(12) United States Patent
Lu et al.

(10) Patent No.: US 9,745,311 B2
(45) Date of Patent: *Aug. 29, 2017

(54) SUBSTITUTED PYRROLO[2,3-B]PYRAZINES AS FGFR INHIBITORS

(71) Applicants: Incyte Corporation, Wilmington, DE (US); Incyte Holdings Corporation, Wilmington, DE (US)

(72) Inventors: Liang Lu, Hockessin, DE (US); Chunhong He, Chadds Ford, PA (US); Wenqing Yao, Chadds Ford, PA (US)

(73) Assignees: Incyte Corporation, Wilmington, DE (US); Incyte Holdings Corporation, Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/181,903

(22) Filed: Jun. 14, 2016

(65) Prior Publication Data

US 2016/0280713 A1    Sep. 29, 2016

Related U.S. Application Data

(63) Continuation of application No. 13/963,569, filed on Aug. 9, 2013, now Pat. No. 9,388,185.

(60) Provisional application No. 61/682,103, filed on Aug. 10, 2012.

(51) Int. Cl.
*C07D 487/04* (2006.01)
*C07D 495/04* (2006.01)
*C07D 519/00* (2006.01)

(52) U.S. Cl.
CPC ......... *C07D 487/04* (2013.01); *C07D 495/04* (2013.01); *C07D 519/00* (2013.01)

(58) Field of Classification Search
CPC .................................................. C07D 487/04
USPC ..... 544/117, 333, 350, 359; 546/199, 268.1; 548/361.1, 364.7, 490, 519, 950; 549/59, 549/356, 434
See application file for complete search history.

(56) References Cited

U.S. PATENT DOCUMENTS

| | | |
|---|---|---|
| 850,370 A | 4/1907 | Hynes |
| 3,894,021 A | 7/1975 | Denzel et al. |
| 4,271,074 A | 6/1981 | Lohmann et al. |
| 4,339,267 A | 7/1982 | Levitt |
| 4,347,348 A | 8/1982 | Chernikhov et al. |
| 4,402,878 A | 9/1983 | D'Alelio et al. |
| 4,405,519 A | 9/1983 | D'Alelio et al. |
| 4,405,520 A | 9/1983 | D'Alelio et al. |
| 4,405,786 A | 9/1983 | D'Alelio et al. |
| 4,460,773 A | 7/1984 | Suzuki et al. |
| 4,874,803 A | 10/1989 | Baron et al. |
| 4,940,705 A | 7/1990 | Boshagen et al. |
| 5,159,054 A | 10/1992 | Keller |
| 5,240,941 A | 8/1993 | Bruneau |
| 5,480,887 A | 1/1996 | Hornback et al. |
| 5,536,725 A | 7/1996 | Cullen et al. |
| 5,541,324 A | 7/1996 | TenBrink et al. |
| 5,783,577 A | 7/1998 | Houghten et al. |
| 5,845,025 A | 12/1998 | Garito et al. |
| 5,994,364 A | 11/1999 | Njoroge et al. |
| 6,465,484 B1 | 10/2002 | Bilodeau et al. |
| 6,998,408 B2 | 2/2006 | Pinto |
| 7,074,801 B1 | 7/2006 | Yoshida et al. |
| 7,125,880 B1 | 10/2006 | Chen |
| 7,642,255 B2 | 1/2010 | Sim |
| 8,754,114 B2 | 6/2014 | Yao et al. |
| 8,889,711 B2 | 11/2014 | Bedjeguelal |
| 2003/0078255 A1 | 4/2003 | Pinto |
| 2003/0078277 A1 | 4/2003 | Hibi et al. |
| 2003/0181622 A1 | 9/2003 | Chiu et al. |
| 2004/0044012 A1 | 3/2004 | Dobrusin et al. |
| 2004/0067948 A1 | 4/2004 | Hallett |
| 2004/0097493 A1 | 5/2004 | Chen et al. |
| 2004/0122029 A1 | 6/2004 | Liu et al. |
| 2004/0204427 A1 | 10/2004 | Chen et al. |

(Continued)

FOREIGN PATENT DOCUMENTS

| | | |
|---|---|---|
| CN | 101007778 | 8/2007 |
| CN | 102399220 | 4/2012 |

(Continued)

OTHER PUBLICATIONS

"Sabiosciences.com" [online]. "FGF Pathway," 2000-2012, [retrieved on Jun. 23, 2015]. Retrieved from the Internet: URL <http://www.sabiosciences.com/pathway.php?sn=FGF_Signaling>, 3 pages.

(Continued)

*Primary Examiner* — Douglas M Willis

(74) *Attorney, Agent, or Firm* — Fish & Richardson P.C.

(57) ABSTRACT

The present invention relates to pyrazine derivatives of Formula I, and pharmaceutical compositions including the same, that are inhibitors of one or more FGFR enzymes and are useful in the treatment of FGFR-associated diseases such as cancer.

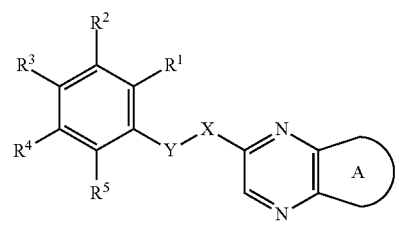

22 Claims, No Drawings

(56) References Cited

U.S. PATENT DOCUMENTS

| | | |
|---|---|---|
| 2005/0070542 A1 | 3/2005 | Hodgetts et al. |
| 2005/0148603 A1 | 7/2005 | Jimenez et al. |
| 2005/0197340 A1 | 9/2005 | Arora et al. |
| 2006/0222637 A1 | 10/2006 | Bamdad |
| 2006/0270849 A1 | 11/2006 | Nishino et al. |
| 2007/0116984 A1 | 5/2007 | Park et al. |
| 2007/0197510 A1 | 8/2007 | Ohmoto et al. |
| 2007/0280943 A1 | 12/2007 | Friedman et al. |
| 2008/0249301 A1 | 10/2008 | Hornberger et al. |
| 2009/0098086 A1 | 4/2009 | Zask et al. |
| 2009/0099165 A1 | 4/2009 | Hurley et al. |
| 2009/0099190 A1 | 4/2009 | Flynn et al. |
| 2009/0105233 A1 | 4/2009 | Chua et al. |
| 2009/0131467 A1 | 5/2009 | Kanazawa et al. |
| 2009/0163545 A1 | 6/2009 | Goldfarb |
| 2009/0246198 A1 | 10/2009 | Dong et al. |
| 2010/0032626 A1 | 2/2010 | Akino |
| 2010/0099684 A1 | 4/2010 | Cook, II et al. |
| 2010/0105661 A1 | 4/2010 | Shirakami et al. |
| 2010/0143547 A1 | 6/2010 | Kriegel et al. |
| 2010/0204235 A1 | 8/2010 | Lizos |
| 2010/0210636 A1 | 8/2010 | Ishikawa et al. |
| 2010/0239496 A1 | 9/2010 | Gangadharmath et al. |
| 2011/0045511 A1 | 2/2011 | Graus Porta et al. |
| 2011/0159604 A1 | 6/2011 | Fan et al. |
| 2011/0160203 A1 | 6/2011 | Liu et al. |
| 2011/0195968 A1 | 8/2011 | Greul et al. |
| 2011/0212077 A1 | 9/2011 | Noronha et al. |
| 2011/0224155 A1 | 9/2011 | Tachdjian et al. |
| 2011/0262525 A1 | 10/2011 | Wang et al. |
| 2011/0313003 A1 | 12/2011 | Shi et al. |
| 2012/0135997 A1 | 5/2012 | Kato et al. |
| 2012/0165305 A1 | 6/2012 | Yao et al. |
| 2012/0295881 A1 | 11/2012 | Lange et al. |
| 2012/0319095 A1 | 12/2012 | Tada et al. |
| 2013/0078731 A1 | 3/2013 | George et al. |
| 2013/0200356 A1 | 8/2013 | Jung et al. |
| 2013/0338134 A1 | 12/2013 | Wu et al. |
| 2014/0045814 A1 | 2/2014 | Lu et al. |
| 2014/0054564 A1 | 2/2014 | Kim et al. |
| 2014/0080892 A1 | 3/2014 | Bhanot et al. |
| 2014/0088100 A1 | 3/2014 | Bifulco, Jr. et al. |
| 2014/0103325 A1 | 4/2014 | Shin et al. |
| 2014/0117318 A1 | 5/2014 | Choi et al. |
| 2014/0148548 A1 | 5/2014 | Yamanaka et al. |
| 2014/0171405 A1 | 6/2014 | Zhuo et al. |
| 2014/0187559 A1 | 7/2014 | Miduturu |
| 2014/0243308 A1 | 8/2014 | Yao et al. |
| 2014/0296233 A1 | 10/2014 | D'Agostino et al. |
| 2014/0315902 A1 | 10/2014 | Sun et al. |
| 2014/0374722 A1 | 12/2014 | Kim et al. |
| 2014/0378468 A1 | 12/2014 | Aichholz et al. |
| 2014/0378481 A1 | 12/2014 | Bifulco, Jr. et al. |
| 2014/0378483 A1 | 12/2014 | Benazet et al. |
| 2015/0011548 A1 | 1/2015 | Linnanen et al. |
| 2015/0011560 A1 | 1/2015 | Legeai-Mallet |
| 2015/0011579 A1 | 1/2015 | Clary-Ceccato et al. |
| 2015/0197519 A1 | 7/2015 | Bifulco |
| 2016/0115164 A1 | 4/2016 | Wu et al. |
| 2016/0244448 A1 | 8/2016 | Lu et al. |
| 2016/0244449 A1 | 8/2016 | Lu et al. |
| 2016/0244450 A1 | 8/2016 | Lu et al. |

FOREIGN PATENT DOCUMENTS

| | | |
|---|---|---|
| CN | 102399233 | 4/2012 |
| CN | 103571502 | 2/2014 |
| CN | 103588771 | 2/2014 |
| CN | 104262330 | 1/2015 |
| DE | 2156720 | 5/1973 |
| DE | 2934578 | 3/1981 |
| DE | 3432983 | 4/1985 |
| DE | 280853 | 7/1990 |
| DE | 3937633 | 5/1991 |
| DE | 4119767 | 12/1992 |
| DE | 19912638 | 9/2000 |
| EP | 0466452 | 1/1992 |
| EP | 0995751 | 4/2000 |
| EP | 1199070 | 4/2002 |
| EP | 1217000 | 6/2002 |
| EP | 1388541 | 2/2004 |
| EP | 2651404 | 10/2015 |
| FR | 2428654 | 1/1980 |
| FR | 2876582 | 4/2006 |
| FR | 2983196 | 5/2013 |
| FR | 2983199 | 5/2013 |
| FR | 2983200 | 5/2013 |
| JP | 62273979 | 11/1987 |
| JP | 63017882 | 1/1988 |
| JP | S 6310630 | 1/1988 |
| JP | 02009895 | 1/1990 |
| JP | H 0348656 | 3/1991 |
| JP | H 03275669 | 12/1991 |
| JP | 04179576 | 6/1992 |
| JP | H 04158084 | 6/1992 |
| JP | H 04328121 | 11/1992 |
| JP | H 05320173 | 12/1993 |
| JP | H 05320515 | 12/1993 |
| JP | H 09188812 | 7/1997 |
| JP | H 1060426 | 3/1998 |
| JP | H 11171865 | 6/1999 |
| JP | 2000123973 | 4/2000 |
| JP | 2001265031 | 9/2001 |
| JP | 2002296731 | 10/2002 |
| JP | 2003335788 | 11/2003 |
| JP | 2004203749 | 7/2004 |
| JP | 2004346145 | 12/2004 |
| JP | 2005015395 | 1/2005 |
| JP | 2005320288 | 11/2005 |
| JP | 200628027 | 2/2006 |
| JP | 2006284843 | 10/2006 |
| JP | 2006316054 | 11/2006 |
| JP | 2008198769 | 8/2008 |
| JP | 2010180147 | 8/2010 |
| JP | 2010248429 | 11/2010 |
| JP | 2010267847 | 11/2010 |
| JP | 2010270245 | 12/2010 |
| JP | 2010272618 | 12/2010 |
| JP | 2010272727 | 12/2010 |
| JP | 2010278114 | 12/2010 |
| JP | 20119348 | 1/2011 |
| JP | 201144637 | 3/2011 |
| JP | 2011116840 | 6/2011 |
| JP | 2011222650 | 11/2011 |
| JP | 2012116825 | 6/2012 |
| JP | 2012136476 | 7/2012 |
| JP | 5120580 | 1/2013 |
| JP | 201349251 | 3/2013 |
| JP | 2013179181 | 9/2013 |
| KR | 20080045536 | 5/2008 |
| KR | 20110023190 | 3/2011 |
| KR | 20110043270 | 4/2011 |
| KR | 20120052034 | 5/2012 |
| KR | 20120078303 | 7/2012 |
| KR | 20130043460 | 4/2013 |
| KR | 20140090411 | 7/2014 |
| KR | 2014009105 | 8/2014 |
| WO | WO 88/03025 | 5/1988 |
| WO | WO 91/09835 | 7/1991 |
| WO | WO 91/10172 | 7/1991 |
| WO | WO 92/06078 | 4/1992 |
| WO | WO 92/22552 | 12/1992 |
| WO | WO 93/24488 | 12/1993 |
| WO | WO 94/13669 | 6/1994 |
| WO | WO 94/15995 | 7/1994 |
| WO | WO 94/25438 | 11/1994 |
| WO | WO 95/20965 | 8/1995 |
| WO | WO 96/15128 | 5/1996 |
| WO | WO 96/40707 | 12/1996 |
| WO | WO 97/47601 | 12/1997 |
| WO | WO 98/05661 | 2/1998 |
| WO | WO 98/06703 | 2/1998 |
| WO | WO 98/11438 | 3/1998 |
| WO | WO 98/18781 | 5/1998 |

(56) References Cited

FOREIGN PATENT DOCUMENTS

| | | |
|---|---|---|
| WO | WO 98/28281 | 7/1998 |
| WO | WO 98/33798 | 8/1998 |
| WO | WO 98/46609 | 10/1998 |
| WO | WO 98/54156 | 12/1998 |
| WO | WO 99/06422 | 2/1999 |
| WO | WO 99/07732 | 2/1999 |
| WO | WO 99/09030 | 2/1999 |
| WO | WO 99/42442 | 8/1999 |
| WO | WO 99/59975 | 11/1999 |
| WO | WO 99/61444 | 12/1999 |
| WO | WO 99/64400 | 12/1999 |
| WO | WO 00/24744 | 5/2000 |
| WO | WO 00/68186 | 11/2000 |
| WO | WO 01/02369 | 1/2001 |
| WO | WO 01/22938 | 4/2001 |
| WO | WO 01/23386 | 4/2001 |
| WO | WO 01/29041 | 4/2001 |
| WO | WO 01/29042 | 4/2001 |
| WO | WO 01/42247 | 6/2001 |
| WO | WO 01/47892 | 7/2001 |
| WO | WO 01/53273 | 7/2001 |
| WO | WO 01/55148 | 8/2001 |
| WO | WO 01/57037 | 8/2001 |
| WO | WO 01/57038 | 8/2001 |
| WO | WO 01/58899 | 8/2001 |
| WO | WO 01/66099 | 9/2001 |
| WO | WO 01/68647 | 9/2001 |
| WO | WO 01/83472 | 11/2001 |
| WO | WO 01/85722 | 11/2001 |
| WO | WO 02/00655 | 1/2002 |
| WO | WO 02/12442 | 2/2002 |
| WO | WO 02/14315 | 2/2002 |
| WO | WO 02/20011 | 3/2002 |
| WO | WO 02/051831 | 7/2002 |
| WO | WO 02/055082 | 7/2002 |
| WO | WO 02/066481 | 8/2002 |
| WO | WO 02/074754 | 9/2002 |
| WO | WO 02/076953 | 10/2002 |
| WO | WO 02/088095 | 11/2002 |
| WO | WO 02/094825 | 11/2002 |
| WO | WO 02/096873 | 12/2002 |
| WO | WO 02/102793 | 12/2002 |
| WO | WO 03/000187 | 1/2003 |
| WO | WO 03/000688 | 1/2003 |
| WO | WO 03/000690 | 1/2003 |
| WO | WO 03/009852 | 2/2003 |
| WO | WO 03/014083 | 2/2003 |
| WO | WO 03/037891 | 5/2003 |
| WO | WO 03/040131 | 5/2003 |
| WO | WO 03/049542 | 6/2003 |
| WO | WO 03/062236 | 7/2003 |
| WO | WO 03/075836 | 9/2003 |
| WO | WO 03/082871 | 10/2003 |
| WO | WO 03/097609 | 11/2003 |
| WO | WO 03/099818 | 12/2003 |
| WO | WO 03/101985 | 12/2003 |
| WO | WO 2004/002986 | 1/2004 |
| WO | WO 2004/011465 | 2/2004 |
| WO | WO 2004/014382 | 2/2004 |
| WO | WO 2004/014907 | 2/2004 |
| WO | WO 2004/018472 | 3/2004 |
| WO | WO 2004/020441 | 3/2004 |
| WO | WO 2004/041821 | 5/2004 |
| WO | WO 2004/041822 | 5/2004 |
| WO | WO 2004/041823 | 5/2004 |
| WO | WO 2004/043367 | 5/2004 |
| WO | WO 2004/048343 | 6/2004 |
| WO | WO 2004/052291 | 6/2004 |
| WO | WO 2004/052862 | 6/2004 |
| WO | WO 2004/056822 | 7/2004 |
| WO | WO 2004/056830 | 7/2004 |
| WO | WO 2004/065378 | 8/2004 |
| WO | WO 2004/083177 | 9/2004 |
| WO | WO 2004/087053 | 10/2004 |
| WO | WO 2004/089955 | 10/2004 |
| WO | WO 2004/094420 | 11/2004 |
| WO | WO 2004/099209 | 11/2004 |
| WO | WO 2004/108139 | 11/2004 |
| WO | WO 2004/110487 | 12/2004 |
| WO | WO 2004/112793 | 12/2004 |
| WO | WO 2004/113307 | 12/2004 |
| WO | WO 2005/007653 | 1/2005 |
| WO | WO 2005/011597 | 2/2005 |
| WO | WO 2005/021533 | 3/2005 |
| WO | WO 2005/028434 | 3/2005 |
| WO | WO 2005/028478 | 3/2005 |
| WO | WO 2005/028480 | 3/2005 |
| WO | WO 2005/040119 | 5/2005 |
| WO | WO 2005/047289 | 5/2005 |
| WO | WO 2005/056524 | 6/2005 |
| WO | WO 2005/063768 | 6/2005 |
| WO | WO 2005/066162 | 7/2005 |
| WO | WO 2005/070430 | 8/2005 |
| WO | WO 2005/070929 | 8/2005 |
| WO | WO 2005/072412 | 8/2005 |
| WO | WO 2005/073232 | 8/2005 |
| WO | WO 2005/080393 | 9/2005 |
| WO | WO 2005/082903 | 9/2005 |
| WO | WO 2005/085210 | 9/2005 |
| WO | WO 2005/085248 | 9/2005 |
| WO | WO 2005/085249 | 9/2005 |
| WO | WO 2005/087765 | 9/2005 |
| WO | WO 2005/092901 | 10/2005 |
| WO | WO 2005/113536 | 12/2005 |
| WO | WO 2005/116035 | 12/2005 |
| WO | WO 2005/121130 | 12/2005 |
| WO | WO 2005/121142 | 12/2005 |
| WO | WO 2006/000420 | 1/2006 |
| WO | WO 2006/024486 | 3/2006 |
| WO | WO 2006/024487 | 3/2006 |
| WO | WO 2006/024834 | 3/2006 |
| WO | WO 2006/028289 | 3/2006 |
| WO | WO 2006/030031 | 3/2006 |
| WO | WO 2006/038112 | 4/2006 |
| WO | WO 2006/050076 | 5/2006 |
| WO | WO 2006/050162 | 5/2006 |
| WO | WO 2006/052712 | 5/2006 |
| WO | WO 2006/055752 | 5/2006 |
| WO | WO 2006/024524 | 6/2006 |
| WO | WO 2006/058120 | 6/2006 |
| WO | WO 2006/062465 | 6/2006 |
| WO | WO 2006/065703 | 6/2006 |
| WO | WO 2006/074293 | 7/2006 |
| WO | WO 2006/087230 | 8/2006 |
| WO | WO 2006/092691 | 9/2006 |
| WO | WO 2006/102588 | 9/2006 |
| WO | WO 2006/102610 | 9/2006 |
| WO | WO 2006/105448 | 10/2006 |
| WO | WO 2006/107644 | 10/2006 |
| WO | WO 2006/112666 | 10/2006 |
| WO | WO 2006/119504 | 11/2006 |
| WO | WO 2006/124462 | 11/2006 |
| WO | WO 2006/124731 | 11/2006 |
| WO | WO 2006/135821 | 12/2006 |
| WO | WO 2006/136442 | 12/2006 |
| WO | WO 2007/013964 | 2/2007 |
| WO | WO 2007/017096 | 2/2007 |
| WO | WO 2007/021795 | 2/2007 |
| WO | WO 2007/022268 | 2/2007 |
| WO | WO 2007/023105 | 3/2007 |
| WO | WO 2007/025949 | 3/2007 |
| WO | WO 2007/030366 | 3/2007 |
| WO | WO 2007/032466 | 3/2007 |
| WO | WO 2007/033780 | 3/2007 |
| WO | WO 2007/038209 | 4/2007 |
| WO | WO 2007/044698 | 4/2007 |
| WO | WO 2007/044729 | 4/2007 |
| WO | WO 2007/048802 | 5/2007 |
| WO | WO 2007/053135 | 5/2007 |
| WO | WO 2007/053452 | 5/2007 |
| WO | WO 2007/053498 | 5/2007 |
| WO | WO 2007/055418 | 5/2007 |
| WO | WO 2007/056023 | 5/2007 |
| WO | WO 2007/056075 | 5/2007 |

(56) References Cited

FOREIGN PATENT DOCUMENTS

| | | |
|---|---|---|
| WO | WO 2007/056170 | 5/2007 |
| WO | WO 2007/058392 | 5/2007 |
| WO | WO 2007/058626 | 5/2007 |
| WO | WO 2007/059108 | 5/2007 |
| WO | WO 2007/061554 | 5/2007 |
| WO | WO 2007/064883 | 6/2007 |
| WO | WO 2007/064931 | 6/2007 |
| WO | WO 2007/066189 | 6/2007 |
| WO | WO 2007/067444 | 6/2007 |
| WO | WO 2007/071752 | 6/2007 |
| WO | WO 2007/084314 | 7/2007 |
| WO | WO 2007/088999 | 8/2007 |
| WO | WO 2007/092879 | 8/2007 |
| WO | WO 2007/093901 | 8/2007 |
| WO | WO 2007/109334 | 9/2007 |
| WO | WO 2007/110868 | 10/2007 |
| WO | WO 2007/112347 | 10/2007 |
| WO | WO 2007/120097 | 10/2007 |
| WO | WO 2007/120339 | 10/2007 |
| WO | WO 2007/125351 | 11/2007 |
| WO | WO 2007/125405 | 11/2007 |
| WO | WO 2007/126841 | 11/2007 |
| WO | WO 2007/134259 | 11/2007 |
| WO | WO 2007/136465 | 11/2007 |
| WO | WO 2007/140957 | 12/2007 |
| WO | WO 2007/143600 | 12/2007 |
| WO | WO 2007/147217 | 12/2007 |
| WO | WO 2008/001070 | 1/2008 |
| WO | WO 2008/003766 | 1/2008 |
| WO | WO 2008/005877 | 1/2008 |
| WO | WO 2008/008234 | 1/2008 |
| WO | WO 2008/008747 | 1/2008 |
| WO | WO 2008/012635 | 1/2008 |
| WO | WO 2008/021389 | 2/2008 |
| WO | WO 2008/021851 | 2/2008 |
| WO | WO 2008/025556 | 3/2008 |
| WO | WO 2008/033858 | 3/2008 |
| WO | WO 2008/033999 | 3/2008 |
| WO | WO 2008/034859 | 3/2008 |
| WO | WO 2008/034860 | 3/2008 |
| WO | WO 2008/042639 | 4/2008 |
| WO | WO 2008/052898 | 5/2008 |
| WO | WO 2008/052934 | 5/2008 |
| WO | WO 2008/060907 | 5/2008 |
| WO | WO 2008/063583 | 5/2008 |
| WO | WO 2008/063609 | 5/2008 |
| WO | WO 2008/071455 | 6/2008 |
| WO | WO 2008/074068 | 6/2008 |
| WO | WO 2008/075068 | 6/2008 |
| WO | WO 2008/076278 | 6/2008 |
| WO | WO 2008/078091 | 7/2008 |
| WO | WO 2008/078100 | 7/2008 |
| WO | WO 2008/079460 | 7/2008 |
| WO | WO 2008/079933 | 7/2008 |
| WO | WO 2008/085942 | 7/2008 |
| WO | WO 2008/089105 | 7/2008 |
| WO | WO 2008/099075 | 8/2008 |
| WO | WO 2008/107436 | 9/2008 |
| WO | WO 2008/107544 | 9/2008 |
| WO | WO 2008/109181 | 9/2008 |
| WO | WO 2008/115974 | 9/2008 |
| WO | WO 2009/109943 | 9/2008 |
| WO | WO 2008/117269 | 10/2008 |
| WO | WO 2008/118454 | 10/2008 |
| WO | WO 2008/123755 | 10/2008 |
| WO | WO 2008/128141 | 10/2008 |
| WO | WO 2008/130584 | 10/2008 |
| WO | WO 2008/131972 | 11/2008 |
| WO | WO 2008/141065 | 11/2008 |
| WO | WO 2008/142720 | 11/2008 |
| WO | WO 2008/144253 | 11/2008 |
| WO | WO 2008/151184 | 12/2008 |
| WO | WO 2008/153207 | 12/2008 |
| WO | WO 2008/153852 | 12/2008 |
| WO | WO 2008/154221 | 12/2008 |
| WO | WO 2009/013335 | 1/2009 |
| WO | WO 2009/013354 | 1/2009 |
| WO | WO 2009/097446 | 1/2009 |
| WO | WO 2009/016253 | 2/2009 |
| WO | WO 2009/019518 | 2/2009 |
| WO | WO 2009/021083 | 2/2009 |
| WO | WO 2009/029473 | 3/2009 |
| WO | WO 2009/029625 | 3/2009 |
| WO | WO 2009/030871 | 3/2009 |
| WO | WO 2009/032861 | 3/2009 |
| WO | WO 2009/036012 | 3/2009 |
| WO | WO 2009/044788 | 4/2009 |
| WO | WO 2009/046606 | 4/2009 |
| WO | WO 2009/047255 | 4/2009 |
| WO | WO 2009/047506 | 4/2009 |
| WO | WO 2009/047522 | 4/2009 |
| WO | WO 2009/047993 | 4/2009 |
| WO | WO 2009/049018 | 4/2009 |
| WO | WO 2009/053737 | 4/2009 |
| WO | WO 2009/055828 | 4/2009 |
| WO | WO 2009/056886 | 5/2009 |
| WO | WO 2009/071535 | 6/2009 |
| WO | WO 2009/073153 | 6/2009 |
| WO | WO 2009/086130 | 7/2009 |
| WO | WO 2009/086509 | 7/2009 |
| WO | WO 2009/087238 | 7/2009 |
| WO | WO 2009/092764 | 7/2009 |
| WO | WO 2009/093209 | 7/2009 |
| WO | WO 2009/093210 | 7/2009 |
| WO | WO 2009/094528 | 7/2009 |
| WO | WO 2009/099982 | 8/2009 |
| WO | WO 2009/103652 | 8/2009 |
| WO | WO 2009/105717 | 8/2009 |
| WO | WO 2009/108332 | 9/2009 |
| WO | WO 2009/108827 | 9/2009 |
| WO | WO 2009/112826 | 9/2009 |
| WO | WO 2009/114870 | 9/2009 |
| WO | WO 2009/114874 | 9/2009 |
| WO | WO 2009/122180 | 10/2009 |
| WO | WO 2009/123967 | 10/2009 |
| WO | WO 2009/125808 | 10/2009 |
| WO | WO 2009/125809 | 10/2009 |
| WO | WO 2009/126584 | 10/2009 |
| WO | WO 2009/128520 | 10/2009 |
| WO | WO 2009/131687 | 10/2009 |
| WO | WO 2009/131926 | 10/2009 |
| WO | WO 2009/132980 | 11/2009 |
| WO | WO 2009/133127 | 11/2009 |
| WO | WO 2009/141386 | 11/2009 |
| WO | WO 2009/144205 | 12/2009 |
| WO | WO 2009/144302 | 12/2009 |
| WO | WO 2009/146034 | 12/2009 |
| WO | WO 2009/150150 | 12/2009 |
| WO | WO 2009/150240 | 12/2009 |
| WO | WO 2009/151997 | 12/2009 |
| WO | WO 2009/153592 | 12/2009 |
| WO | WO 2009/157423 | 12/2009 |
| WO | WO 2010/006947 | 1/2010 |
| WO | WO 2010/007099 | 1/2010 |
| WO | WO 2010/007116 | 1/2010 |
| WO | WO 2010/009155 | 1/2010 |
| WO | WO 2010/009195 | 1/2010 |
| WO | WO 2010/009207 | 1/2010 |
| WO | WO 2010/015643 | 2/2010 |
| WO | WO 2010/017047 | 2/2010 |
| WO | WO 2010/019210 | 2/2010 |
| WO | WO 2010/019899 | 2/2010 |
| WO | WO 2010/030027 | 3/2010 |
| WO | WO 2010/038081 | 4/2010 |
| WO | WO 2010/045371 | 4/2010 |
| WO | WO 2010/049731 | 5/2010 |
| WO | WO 2010/051043 | 5/2010 |
| WO | WO 2010/052448 | 5/2010 |
| WO | WO 2010/059552 | 5/2010 |
| WO | WO 2010/059658 | 5/2010 |
| WO | WO 2010/064621 | 6/2010 |
| WO | WO 2010/064875 | 6/2010 |
| WO | WO 2010/067886 | 6/2010 |
| WO | WO 2010/067888 | 6/2010 |

(56) References Cited

FOREIGN PATENT DOCUMENTS

| | | |
|---|---|---|
| WO | WO 2010/077647 | 7/2010 |
| WO | WO 2010/077680 | 7/2010 |
| WO | WO 2010/078421 | 7/2010 |
| WO | WO 2010/078427 | 7/2010 |
| WO | WO 2010/080503 | 7/2010 |
| WO | WO 2010/080712 | 7/2010 |
| WO | WO 2010/083145 | 7/2010 |
| WO | WO 2010/083283 | 7/2010 |
| WO | WO 2010/086089 | 8/2010 |
| WO | WO 2010/092181 | 8/2010 |
| WO | WO 2010/099938 | 9/2010 |
| WO | WO 2010/103306 | 9/2010 |
| WO | WO 2010/104047 | 9/2010 |
| WO | WO 2010/107765 | 9/2010 |
| WO | WO 2010/107768 | 9/2010 |
| WO | WO 2010/111303 | 9/2010 |
| WO | WO 2010/111573 | 9/2010 |
| WO | WO 2010/115279 | 10/2010 |
| WO | WO 2010/117425 | 10/2010 |
| WO | WO 2010/119284 | 10/2010 |
| WO | WO 2010/119285 | 10/2010 |
| WO | WO 2010/117323 | 11/2010 |
| WO | WO 2010/125216 | 11/2010 |
| WO | WO 2010/126960 | 11/2010 |
| WO | WO 2010/127212 | 11/2010 |
| WO | WO 2010/129509 | 11/2010 |
| WO | WO 2010/136031 | 12/2010 |
| WO | WO 2010/142801 | 12/2010 |
| WO | WO 2010/151689 | 12/2010 |
| WO | WO 2011/002038 | 1/2011 |
| WO | WO 2011/007819 | 1/2011 |
| WO | WO 2011/011597 | 1/2011 |
| WO | WO 2011/012816 | 2/2011 |
| WO | WO 2011/014535 | 2/2011 |
| WO | WO 2011/015037 | 2/2011 |
| WO | WO 2011/016472 | 2/2011 |
| WO | WO 2011/016528 | 2/2011 |
| WO | WO 2011/018894 | 2/2011 |
| WO | WO 2011/022439 | 2/2011 |
| WO | WO 2011/026579 | 3/2011 |
| WO | WO 2011/028947 | 3/2011 |
| WO | WO 2011/031740 | 3/2011 |
| WO | WO 2011/032050 | 3/2011 |
| WO | WO 2011/039344 | 4/2011 |
| WO | WO 2011/041143 | 4/2011 |
| WO | WO 2011/042389 | 4/2011 |
| WO | WO 2011/042474 | 4/2011 |
| WO | WO 2011/045344 | 4/2011 |
| WO | WO 2011/049825 | 4/2011 |
| WO | WO 2011/049988 | 4/2011 |
| WO | WO 2011/050245 | 4/2011 |
| WO | WO 2011/051425 | 5/2011 |
| WO | WO 2011/054843 | 5/2011 |
| WO | WO 2011/055911 | 5/2011 |
| WO | WO 2011/057022 | 5/2011 |
| WO | WO 2011/060295 | 5/2011 |
| WO | WO 2011/062253 | 5/2011 |
| WO | WO 2011/062885 | 5/2011 |
| WO | WO 2011/063159 | 5/2011 |
| WO | WO 2011/068899 | 6/2011 |
| WO | WO 2011/071821 | 6/2011 |
| WO | WO 2011/075515 | 6/2011 |
| WO | WO 2011/075620 | 6/2011 |
| WO | WO 2011/077043 | 6/2011 |
| WO | WO 2011/077044 | 6/2011 |
| WO | WO 2011/079231 | 6/2011 |
| WO | WO 2011/080755 | 7/2011 |
| WO | WO 2011/082234 | 7/2011 |
| WO | WO 2011/082266 | 7/2011 |
| WO | WO 2011/082267 | 7/2011 |
| WO | WO 2011/082488 | 7/2011 |
| WO | WO 2011/087776 | 7/2011 |
| WO | WO 2011/090666 | 7/2011 |
| WO | WO 2011/090738 | 7/2011 |
| WO | WO 2011/090760 | 7/2011 |
| WO | WO 2011/093672 | 8/2011 |
| WO | WO 2011/094890 | 8/2011 |
| WO | WO 2011/097717 | 8/2011 |
| WO | WO 2011/101806 | 8/2011 |
| WO | WO 2011/102441 | 8/2011 |
| WO | WO 2011/103196 | 8/2011 |
| WO | WO 2011/103441 | 8/2011 |
| WO | WO 2011/103460 | 8/2011 |
| WO | WO 2011/103557 | 8/2011 |
| WO | WO 2011/105161 | 9/2011 |
| WO | WO 2011/109237 | 9/2011 |
| WO | WO 2011/111880 | 9/2011 |
| WO | WO 2011/112687 | 9/2011 |
| WO | WO 2011/112995 | 9/2011 |
| WO | WO 2011/115725 | 9/2011 |
| WO | WO 2011/119894 | 9/2011 |
| WO | WO 2011/120327 | 10/2011 |
| WO | WO 2011/123493 | 10/2011 |
| WO | WO 2011/128403 | 10/2011 |
| WO | WO 2011/130390 | 10/2011 |
| WO | WO 2011/133722 | 10/2011 |
| WO | WO 2011/133750 | 10/2011 |
| WO | WO 2011/133888 | 10/2011 |
| WO | WO 2011/135376 | 11/2011 |
| WO | WO 2011/137313 | 11/2011 |
| WO | WO 2011/140338 | 11/2011 |
| WO | WO 2011/141756 | 11/2011 |
| WO | WO 2011/141848 | 11/2011 |
| WO | WO 2011/143033 | 11/2011 |
| WO | WO 2011/143318 | 11/2011 |
| WO | WO 2011/143430 | 11/2011 |
| WO | WO 2011/147198 | 12/2011 |
| WO | WO 2011/147199 | 12/2011 |
| WO | WO 2011/151360 | 12/2011 |
| WO | WO 2011/153553 | 12/2011 |
| WO | WO 2011/155983 | 12/2011 |
| WO | WO 2011/156610 | 12/2011 |
| WO | WO 2012/000103 | 1/2012 |
| WO | WO 2012/003544 | 1/2012 |
| WO | WO 2012/004217 | 1/2012 |
| WO | WO 2012/004731 | 1/2012 |
| WO | WO 2012/004732 | 1/2012 |
| WO | WO 2012/008563 | 1/2012 |
| WO | WO 2012/008564 | 1/2012 |
| WO | WO 2012/008999 | 1/2012 |
| WO | WO 2012/009258 | 1/2012 |
| WO | WO 2012/009309 | 1/2012 |
| WO | WO 2012/013619 | 2/2012 |
| WO | WO 2012/015274 | 2/2012 |
| WO | WO 2012/019093 | 2/2012 |
| WO | WO 2012/020133 | 2/2012 |
| WO | WO 2012/027236 | 3/2012 |
| WO | WO 2012/027239 | 3/2012 |
| WO | WO 2012/030990 | 3/2012 |
| WO | WO 2012/031004 | 3/2012 |
| WO | WO 2012/032031 | 3/2012 |
| WO | WO 2012/032065 | 3/2012 |
| WO | WO 2012/032067 | 3/2012 |
| WO | WO 2012/032334 | 3/2012 |
| WO | WO 2012/035996 | 3/2012 |
| WO | WO 2012/036233 | 3/2012 |
| WO | WO 2012/038743 | 3/2012 |
| WO | WO 2012/047699 | 4/2012 |
| WO | WO 2012/054364 | 4/2012 |
| WO | WO 2012/057260 | 5/2012 |
| WO | WO 2012/058211 | 5/2012 |
| WO | WO 2012/061337 | 5/2012 |
| WO | WO 2012/062462 | 5/2012 |
| WO | WO 2012/063207 | 5/2012 |
| WO | WO 2012/064715 | 5/2012 |
| WO | WO 2012/065297 | 5/2012 |
| WO | WO 2012/065546 | 5/2012 |
| WO | WO 2012/066578 | 5/2012 |
| WO | WO 2012/068343 | 5/2012 |
| WO | WO 2012/073017 | 6/2012 |
| WO | WO 2012/080727 | 6/2012 |
| WO | WO 2012/080729 | 6/2012 |
| WO | WO 2012/083866 | 6/2012 |
| WO | WO 2012/083953 | 6/2012 |

(56) References Cited

FOREIGN PATENT DOCUMENTS

| | | |
|---|---|---|
| WO | WO 2012/083954 | 6/2012 |
| WO | WO 2012/087784 | 6/2012 |
| WO | WO 2012/088266 | 6/2012 |
| WO | WO 2012/091240 | 7/2012 |
| WO | WO 2012/093731 | 7/2012 |
| WO | WO 2012/098068 | 7/2012 |
| WO | WO 2012/101239 | 8/2012 |
| WO | WO 2012/106995 | 8/2012 |
| WO | WO 2012/112961 | 8/2012 |
| WO | WO 2012/112965 | 8/2012 |
| WO | WO 2012/116237 | 8/2012 |
| WO | WO 2012/125812 | 9/2012 |
| WO | WO 2012/127012 | 9/2012 |
| WO | WO 2012/134943 | 10/2012 |
| WO | WO 2012/138975 | 10/2012 |
| WO | WO 2012/140114 | 10/2012 |
| WO | WO 2012/158704 | 11/2012 |
| WO | WO 2012/158795 | 11/2012 |
| WO | WO 2012/158994 | 11/2012 |
| WO | WO 2012/161812 | 11/2012 |
| WO | WO 2012/167247 | 12/2012 |
| WO | WO 2012/173370 | 12/2012 |
| WO | WO 2013/016197 | 1/2013 |
| WO | WO 2013/024002 | 2/2013 |
| WO | WO 2013/024895 | 2/2013 |
| WO | WO 2013/033981 | 3/2013 |
| WO | WO 2013/039854 | 3/2013 |
| WO | WO 2013/049352 | 4/2013 |
| WO | WO 2013/063000 | 5/2013 |
| WO | WO 2013/063003 | 5/2013 |
| WO | WO 2013/108809 | 7/2013 |
| WO | WO 2013/109027 | 7/2013 |
| WO | WO 2013/124316 | 8/2013 |
| WO | WO 2013/136249 | 9/2013 |
| WO | WO 2013/144339 | 10/2013 |
| WO | WO 2014/007951 | 1/2014 |
| WO | WO 2014/011284 | 1/2014 |
| WO | WO 2014/011900 | 1/2014 |
| WO | WO 2014/019186 | 2/2014 |
| WO | WO 2014/022528 | 2/2014 |
| WO | WO 2014/026125 | 2/2014 |
| WO | WO 2014/044846 | 3/2014 |
| WO | WO 2014/048878 | 4/2014 |
| WO | WO 2014/062454 | 4/2014 |
| WO | WO 2014/085216 | 5/2014 |
| WO | WO 2014/089913 | 6/2014 |
| WO | WO 2014/105849 | 7/2014 |
| WO | WO 2014/113191 | 7/2014 |
| WO | WO 2014/136972 | 9/2014 |
| WO | WO 2014/138485 | 9/2014 |
| WO | WO 2014/140184 | 9/2014 |
| WO | WO 2014/144737 | 9/2014 |
| WO | WO 2014/160160 | 10/2014 |
| WO | WO 2014/160478 | 10/2014 |
| WO | WO 2014/160521 | 10/2014 |
| WO | WO 2014/162039 | 10/2014 |
| WO | WO 2014/171755 | 10/2014 |
| WO | WO 2014/172644 | 10/2014 |
| WO | WO 2014/174307 | 10/2014 |
| WO | WO 2014/182829 | 11/2014 |
| WO | WO 2014/198942 | 12/2014 |
| WO | WO 2014/206343 | 12/2014 |
| WO | WO 2014/206344 | 12/2014 |
| WO | WO 2015/000715 | 1/2015 |
| WO | WO 2015/006492 | 1/2015 |
| WO | WO 2015/006754 | 1/2015 |
| WO | WO 2015/030021 | 3/2015 |
| WO | WO 2015/057938 | 4/2015 |
| WO | WO 2015/057963 | 4/2015 |
| WO | WO 2015/059668 | 4/2015 |
| WO | WO 2015/061572 | 4/2015 |
| WO | WO 2015/066452 | 5/2015 |
| WO | WO 2015/108992 | 7/2015 |
| WO | WO 2016/064960 | 4/2016 |

OTHER PUBLICATIONS

"Substance Record for SID 240993001," Feb. 13, 2015, pp. 1-8.

Acevedo et al., "Inducible FGFR-1 Activation Leads to Irreversible Prostate Adenocarcinoma and an Epithelial-to-Mesenchymal Transition," Cancer Cell, Dec. 2007, 12: 559-571.

Ali et al., "Synthesis and structure activity relationship of substituted N,6-diphenyl-5,6-dihydrobenzo[h]quinazolin-2-amine as inhibitors of fibroblast growth factor receptors (FGFR)" Cancer Res, Apr. 15, 2012, 72; 3905.

Angevin et al., "TKI258 (dovitinib lactate) in metastatic renal cell carcinoma (mRCC) patients refractory to approved targeted therapies: A phase I/II dose finding and biomarker study," Journal of Clinical Oncology, May 20, 2009, 27:15S, 1 page.

Antonios-McCrea et al., "LHMDS mediated tandem acylation-cyclization of 2-aminobenzenecarbonitriles with 2-benzymidazol-2-ylacetates: a short and efficient route to the synthesis of 4-amino-3-benzimidazol-2-ylhydroquinolin-2-ones," Tetrahedron Letters, 2006, 657-660.

Avet-Loiseau et al., "Impact of high-risk cytogenetics and prior therapy on outcomes in patients with advanced relapsed or refractory multiple myeloma treated with lenalidomide plus dexamethasone," Leukemia, 2010, 623-628.

Bai et al., "GP369, an FGFR2-IIIb specific antibody, exhibits potent antitumor activity against human cancers driven by activated FGFR2 signaling," Am. Assoc. for Cancer Research, Aug. 17, 2010, 30 pages.

Bansal et al., "Specific inhibitor of FGF receptor signaling: FGF-2-mediated effects on proliferation, differentiation, and MAPK activation are inhibited by PD173074 in oligodendrocyte-lineage cells," J. Neurosci. Res., 2003, 74: 486.

Beekman et al., "New Molecular Targets and Novel Agents in the Treatment of Advanced Urothelial Cancer," Semin Oncol, 2007, 34: 154-164.

Bello et al., "E-3810 is a potent dual inhibitor of VEGFR and FGFR that exerts antitumor activity in multiple preclinical models," Cancer Res, 2011.

Bello et al., "E-3810 is a potent dual inhibitor of VEGFR and FGFR that exerts antitumor activity in multiple preclinical models," Cancer Res, 2011, Supplemental figures, 4 pages.

Bello et al., "E-3810 is a potent dual inhibitor of VEGFR and FGFR that exerts antitumor activity in multiple preclinical models," Cancer Res, 2011, Supplemental table, 3 pages.

Bello et al., "E-3810 is a potent dual inhibitor of VEGFR and FGFR that exerts antitumor activity in multiple preclinical models," Cancer Res, 2011, Supplementary data, 4 pages.

Benet-Pages et al., "An FGF23 missense mutation causes familial tumoral calcinosis with hyperphosphatemia," Human Molecular Genetics, 2005, 14(3):385-390.

Berge et al., "Pharmaceutical Salts", Journal of Pharmaceutical Science, 66(2):1-19 (1977).

Bergwitz and Juppner, "Regulation of Phosphate Homeostasis by PTH, Vitamin D, and FGF23," Annu. Rev. Med., 2010, 61:91-104.

Bhide et al., "Discovery and Preclinical Studies of (R )-1-(4-(4-Fluoro-2-methyl-1H-indol-5-yloxy)-5-methylpyrrolo[2,1-f][1,2,4]triazin-6-yloxy)propan-2-ol (BMS-540215), an In Vivo Active Potent VEGFR-2 Inhibitor," Journal of Medicinal Chemistry, 2006, 49(7): 2143-2146.

Billottet et al., "Targets of Fibroblast Growth Factor 1 (FGF-1) and FGF-2 Signaling Involved in the Invasive and Tumorigenic Behavior of Carchinoma Cells," Molecular Biology of the Cell, Oct. 2004, 15: 4725-4734.

BioCentury, Week of Nov. 10, 2014, 52 pages.

Bisping et al., "Bortezomib, Dexamethasone, and Fibroblast Growth Factor Receptor 3-Specific Tyrosine Kinase Inhibitor in t(4;14) Myeloma," Clin Cancer Res, Jan. 2009, 15(2):520-531.

Black et al., "Targeted therapies in bladder cancer—an update," Urologic Oncology: Seminars and Original Investigations, 2007, 433-438.

Blom et al., "Optimizing Preparative LC-MS Configurations and Methods for Parallel Synthesis Purification", *J. Combi Chem.*, 5, 670 (2003).

(56) References Cited

OTHER PUBLICATIONS

Blom et al., Preparative LC-MS Purification: Improved Compound Specific Method Optimization, J. Combi. Chem. 2004, 6(6), 874-883.

Blom, K., "Two-Pump at Column Dilution Configuration for Preparative LC-MS", *J. Combi Chem.*, 4, 295 (2002).

Bonaventure et al., "Common Mutations in the Fibroblast Growth Factor Receptor 3 (FRFR3) Gene Account for Achondroplasia, Hypochondroplasia and Thanatophoric Dwarfism," Clin Pediatr Endocrinol, 1997, 105-113.

Bono et al , "Inhibition of Tumor Angiogenesis and Growth by a Small-Molecule Multi-FGF Receptor Blocker with Allosteric Properties," Cancer Cell, Apr. 2013, 477-488.

Brooks et al., "Fibroblast growth factor signaling: a new therapeutic opportunity in cancer," Clinical Cancer Research, 2012, 1-23.

Cancer [online], [retrieved on Jul. 6, 2007] Retrieved from the Internet, URL: http://www.nlm.nih.gov/medlineplus/cancer.html.

Cappellen et al., "Frequent activating mutations of FGFR3 in human bladder and cervix carcinomas," Nature Genetics, Sep. 1999, 23: 18-20.

Carmichael et al., "Familial Tumoral Calcinosis: A Forty-Year Follow-up on One Family," The Journal of Bone & Joint Surgery, 2009, 664-671.

Cha et al., "Aberrant Receptor Internalization and Enhanced FRS2-dependent Signaling Contribute to the Transforming Activity of the Fibroblast Growth Factor Receptor 2 IIIb C3 Isoform," The Journal of Biological Chemistry, Mar. 2009, 284(10): 6227-6240.

Chase et al., "Activity of TKI258 against primary cells and cell lines with FGFR1 fusion genes associated with the 8p11 myeloproliferative syndryome," Blood, 2007, 110:3729-3734.

Chefetz and Sprecher, "Familial tumoral calcinosis and the role of O-glycosylation in the maintenance of phosphate homeostasis," Biochimica et Biophysica Acta, 2009, 847-852.

Chefetz et al., "A novel homozygous missense mutation in FGF23 causes Familial Tumoral Calcinosis associated with disseminated visceral calcification," Hum Genet, 2005, 118:261-266.

Chell et al., "Tumour cell responses to new fibroblast growth factor receptor tyrosine kinase inhibitors and identification of a gatekeeper mutation in FGFR3 as a mechanism of acquired resistance," Oncogene, 2012, 1-12.

Chen et al., "Acenaphtho[1,2-b]pyrrole-Based Selective Fibroblast Growth Factor Receptors 1 (FRGR1) Inhibitors: Design, Synthesis, and Biological Activity," Jounal of Medicinal Chemistry, 2011, 54: 3732-3745.

Chen et al., "FGFR3 as a therapeutic target of the small molecule inhibitor PKC412 in hematopoietic malignancies," Oncogene, 2005, 24: 8259-8267.

Chesi et al., "Activated fibroblast growth factor receptor 3 is an oncogene that contributes to tumor progression in multiple myeloma," Blood, 2001, 97:729-736.

Chesi et al., "Frequent translocation t(4;14)(p16.3;q32.3) in multiple myeloma is associated with increased expression and activating mutations of fibroblast growth factor receptor 3," Nature Genetics, 1997, 260-264.

Chinese Office Action in Chinese Application No. 201480028858.7, dated Aug. 19, 2016, 18 pages (English Translation).

Chng et al., "Translocation t(4;14) retains prognostic significance even in the setting of high-risk molecular signature," Leukemia, 2008, 2: 459-461.

Chuaqui et al., "Interaction Profiles of Protein Kinase—Inhibitor Complexes and Their Application to Virtual Screening," J. Med. Chem., 2005, 48: 121-133.

Cole et al , "Inhibition of FGFR2 and FGFR1 increases cisplatin sensitivity in ovarian cancer," Cancer Biol. Therapy, Sep. 1, 2010, 10(5):495-504.

Coleman, "Positive and negative regulation of cellular sensitivity to anti-cancer drugs by FGF-2," Drug Resistance Updates, 2003, 85-94.

Corre et al., "Synthesis and biological evaluation of a triazole-based library of pyrido [2,3-d]pyrimidines as FGFR3 tyrosine kinase inhibitors," Organic & Biomolecular Chemistry, 2010, 8:2164-2173.

Costa Rican Opposition in Costa Rican Application No. PCT/US2013/045309, dated Jun. 29, 2015, 14 pages (English Translation).

Covic et al., "Vascular calcification in chronic kidney disease," Clinical Science, 2010, 119: 111-121.

Crose et al., "FGFR4 Blockade Exerts Distinct Antitumorigenic Effects in Human Embryonal versus Alveolar Rhabdomyosarcoma," Clin Cancer Res., 2012, 18:3780-3790.

Dailey et al., "Mechanisms underlying differential responses to FGF signaling," Cytokine & Growth Factor Reviews, 2005, 233-247.

Dash et al., "A Role for Neoadjuvant Gemcitabine Plus Cisplatin in Muscle-Invasive Urothelial Carcinoma o the Bladder: A Retrospective Experience," Cancer, 2008, 113(9): 2471-2477.

Dey et al., "Targeting Fibroblast Growth Factor Receptors Blocks PI3K/AKT Signaling, Induces Apoptosis, and Impairs Mammary Tumor Outgrowth and Metastasis," Cancer Research, 2010, 4151-4162.

Dieci et al., "Fibroblast Growth Factor Receptor Inhibitors as a Cancer Treatment: From a Biologic Rationale to Medical Perspectives," Cancer Discovery, 2013, 1-16.

Dienstmann et al., "Genomic aberrations in the FGFR pathway: opportunities for targeted therapies in solid tumors," Annals of Oncology, 2013, 1-12.

Diller and Li, "Kinases, Homology Models, and High Throughput Docking," J. Med. Chem., 2003, 46: 4638-4647.

Dimopoulos et al., "Lenalidomide plus Dexamethasone for Relapsed or Refractory Multiple Myeloma," The New England Journal of Medicine, 2007, 357:2123-2132.

Dovedi and Davies, "Emerging targeted therapies for bladder cancer: a disease waiting for a drug," Cancer Metastasis Rev, 2009, 28:355-367.

Dring et al., "A Global Expression-based Analysis of the Consequences of the t(4;14) Translocation in Myeloma," Clinical Cancer Research, Sep. 2004, 10: 5692-5701.

Dutt et al., "Drug-sensitive FGFR2 mutations in endometrial carcinoma," PNAS, Jun. 24, 2008, 105(25):8713-8717.

Dutt et al., "Drug-sensitive FGFR2 mutations in endometrial carcinoma," Supporting Information, Jun. 2008, 8 pages.

Eissa, "Synthesis and evaluation of some surface active agents from long chain fatty amine," Spanish National Research Council, Jan. 2007, 58(4):379-389.

Elsheikh et al., "FGFR1 amplification in breast carcinomas: a chromogenic in situ hybridisation analysis," Breast Cancer Research, Mar. 2007, 9(2): 1-12.

Eskens and Verweij, "The clinical toxicity profile of vascular endothelial growth factor (VEGF) and vascular endothelial growth factor receptor (VEGFR) targeting angiogenesis inhibitors; A review," European Journal of Cancer, 2006, 3127-3139.

Eswarakumar and Schlessinger, "Cellular signaling by fibroblast growth factor receptors," Cytokine & Growth Factor Reviews, 2005, 139-149.

Faul et al., "FGF23 induces left ventricular hypertrophy," The Journal of Clinical Investigation, 2010, 1-16.

Feng et al., "Targeting Fibroblast Growth Factor Receptor Signaling Inhibits Prostate Cancer Progression," Clinical Cancer Research, 2012, 1-9.

Ferrera et al., "Bevacizumab (Avastin), a humanized anti-VEGF monoclonal antibody for cancer therapy," Biochemical and Biophysical Research Communications, 2005, 328-335.

Fillmore et al., "Estrogen expands breast cancer stem-like cells through paracrine FGF/Tbx3 signaling," PNAS, 2010, 1-6.

Fischer et al., "Fibroblast growth factor receptor-mediated signals contribute to the malignant phenotype of non-small cel lung cancer cells: therapeutic implications and synergism with epidermal growth factor receptor inhibition," Mol Cancer Therapy, 2008, 3408-3419.

French et al., "Targeting FGFR4 Inhibits Hepatocellular Carcinoma in Preclinical Mouse Models," PLoS One, 2012, 7(5):e36713, 1-12.

(56) References Cited

OTHER PUBLICATIONS

Frishberg et al., "Hypertosis-Hyperphosphatemia Syndrome: A Congenital Disorder of O-Glycosylation Associated With Augmented Processing of Fibroblast Growth Factor 23," Journal of Bone and Mineral Research, 2007, 22(2): 235-242.
Frishberg et al., "Identification of a recurrent mutation in GALNT3 demonstrates that hyperstosis-hyperphosphatemia syndrome and familial tumoral calcinosis are allelic disorders," J Mol Med, 2005, 83:33-38.
Fukumoto and Yamashita, "FGF23 is a hormone-regulating phophate metabolism—Unique biological characteristics of FGF23," Bone, 2007, 1190-1195.
Galdemard et al., "Regulation of FGF-3 Gene Expression in Tumorigenic and Non-tumorigenic Clones of a Human Colon Carcinoma Cell Line," The Journal of Biological Chemistry, 2000, 275(23): 17364-17373.
Garringer et al., "Molecular genetic and biochemical analyses of FGF23 mutations in familial tumoral calcinosis," Am J Physiol Endocrinol Metab, 2008, 929-937.
Gattineni et al., "FGF23 decreases renal NaPi-2a and NaPi-2c expression and induces hypophosphatemia in vivo predominantly via FGF receptor 1," Am J Physiol Renal Physiol, 2009, 297: 282-291.
Gavine et al., "AZD4547: An Orally Bioavailable, Potent, and Selective Inhibitor of the Fibroblast Growth Factor Receptor Tyrosine Kinase Family," American Association for Cancer Research, Apr. 2012, 72(8): 2045-2056.
Gerby et al., "2-Arylidenedihydroindole-3-ones: Design, synthesis, and biological activity on bladder carcinoma cell lines," Bioorganic & Medicinal Chemistry Letters, 2007, 208-213.
Ghorab et al., "Synthesis of some sulfur containing Tetrahydrobenzoabuthieno [b] Thieno(Pyridines, Quinolines, Oxazins and Pyrimidines) as possible radioprotective and Antineoplastic agents," Phosphorus, Sulfur and Silicon, Jan. 1998, 134/135:57-76.
Goetz et al., "Isolated C-terminal tail of FGF23 alleviates hypophosphatemia by inhibiting FGF23-FGFR-Klotho complex formation," PNAS, Jan. 2010, 107(1): 407-412.
Golub et al., "Molecular Classification of Cancer: Class Discovery and Class Prediction by Gene Expression Monitoring," Science, 1999, 286: 531-537.
Gomez-Rivera et al., "The Tyrosine Kinase Inhibitor, AZD2171, Inhibits Vascular Endothelial Growth Factor Receptor Signaling and Growth of Anaplastic Thyroid Cancer in an Orthotopic Nude Mouse Model," Clin Cancer Res, Aug. 2007, 4519-4527.
Govindan, "Summary of Presentations from the Ninth Annual Targeted Therapies in Lung Cancer Symposium," Journal of Thoracic Oncology, Nov. 2009, 4(11): 1045-1089.
Gozgit et al., "Ponatinib (AP24534), a Multitargeted Pan-FGFR Inhibitor with Activity in Multiple FGFR-Amplified or Mutated Cancer Models," Mol Cancer Ther, 2012, 11: 690-699.
Grand et al., "Targeting FGFR3 in multiple myeloma inhibition of t(4;14)-positive cells by SU5402 and PD173074," Leukemia, 2004, 18: 962-966.
Greene, T. W. and Wuts, P. G. M., "Protective Groups in Organic Synthesis", 3rd Ed., Wiley & Sons, Inc., New York (1999) **Too Voluminous to Provide.
Greulich and Pollock, "Targeting mutant fibroblast growth factor receptors in cancer," Cell Press, May 2011, 17(5): 283-292.
Grose and Dickson, "Fibroblast growth factor signaling in tumorigenesis," Cytokine & Growth Factor Reviews, 2005, 179-186.
Gu et al., "Phosphotyrosine profiling identifies the KG-1 cell line as a model for the study of FGFR1 fusions in acute myeloid leukemia," Blood, Dec. 15, 2006, 108(13):4202-42040.
Guagnano et al., "Discovery of 3-(2,6-Dichloro-3,5-dimethoxyphenyl)-1-{6-[4-(4-ethyl-piperazin-1-yl)-phenylamino]-pyrimidin-4-yl}-1-methyl-urea (NVP-BGJ398), a Potent and Selective Inhibitor of the Fibroblast Growth Factor Receptor Family of Receptor Tyrosine Kinase," J. Med. Chem., 2011, 54: 7066-7083.

Guan et al., "Design and synthesis of aminopropyl tetrahydroindole-based indolin-2-ones as selective and potent inhibitors of Src and Yes tyrosine kinase," Bioorganic & Medicinal Chemistry Letters, 2004, 187-190.
Hackam, et al. JAMA, 296(14), 2006, 1731-1732.
Hafner et al., "High Frequency of FGFR3 Mutations in Adenoid Seborrheic Keratoses," Journal of Investigative Dermatology, 2006, 126: 2404-2407.
Hafner, "Seborrheic keratoses and epidermal nevi: new pathogenetic insights and therapeutic implications," Expert Rev Dermatol, 2006, 1(6): 759-761.
Hagel et al., "First Selective Small Molecule Inhibitor of FGFR4 for the Treatment of Hepatocellular Carcinomas with an Activated FGFR4 Signaling Pathway," Cancer Discovery, Apr. 2015, 1-14.
Hara and Saito, "CARD9 versus CARMA1 in innate and adaptive immunity," Cell Press, 2009, 234-242.
Heinzle et al., "Is fibroblast growth factor receptor 4 a suitable target of cancer therapy?," Cur. Pharm. Des. 2014, 20:2881-98.
Heinzle et al., "Targeting fibroblast-growth-factor-receptor-dependent signaling for cancer therapy," Expert Opinion, 2011, 1-18.
Hideshima and Anderson, "Preclinical Studies of Novel Targeted Therapies," Hematol Oncol Clin N Am, 2007, 1071-1091.
Honigberg et al., "The Bruton tyrosine kinase inhibitor PCI-32765 blocks B-cell activation and is efficacious in models of autoimmune disease and B-cell malignancy," Supporting Information, PNAS, Jul. 20, 2010, 107:29.
Hruska et al., "The Pathogenesis of Vascular Calcification in the Chronic Kidney Disease Mineral Bone Disorder (CKD-MBD): The Links Between Bone and Vasculature," Semin Nephrol, Mar. 2009, 29(2): 156-165.
Huynh, "Tyrosine kinase inhibitors to treat liver cancer," Expert Opinion, 2010, 13-26.
Hynes and Dey, "Potential for Targeting the Fibroblast Growth Factor Receptors in Breast Cancer," Cancer Res, 2010, 70:5199-5202.
Ichikawa et al., "A homozygous missense mutation in human KLOTHO causes severe tumoral calcinosis," The Journal of Clinical Investigation, Sep. 2007, 117(9): 2684-2691.
Ichikawa et al., "A Novel GALNT3 Mutation in a Pseudoautosomal Dominant Form of Tumoral Calcinosis: Evidence That the Disorder Is Autosomal Recessive," J. Clin. Endocrinol. Metab., 2005, 90:2420-2423.
Ichikawa et al., "Clinical Variability of Familial Tumoral Calcinosis Caused by Novel GALNT3 Mutations," American Journal of Medical Genetics, 2009, 896-903.
Ichikawa et al., "Novel GALNT3 Mutations Causing Hyperostosis-Hyperphosphatemia Syndrome Result in Low Intact Fibroblast Growth Factor 23 Concentrations," J. Clin. Endocrinol. Metab., 2007, 92:1943-1947.
Ichikawa et al., "Tumoral Calcinosis Presenting with Eyelid Calcifications due to Novel Missense Mutations in the Glycosyl Transferase Domain of the GALNT3 Gene," J. Clin. Endocrinol. Metab., 2006, 91: 4472-4475.
International Preliminary Report on Patentability and Written Opinion in International Application No. PCT/US2011/066473, issued Jun. 25, 2013, 10 pages.
International Preliminary Report on Patentability in International Application No. PCT/US2013/045309, mailed Dec. 24, 2014, 11 pages.
International Preliminary Report on Patentability in International Application No. PCT/US2013/054361, mailed Feb. 19, 2015, 7 pages.
International Preliminary Report on Patentability in International Application No. PCT/US2014/034662, dated Oct. 29, 2015, 12 pages.
International Search Report and Written Opinion for International Application No. PCT/US2015/056583, dated Dec. 15, 2015, 10 pages.
International Search Report and Written Opinion in International Application No. PCT/US2013/045309, mailed on Jan. 22, 2014, 19 pages.

(56) References Cited

OTHER PUBLICATIONS

International Search Report and Written Opinion in International Application No. PCT/US2013/054361, dated Oct. 16, 2013, 12 pages.
International Search Report and Written Opinion in International Application No. PCT/US2014/034662, mailed Oct. 24, 2014, 18 pages.
International Search Report and Written Opinion in International Application No. PCT/US2016/018737, dated Jun. 2, 2016, 12 pages.
International Search Report and Written Opinion in International Application No. PCT/US2016/018770, dated Jun. 2, 2016, 14 pages.
International Search Report and Written Opinion in International Application No. PCT/US2016/018787, dated Jun. 2, 2016, 12 pages.
International Search Report dated Jun. 19, 2012 for International Appln. No. PCT/US2011/066473 (15 pgs.).
Invitation to Pay Additional Fees and, Where Applicable, Protest Fee in International Application No. PCT/US2013/045309, mailed Nov. 25, 2013, 5 pages.
Isakova et al., "Fibroblast Growth Factor 23 and Risks of Mortality and End-Stage Renal Disease in Patients With Chronic Kidney Disease," JAMA, Jun. 15, 2011, 305:23, 2432-2439.
Ishikawa et al., "Accelerated proliferation of myeloma cells by interleukin-6 cooperating with fibroblast growth factor receptor 3-mediated signals," Oncogene, 2005, 24:6328-6332.
Jan de Beur, "Tumoral Calcinosis: A Look into the Metabolic Mirror of Phosphate Homeostasis," The Journal of Clinical Endocrinology & Metabolism, 2005, 90: 2469-2471.
Jebar et al., "FGFR3 and Ras gene mutations are mutually exclusive genetic events in urothelial cell carcinoma," Oncogene, 2005, 24: 5218-5225.
Johnson et al., "Pharmacological and Functional Comparison of the Polo-like Kinase Family: Insight into Inhibitor and Substrate Specificity," Biochemistry, 2007, 46: 9551-9563.
Jonker et al., "A phase I study to determine the safety, pharmacokinetics and pharmacodynamics of a dual VEGFR and FGFR inhibitor, brivanib, in patients with advanced or metastatic solid tumors," Annals of Oncology, 2010, 1-7.
Jordan, V.C. Nature Reviews: Drug Discovery, 2, 2003, 205.
Kang et al., FGFR3 Activates RSK2 to Mediate Hematopoietic Transformation through Tyrosine Phosphorylation of RSK2 and Activation of the MEK/ERK Pathway, Cancer Cell, Sep. 2007, 12:201-214.
Kassack et al., "Structure-activity relationships of analogues of NF449 confirm NF449 as the most potent and selective known P2X$_1$ receptor antagonist," European Journal of Medicinal Chemisty, 2004, 345-357.
Katoh and Katoh, "FGF signaling network in the gastrointestinal tract (Review)," International Journal of Oncology, 2006, 29: 163-168.
Keats et al., "Ten years and counting: so what do we know about t(4;14) (p16;q32) multiple myeloma," Leukemia & Lymphoma, Nov. 2006, 47(11): 2289-2300.
Keer et al., "Enrolling a Rare Patient Population. Establishing Proof of Concept for FP-1039, an FGF "Trap," in Endometrial Cancer Patients with the S252W FGFR2 Mutation," Journal of Clinical Oncology, 2010 ASCO Annual Meeting Abstracts, 28:15, May 20 Supplement, 1 page.
Kim et al., "Phase I/II and Pharmacodynamic Study of Dovitinib (TKI258), an Inhibitor of Fibroblast Growth Factor Receptors and VEGF Receptors, in Patients with Advanced Melanoma," Clin Cancer Res, 2011, 17: 7451-7461.
Kim et al., "The design, synthesis, and biological evaluation of potent receptor tyrosine kinase inhibitors," Bioorganic & Medicinal Chemistry Letters, 2012, 4979-4985.
Klein et al., "FGFR1 Kinase Inhibitors: Close Regioisomers Adopt Divergent Binding Modes and Display Distinct Biophysical Signatures," American Chemical Society, 2014, 166-171.

Knights and Cook, "De-regulated FGF receptors as therapeutic targets in cancer," Pharmacology & Therapeutics, 2010, 125:105-117.
Kompier et al., "Bladder cancer: Novel molecular characteristics, diagnostic, and therapeutic implications," Urologic Oncology: Seminars and Original Investigations, 2010, 91-96.
Kompier et al., "FGFR3, HRAS, KRAS, NRAS and PIK3CA Mutations in Bladder Cancer and Their Potential as Biomarkers for Surveillance and Therapy," PLoS One, Nov. 2010, 5(11): 1-13.
Kono et al., "The fibroblast growth factor receptor signaling pathway as a mediator of intrinsic resistance to EGFR-specific tyrosine kinase inhibitors in non-small cell lung cancer," Drug Resistance Updates, 2009, 95-102.
Koziczak and Hynes, "Cooperation between Fibroblast Growth Factor Receptor-4 and ErbB2 in Regulation of Cyclin D1 Translation," The Journal of Biological Chemistry, 2004, 279(48): 50004-50011.
Koziczak et al., "Blocking of FGFR signaling inhibits breast cancer cell proliferation through downregulation of D-type cyclins," Oncogene, 2004, 23:3501-3508.
Krejci et al., "Molecular pathology of the fibroblast growth factor family," Hum Mutat, Sep. 2009, 30(9): 1245-1255.
Krejci et al., "NF449 Is a Novel Inhibitor of Fibroblast Growth Factor Receptor 3 (FGFR3) Signaling Active in Chondrocytes and Multiple Myeloma Cells," The Journal of Biological Chemistry, Jul. 2010, 285(27): 20644-20653.
Krejci et al., "NF449 is a novel inhibitor of fibroblast growth factor receptor 3 (FGFR3) signaling active in chondrocytes and multiple myeloma cells," The American Society for Biochemistry and Molecular Biology, 2010, 1-20.
Kunii et al., "FGFR2-Amplified Gastric Cancer Cell Lines Require FGFR2 and Erbb3 Signaling for Growth and Survival," Cancer Res., Apr. 1, 2008, 68(7):2340-2348.
Kunii et al., "FGFR2-Amplified Gastric Cancer Cell Lines Require FGFR2 and Erbb3 Signaling for Growth and Survival," Cancer Res., Apr. 1, 2008, Supplemental figures, 11 pages.
Kurosu et al., "Regulation of Fibroblast Growth Factor-23 Signaling by Klotho," The Journal of Biological Chemistry, Mar. 2006, 281(10): 6120-6123.
Lala et al., "Role of nitric oxide in tumor progression: Lessons from experimental tumors," Cancer and Metastasis Reviews, 1998, 17: 91-106.
Lammoglia and Mericq, "Familial Tumoral Calcinosis Caused by a Novel FGF23 Mutation: Response to Induction of Tubular Renal Acidosis with Acetazolamide and the Non-Calcium Phosphate Binder Sevelamer," Horm Res, 2009, 71:178-184.
Lamont et al., "Small molecule FGF receptor inhibitors block FGFR-dependent urothelial carcinoma growth in vitro and in vivo," Br. J Cancer, 2010, 1-8.
Lamont et al., "Small molecule FGF receptor inhibitors block FGFR-dependent urothelial carcinoma growth in vitro and in vivo," Br. J Cancer, 2011, 104:75-82.
Le Corre et al., "Synthesis and biological evaluation of a triazole-based library of pyrido [2,3-d]pyrimidines as FGFR3 tyrosine kinase inhibitors," Org. Biomol. Chem., 2010, 8, 2164-2173.
Lee et al., "In vivo Target Modulation and Biological Activity of CHIR-258, a Multitargeted Growth Factor Receptor Kinase Inhibitor, in Colon Cancer Models," Clin Cancer Res, May 2005, 3633-3641.
L'Hote and Knowles, "Cell responses to FGFR3 signalling: growth, differentiation and apoptosis," Experimental Cell Research, 2005, 417-431.
Li et al., "Compound deletion of Fgfr3 and Fgfr4 partially rescues the Hyp mouse phenotype," Am. J. Physiology—Endocrinol Metab, Dec. 7, 2010, 300:3, 29 pages.
Liang et al., "Anticancer molecules targeting fibroblast growth factor receptors," Cell Press, 2012, 11 pages.
Liu et al., "Developing Irreversible Inhibitors of the Protein Kinase Cysteinome," Chemistry & Biology, Feb. 2013, 146-159.
Liu et al., "FRFR3 and FRFR4 Do not Mediate Renal Effects of FGF23," J Am Soc Nephrol, 2008, 19:2342-2350.
Liu et al., "Pathogenic role of Fgf23 in Hyp mice," Am J Physiol Endocrinol Metab 291, Jan. 31, 2006, E38-E49.

(56) References Cited

OTHER PUBLICATIONS

Lopes de Menezes et al., "CHIR-258: A Potent Inhibitor of FLT3 Kinase in Experimental Tumor Xenograft Models of Human Acute Myelogenous Leukemia," Clin Cancer Res, Jul. 2005, 5281-5291.

Marek et al., "Fibroblast Growth Factor (FGF) and FGF Receptor-Mediated Autocrine Signaling in Non-Small-Cell Lung Cancer Cells," Molecular Pharmacology, 2009, 75:196-207.

Marfe and Stefano, "In vitro Anti-leukaemia Activity of Pyrrolo[1,2-b][1,2,5]benzothiadiaze-pines (PBTDs)," Recent Patents on Anti-Cancer Drug Discovery, 2010, 58-68.

Marshall et al., "Fibroblast Growth Factor Receptors are Components of Autocrine Signaling Networks in Head and Neck Squamous Cell Carcinoma Cells," Clin Cancer Res., 2011, 17:5016-5025.

Martinez-Torrecuadrada et al., "Targeting the Extracellular Domain of Fibroblast Growth Factor Receptor 3 with Human Single-Chain Fv Antibodies Inhibits Bladder Carcinoma Cell Line Proliferation," Clin Cancer Res, Sep. 2005, 6280-6290.

Matsuda et al., "Fibroblast Growth Factor Receptor 2 IIIc as a Therapeutic Target for Colorectal Cancer Cells," Mol Cancer Ther., 2012, 52 pages.

McConkey et al., "Molecular genetics of bladder cancer: Emerging mechanisms of tumor initiation and progression," Urologic Oncology: Seminars and Original Investigations, 2010, 429-440.

McMahon, "VEGF Receptor Signaling in Tumor Angiogenesis," Oncologist, 2000, 5(suppl 1):3-10.

Meijer et al., "Fibroblast growth factor receptor 4 predicts failure on tamoxifen therapy in patients with recurrent breast cancer," Endocrine-Related Cancer, 2008, 15:101-111.

Mellor, "Targeted inhibition of the FGF19-FGFR4 pathway in hepatocellular carcinoma; translational safety considerations," Liver International, 2013, 1-9.

Memon et al., "Does Fgf23-klotho activity influence vascular and soft tissue calcification through regulating phosphate homeostasis," Kidney Int., 2008, 74(5): 566-570.

Metzner, "Fibroblast Growth Factor Receptors as Therapeutic Targets in Human Melanoma: Synergism with BRAF Inhibition," J Investigative Dermatol., 2011, 131:2087-2095.

Miyake et al., "1-tert-Butyl-3[6-(3,5-dimethoxy-phenyl)-2-(4-diethylamino-butylamino)-pyrido[2,3-d]pyrimidin-7-yl]urea (PD173074), a Selective Tyrosine Kinase Inhibitor of Fibroblast Growth Factor Receptor-3 (FGFR3), Inhibits Cell Proliferation of Bladder Cancer Carrying the FGFR3 Gene Mutation along with Up-Regulation of p27/Kip1 and $G_1/G_0$ Arrest," The Journal of Pharmacology and Experimental Therapeutics, 2010, 332(3):795-802.

Mohammadi et al., "Crystal structure of an angiogenesis inhibitor bound to the FGF receptor tyrosine kinase domain," The EMBO Journal, 1998, 5896-5904.

Mohammadi et al., "Structures of the Tyrosine Kinase Domain of Fibroblast Growth Factor Receptor in Complex with Inhibitors," Science, May 1997, 276:955-960.

Murphy et al., "Evidence for distinct alterations in the FGF axis in prostate cancer progression to an aggressive clinical phenotype," J Pathol., 2010, 220:452-460.

Naito et al., "Progressive tumoral calcinosis as the presenting feature of sarcoidosis in a patient on haemodialysis treatment," Nephrol Dial Transplant, 1999, 14:2716-2719.

Nakatani et al., "In vivo genetic evidence for klotho-dependent, fibroblast growth factor 23 (Fgf23)-mediated regulation of systemic phosphate homeostasis," The FASEB Journal, Feb. 2009, 23:433-441.

Natajaran et al., "p38 MAP kinase inhibitors. Part 3: SAR on 3,4-dihydropyrimido-[4,5-d]pyrimidin-2-ones and 3,4-dihydropyrido[4,3-d]-pyrimidin-2-ones," Bioorgan Med. Chem. Lett., 2006, 4400-4404.

Nitta, "Relationship between Fibroblast Growth Factor-23 and Mineral Metabolism in Chronic Kidney Disease," International Journal of Nephrology, 2010, 1-7.

Nomura et al., "FGF10/FGFR20 signal induces cell migration and invasion in pancreatic cancer," Br. J Cancer, 2008, 99:305-313.

Norman et al., "Protein-Ligand Crystal Structures Can Guide the Design of Selective Inhibitors of the FGFR Tyrosine Kinase," J. Med. Chem., 2012, 55(11):5003-5012.

Ornitz et al., "Receptor Specificity of the Fibroblast Growth Factor Family," The Journal of Biological Chemistry, 1996, 271(25): 15292-15297.

Pai et al., "Antibody-Mediated Inhibition of Fibroblast Growth Factor 19 Results in Increased Bile Acids Synthesis and Ileal Malabsortion of Bile Acides in Cynomolgus Monkeys," Toxicological Sciences, 2012, 126(2): 446-456.

Pan et al., "MK-2461, a Novel Multitargeted Kinase Inhibitor, Preferentially Inhibits the Activated c-Met Receptor," Cancer Res, Feb. 2010, 1524-1533.

Pandith et al., "Oncogenic role of fibroblast growth factor receptor 3 in tumorigenesis of urinary bladder cancer," Urologic Oncology: Seminars and Original Investigations, 2010, 1-9.

Pardo et al., "The Fibroblast Growth Factor Receptor Inhibitor PD173074 Blocks Small Cell Lung Cancer Growth In vitro and In vivo," Cancer Res, Nov. 2009, 8645-8651.

Paterson et al., "Preclinical studies of fibroblast growth factor receptor 3 as a therapeutic target in multiple myeloma," British Journal of Haematology, 2004, 124:595-603.

Piazza et al., "Towards a new age in the treatment of multiple myeloma," Ann Hematol, 2007, 86:159-172.

Pinedo and Slamon, "Translational Research: The Role of VEGF in Tumor Angiogenesis," Oncologist, 2000, 5(suppl 1):1-2.

Platt et al., "Spectrum of Phosphatidylinositol 3-Kinase Pathway Gene Alterations in Bladder Cancer," Clin Cancer Res, Oct. 2009, 6008-6017.

Pliarchopoulou et al., "Current chemotherapeutic options for the treatment of advanced bladder cancer: A review," Urologic Oncology: Seminars and Original Investigations, 2010, 1-9.

Plowright et al., "Ectopic expression of fibroblast growth factor receptor 3 promotes myeloma cell proliferation and prevents apoptosis," Blood, Feb. 2000, 95(3): 992-998.

Podar et al., "Emerging therapies for multiple myeloma," Expert Opin. Emerging Drugs, 2009, 14(1):9-127.

Podar et al., "Targeting signalling pathways for the treatment of multiple myeloma," Expert Opin. Ther. Targets, 2005, 359-381.

Pollett et al., "Overexpression of the myeloma-associated oncogene fibroblast growth factor receptor 3 confers dexamethasone resistance," Blood, Nov. 2002, 100(10): 3819-3821.

Pollock et al., "Frequent activating FGFR2 mutations in endometrial carcinomas parallel germline mutations associated with craniosynostosis and skeletal dysplasia syndromes," Oncogene, 2007, 26:7158-7162.

Propper et al., "Phase I and Pharmacokinetic Study of PKC412, an Inhibitor of Protein Kinase C," J Clin Oncol, 2001, 19(5):1485-1492.

Qian et al., "Targeting Tumor Angiogenesis with Histone Deacetylase Inhibitors: the Hydroxamic Acid Derivative LBH589," Clin Cancer Res, Jan. 2006, 634-642.

Qing et al., "Antibody-based targeting of FGFR3 in bladder carcinoma and t(4;14)-positive multiple myeloma in mice," The Journal of Clinical Investigation, May 2009, 119(5): 1216-1229.

Qing et al., "Antibody-based targeting of FGFR3 in bladder carcinoma and t(4;14)-positive multiple myeloma in mice," The Journal of Clinical Investigation, May 2009, Supplemental Table 1: Summary of crystallographic analysis, 21 pages.

Raab et al., "Multiple myeloma," Lancet, 2009, 374: 324-339.

Ravindranathan et al., "Discovery of Novel Fibroblast Growth Factor Receptor 1 Kinase Inhibitors by Structure-Based Virtual Screening," J. Med. Chem., 2010, 53: 1662-1672.

Razzaque, "FGF23-mediated regulation of systemic phosphate homeostasis: is Klotho an essential player?," Am J Physiol Renal Physiol, 2009, 470-476.

Reimers et al., "NoBP, a Nuclear Fibroblast Growth Factor 3 Binding Protein, Is Cell Cycle Regulated and Promotes Cell Growth," Molecular and Cellular Biology, Aug. 2001, 21(15): 4996-5007.

(56) References Cited

OTHER PUBLICATIONS

Reis-Filho et al., "FGFR1 Emerges as a Potential Therapeutic Target for Lobular Breast Carcinomas," Clin Cancer Res, Nov. 2006, 6652-6662.
Reiter et al., "Consistent Fusion of ZNF198 to the Fibroblast Growth Factor Receptor-1 in the t(8;13)(p11;q12) Myeloproliferative Syndrome," Blood, Sep. 1998, 92(5): 1735-1742.
Remington's Pharmaceutical Sciences, 17th ed., Mack Publishing Company, Easton, Pa., 1985, p. 1418*.
Renhowe et al., "Design, Structure-Activity Relationships and in Vivo Characterization of 4-Amino-3-benzimidazol-2-ylhydroquinolin-2-ones: A Novel Class of Receptor Tyrosine Kinase Inhibitors," J. Med. Chem., 2009, 52: 278-292.
Ribatti et al., "The discovery of basic fibroblast growth factor/fibroblast growth factor-2 and its role in haematological malignancies," Cytokine & Growth Factor Reviews, 2007, 18: 327-334.
Ribatti, "Tyrosine Kinase Inhibitors as Antiangiogenic Drugs in Multiple Myeloma," Pharmaceuticals, 2010, 3: 1225-1231.
Roidl et al., "Resistance to Chemotherapy Is Associated with Fibroblast Growth Factor Receptor 4 Up-Regulation," Clin Cancer Res, Mar. 2009, 2058-2066.
Ronchetti et al., "Deregulated FGFR3 mutants in multiple myeloma cell lines with t(4;14): comparative analysis of Y373C, K650E and the novel G384D mutations," Oncogene, 2001, 20: 3553-3562.
Roumiantsev et al., "Distinct stem cell myeloproliferative/T lymphoma syndromes induced by ZNF198-FGFR1 and BCR-FGFR1 fusion genes from 8p11 translocations," Cancer Cell, Mar. 2004, 5: 287-298.
Ryan et al., "Toxicologic Pathology of Unique Biotechnology Agents and Biotherapies," Toxicologic Pathology, 1999, 27(1): 78-86.
Sakurai et al., "A novel angiogenesis inhibitor, Ki23057, is useful for preventing the progression of colon cancer and the spreading of cancer cells to the liver," European Journal of Cancer, 2007, 2612-2620.
Sarker et al., "A Phase I Pharmacokinetic and Pharmacodynamic Study of TKI258, an Oral, Multitargeted Receptor Tyrosine Kinase Inhibitor in Patients with Advanced Solid Tumors," Clin Cancer Res, Apr. 2008, 2075-2081.
Saxty et al., "Fragment-based drug discovery of selective inhibitors of fibroblast growth factor receptor (FGFr)," Cancer Res, Apr. 15, 2010, 70, 5778.
Schenone et al., "Small Molecules ATP-Comptetitive Inhibitors of FLT3: A Chemical Overview," Current Medicinal Chemistry, 2008, 15(29): 3113-3132.
Schlapbach et al., "A novel Pd-catalyzed cyclization rection of ureas for the synthesis of dihydroquinazolinone p38 kinase inhibitors," Bioorg. Med. Chem. Lett., 2004, 357-360.
Science IP Order 3032627, Chemical Structure Search , Science IP, Apr. 2012, 78 pages.
Science IP Order 3101926, Chemical Structure Search , Science IP, Jan. 2015, 50 pages.
Science IP Order 3101983, Chemical Structure Search , Science IP, Jan. 2015, 70 pages.
Science IP Order 3104564, Patent Chemical Structure Search , Science IP, Mar. 2015, 90 pages.
Science IP Order 3104565, Patent Chemical Structure Search , Science IP, Mar. 2015, 521 pages.
Segev et al., "Restrained chondrocyte proliferation and maturation with abnormal growth plate vascularization and ossification in human FRFR-3$^{G380R}$ trasngenic mice," Human Molecular Genetics, 2000, 9(2): 249-258.
Shariat et al., "Association of Angiogenesis Related Markers With Bladder Cancer Outcomes and Other Molecular Markers," The Journal of Urology, May 2010, 183: 1744-1750.
Sharkey et al., "PKC412 demonstrates JNK-dependent activity against human multiple myeloma cells," Blood, Feb. 2007, 109(4): 1712-1719.
Shinya et al., "Fgf signalling through MAPK cascade is required for development of the subpallial telencephalon in zebrafish embryos," Development, 2001, 4153-4164.
Singh et al., "Transforming Fusions of FGFR and TACC Genes in Human Glioblastoma," Science, Sep. 2012, 337:1231-1235.
Slavin et al., "Familial Tumoral Calcinosis," The American Journal of Surgican Pathology, 1993, 17(8): 188-802.
Smith et al., "Circulating αKlotho influences phosphate handling by controlling FGF23 production," The Journal of Clinical Investigation, Dec. 2012, 122(12): 4710-4715.
Song et al., "Fibroblast growth factors: An epigenetic mechanism of broad spectrum resistance to anticancer drugs," PNAS, Jul. 2000, 97(15): 8658-8663.
Sonvilla et al., "Fibroblast growth factor receptor 3-111c mediates colorectal cancer growth and migration," British Journal of Cancer, 2010, 1-12.
Soria, "FGFR inhibition overview of clinical development programs," Presentation, presented at TAT in Washington DC on Mar. 5-7, 2014, 54 pages.
Soverini et al., "Novel mutation and RNA splice variant of fibroblast growth factor receptor 3 in multiple myeloma patients at diagnosis," Haematologica, 2002, 87: 1036-1040.
Specktor et al., "Hyperphosphatemic familial tumoral calcinosis caused by a mutation in GALNT3 in a European kindred," J Hum Genet, 2006, 51:487-490.
Squires et al., "Development of inhibitors of the fibroblast growth factor receptor (FGFR) kinase using a fragment based approach," Cancer Res 70, Apr. 15, 2010, 3626.
Squires et al., "Development of inhibitors of the fibroblast growth factor receptor (FGFR) kinase using a fragment based approach," Cancer Res, 2008, 1 page.
Sun et al., "Design, Synthesis, and Evaluations of Substituted 3-[(3- or 4-Carboxyethylpyrrol-2-yl)methylidenyl]indolin-2-ones as Inhibitors of VEGF, FGF, and PDGF Receptor Tyrosine Kinases," J. Med. Chem., 1999, 42: 5120-5130.
Sun et al., "Identification of Substituted 3-[(4,5,6,7-Tetrahydro-1H-indol-2-yl)methylene]-1,3-dihydroindol-2-ones as Growth Factor Receptor Inhibitors for VEGF-R2 (Flk-1/KDR), FGF-R1, and PDGF-Rβ Tyrosine Kinases," J. Med. Chem., 2000, 43: 2655-2663.
Sun et al., "Synthesis and Biological Evaluations of 3-Substituated Indolin-2-ones: A Novel Class of Tyrosine Kinase Inhibitors That Exhibit Selectivity toward Particular Receptor Tyrosine Kinases," J. Med. Chem., 1998, 41: 2588-2603.
Takeda et al., "AZD2171 Shows Potent Antitumor Activity Against Gastric Cancer Over-Expressing Fibroblast Growth Factor Receptor 2/Keratinocyte Growth Factor Receptor," Clin Cancer Res, May 2007, 3051-3057.
Tan et al., "Development of covalent inhibitors that can overcome resistance to first-generation FGFR kinase inhibitors," PNAS, Oct. 2014, E4869-E4877.
Taylor et al., "Identification of FGFR4-activating mutations in human rhabdomyasarcomas that promote metastasis in xenotransplanted models," J Clin Invest, Nov. 2009, 119(11): 3395-407.
Taylor, "Inhibitor PD-173074 Bound to the Tyrosine Kinase Domain of FGFR 1," Molecular & Behavioral Neuroscience Institute , Feb. 2006, 1 page.
Taylor, "Inhibitor SU-5402 Bound to the Tyrosine Kinase Domain of FGFR 1," Molecular & Behavioral Neuroscience Institute , Apr. 2006, 1 page.
Terai et al., "Vascular calcification and secondary hyperparathyroidism of severe chronic kidney disease and its relation to serum phosphate and calcium levels," British Journal of Pharmacology, 2009, 156: 1267-1278.
Thome and Weil, "Post-translational modifications regulate distinct functions of CARMA1 and BCL10," TRENDS in Immunology, 2007, 28(6): 281-288.
Thompson et al., "3-(3,5-Dimethoxyphenyl)-1,6-naphthyridine-2,7-diamines and Related 2-Urea Derivatives Are Potent and Selective Inhibitors of the FGF Receptor-1 Tyrosine Kinase," J. Med. Chem., 2000, 43: 4200-4211.
Thompson et al., "Synthesis and Structure—Activity Relationships of Soluble 7-Substituted 3-(3,5-Dimethoxyphenyl)-1,6-

(56) References Cited

OTHER PUBLICATIONS naphthyridin-2-amines and Related Ureas as Dual Inhibitors of the Fibroblast Growth Factor Receptor-1 and Vascular Endothelial Growth Factor Receptor-2 Tyrosine Kinases," J. Med. Chem., 2005, 48: 4628-2653.
Tolcher et al., "381 Preliminary results of a dose escalation study of the Fibroblast Growth Factor (FGF) "trap" FP-1039 (FGFR1:Fc) in patients with advanced malignancies," EJC Supplements, Nov. 2010, 8:7, p. 121.
Tomlinson et al., "FGFR3 protein expression and its relationship to mutation status and prognostic variables in bladder cancer," J Pathol, Sep. 2007, 213(1): 91-98.
Tomlinson et al., "Fibroblast Growth Factor Receptor 1 Promotes Proliferation and Survival via Activation of the Mitogen-Activated Protein Kinase Pathway in Bladder Cancer," Cancer Res, 2009, 4613-4620.
Tomlinson et al., "Knockdown by shRNA identifies S249C mutant FGFR3 as a potential therapeutic target in bladder cancer," Oncogene, 2007, 26: 5889-5899.
Topaz et al., "Mutations in GALNT3, encoding a protein involved in O-linked glycosylation, cause familial tumoral calcinosis," Nature Genetics, 2004, 1-3.
Traxler and Furet, "Strategies toward the Design of Novel and Selective Protein Tyrosine Kinase Inhibitors," Pharmacol. Ther., 1999, 82(2-3): 195-206.
Trudel et al., "CHIR-258, a novel, multitargeted tyrosine kinase inhibitor for the potential treatment of t(4;14) multiple myeloma," Blood, Apr. 2005, 105(7): 2941-2948.
Trudel et al , "Inhibition of fibroblast growth factor receptor 3 induces differentiation and apoptosis in t(4;14) myeloma," Blood, May 2004, 103(9):3521-3528.
Trudel et al., "The inhibitory anti-FGFR3 antibody, PRO-001, is cytotoxic to t(4;14) multiple myeloma cells," Blood, May 2006, 107(10): 4039-4046.
Trudel, "CHIR-258, a Novel Multi-targeted Tyrosine KinaseInhibitor, for the Treatment of t(4;14) Multiple Myeloma," Presentation, Presented at International Myeloma Foundation, Apr. 2005, 18 pages.
Turner and Grose, "Fibroblast growth factor signalling: from development to cancer," Nature Reviews Cancer, 2010, 10:116-129.
Turner et al., "FGFR1 Amplification Drives Endocrine Therapy Resistance and Is a Therapeutic Target in Breast Cancer," Cancer Res., Mar. 2010, 2085-2094.
Tvorogov et al., "Effective Suppression of Vascular Network Formation by Combination of Antibodies Blocking VEGFR Ligand Binding and Receptor Dimerization," Cancer Cell, Dec. 2010, 18: 630-640.
Urakawa et al., "Klotho converts canonical FGF receptor into a specific receptor for FGF23," Nature, Dec. 2006, 444: 770-774.
Uzawa et al., "Targeting fibroblast growth factor receptor 3 enhances radiosensitivity in human squamous cancer cells," Oncogene, 2011, 1-6.
van Oers et al., "FGFR3 Mutations Indicate Better Survival in Invasive Upper Urinary Tract and Bladder Tumours," European Urology, 2009, 650-658.
Våtsveen et al., "FGFR3 is expressed and is important for survival in INA-6, a human myeloma cell line without a t(4;14)," Eur. J. Haematol., 83:5, Jul. 6, 2009, 471-476.
Wang and Becker, "Antisense targeting of basic fibroblast growth factor and fibroblast growth factor receptor-1 in human melanomas blocks intratumoral angiogenesis and tumor growth," Nature Medicine, Aug. 1997, 887-893.
Ware et al., "Rapidly Acquired Resistance to EFGR Tyrosine Kinase Inhibitors in NSCLC Cell Lines through De-Repression of FGFR2 and FGFR3 Expression," PLoS, Nov. 2010, 5(11): 1-9.
Weiss et al., Frequent and Focal FGFR1 Amplification Associates with Therapeutically Tractable FGFR1 Dependency in Squamous Cell Lung Cancer, Sci. Transl. Med., 2010, 2(62):62ra93, pp. 1-7.
Wu, "Urothelial Tumorigenesis: A Tale of Divergent Pathways," Nature Reviews, Sep. 2005, 5: 713-725.
Wöhrle et al., "FGF Receptors Control Vitamin D and Phosphate Homeostasis by Mediating Renal FGF-23 Signaling and Regulating FGF-23 Expression in Bone," Journal of Bone and Mineral Research, Oct. 2011, 26(10): 2486-2497.
Wöhrle et al., "Pharmacological inhibition of FGFR signaling ameliorates FGF23-mediated hypophosphatemic rickets," Journal of Bone and Mineral Research, 2012, 1-36.
Xian et al., "Pleiotropic effects of FGFR1 on cell proliferation, survival, and migration in a 3D mammary epithelial cell model," JCB, 2005, 171(4): 663-673.
Xin et al., "CHIR-258 Is Efficacious in a Newly Developed Fibroblast Growth Factor Receptor 3-Expressing Orthotopic Multiple Myeloma Model in Mice," Clin Cancer Res, Aug. 2006, 4908-4915.
Yu et al., "Analysis of the Biochemical Mechanisms for the Endocrine Actions of Firbroblast Growth Factor-23," Endocrinology, Nov. 2005, 146(11): 4647-4656.
Zaid et al., "Identification of FGFR4 as a Potential Therapeutic Target for Advanced-Stage, High-Grade Serous Ovarian Cancer," Clin Cancer Res, 2013, 19(4): 809-820.
Zhang et al., "AZD4547, a potent and selective FGF-receptor inhibitor induces tumor regressions in a human primary model of FGF-receptor 2 amplified gastric cancer and is efficacious in combination with chemotherapy," 2012.
Zhang et al., "Direct Cell Cycle Regulation by the Fibroblast Growth Factor Receptor (FGFR) Kinase through Phosphorylation-dependent Release of Cks1 from FGFR Substrate 2," The Journal of Biological Chemistry, 2004, 279(53): 55348-55354.
Zhang et al., "FP-1039 (FGFR1:Fc), A Soluble FGFR1 Receptor Antagonist, Inhibits Tumor Growth and Angiogenesis," Mol Cancer Ther, 6, Nov. 2007, B55.
Zhang et al., "Receptor Specificity of the Fibroblast Growth Factor Family," Journal of Biological Chemistry, Jun. 2006, 281(23): 15694-15700.
Zhang et al., "Translating the therapeutic potential of AZD4547 in FGFR1-amplified non-small cell lung cancer through the use of patient derived tumor xenograft (PDTX) models," Clin cancer Res, Oct. 18, 2012, 40 pages.
Zhao et al., "A Novel, Selective Inhibitor of Fibroblast Growth Factor Receptors That Shows a Potent Broad Spectrum of Antitumor Activity in Several Tumor Xenograft Models," Mol Cancer Ther, Nov. 2011, 2200-2210.
Zhao et al., "Homozygous Deletions and Chromosome Amplifications in Human Lung Carcinomas Revealed by Single Nucleotide Polymorphism Array Analysis," Cancer Res, Jul. 2005, 5561-5570.
Zhou et al., "A Structure-Guided Approach to Creating Covalent FGFR Inhibitors," Chemistry and Biology, Mar. 2010, 285-295.
Zhu et al., "Fibroblast growth factor receptor 3 inhibition by short hairpin RNAs leads to apoptosis in multiple myeloma," Mol Cancer Ther, May 2005, 787-798.
Zieger et al., "Role of Activating Fibroblast Growth Factor Receptor 3 Mutations in the Development of Bladder Tumors," Clin Cancer Res, Nov. 2005, 7709-7719.
Zingone et al., "Ectopic expression of wild-type FGFR3 cooperates with MYC to accelerate development of B-cell lineage neoplasms," Leukemia, 2010, 1171-1178.
Chilean Office Action in Chilean Application No. 3355-2014, dated Jan. 18, 2017, 17 pages (with English translation).
Chilean Opposition in Chilean Application No. 3355-2014, received Feb. 3, 2017, 3 pages (English translation only).
Chinese Office Action in Chinese Application No. 201380041027.9, dated Feb. 13, 2017, 10 pages (with English translation).
Chinese Office Action in Chinese Application No. 201380041027.9, dated Jul. 12, 2016, 11 pages (with English translation).
Chinese Office Action in Chinese Application No. 201380041027.9, dated Oct. 28, 2015, 17 pages (with English translation).
Columbian Office Action in Columbian Application No. 14-275934-6, dated May 31, 2016, 3 pages (English translation only).
Columbian Office Action in Columbian Application No. 14-275934-6, dated Nov. 17, 2015, 12 pages (English translation only).
Eurasian Office Aciton in Eurasian Application No. 201590005, dated Oct. 30, 2015, 6 pages.
European Communication pursuant to Article 94(3) EPC in European Application No. 13783125.1, dated Jan. 26, 2016, 4 pages.

(56) References Cited

OTHER PUBLICATIONS

European search report in European Application No. 16203866.5, dated Mar. 1, 2017, 7 pages.
Japanese Office Action in Japanese Application No. 2015-517376, dated Feb. 21, 2017, 6 pages (with English translation).
New Zealand Office Action in New Zealand Application No. 702747, dated Sep. 16, 2016, 3 pages.
Office Action from the Intellectual Property Office of the Philippines in Application No. 1-2014-502772, dated Mar. 17, 2016, 3 pages.
Taiwanese Office Action in Taiwan Application No. 102120946, dated Nov. 9, 2016, 9 pages (with English translation).
Thai Office Action in Thai Application No. 1401007417, dated Jun. 5, 2016, 7 pages (with English translation).
Thompson et al., "Photochemical Preparation of a Pyridone Containing Tetracycle: A Jak Protein Kinase Inhibitor," Bioorganic & Medicinal Chemistry Letters 12:1219-1223, 2002.
Ukraine Office Action in Ukraine Application No. a201500191, dated Dec. 13, 2016, 10 pages (with English translation).
Vietnamese Office Action in Vietnamese Application No. 1-2015-00102, dated Mar. 18, 2015, 4 pages.

SUBSTITUTED PYRROLO[2,3-B]PYRAZINES AS FGFR INHIBITORS

FIELD OF THE INVENTION

The present invention relates to pyrazine derivatives, and pharmaceutical compositions including the same, that are inhibitors of one or more FGFR enzymes and are useful in the treatment of FGFR-associated diseases such as cancer.

BACKGROUND OF THE INVENTION

The Fibroblast Growth Factor Receptors (FGFR) are receptor tyrosine kinases that bind to fibroblast growth factor (FGF) ligands. There are four FGFR proteins (FGFR1-4) that are capable of binding ligands and are involved in the regulation of many physiological processes including tissue development, angiogenesis, wound healing, and metabolic regulation. Upon ligand binding, the receptors undergo dimerization and phosphorylation leading to stimulation of the protein kinase activity and recruitment of many intracellular docking proteins. These interactions facilitate the activation of an array of intracellular signaling pathways including Ras-MAPK, AKT-PI3K, and phospholipase C that are important for cellular growth, proliferation and survival (Reviewed in Eswarakumar et al. Cytokine & Growth Factor Reviews, 2005).

Aberrant activation of this pathway either through overexpression of FGF ligands or FGFR or activating mutations in the FGFRs can lead to tumor development, progression, and resistance to conventional cancer therapies. In human cancer, genetic alterations including gene amplification, chromosomal translocations and somatic mutations that lead to ligand-independent receptor activation have been described. Large scale DNA sequencing of thousands of tumor samples has revealed that components of the FGFR pathway are among the most frequently mutated in human cancer. Many of these activating mutations are identical to germline mutations that lead to skeletal dysplasia syndromes. Mechanisms that lead to aberrant ligand-dependent signaling in human disease include overexpression of FGFs and changes in FGFR splicing that lead to receptors with more promiscuous ligand binding abilities (Reviewed in Knights and Cook Pharmacology & Therapeutics, 2010; Turner and Grose, Nature Reviews Cancer, 2010). Therefore, development of inhibitors targeting FGFR may be useful in the clinical treatment of diseases that have elevated FGF or FGFR activity.

The cancer types in which FGF/FGFRs are implicated include, but are not limited to: carcinomas (e.g., bladder, breast, cervical, colorectal, endometrial, gastric, head and neck, kidney, liver, lung, ovarian, prostate); hematopoietic malignancies (e.g., multiple myeloma, chronic lymphocytic lymphoma, adult T cell leukemia, acute myelogenous leukemia, non-Hodgkin lymphoma, myeloproliferative neoplasms, and Waldenstrom's Macroglubulinemia); and other neoplasms (e.g., glioblastoma, melanoma, and rhabdosarcoma). In addition to a role in oncogenic neoplasms, FGFR activation has also been implicated in skeletal and chondrocyte disorders including, but not limited to, achrondroplasia and craniosynostosis syndromes.

There is a continuing need for the development of new drugs for the treatment of cancer and other diseases, and the FGFR inhibitors described herein help address this need.

SUMMARY OF THE INVENTION

The present invention provides, inter alia, a compound of Formula I:

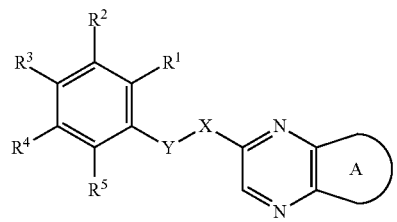

or a pharmaceutically acceptable salt thereof, wherein constituent variables are defined herein.

The present invention further provides a composition comprising a compound of Formula I and at least one pharmaceutically acceptable carrier.

The present invention further provides a method of treating cancer in a patient comprising administering to the patient a therapeutically effective amount of a compound of Formula I, or a pharmaceutically acceptable salt thereof.

The present invention further provides a method of treating a myeloproliferative disorder in a patient comprising administering to the patient a therapeutically effective amount of a compound of Formula I, or a pharmaceutically acceptable salt thereof.

The present invention further provides a skeletal or chondrocyte disorder in a patient comprising administering to the patient a therapeutically effective amount of Formula I, or a pharmaceutically acceptable salt thereof.

DETAILED DESCRIPTION

The present invention is related to FGFR inhibitors such as a compound of Formula I:

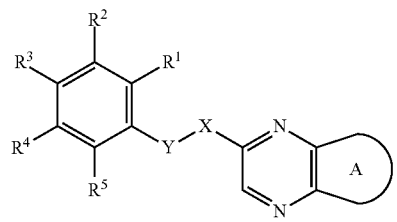

or a pharmaceutically acceptable salt thereof, wherein:
X and Y are each independently selected from CH$_2$, O, and S, wherein no more than one of X and Y is selected from O and S;
ring A is selected from

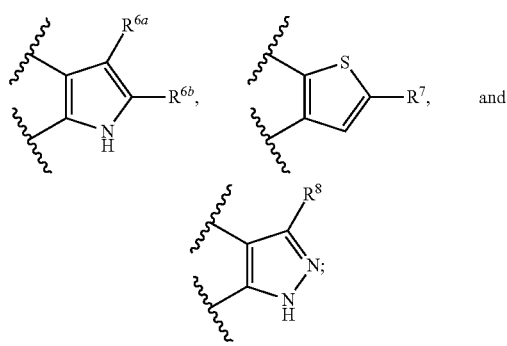

$R^1$, $R^2$, $R^3$, $R^4$, and $R^5$ are each independently selected from H, halo, $C_{1-6}$ alkyl, $C_{2-6}$ alkenyl, $C_{2-6}$ alkynyl, $C_{1-6}$ haloalkyl, CN, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)OR^a$, $NR^cC(O)NR^cR^d$, $C(=NR^e)R^b$, $C(=NR^e)NR^cR^d$, $NR^cC(=NR^e)NR^cR^d$, $NR^cS(O)R^b$, $NR^cS(O)_2R^b$, $NR^cS(O)_2NR^cR^d$, $S(O)R^b$, $S(O)NR^cR^d$, $S(O)_2R^b$, and $S(O)_2NR^cR^d$; wherein said $C_{1-6}$ alkyl, $C_{2-6}$ alkenyl, $C_{2-6}$ alkynyl are each optionally substituted with 1, 2, or 3 substituents independently selected from halo, $C_{1-6}$ haloalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $C(=NR^e)NR^cR^d$, $NR^cC(=NR^e)NR^cR^d$, $NR^cR^d$, $NR^cC(O)R^b$, $NR^cC(O)OR^a$, $NR^cC(O)NR^cR^d$, $NR^cS(O)R^b$, $NR^cS(O)_2R^b$, $NR^cS(O)_2NR^cR^d$, $S(O)R^b$, $S(O)NR^cR^d$, $S(O)_2R^b$, and $S(O)_2NR^cR^d$;

each $R^a$, $R^b$, $R^c$, and $R^d$ is independently selected from H, $C_{1-6}$ alkyl, $C_{1-4}$ haloalkyl, $C_{2-6}$ alkenyl, and $C_{2-6}$ alkynyl;

$R^e$ is selected from H, $C_{1-4}$ alkyl, CN, and $C_{1-4}$ alkoxy;

$R^{6a}$, $R^{6b}$, $R^7$ and $R^8$ are each independently selected from H, halo, $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-10 membered heteroaryl, 4-10 membered heterocycloalkyl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $C(=NR^{e1})R^{b1}$, $C(=NR^{e1})NR^{c1}R^{d1}$, $NR^cC(=NR^{e1})NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, and $S(O)_2NR^{c1}R^{d1}$; wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, and 4-10 membered heterocycloalkyl are each optionally substituted with 1, 2, 3, 4, or 5 substituents independently selected from $R^9$;

each $R^9$ is independently selected from $Cy^1$, halo, $C_{1-6}$ alkyl, $C_{2-6}$ alkenyl, $C_{2-6}$ alkynyl, $C_{1-6}$ haloalkyl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $C(=NR^{e1})NR^{c1}R^{d1}$, $NR^{c1}C(=NR^{e1})NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, and $S(O)_2NR^{c1}R^{d1}$, wherein said $C_{1-6}$ alkyl, $C_{2-6}$ alkenyl, and $C_{2-6}$ alkynyl are each optionally substituted with 1, 2, or 3 substituents independently selected from $Cy^1$, halo, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $C(=NR^{e1})NR^{c1}R^{d1}$, $R^{c1}C(=NR^{e1})NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, and $S(O)_2NR^{c1}R^{d1}$;

each $Cy^1$ is independently selected from $C_{6-10}$ aryl, $C_{3-10}$ cycloalkyl, 5-10 membered heteroaryl, 4-10 membered heterocycloalkyl, each of which is optionally substituted by 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-10 membered heteroaryl, 4-10 membered heterocycloalkyl, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)OR^{a2}$, $NR^{c2}C(O)NR^{c2}R^{d2}$, $C(=NR^{e2})R^{b2}$, $C(=NR^{e2})NR^{c2}R^{d2}$, $NR^{c2}C(=NR^{e2})NR^{c2}R^{d2}$, $NR^{c2}S(O)R^{b2}$, $NR^{c2}S(O)_2R^{b2}$, $NR^{c2}S(O)_2NR^{c2}R^{d2}$, $S(O)R^{b2}$, $S(O)NR^{c2}R^{d2}$, $S(O)_2R^{b2}$, and $S(O)_2NR^{c2}R^{d2}$; wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, and 4-10 membered heterocycloalkyl are each optionally substituted with 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $C(=NR^{e2})NR^{c2}R^{d2}$, $NR^{c2}C(=NR^{e2})NR^{c2}R^{d2}$, $NR^{c2}R^{d2}$, $NR^{c2}C(O)R^{b2}$, $NR^{c2}C(O)OR^{a2}$, $NR^{c2}C(O)NR^{c2}R^{d2}$, $NR^{c2}S(O)R^{b2}$, $NR^{c2}S(O)_2R^{b2}$, $NR^{c2}S(O)_2NR^{c2}R^{d2}$, $S(O)R^{b2}$, $S(O)NR^{c2}R^{d2}$, $S(O)_2R^{b2}$, and $S(O)_2NR^{c2}R^{d2}$;

each $R^{a1}$, $R^{b1}$, $R^{c1}$, $R^{d1}$, $R^{a2}$, $R^{b2}$, $R^{c2}$, and $R^{d2}$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl, $C_{3-10}$ cycloalkyl-$C_{1-4}$ alkyl, (5-10 membered heteroaryl)-$C_{1-4}$ alkyl, or (4-10 membered heterocycloalkyl)-$C_{1-4}$ alkyl, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl, $C_{3-10}$ cycloalkyl-$C_{1-4}$ alkyl, (5-10 membered heteroaryl)-$C_{1-4}$ alkyl, and (4-10 membered heterocycloalkyl)-$C_{1-4}$ alkyl is optionally substituted with 1, 2, 3, 4, or 5 substituents independently selected from $C_{1-4}$ alkyl, $C_{1-4}$ haloalkyl, halo, CN, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)NR^{c3}R^{d3}$, $NR^{c3}C(O)OR^{a3}$, $C(=NR^{e3})NR^{c3}R^{d3}$, $NR^{c3}C(=NR^{e3})NR^{c3}R^{d3}$ $S(O)R^{b3}$, $S(O)NR^{c3}R^{d3}$, $S(O)_2R^{b3}$, $NR^{c3}S(O)_2R^{b3}$, $NR^{c3}S(O)_2NR^{c3}R^{d3}$, and $S(O)_2NR^{c3}R^{d3}$;

or any $R^{c1}$ and $R^{d1}$ together with the N atom to which they are attached form a 4-, 5-, 6-, or 7-membered heterocycloalkyl group optionally substituted with 1, 2, or 3 substituents independently selected from $C_{1-6}$ alkyl, $C_{3-7}$ cycloalkyl, 4-7 membered heterocycloalkyl, $C_{6-10}$ aryl, 5-6 membered heteroaryl, $C_{1-6}$ haloalkyl, halo, CN, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)NR^{c3}R^{d3}$, $NR^{c3}C(O)OR^{a3}$, $C(=NR^{e3})NR^{c3}R^{d3}$, $NR^{c3}C(=NR^{e3})NR^{c3}R^{d3}$, $S(O)R^{b3}$, $S(O)NR^{c3}R^{d3}$, $S(O)_2R^{b3}$, $NR^{c3}S(O)_2R^{b3}$, $NR^{c3}S(O)_2NR^{c3}R^{d3}$, and $S(O)_2NR^{c3}R^{d3}$, wherein said $C_{1-6}$ alkyl, $C_{3-7}$ cycloalkyl, 4-7 membered heterocycloalkyl, $C_{6-10}$ aryl, and 5-6 membered heteroaryl are optionally substituted by 1, 2, or 3 substituents independently selected from halo, CN, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)NR^{c3}R^{d3}$, $NR^{c3}C(O)OR^{a3}$, $C(=NR^{e3})NR^{c3}R^{d3}$, $NR^{c3}C(=NR^{e3})NR^{c3}R^{d3}$, $S(O)R^{b3}$, $S(O)NR^{c3}R^{d3}$, $S(O)_2R^{b3}$, $NR^{c3}S(O)_2R^{b3}$, $NR^{c3}S(O)_2NR^{c3}R^{d3}$, and $S(O)_2NR^{c3}R^{d3}$;

or any $R^{c2}$ and $R^{d2}$ together with the N atom to which they are attached form a 4-, 5-, 6-, or 7-membered heterocycloalkyl group optionally substituted with 1, 2, or 3 substituents independently selected from $C_{1-6}$ alkyl, $C_{3-7}$ cycloalkyl, 4-7 membered heterocycloalkyl, $C_{6-10}$ aryl, 5-6 membered heteroaryl, $C_{1-6}$ haloalkyl, halo, CN, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)NR^{c3}R^{d3}$, $NR^{c3}C(O)OR^{a3}$, $C(=NR^{e3})NR^{c3}R^{d3}$, $NR^{c3}C(=NR^{e3})NR^{c3}R^{d3}$, $S(O)R^{b3}$, $S(O)NR^{c3}R^{d3}$, $S(O)_2R^{b3}$, $NR^{c3}S(O)_2R^{b3}$, $NR^{c3}S(O)_2NR^{c3}R^{d3}$, and $S(O)_2NR^{c3}R^{d3}$, wherein said $C_{1-6}$ alkyl, $C_{3-7}$ cycloalkyl, 4-7 membered heterocycloalkyl, $C_{6-10}$ aryl, and 5-6 membered heteroaryl are optionally substituted by 1, 2, or 3 substituents independently selected from halo, CN, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)NR^{c3}R^{d3}$, $NR^{c3}C(O)OR^{a3}$, $C(=NR^{e3})NR^{c3}R^{d3}$, $NR^{c3}C(=NR^{e3})NR^{c3}R^{d3}$, $S(O)R^{b3}$, $S(O)NR^{c3}R^{d3}$, $S(O)_2R^{b3}$, $NR^{c3}S(O)_2R^{b3}$, $NR^{c3}S(O)_2NR^{c3}R^{d3}$, and $S(O)_2NR^{c3}R^{d3}$;

each $R^{e1}$ and $R^{e2}$ is independently selected from H, $C_{1-4}$ alkyl, CN, $OR^{a3}$, $SR^{b3}$, $S(O)_2R^{b3}$, $C(O)R^{b3}$, $S(O)_2NR^{c3}R^{d3}$, and $C(O)NR^{c3}R^{d3}$;

each $R^{a3}$, $R^{b3}$, $R^{c3}$, and $R^{d3}$ is independently selected from H, $C_{1-4}$ alkyl, $C_{1-4}$ haloalkyl, $C_{2-4}$ alkenyl, and $C_{2-4}$ alkynyl, wherein said $C_{1-4}$ alkyl, $C_{2-4}$ alkenyl, and $C_{2-4}$ alkynyl, is optionally substituted with 1, 2, or 3 substituents independently selected from OH, CN, amino, halo, $C_{1-4}$ alkyl, $C_{1-4}$ alkoxy, $C_{1-4}$ alkylthio, $C_{1-4}$ alkylamino, di($C_{1-4}$ alkyl)amino, $C_{1-4}$ haloalkyl, and $C_{1-4}$ haloalkoxy;

or any $R^{c3}$ and $R^{d3}$ together with the N atom to which they are attached form a 3-, 4-, 5-, 6-, or 7-membered heterocycloalkyl group optionally substituted with 1, 2, or 3 substituents independently selected from OH, CN, amino, halo, $C_{1-6}$ alkyl, $C_{1-4}$ alkoxy, $C_{1-4}$ alkylthio, $C_{1-4}$ alkylamino, di($C_{1-4}$ alkyl)amino, $C_{1-4}$ haloalkyl, and $C_{1-4}$ haloalkoxy; and each $R^{e3}$ is independently selected from H, $C_{1-4}$ alkyl, and CN;

wherein when ring A is

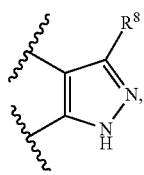

$R^8$ is H, and X is O, then at least one of $R^1$, $R^2$, $R^3$, $R^4$, and $R^5$ is other than H.

In some embodiments, X and Y are both $CH_2$.

In some embodiments, ring A is

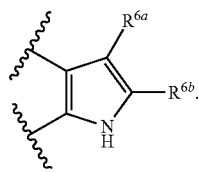

In some embodiments, $R^{6a}$ is H, halo, $C_{1-6}$ alkyl, CN, or $C(O)NR^{c1}R^{d1}$.

In some embodiments, $R^{6a}$ is H, Br, Cl, methyl, ethyl, CN, or $C(O)NHCH_3$.

In some embodiments, $R^{6a}$ is H.

In some embodiments, $R^{6b}$ is other than H.

In some embodiments, $R^{6b}$ is $C_{1-6}$ alkyl, $C_{2-6}$ alkynyl, $C_{6-10}$ aryl, 5-10 membered heteroaryl, 4-10 membered heterocycloalkyl, or $C(O)NR^{c1}R^{d1}$; wherein said $C_{1-6}$ alkyl, $C_{2-6}$ alkynyl, $C_{6-10}$ aryl, 5-10 membered heteroaryl, and 4-10 membered heterocycloalkyl are each optionally substituted with 1, 2, 3, 4, or 5 substituents independently selected from $R^9$.

In some embodiments, $R^{6b}$ is phenyl, thienyl, pyrazolyl, pyridyl, pyrimidinyl, benzodioxolyl, 1,2,3,6-tetrahydropyridinyl, 1H-indazolyl, piperidinyl, pyridopyrazinyl, indolinonyl; wherein said phenyl, thienyl, pyrazolyl, pyridyl, pyrimidinyl, benzodioxolyl, 1,2,3,6-tetrahydropyridinyl, 1H-indazolyl, piperidinyl, pyridopyrazinyl, indolinonyl are each optionally substituted with 1, 2, or 3 substituents independently selected from $R^9$.

In some embodiments, $R^{6b}$ is propyl or propynyl; wherein said propyl or propynyl are each optionally substituted with 1, 2, or 3 substituents independently selected from $R^9$.

In some embodiments, $R^{6b}$ is $C(O)NHCH_3$ or $C(O)N(CH_3)_2$.

In some embodiments, $R^{6b}$ is propyl, propynyl, phenyl, thienyl, pyrazolyl, pyridyl, pyrimidinyl, a benzo[d][1,3]dioxole ring, 1,2,3,6-tetrahydropyridinyl, 1H-indazolyl, piperidinyl, pyrido[2,3-b]pyrazinyl, an indolin-2-one ring, $C(O)NHCH_3$, or $C(O)N(CH_3)_2$; wherein said propyl, propynyl, phenyl, thienyl, pyrazolyl, pyridyl, pyrimidinyl, benzo[d][1,3]dioxole ring, 1,2,3,6-tetrahydropyridinyl, 1H-indazolyl, piperidinyl, pyrido[2,3-b]pyrazinyl, and indolin-2-one ring are each optionally substituted with 1, 2, or 3 substituents independently selected from $R^9$.

In some embodiments, $R^9$ is $Cy^1$, halo, $C_{1-6}$ alkyl, $C_{1-6}$ haloalkyl, CN, $OR^{a1}$, $C(O)NR^{c1}R^{d1}$, $C(O)OR^{a1}$, $NR^{c1}R^{d1}$, or $NR^{c1}C(O)R^{b1}$, wherein said $C_{1-6}$ alkyl, is optionally substituted with 1, 2, or 3 substituents independently selected from $Cy^1$, halo, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $C(=NR^{e1})NR^{c1}R^{d1}$, $NR^{c1}C(=NR^{e1})NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, and $S(O)_2NR^{c1}R^{d1}$.

In some embodiments $Cy^1$ is morpholinyl pyrrolidinyl, piperazinyl, piperidinyl, tetrahydropyranyl, tetrahyropyridinyl, pyrrolidinonyl, piperazinonyl, or piperidinonyl, wherein said $Cy^1$ is optionally substituted with 1, 2, or 3 substituents independently selected from halo, $C_{1-6}$ alkyl, and $OR^{a2}$.

In some embodiments, at least two of $R^1$, $R^2$, $R^3$, $R^4$, and $R^5$ are other than H.

In some embodiments, at least three of $R^1$, $R^2$, $R^3$, $R^4$, and $R^5$ are other than H.

In some embodiments, at least four of $R^1$, $R^2$, $R^3$, $R^4$, and $R^5$ are other than H.

In some embodiments, $R^3$ is H and $R^2$ and $R^5$ are other than H.

In some embodiments, $R^3$ is H and $R^1$, $R^2$, $R^4$, and $R^5$ are other than H.

In some embodiments, $R^1$, $R^2$, $R^3$, $R^4$, and $R^5$ are each independently selected from H, halo, and $C_{1-4}$ alkoxy.

In some embodiments, $R^1$, $R^2$, $R^3$, $R^4$, and $R^5$ are each independently selected from H, halo, and $OR^a$.

In some embodiments, $R^3$ is H and $R^1$, $R^2$, $R^4$, and $R^5$ are each independently selected from halo and $OR^a$.

In some embodiments, $R^3$ is H and $R^1$, $R^2$, $R^4$, and $R^5$ are each independently selected from halo and $C_{1-4}$ alkoxy.

In some embodiments, $R^1$, $R^2$, $R^3$, $R^4$, and $R^5$ are each independently selected from H, F, and methoxy.

In some embodiments, $R^1$ is H or F, $R^2$ is methoxy, $R^3$ is H, $R^4$ is methoxy, and $R^5$ is H or F.

In some embodiments, $R^1$ is H, $R^2$ is methoxy, $R^3$ is H, $R^4$ is methoxy, and $R^5$ is H.

In some embodiments, $R^1$ is F, $R^2$ is methoxy, $R^3$ is H, $R^4$ is methoxy, and $R^5$ is F.

In some embodiments, the compounds of the invention have Formula IIa:

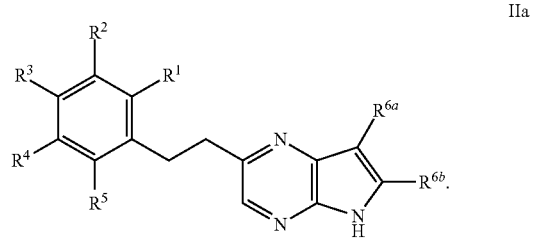

IIa

In some embodiments, the compounds of the invention have Formula IIb:

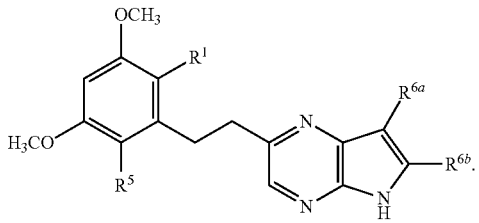

In some embodiments, the compounds of the invention have Formula III:

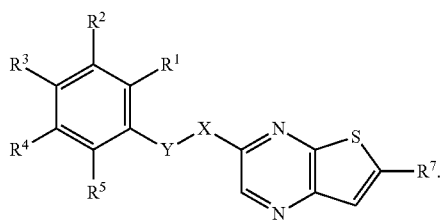

In some embodiments, the compounds of the invention have Formula IV:

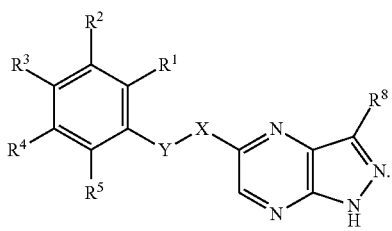

It is further appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable subcombination.

At various places in the present specification, substituents of compounds of the invention are disclosed in groups or in ranges. It is specifically intended that the invention include each and every individual subcombination of the members of such groups and ranges. For example, the term "$C_{1-6}$ alkyl" is specifically intended to individually disclose methyl, ethyl, $C_3$ alkyl, $C_4$ alkyl, $C_5$ alkyl, and $C_6$ alkyl.

At various places in the present specification various aryl, heteroaryl, cycloalkyl, and heterocycloalkyl rings are described. Unless otherwise specified, these rings can be attached to the rest of the molecule at any ring member as permitted by valency. For example, the term "pyridyl," "pyridinyl," or "a pyridine ring" may refer to a pyridin-2-yl, pyridin-3-yl, or pyridin-4-yl ring.

The term "n-membered" where n is an integer typically describes the number of ring-forming atoms in a moiety where the number of ring-forming atoms is n. For example, piperidinyl is an example of a 6-membered heterocycloalkyl ring, pyrazolyl is an example of a 5-membered heteroaryl ring, pyridyl is an example of a 6-membered heteroaryl ring, and 1,2,3,4-tetrahydro-naphthalene is an example of a 10-membered cycloalkyl group.

For compounds of the invention in which a variable appears more than once, each variable can be a different moiety independently selected from the group defining the variable. For example, where a structure is described having two R groups that are simultaneously present on the same compound, the two R groups can represent different moieties independently selected from the group defined for R.

As used herein, the phrase "optionally substituted" means unsubstituted or substituted.

As used herein, the term "substituted" means that a hydrogen atom is replaced by a non-hydrogen group. It is to be understood that substitution at a given atom is limited by valency.

As used herein, the term "$C_{i-j}$", where i and j are integers, employed in combination with a chemical group, designates a range of the number of carbon atoms in the chemical group with i-j defining the range. For example, $C_{1-6}$ alkyl refers to an alkyl group having 1, 2, 3, 4, 5, or 6 carbon atoms.

As used herein, the term "alkyl", employed alone or in combination with other terms, refers to a saturated hydrocarbon group that may be straight-chain or branched. In some embodiments, the alkyl group contains 1 to 6, 1 to 4, or 1 to 3 carbon atoms. Examples of alkyl moieties include, but are not limited to, chemical groups such as methyl, ethyl, n-propyl, isopropyl, n-butyl, isobutyl, sec-butyl, tert-butyl, n-pentyl, 2-methyl-1-butyl, 3-pentyl, n-hexyl, 1,2,2-trimethylpropyl, and the like. In some embodiments, the alkyl group is methyl, ethyl, or propyl.

As used herein, "alkenyl", employed alone or in combination with other terms, refers to an alkyl group having one or more carbon-carbon double bonds. In some embodiments, the alkenyl moiety contains 2 to 6 or 2 to 4 carbon atoms. Example alkenyl groups include, but are not limited to, ethenyl, n-propenyl, isopropenyl, n-butenyl, sec-butenyl, and the like.

As used herein, "alkynyl", employed alone or in combination with other terms, refers to an alkyl group having one or more carbon-carbon triple bonds. Example alkynyl groups include, but are not limited to, ethynyl, propyn-1-yl, propyn-2-yl, and the like. In some embodiments, the alkynyl moiety contains 2 to 6 or 2 to 4 carbon atoms.

As used herein, "halo" or "halogen", employed alone or in combination with other terms, includes fluoro, chloro, bromo, and iodo. In some embodiments, halo is F or Cl.

As used herein, the term "haloalkyl", employed alone or in combination with other terms, refers to an alkyl group having up to the full valency of halogen atom substituents, which may either be the same or different. In some embodiments, the halogen atoms are fluoro atoms. In some embodiments, the alkyl group has 1 to 6 or 1 to 4 carbon atoms. Example haloalkyl groups include $CF_3$, $C_2F_5$, $CHF_2$, $CCl_3$, $CHCl_2$, $C_2Cl_5$, and the like.

As used herein, the term "alkoxy", employed alone or in combination with other terms, refers to a group of formula —O-alkyl. Example alkoxy groups include methoxy, ethoxy, propoxy (e.g., n-propoxy and isopropoxy), t-butoxy, and the like. In some embodiments, the alkyl group has 1 to 6 or 1 to 4 carbon atoms.

As used herein, "haloalkoxy", employed alone or in combination with other terms, refers to a group of formula —O-(haloalkyl). In some embodiments, the alkyl group has 1 to 6 or 1 to 4 carbon atoms. An example haloalkoxy group is —OCF$_3$.

As used herein, "amino", employed alone or in combination with other terms, refers to NH$_2$.

As used herein, the term "alkylamino", employed alone or in combination with other terms, refers to a group of formula —NH(alkyl). In some embodiments, the alkylamino group has 1 to 6 or 1 to 4 carbon atoms. Example alkylamino groups include methylamino, ethylamino, propylamino (e.g., n-propylamino and isopropylamino), and the like.

As used herein, the term "dialkylamino", employed alone or in combination with other terms, refers to a group of formula —N(alkyl)$_2$. Example dialkylamino groups include dimethylamino, diethylamino, dipropylamino (e.g., di(n-propyl)amino and di(isopropyl)amino), and the like. In some embodiments, each alkyl group independently has 1 to 6 or 1 to 4 carbon atoms.

As used herein, the term "alkylthio", employed alone or in combination with other terms, refers to a group of formula —S-alkyl. In some embodiments, the alkyl group has 1 to 6 or 1 to 4 carbon atoms.

As used herein, the term "cycloalkyl", employed alone or in combination with other terms, refers to a non-aromatic cyclic hydrocarbon including cyclized alkyl and alkenyl groups. Cycloalkyl groups can include mono- or polycyclic (e.g., having 2, 3, or 4 fused, bridged, or spiro rings) ring systems. Also included in the definition of cycloalkyl are moieties that have one or more aromatic rings (e.g., aryl or heteroaryl rings) fused (i.e., having a bond in common with) to the cycloalkyl ring, for example, benzo derivatives of cyclopentane, cyclohexene, cyclohexane, and the like, or pyrido derivatives of cyclopentane or cyclohexane. Ring-forming carbon atoms of a cycloalkyl group can be optionally substituted by oxo. Cycloalkyl groups also include cycloalkylidenes. The term "cycloalkyl" also includes bridgehead cycloalkyl groups (e.g., non-aromatic cyclic hydrocarbon moieties containing at least one bridgehead carbon, such as admantan-1-yl) and spirocycloalkyl groups (e.g., non-aromatic hydrocarbon moieties containing at least two rings fused at a single carbon atom, such as spiro[2.5]octane and the like). In some embodiments, the cycloalkyl group has 3 to 10 ring members, or 3 to 7 ring members. In some embodiments, the cycloalkyl group is monocyclic or bicyclic. In some embodiments, the cycloalkyl group is monocyclic. In some embodiments, the cycloalkyl group is a C$_{3-7}$ monocyclic cycloalkyl group. Example cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcarnyl, tetrahydronaphthalenyl, octahydronaphthalenyl, indanyl, and the like. In some embodiments, the cycloalkyl group is cyclopropyl, cyclobutyl, cyclopentyl, or cyclohexyl.

As used herein, the term "cycloalkylalkyl", employed alone or in combination with other terms, refers to a group of formula cycloalkyl-alkyl-. In some embodiments, the alkyl portion has 1 to 4, 1 to 3, 1 to 2, or 1 carbon atom(s). In some embodiments, the alkyl portion is methylene. In some embodiments, the cycloalkyl portion has 3 to 10 ring members or 3 to 7 ring members. In some embodiments, the cycloalkyl group is monocyclic or bicyclic. In some embodiments, the cycloalkyl portion is monocyclic. In some embodiments, the cycloalkyl portion is a C$_{3-7}$ monocyclic cycloalkyl group.

As used herein, the term "heterocycloalkyl", employed alone or in combination with other terms, refers to a non-aromatic ring or ring system, which may optionally contain one or more alkenylene or alkynylene groups as part of the ring structure, which has at least one heteroatom ring member independently selected from nitrogen, sulfur, oxygen, and phosphorus. Heterocycloalkyl groups can include mono- or polycyclic (e.g., having 2, 3 or 4 fused, bridged, or spiro rings) ring systems. In some embodiments, the heterocycloalkyl group is a monocyclic or bicyclic group having 1, 2, 3, or 4 heteroatoms independently selected from nitrogen, sulfur and oxygen. Also included in the definition of heterocycloalkyl are moieties that have one or more aromatic rings (e.g., aryl or heteroaryl rings) fused (i.e., having a bond in common with) to the non-aromatic heterocycloalkyl ring, for example, 1,2,3,4-tetrahydro-quinoline and the like. Heterocycloalkyl groups can also include bridgehead heterocycloalkyl groups (e.g., a heterocycloalkyl moiety containing at least one bridgehead atom, such as azaadmantan-1-yl and the like) and spiroheterocycloalkyl groups (e.g., a heterocycloalkyl moiety containing at least two rings fused at a single atom, such as [1,4-dioxa-8-aza-spiro[4.5]decan-N-yl] and the like). In some embodiments, the heterocycloalkyl group has 3 to 10 ring-forming atoms, or about 3 to 8 ring forming atoms. In some embodiments, the heterocycloalkyl group has 2 to 20 carbon atoms, 2 to 15 carbon atoms, 2 to 10 carbon atoms, or about 2 to 8 carbon atoms. In some embodiments, the heterocycloalkyl group has 1 to 5 heteroatoms, 1 to 4 heteroatoms, 1 to 3 heteroatoms, or 1 to 2 heteroatoms. The carbon atoms or heteroatoms in the ring(s) of the heterocycloalkyl group can be oxidized to form a carbonyl, an N-oxide, or a sulfonyl group (or other oxidized linkage) or a nitrogen atom can be quaternized. In some embodiments, the heterocycloalkyl portion is a C$_{2-7}$ monocyclic heterocycloalkyl group. In some embodiments, the heterocycloalkyl group is a morpholine ring, pyrrolidine ring, piperazine ring, piperidine ring, tetrahydropyran ring, tetrahyropyridine, azetidine ring, tetrahydrofuran ring, indoline ring, pyrrolidinone ring, piperazinone ring, piperidinone ring, or indolinone ring.

As used herein, the term "heterocycloalkylalkyl", employed alone or in combination with other terms, refers to a group of formula heterocycloalkyl-alkyl-. In some embodiments, the alkyl portion has 1 to 4, 1 to 3, 1 to 2, or 1 carbon atom(s). In some embodiments, the alkyl portion is methylene. In some embodiments, the heterocycloalkyl portion has 3 to 10 ring members or 3 to 7 ring members. In some embodiments, the heterocycloalkyl group is monocyclic or bicyclic. In some embodiments, the heterocycloalkyl portion is monocyclic. In some embodiments, the heterocycloalkyl portion is a C$_{2-7}$ monocyclic heterocycloalkyl group.

As used herein, the term "aryl", employed alone or in combination with other terms, refers to a monocyclic or polycyclic (e.g., having 2 fused rings) aromatic hydrocarbon moiety, such as, but not limited to, phenyl, 1-naphthyl, 2-naphthyl, and the like. In some embodiments, aryl groups have from 6 to 10 carbon atoms or 6 carbon atoms. In some embodiments, the aryl group is a monocyclic or bicyclic group. In some embodiments, the aryl group is phenyl or naphthyl.

As used herein, the term "arylalkyl", employed alone or in combination with other terms, refers to a group of formula aryl-alkyl-. In some embodiments, the alkyl portion has 1 to 4, 1 to 3, 1 to 2, or 1 carbon atom(s). In some embodiments, the alkyl portion is methylene. In some embodiments, the aryl portion is phenyl. In some embodiments, the aryl group is a monocyclic or bicyclic group. In some embodiments, the arylalkyl group is benzyl.

As used herein, the term "heteroaryl", employed alone or in combination with other terms, refers to a monocyclic or polycyclic (e.g., having 2 or 3 fused rings) aromatic hydrocarbon moiety, having one or more heteroatom ring members independently selected from nitrogen, sulfur and oxygen. In some embodiments, the heteroaryl group is a monocyclic or bicyclic group having 1, 2, 3, or 4 heteroatoms independently selected from nitrogen, sulfur and oxygen. Example heteroaryl groups include, but are not limited to, pyridyl, pyrimidinyl, pyrazinyl, pyridazinyl, triazinyl, furyl, thienyl, imidazolyl, thiazolyl, indolyl, pyrryl, oxazolyl, benzofuryl, benzothienyl, benzthiazolyl, benzodioxolyl, isoxazolyl, pyrazolyl, triazolyl, tetrazolyl, indazolyl, 1,2,4-thiadiazolyl, isothiazolyl, purinyl, carbazolyl, benzimidazolyl, pyrrolyl, azolyl, quinolinyl, isoquinolinyl, benzisoxazolyl, imidazo[1,2-b]thiazolyl, pyridopyrazinyl, or the like. The carbon atoms or heteroatoms in the ring(s) of the heteroaryl group can be oxidized to form a carbonyl, an N-oxide, or a sulfonyl group (or other oxidized linkage) or a nitrogen atom can be quaternized, provided the aromatic nature of the ring is preserved. In some embodiments, the heteroaryl group has from 3 to 10 carbon atoms, from 3 to 8 carbon atoms, from 3 to 5 carbon atoms, from 1 to 5 carbon atoms, or from 5 to 10 carbon atoms. In some embodiments, the heteroaryl group contains 3 to 14, 4 to 12, 4 to 8, 9 to 10, or 5 to 6 ring-forming atoms. In some embodiments, the heteroaryl group has 1 to 4, 1 to 3, or 1 to 2 heteroatoms.

As used herein, the term "heteroarylalkyl", employed alone or in combination with other terms, refers to a group of formula heteroaryl-alkyl-. In some embodiments, the alkyl portion has 1 to 4, 1 to 3, 1 to 2, or 1 carbon atom(s). In some embodiments, the alkyl portion is methylene. In some embodiments, the heteroaryl portion is a monocyclic or bicyclic group having 1, 2, 3, or 4 heteroatoms independently selected from nitrogen, sulfur and oxygen. In some embodiments, the heteroaryl portion has 5 to 10 carbon atoms.

The compounds described herein can be asymmetric (e.g., having one or more stereocenters). All stereoisomers, such as enantiomers and diastereomers, are intended unless otherwise indicated. Compounds of the present invention that contain asymmetrically substituted carbon atoms can be isolated in optically active or racemic forms. Methods on how to prepare optically active forms from optically inactive starting materials are known in the art, such as by resolution of racemic mixtures or by stereoselective synthesis. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms.

Resolution of racemic mixtures of compounds can be carried out by any of numerous methods known in the art. An example method includes fractional recrystallizaion using a chiral resolving acid which is an optically active, salt-forming organic acid. Suitable resolving agents for fractional recrystallization methods are, for example, optically active acids, such as the D and L forms of tartaric acid, diacetyltartaric acid, dibenzoyltartaric acid, mandelic acid, malic acid, lactic acid or the various optically active camphorsulfonic acids. Other resolving agents suitable for fractional crystallization methods include stereoisomerically pure forms of methylbenzyl-amine (e.g., S and R forms, or diastereomerically pure forms), 2-phenylglycinol, norephedrine, ephedrine, N-methylephedrine, cyclohexylethylamine, 1,2-diaminocyclohexane, and the like. Resolution of racemic mixtures can also be carried out by elution on a column packed with an optically active resolving agent (e.g., dinitrobenzoylphenylglycine). Suitable elution solvent composition can be determined by one skilled in the art.

Compounds of the invention also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone—enol pairs, amide—imidic acid pairs, lactam—lactim pairs, enamine—imine pairs, and annular forms where a proton can occupy two or more positions of a heterocyclic system, for example, 1H- and 3H-imidazole, 1H-, 2H- and 4H-1,2,4-triazole, 1H- and 2H-isoindole, and 1H- and 2H-pyrazole. Tautomeric forms can be in equilibrium or sterically locked into one form by appropriate substitution.

Compounds of the invention also include all isotopes of atoms occurring in the intermediates or final compounds. Isotopes include those atoms having the same atomic number but different mass numbers. For example, isotopes of hydrogen include tritium and deuterium.

The term, "compound," as used herein is meant to include all stereoisomers, geometric isomers, tautomers, and isotopes of the structures depicted.

All compounds, and pharmaceutically acceptable salts thereof, can be found together with other substances such as water and solvents (e.g., in the form of hydrates and solvates) or can be isolated.

In some embodiments, the compounds of the invention, or salts thereof, are substantially isolated. By "substantially isolated" is meant that the compound is at least partially or substantially separated from the environment in which it was formed or detected. Partial separation can include, for example, a composition enriched in the compounds of the invention.

Substantial separation can include compositions containing at least about 50%, at least about 60%, at least about 70%, at least about 80%, at least about 90%, at least about 95%, at least about 97%, or at least about 99% by weight of the compounds of the invention, or salt thereof.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The present invention also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the non-toxic salts of the parent compound formed, for example, from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, alcohols (e.g., methanol, ethanol, iso-propanol, or butanol) or acetonitrile (ACN) are preferred. Lists of suitable salts are found in *Remington's Pharmaceutical Sciences*, 17th ed., Mack Publishing Company, Easton, Pa., 1985, p. 1418 and Berge et al., *Journal of Pharmaceutical Science*, 66, 2 (1977), each of which is incorporated herein by reference in its entirety.

Synthesis

Compounds of the invention, including salts thereof, can be prepared using known organic synthesis techniques and can be synthesized according to any of numerous possible synthetic routes.

The reactions for preparing compounds of the invention can be carried out in suitable solvents which can be readily selected by one of skill in the art of organic synthesis. Suitable solvents can be substantially nonreactive with the starting materials (reactants), the intermediates, or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected by the skilled artisan.

Preparation of compounds of the invention can involve the protection and deprotection of various chemical groups. The need for protection and deprotection, and the selection of appropriate protecting groups, can be readily determined by one skilled in the art. The chemistry of protecting groups can be found, for example, in T. W. Greene and P. G. M. Wuts, *Protective Groups in Organic Synthesis*, 3rd. Ed., Wiley & Sons, Inc., New York (1999), which is incorporated herein by reference in its entirety.

Reactions can be monitored according to any suitable method known in the art. For example, product formation can be monitored by spectroscopic means, such as nuclear magnetic resonance spectroscopy (e.g., $^1$H or $^{13}$C), infrared spectroscopy, spectrophotometry (e.g., UV-visible), or mass spectrometry, or by chromatography such as high performance liquid chromatography (HPLC) or thin layer chromatography.

The expressions, "ambient temperature," "room temperature," and "r.t.", as used herein, are understood in the art, and refer generally to a temperature, e.g. a reaction temperature, that is about the temperature of the room in which the reaction is carried out, for example, a temperature from about 20° C. to about 30° C.

Compounds of the invention can be prepared according to numerous preparatory routes known in the literature. Example synthetic methods for preparing compounds of the invention are provided in the Schemes below.

The following abbreviations are used throughout: potassium acetate (KOAc), trimethylsilyl (TMS), N-methylpyrrolidone (NMP), lithium diisopropylamide (LDA), lithium bis(trimethylsilyl)amide (LiHMDS), sodium bis(trimethylsilyl)amide (NaHMDS), N-chlorosuccinimide (NCS), tetrahydrofuran (THF), 2-(1H-7-azabenzotriazol-1-yl)-1,1,3,3-tetramethyluronoium hexafluorphosphate (HATU), 2-(1H-benzotriazole-1-yl)-1,1,3,3-tetramethyluronium hexafluorophosphate (HBTU), benzotriazole-1-yl-oxy-tris-(dimethylamino)-phosphonium hexafluorophosphate (BOP), 1-ethyl-3-(3-dimethylaminopropyl) carbodiimide (EDCI), N-hydroxybenzotriazole (HOBT), 1-hydroxy-7-azabenzotriazole (HOAT), 1,1'-carbonyldiimidazole (CDI), N-bromosuccinimide (NBS), N-iodosuccinimide (NIS), 2-trimethylsilylethyoxymethyl chloride (SEMC1), and diethyl azodicarboxylate (DEAD).

Compounds of formula 4 can be prepared by the methods outlined in Scheme 1. Halide 2 ($X^1$=Cl, Br, or I) can be coupled to compound 1, where M is a boronic acid, boronic ester or an appropriately substituted metal (e.g., M is B(OH)$_2$, Sn(Bu)$_3$, or ZnBr), under standard Suzuki conditions or standard Stille conditions (e.g., in the presence of a palladium catalyst, such as, but not limited to, Pd(dppf)Cl$_2$ and a phosphate or carbonate base) or standard Negishi conditions (e.g., in the presence of a palladium(0) catalyst, such as, but not limited to, tetrakis(triphenylphosphine) palladium(0)), to give compound 3. The following hydrogenation of compound 3 using a suitable catalyst, such as, but not limited to, palladium (0) on carbon can afford formula 4.

Scheme 1

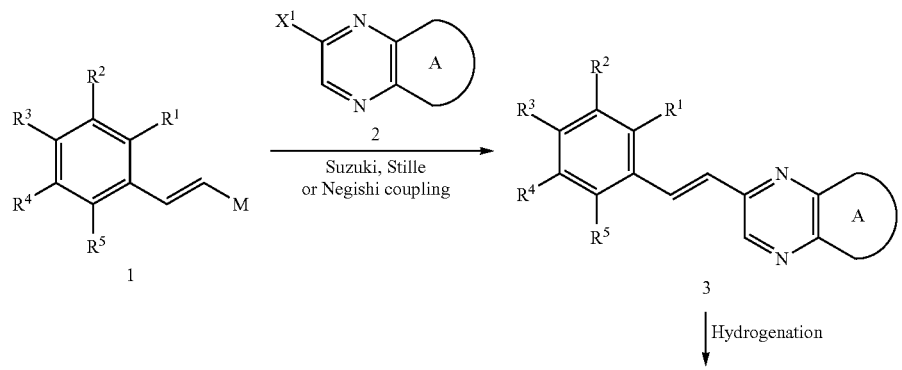

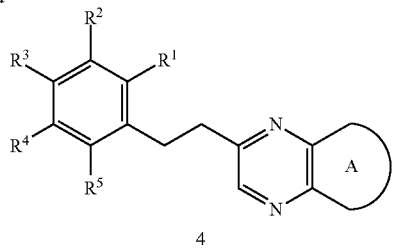

4

Compounds of formula 1 can be prepared by the methods outlined in Scheme 2. Vinyl bromide 6 can be prepared from aldehyde 5 using standard Wittig reaction conditions (e.g., in the presence of (bromomethyl)triphenylphosphonium bromide and a strong base such as, but not limited to, NaH, LiHMDS, KOtBu). Vinyl bromide 6 can be converted to the corresponding compound 1 under various conditions such as, but not limited to, bis(pinacolato)diboron/Pd(dppf)Cl$_2$/KOAc for M=boronic ester, nBuLi/Bu$_3$SnCl for M=Sn(Bu)$_3$, and nBuLi/ZnBr$_2$ for M=ZnBr.

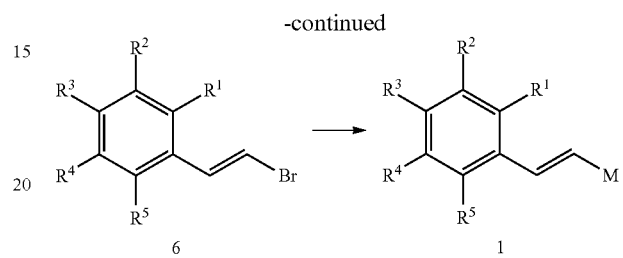

Alternatively, a series of compounds of formula 4 can be prepared by the methods outlined in Scheme 3. Appropriate aniline derivatives 7 can be converted to the corresponding halide 8 ($X^1$=Cl, Br, or I) under standard Sandmeyer reaction conditions (e.g., aniline 7 reacts with sodium nitrite and hydrogen chloride to form an aryl diazonium salt, which decomposes in the presence of copper (I) bromide or potassium iodide to form the desired aryl halide.). Halide 8 can be coupled with trimethylsilyacetylene under standard Sonogashira conditions (e.g., in the presence of a palladium(II) catalyst, such as, but not limited to, bis(triphenylphosphine)-palladium(II) dichloride, a Cu(I) salt, such as CuI or CuCN, and an amine, such as triethylamine). The removal of the trimethylsilyl group can generate compound 9. Compound 10 can be prepared by the coupling between compound 9 and halide 2 ($X^1$=Cl, Br, or I) under the standard Sonogashira conditions (e.g., in the presence of a palladium(II) catalyst, such as, but not limited to, bis(triphenylphosphine) palladium(II) dichloride, a Cu(I) salt, such as CuI or CuCN, and an amine, such as triethylamine). Hydrogenation of compound 10 using a suitable catalyst, such as, but not limited to, palladium (0) on carbon can afford formula 4.

Scheme 2

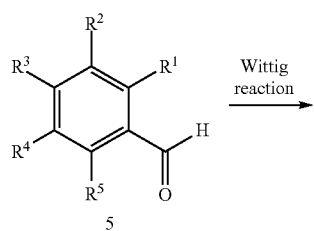

Scheme 3

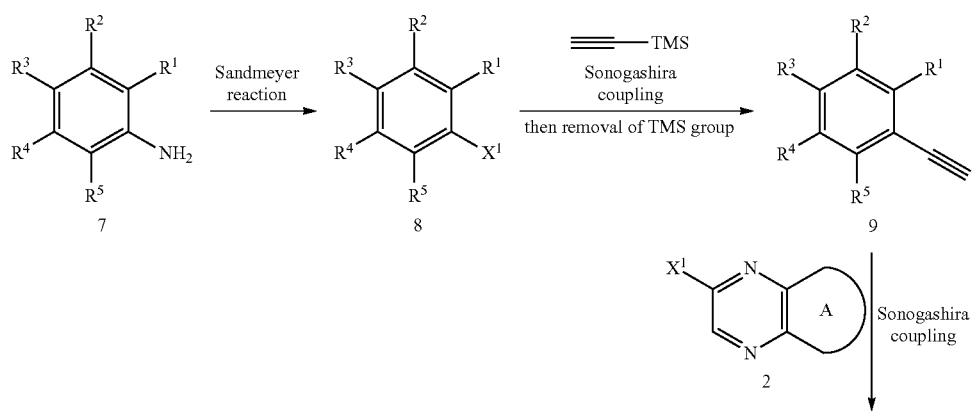

17

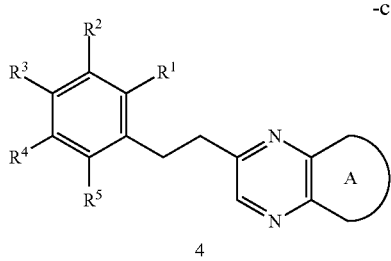
4

← Hydrogenation

18

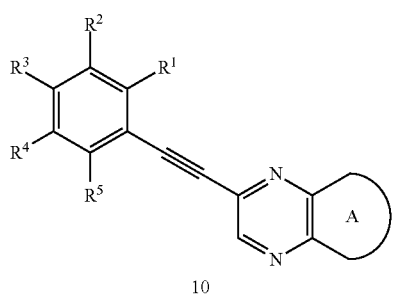
10

-continued

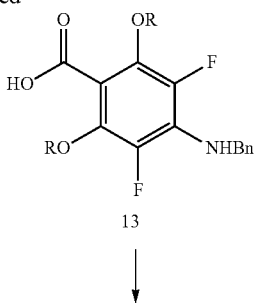
13

↓

A series of aniline derivatives 15 can be prepared according to the procedures described in Scheme 4 (see, e.g., WO 2011/093672). Displacement of fluorine in compound 11 with benzylamine provides the aniline 12 which can be converted to bis-ether by reacting with a suitable sodium alkoxide (NaOR where R is, e.g., methyl, alkyl). The following saponification can provide acid 13. Decarboxylation of benzoic acid 13, followed by hydrogenation using Pd(OH)$_2$/C can afford aniline 15.

Scheme 4

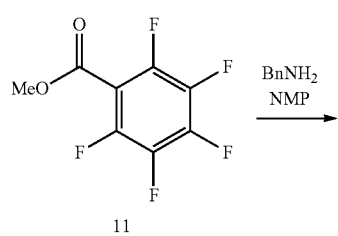
11

$\xrightarrow{\text{BnNH}_2}{\text{NMP}}$

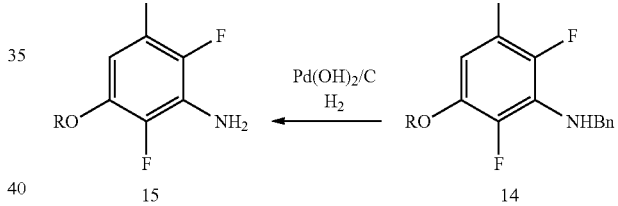
15      14

$\xleftarrow[\text{H}_2]{\text{Pd(OH)}_2/\text{C}}$

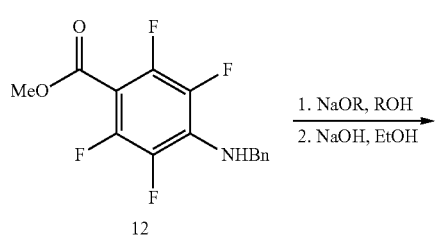
12

$\xrightarrow[\text{2. NaOH, EtOH}]{\text{1. NaOR, ROH}}$

A series of 5H-pyrrolo[2,3-b]pyrazine derivatives 18 can be prepared according to the procedures outlined in Scheme 5. The halide 17 ($X^1$=Cl, Br, or I) can be generated by the treatment of the compound 16, which is prepared using procedures as described in Scheme 1, with a strong base such as, but not limited to, LDA, LiHMDS, NaHMDS or butyllithium in an inert solvent such as THF, ether at low temperature to provide the metallated intermediate, and followed by the treatment with a halogen reagent such as, but not limited to, NCS, 1,2-dibromo-1,1,2,2-tetrachloroethane, or iodine. Halide 17 ($X^1$=Cl, Br, or I) can be coupled to $R^{6b}$-M, where M is a boronic acid, boronic ester or an appropriately substituted metal (e.g., M is B(OH)$_2$, Sn(Bu)$_3$, or ZnBr), under standard Suzuki conditions or standard Stille conditions (e.g., in the presence of a palladium catalyst, such as, but not limited to, Pd(dppf)Cl$_2$ and a phosphate or carbonate base) or standard Negishi conditions (e.g., in the presence of a palladium(0) catalyst, such as, but not limited to, tetrakis(triphenylphosphine)palladium(0)). Removal of the protecting group can afford compound 18.

Scheme 5

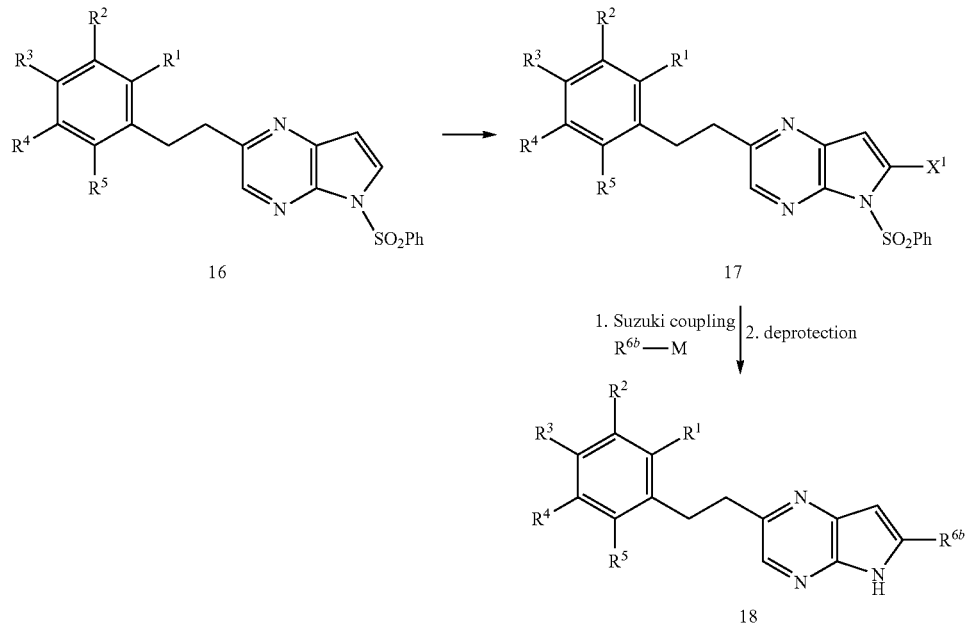

A series of amide derivatives 20 can be prepared according to the methods outlined in Scheme 6. The carboxylic acid 19 can be obtained by treating the compound 16 with a strong base such as, but not limited to, LDA, LiHMDS, NaHMDS, butyllithium in an inert solvent such as THF, ether at low temperature, and followed by addition of dry ice to the reaction mixture. Carboxylic acid 19 can be converted to the corresponding amide by coupling with an appropriate amine $NHR^{c1}R^{d1}$ in the presence of a suitable amide coupling reagent such as, but not limited to, HATU, HBTU, BOP, EDCI/HOBT, EDCI/HOAT, or CDI. Removal of the protecting group using a base such as, but not limited to, $K_2CO_3$ or KOtBu can provide amide 20.

Scheme 6

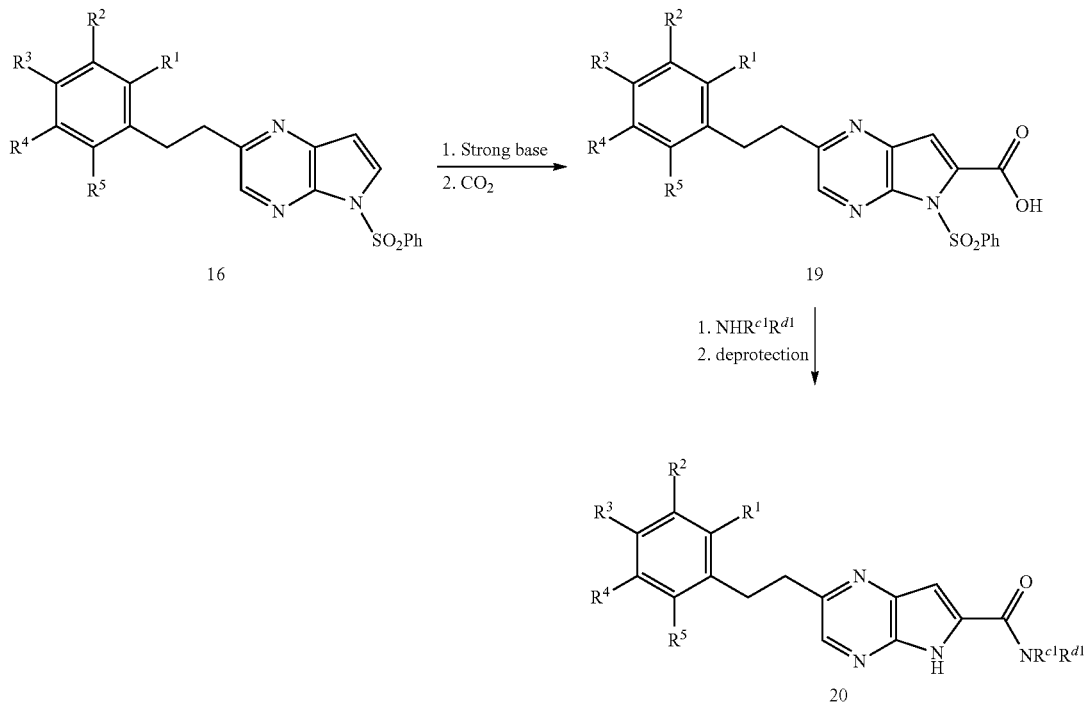

A series of 5H-pyrrolo[2,3-b]pyrazine derivatives 24 can be prepared according to the procedures outlined in Scheme 7. Halogenation of compound 18 using a halogenating reagent such as, but not limited to, NCS, NBS or NIS can give the corresponding halide 21 ($X^1$=Cl, Br, or I). Protection of halide 21 with suitable protection reagents such as, but not limited to, SEMCl under basic conditions can afford compound 22. Halide 22 ($X^1$=Cl, Br, or I) can be coupled to $R^{6a}$-M, where M is a boronic acid, boronic ester or an appropriately substituted metal (e.g., M is $B(OH)_2$, $Sn(Bu)_3$, or ZnBr), under standard Suzuki conditions or standard Stille conditions (e.g., in the presence of a palladium catalyst, such as, but not limited to, $Pd(dppf)Cl_2$ and a phosphate or carbonate base) or standard Negishi conditions (e.g., in the presence of a palladium(0) catalyst, such as, but not limited to, tetrakis(triphenylphosphine)palladium(0)), to give compound 23. Removal of the protecting group can afford compound 24.

Scheme 7

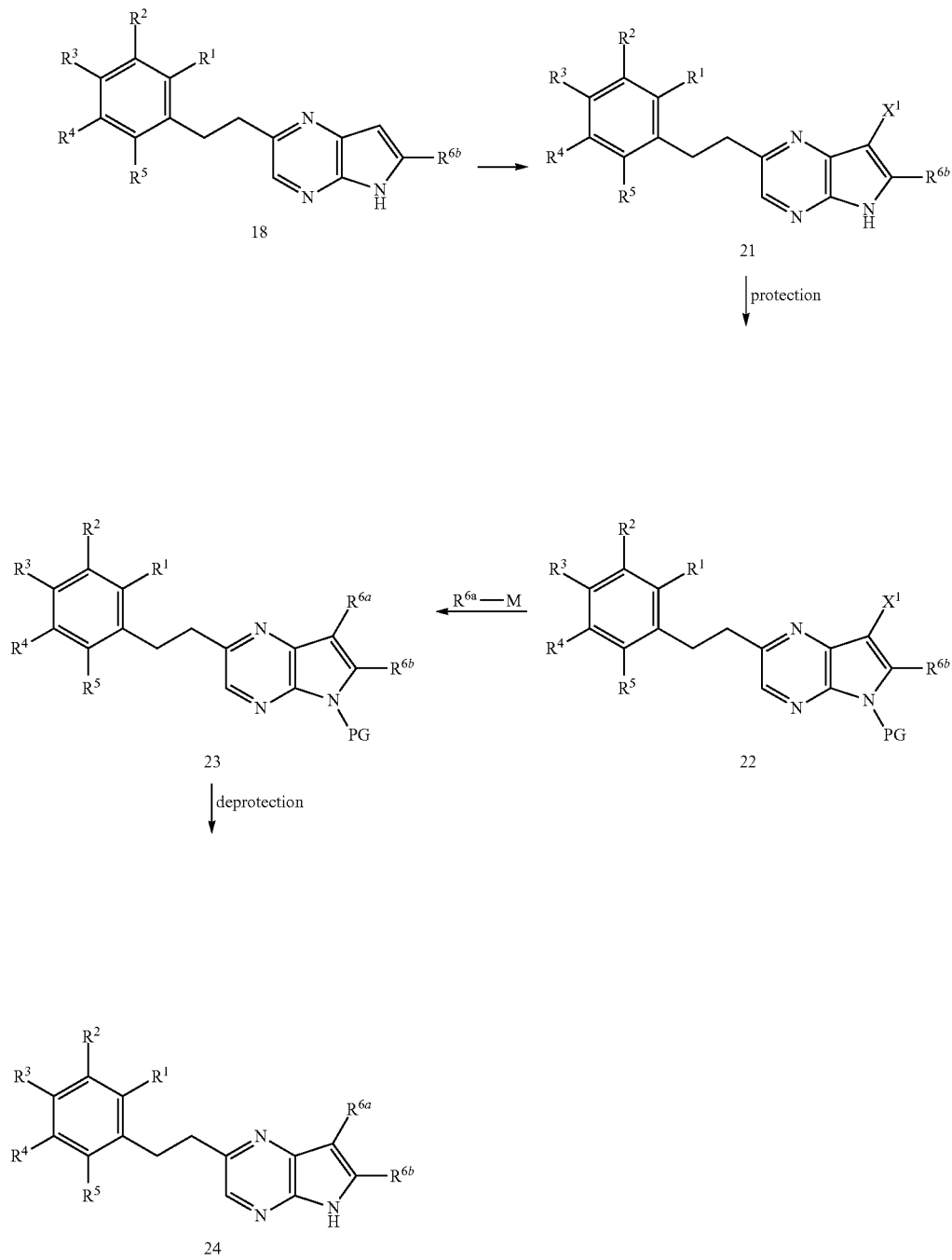

A series of 5H-pyrrolo[2,3-b]pyrazine derivatives 26 can be prepared according to the procedures outlined in Scheme 8. The carboxylic acid 25 can be obtained by treating the compound 22 with a strong base such as, but not limited to, LDA, or n-butyllithium in an inert solvent such as THF, ether at low temperature, and followed by addition of dry ice to the reaction mixture. Carboxylic acid 25 can be converted to the corresponding amide by coupling with an appropriate amine $NHR^{c1}R^{d1}$ in the presence of a suitable amide coupling reagent such as, but not limited to, HATU, HBTU, BOP, EDCI/HOBT, EDCI/HOAT, or CDI. Removal of the protecting group can provide compound 26.

Scheme 8

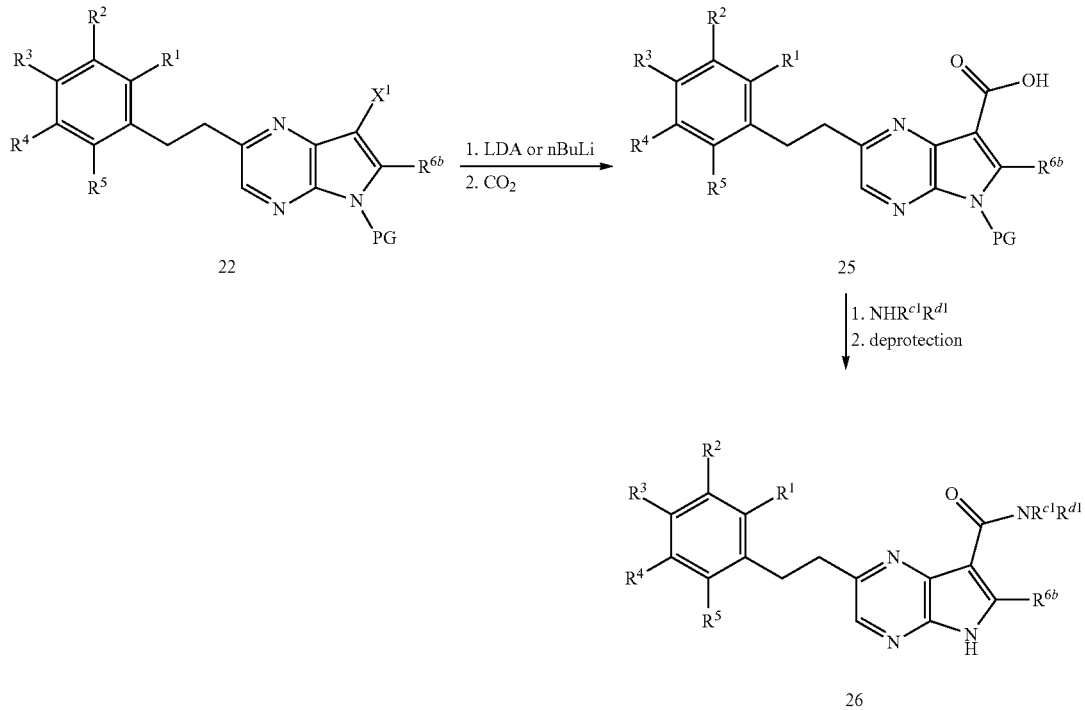

A series of 5H-pyrrolo[2,3-b]pyrazine derivatives 29 can be prepared according to the procedures outlined in Scheme 9. Compound 27 can be prepared using procedures as described in the Scheme 7. Chlorination of compound 27 using appropriate reagents such as, but not limited to, sulfuryl chloride can give the corresponding monochloride ($X^1$=H, $X^2$=Cl) or dichloride ($X^1$=$X^2$=Cl). Alternatively, treating compound 27 with appropriate reagents such as, but not limited to, Selectfluor® can yield the corresponding monofluoride ($X^1$=H, $X^2$=F) or difluoride ($X^1$=$X^2$=F). The protecting group of compound 28 can be removed to give 5H-pyrrolo[2,3-b]pyrazine derivatives 29.

Scheme 9

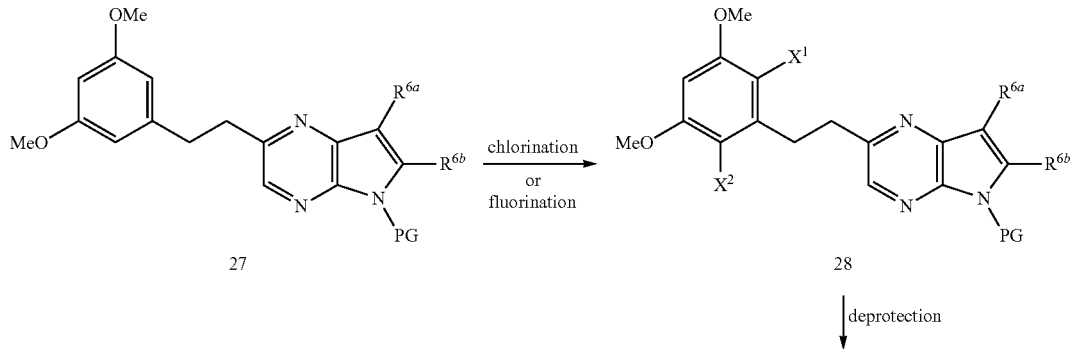

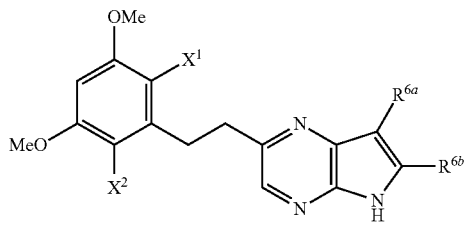

29

A series of 5H-pyrrolo[2,3-b]pyrazine derivatives 31 can be prepared according to the procedures outlined in Scheme 10. Monofluoride 30 can be prepared using procedures as described in the Scheme 9. Chlorination of compound 30 using appropriate reagents such as, but not limited to, sulfuryl chloride, followed by the deprotection can give 5H-pyrrolo[2,3-b]pyrazine derivatives 31.

Scheme 10

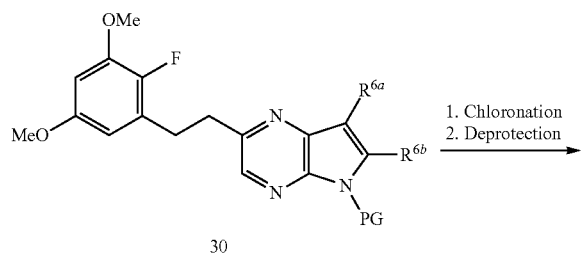

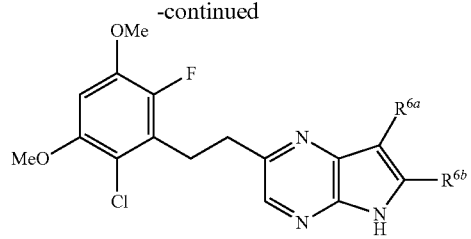

31

A series of thieno[3,2-b]pyrazine derivatives 34 can be prepared according to the procedures outlined in Scheme 11. Compound 32 can be generated using procedures as described in the Scheme 3. Halogenation of compound 32 using a halogenating reagent such as, but not limited to, NCS, NBS, NIS can give halide 33 ($X^1$=Cl, Br, or I). Halide 33 ($X^1$=Cl, Br, or I) can be coupled to $R^7$-M, where M is a boronic acid, boronic ester or an appropriately substituted metal (e.g., M is $B(OH)_2$, $Sn(Bu)_3$, or ZnBr), under standard Suzuki conditions or standard Stille conditions (e.g., in the presence of a palladium catalyst, such as, but not limited to, $Pd(dppf)Cl_2$ and a phosphate or carbonate base) or standard Negishi conditions (e.g., in the presence of a palladium(0) catalyst, such as, but not limited to, tetrakis(triphenylphosphine)palladium(0)), to give compound 34.

Scheme 11

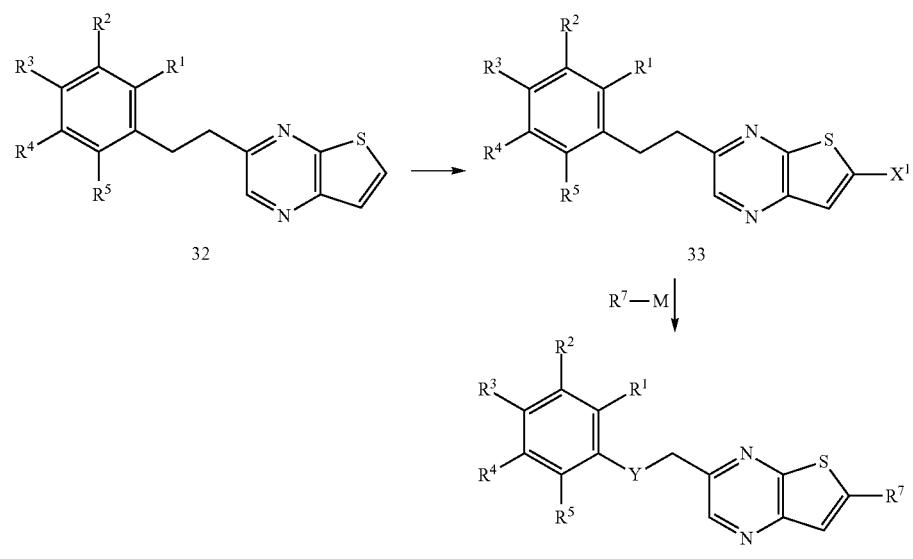

A series of 1H-pyrazolo[3,4-b]pyrazine derivatives 37 can be prepared according to the procedures outlined in Scheme 12. Compound 35 can be generated using procedures as described in the Scheme 3. Halogenation of compound 35 using a halogenating reagent such as NCS, NBS, or NIS can give halide 36 ($X^1$=Cl, Br, or I). Halide 36 ($X^1$=Cl, Br, or I) can be coupled to $R^8$-M, where M is a boronic acid, boronic ester or an appropriately substituted metal (e.g., M is $B(OH)_2$, $Sn(Bu)_3$, or ZnBr), under standard Suzuki conditions or standard Stille conditions (e.g., in the presence of a palladium catalyst, such as, but not limited to, $Pd(dppf)Cl_2$ and a phosphate or carbonate base) or standard Negishi conditions (e.g., in the presence of a palladium(0) catalyst, such as, but not limited to, tetrakis(triphenylphosphine)palladium(0)), to give compounds of formula 37.

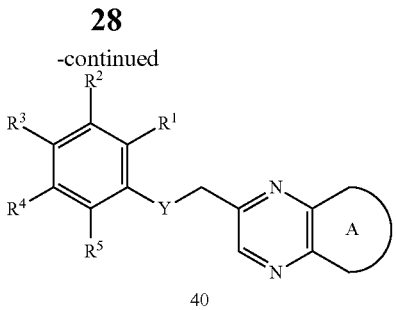

Compounds of formula 43 can be prepared according to the procedures outlined in Scheme 14. The treatment of compound 41 (X=O or S) with a strong base such as, but not limited to, NaH, LiHMDS, KOtBu, followed by the addition of compound 42 (LG=leaving group, such as, but not limited to, Cl, Br, or OMs) can afford compounds 43.

Scheme 12

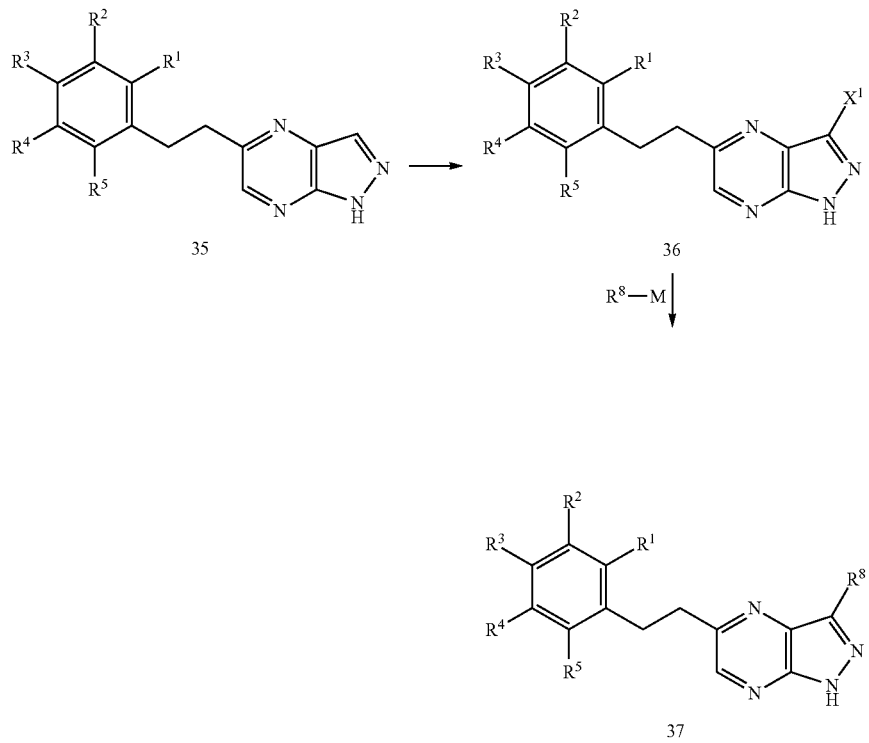

Compounds of formula 40 can be prepared according to the procedures outlined in Scheme 13. Compound 38 (Y=O or S) can be coupled to alcohol 39 under standard Mitsunobu conditions (e.g., in the presence of $PPh_3$ and DEAD) to afford compound 40 (Y=O or S).

Scheme 13

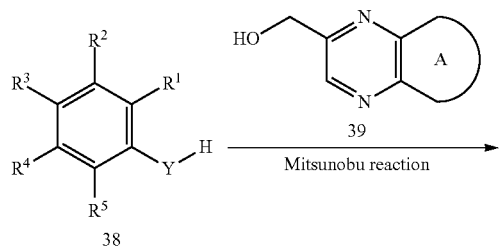

Scheme 14

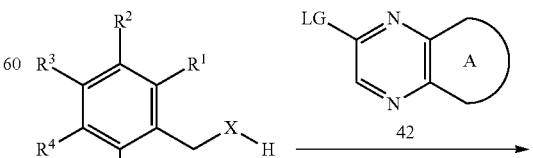

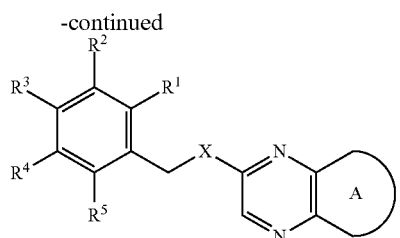

Methods of Use

Compounds of the invention can inhibit activity of one or more FGFR enzymes. For example, the compounds of the invention can be used to inhibit activity of an FGFR enzyme in a cell or in an individual or patient in need of inhibition of the enzyme by administering an inhibiting amount of a compound of the invention to the cell, individual, or patient.

In some embodiments, the compounds of the invention are inhibitors of one or more of FGFR1, FGFR2, FGFR3, and FGFR4. In some embodiments, the compounds of the invention inhibit each of FGFR1, FGFR2, and FGFR3. In some embodiments, the compounds of the invention are selective for one or more FGFR enzymes. In some embodiments, the compounds of the invention are selective for one or more FGFR enzymes over VEGFR2. In some embodiments, the selectivity is 2-fold or more, 3-fold or more, 5-fold or more, 10-fold or more, 50-fold or more, or 100-fold or more.

As FGFR inhibitors, the compounds of the invention are useful in the treatment of various diseases associated with abnormal expression or activity of FGFR enzymes or FGFR ligands.

For example, the compounds of the invention are useful in the treatment of cancer. Example cancers include bladder cancer, breast cancer, cervical cancer, colorectal cancer, endometrial cancer, gastric cancer, head and neck cancer, kidney cancer, liver cancer, lung cancer (e.g., adenocarcinoma, small cell lung cancer and non-small cell lung carcinomas), ovarian cancer, prostate cancer, esophageal cancer, gall bladder cancer, pancreatic cancer (e.g. exocrine pancreatic carcinoma), stomach cancer, thyroid cancer, skin cancer (e.g., squamous cell carcinoma).

Further example cancers include hematopoietic malignancies such as leukemia, multiple myeloma, chronic lymphocytic lymphoma, adult T cell leukemia, B-cell lymphoma, acute myelogenous leukemia, Hodgkin's or non-Hodgkin's lymphoma, myeloproliferative neoplasms (e.g., polycythemia vera, essential thrombocythemia, and primary myelofibrosis), Waldenstrom's Macroglubulinemia, hairy cell lymphoma, and Burkett's lymphoma.

Other cancers treatable with the compounds of the invention include glioblastoma, melanoma, and rhabdosarcoma.

In addition to oncogenic neoplasms, the compounds of the invention can be useful in the treatment of skeletal and chondrocyte disorders including, but not limited to, achrondroplasia, hypochondroplasia, dwarfism, thanatophoric dysplasia (TD) (clinical forms TD I and TD II), Apert syndrome, Crouzon syndrome, Jackson-Weiss syndrome, Beare-Stevenson cutis gyrate syndrome, Pfeiffer syndrome, and craniosynostosis syndromes.

The compounds of the invention may further be useful in the treatment of fibrotic diseases, such as where a disease symptom or disorder is characterized by fibrosis. Example fibrotic diseases include liver cirrhosis, glomerulonephritis, pulmonary fibrosis, systemic fibrosis, rheumatoid arthritis, and wound healing.

As used herein, the term "cell" is meant to refer to a cell that is in vitro, ex vivo or in vivo. In some embodiments, an ex vivo cell can be part of a tissue sample excised from an organism such as a mammal. In some embodiments, an in vitro cell can be a cell in a cell culture. In some embodiments, an in vivo cell is a cell living in an organism such as a mammal.

As used herein, the term "contacting" refers to the bringing together of indicated moieties in an in vitro system or an in vivo system. For example, "contacting" the FGFR enzyme with a compound of the invention includes the administration of a compound of the present invention to an individual or patient, such as a human, having FGFR, as well as, for example, introducing a compound of the invention into a sample containing a cellular or purified preparation containing the FGFR enzyme.

As used herein, the term "individual" or "patient," used interchangeably, refers to any animal, including mammals, preferably mice, rats, other rodents, rabbits, dogs, cats, swine, cattle, sheep, horses, or primates, and most preferably humans.

As used herein, the phrase "therapeutically effective amount" refers to the amount of active compound or pharmaceutical agent that elicits the biological or medicinal response in a tissue, system, animal, individual or human that is being sought by a researcher, veterinarian, medical doctor or other clinician.

As used herein the term "treating" or "treatment" refers to 1) preventing the disease; for example, preventing a disease, condition or disorder in an individual who may be predisposed to the disease, condition or disorder but does not yet experience or display the pathology or symptomatology of the disease; 2) inhibiting the disease; for example, inhibiting a disease, condition or disorder in an individual who is experiencing or displaying the pathology or symptomatology of the disease, condition or disorder (i.e., arresting further development of the pathology and/or symptomatology), or 3) ameliorating the disease; for example, ameliorating a disease, condition or disorder in an individual who is experiencing or displaying the pathology or symptomatology of the disease, condition or disorder (i.e., reversing the pathology and/or symptomatology).

Combination Therapy

One or more additional pharmaceutical agents or treatment methods such as, for example, anti-viral agents, chemotherapeutics or other anti-cancer agents, immune enhancers, immunosuppressants, radiation, anti-tumor and anti-viral vaccines, cytokine therapy (e.g., IL2, GM-CSF, etc.), and/or tyrosine kinase inhibitors can be used in combination with the compounds of the present invention for treatment of FGFR-associated diseases, disorders or conditions. The agents can be combined with the present compounds in a single dosage form, or the agents can be administered simultaneously or sequentially as separate dosage forms.

Suitable antiviral agents contemplated for use in combination with the compounds of the present invention can comprise nucleoside and nucleotide reverse transcriptase inhibitors (NRTIs), non-nucleoside reverse transcriptase inhibitors (NNRTIs), protease inhibitors and other antiviral drugs.

Example suitable NRTIs include zidovudine (AZT); didanosine (ddI); zalcitabine (ddC); stavudine (d4T); lamivudine (3TC); abacavir (1592U89); adefovir dipivoxil [bis (POM)-PMEA]; lobucavir (BMS-180194); BCH-10652;

emitricitabine [(−)-FTC]; beta-L-FD4 (also called beta-L-D4C and named beta-L-2', 3'-dicleoxy-5-fluoro-cytidene); DAPD, ((−)-beta-D-2,6,-diamino-purine dioxolane); and lodenosine (FddA). Typical suitable NNRTIs include nevirapine (BI-RG-587); delaviradine (BHAP, U-90152); efavirenz (DMP-266); PNU-142721; AG-1549; MKC-442 (1-(ethoxy-methyl)-5-(1-methylethyl)-6-(phenylmethyl)-(2,4 (1H,3H)-pyrimidinedione); and (+)-calanolide A (NSC-675451) and B. Typical suitable protease inhibitors include saquinavir (Ro 31-8959); ritonavir (ABT-538); indinavir (MK-639); nelfnavir (AG-1343); amprenavir (141W94); lasinavir (BMS-234475); DMP-450; BMS-2322623; ABT-378; and AG-1 549. Other antiviral agents include hydroxyurea, ribavirin, IL-2, IL-12, pentafuside and Yissum Project No. 11607.

Suitable chemotherapeutic or other anti-cancer agents include, for example, alkylating agents (including, without limitation, nitrogen mustards, ethylenimine derivatives, alkyl sulfonates, nitrosoureas and triazenes) such as uracil mustard, chlormethine, cyclophosphamide (Cytoxan™), ifosfamide, melphalan, chlorambucil, pipobroman, triethyl-ene-melamine, triethylenethiophosphoramine, busulfan, carmustine, lomustine, streptozocin, dacarbazine, and temozolomide.

Other suitable agents for use in combination with the compounds of the present invention include: dacarbazine (DTIC), optionally, along with other chemotherapy drugs such as carmustine (BCNU) and cisplatin; the "Dartmouth regimen," which consists of DTIC, BCNU, cisplatin and tamoxifen; a combination of cisplatin, vinblastine, and DTIC; or temozolomide. Compounds according to the invention may also be combined with immunotherapy drugs, including cytokines such as interferon alpha, interleukin 2, and tumor necrosis factor (TNF) in.

Suitable chemotherapeutic or other anti-cancer agents include, for example, antimetabolites (including, without limitation, folic acid antagonists, pyrimidine analogs, purine analogs and adenosine deaminase inhibitors) such as methotrexate, 5-fluorouracil, floxuridine, cytarabine, 6-mercaptopurine, 6-thioguanine, fludarabine phosphate, pentostatine, and gemcitabine.

Suitable chemotherapeutic or other anti-cancer agents further include, for example, certain natural products and their derivatives (for example, vinca alkaloids, antitumor antibiotics, enzymes, lymphokines and epipodophyllotoxins) such as vinblastine, vincristine, vindesine, bleomycin, dactinomycin, daunorubicin, doxorubicin, epirubicin, idarubicin, ara-C, paclitaxel (TAXOL™), mithramycin, deoxycoformycin, mitomycin-C, L-asparaginase, interferons (especially IFN-a), etoposide, and teniposide.

Other cytotoxic agents include navelbene, CPT-11, anastrazole, letrazole, capecitabine, reloxafine, cyclophosphamide, ifosamide, and droloxafine.

Also suitable are cytotoxic agents such as epidophyllotoxin; an antineoplastic enzyme; a topoisomerase inhibitor; procarbazine; mitoxantrone; platinum coordination complexes such as cis-platin and carboplatin; biological response modifiers; growth inhibitors; antihormonal therapeutic agents; leucovorin; tegafur; and haematopoietic growth factors.

Other anti-cancer agent(s) include antibody therapeutics such as trastuzumab (Herceptin), antibodies to costimulatory molecules such as CTLA-4, 4-1BB and PD-1, or antibodies to cytokines (IL-10, TGF-β, etc.).

Other anti-cancer agents also include those that block immune cell migration such as antagonists to chemokine receptors, including CCR2 and CCR4.

Other anti-cancer agents also include those that augment the immune system such as adjuvants or adoptive T cell transfer.

Anti-cancer vaccines include dendritic cells, synthetic peptides, DNA vaccines and recombinant viruses.

Methods for the safe and effective administration of most of these chemotherapeutic agents are known to those skilled in the art. In addition, their administration is described in the standard literature. For example, the administration of many of the chemotherapeutic agents is described in the "Physicians' Desk Reference" (PDR, e.g., 1996 edition, Medical Economics Company, Montvale, N.J.), the disclosure of which is incorporated herein by reference as if set forth in its entirety.

Pharmaceutical Formulations and Dosage Forms

When employed as pharmaceuticals, the compounds of the invention can be administered in the form of pharmaceutical compositions which refers to a combination of a compound of the invention, or its pharmaceutically acceptable salt, and at least one pharmaceutically acceptable carrier. These compositions can be prepared in a manner well known in the pharmaceutical art, and can be administered by a variety of routes, depending upon whether local or systemic treatment is desired and upon the area to be treated. Administration may be topical (including ophthalmic and to mucous membranes including intranasal, vaginal and rectal delivery), pulmonary (e.g., by inhalation or insufflation of powders or aerosols, including by nebulizer; intratracheal, intranasal, epidermal and transdermal), ocular, oral or parenteral. Methods for ocular delivery can include topical administration (eye drops), subconjunctival, periocular or intravitreal injection or introduction by balloon catheter or ophthalmic inserts surgically placed in the conjunctival sac. Parenteral administration includes intravenous, intraarterial, subcutaneous, intraperitoneal, or intramuscular injection or infusion; or intracranial, e.g., intrathecal or intraventricular, administration. Parenteral administration can be in the form of a single bolus dose, or may be, for example, by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

This invention also includes pharmaceutical compositions which contain, as the active ingredient, one or more of the compounds of the invention above in combination with one or more pharmaceutically acceptable carriers. In making the compositions of the invention, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g. about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

The compositions can be formulated in a unit dosage form, each dosage containing from about 5 to about 100 mg, more usually about 10 to about 30 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

The active compound can be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient is mixed with a pharmaceutical excipient to form a solid pre-formulation composition containing a homogeneous mixture of a compound of the present invention. When referring to these pre-formulation compositions as homogeneous, the active ingredient is typically dispersed evenly throughout the composition so that the composition can be readily subdivided into equally effective unit dosage forms such as tablets, pills and capsules. This solid pre-formulation is then subdivided into unit dosage forms of the type described above containing from, for example, 0.1 to about 500 mg of the active ingredient of the present invention.

The tablets or pills of the present invention can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compounds and compositions of the present invention can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions in can be nebulized by use of inert gases. Nebulized solutions may be breathed directly from the nebulizing device or the nebulizing device can be attached to a face masks tent, or intermittent positive pressure breathing machine. Solution, suspension, or powder compositions can be administered orally or nasally from devices which deliver the formulation in an appropriate manner.

The amount of compound or composition administered to a patient will vary depending upon what is being administered, the purpose of the administration, such as prophylaxis or therapy, the state of the patient, the manner of administration, and the like. In therapeutic applications, compositions can be administered to a patient already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient, and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers, or stabilizers will result in the formation of pharmaceutical salts.

The therapeutic dosage of the compounds of the present invention can vary according to, for example, the particular use for which the treatment is made, the manner of administration of the compound, the health and condition of the patient, and the judgment of the prescribing physician. The proportion or concentration of a compound of the invention in a pharmaceutical composition can vary depending upon a number of factors including dosage, chemical characteristics (e.g., hydrophobicity), and the route of administration. For example, the compounds of the invention can be provided in an aqueous physiological buffer solution containing about 0.1 to about 10% w/v of the compound for parenteral administration. Some typical dose ranges are from about 1 µg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

The compounds of the invention can also be formulated in combination with one or more additional active ingredients which can include any pharmaceutical agent such as antiviral agents, vaccines, antibodies, immune enhancers, immune suppressants, anti-inflammatory agents and the like.

Labeled Compounds and Assay Methods

Another aspect of the present invention relates to fluorescent dye, spin label, heavy metal or radio-labeled compounds of the invention that would be useful not only in imaging but also in assays, both in vitro and in vivo, for localizing and quantitating the FGFR enzyme in tissue samples, including human, and for identifying FGFR enzyme ligands by inhibition binding of a labeled compound. Accordingly, the present invention includes FGFR enzyme assays that contain such labeled compounds.

The present invention further includes isotopically-labeled compounds of the invention. An "isotopically" or "radio-labeled" compound is a compound of the invention where one or more atoms are replaced or substituted by an atom having an atomic mass or mass number different from the atomic mass or mass number typically found in nature (i.e., naturally occurring). Suitable radionuclides that may be incorporated in compounds of the present invention include but are not limited to $^2$H (also written as D for deuterium), $^3$H (also written as T for tritium), $^{11}$C, $^{13}$C, $^{14}$C, $^{13}$N, $^{15}$N, $^{15}$O, $^{17}$O, $^{18}$O, $^{18}$F, $^{35}$S, $^{36}$Cl, $^{82}$Br, $^{75}$Br, $^{76}$Br, $^{77}$Br, $^{123}$I, $^{124}$I, $^{125}$I and $^{131}$I. The radionuclide that is incorporated in the instant radio-labeled compounds will depend on the specific application of that radio-labeled compound. For example, for in vitro FGFR enzyme labeling and competition assays, compounds that incorporate $^3$H, $^{14}$C, $^{82}$Br, $^{125}$I, $^{131}$I, or $^{35}$S will generally be most useful. For radio-imaging applications $^{11}$C, $^{18}$F, $^{125}$I, $^{123}$I, $^{124}$I, $^{131}$I, $^{75}$Br, $^{76}$Br or $^{77}$Br will generally be most useful.

It is understood that a "radio-labeled" or "labeled compound" is a compound that has incorporated at least one radionuclide. In some embodiments the radionuclide is selected from the group consisting of $^3$H, $^{14}$C, $^{125}$I, $^{35}$S and $^{82}$Br.

Synthetic methods for incorporating radio-isotopes into organic compounds are applicable to compounds of the invention and are well known in the art.

A radio-labeled compound of the invention can be used in a screening assay to identify/evaluate compounds. In general terms, a newly synthesized or identified compound (i.e., test compound) can be evaluated for its ability to reduce binding of the radio-labeled compound of the invention to the FGFR enzyme. Accordingly, the ability of a test compound to compete with the radio-labeled compound for binding to the FGFR enzyme directly correlates to its binding affinity.

Kits

The present invention also includes pharmaceutical kits useful, for example, in the treatment or prevention of FGFR-associated diseases or disorders, obesity, diabetes and other diseases referred to herein which include one or more containers containing a pharmaceutical composition comprising a therapeutically effective amount of a compound of the invention. Such kits can further include, if desired, one or more of various conventional pharmaceutical kit components, such as, for example, containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, can also be included in the kit.

The invention will be described in greater detail by way of specific examples. The following examples are offered for illustrative purposes, and are not intended to limit the invention in any manner. Those of skill in the art will readily recognize a variety of non-critical parameters which can be changed or modified to yield essentially the same results. The compounds of the Examples were found to be inhibitors of one or more FGFR's as described below.

EXAMPLES

Experimental procedures for compounds of the invention are provided below. Preparatory LC-MS purifications of some of the compounds prepared were performed on Waters mass directed fractionation systems. The basic equipment setup, protocols, and control software for the operation of these systems have been described in detail in the literature. See e.g. "Two-Pump At Column Dilution Configuration for Preparative LC-MS", K. Blom, *J. Combi. Chem.*, 4, 295 (2002); "Optimizing Preparative LC-MS Configurations and Methods for Parallel Synthesis Purification", K. Blom, R. Sparks, J. Doughty, G. Everlof, T. Haque, A. Combs, *J. Combi. Chem.*, 5, 670 (2003); and "Preparative LC-MS Purification: Improved Compound Specific Method Optimization", K. Blom, B. Glass, R. Sparks, A. Combs, *J. Combi. Chem.*, 6, 874-883 (2004). The compounds separated were typically subjected to analytical liquid chromatography mass spectrometry (LCMS) for purity check under the following conditions: Instrument; Agilent 1100 series, LC/MSD, Column: Waters Sunfire™ $C_{18}$ 5 µm, 2.1×5.0 mm, Buffers: mobile phase A: 0.025% TFA in water and mobile phase B: 0.025% TFA in acetonitrile; gradient 2% to 80% of B in 3 minutes with flow rate 1.5 mL/minute.

Some of the compounds prepared were also separated on a preparative scale by reverse-phase high performance liquid chromatography (RP-HPLC) with MS detector or flash chromatography (silica gel) as indicated in the Examples. Typical preparative reverse-phase high performance liquid chromatography (RP-HPLC) column conditions are as follows:

pH=2 purifications: Waters Sunfire™ $C_{18}$ 5 µm, 19×100 mm column, eluting with mobile phase A: 0.1% TFA (trifluoroacetic acid) in water and mobile phase B: 0.1% TFA in acetonitrile; the flow rate was 30 mL/minute, the separating gradient was optimized for each compound using the Compound Specific Method Optimization protocol as described in the literature [see "Preparative LCMS Purification: Improved Compound Specific Method Optimization", K. Blom, B. Glass, R. Sparks, A. Combs, *J. Comb. Chem.*, 6, 874-883 (2004)]. Typically, the flow rate used with the 30×100 mm column was 60 mL/minute.

pH=10 purifications: Waters XBridge $C_{18}$ 5 µm, 19×100 mm column, eluting with mobile phase A: 0.15% NH$_4$OH in water and mobile phase B: 0.15% NH$_4$OH in acetonitrile; the flow rate was 30 mL/minute, the separating gradient was optimized for each compound using the Compound Specific Method Optimization protocol as described in the literature [See "Preparative LCMS Purification: Improved Compound Specific Method Optimization", K. Blom, B. Glass, R. Sparks, A. Combs, *J. Comb. Chem.*, 6, 874-883 (2004)]. Typically, the flow rate used with 30×100 mm column was 60 mL/minute.

Example 1

2-[2-(3,5-dimethoxyphenyl)ethyl]-6-[4-(4-methyl-piperazin-1-yl)phenyl]-5H-pyrrolo[2,3-b]pyrazine

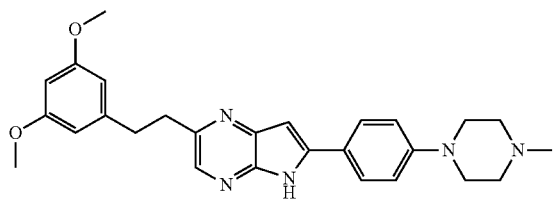 [SMILES: COc1cc(CCc2cnc3[nH]c(-c4ccc(N5CCN(C)CC5)cc4)cc3n2)cc(OC)c1]

Step 1. 2-bromo-5-(phenylsulfonyl)-5H-pyrrolo[2,3-b]pyrazine

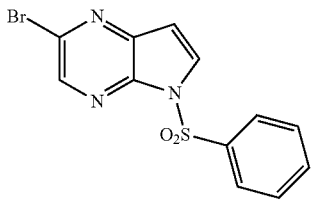 [SMILES: O=S(=O)(c1ccccc1)n1ccc2nc(Br)cnc21]

To a stirred solution of 2-bromo-5H-pyrrolo[2,3-b]pyrazine (from Ark Pharm, cat#AK-23813, 1.00 g, 5.05 mmol) in tetrahydrofuran (10 mL), NaH (60% w/w dispersion form in mineral oil, 283 mg, 7.07 mmol) was added at 0° C. After 0.5 hour, benzenesulfonyl chloride (644 µL, 5.05 mmol) was added dropwise. After another 1 hour, the reaction mixture was quenched with saturated aqueous $NH_4Cl$ and extracted with methylene chloride. The combined organic layers were dried over $MgSO_4$, filtered, and concentrated. The residue was purified on silica gel (eluting with 0 to 50% ethyl acetate (EtOAc) in hexanes) to give the desired product (1.50 g, 88%). LCMS calculated for $C_{12}H_9BrN_3O_2S$ $(M+H)^+$: m/z=339.2. Found: 339.2.

Step 2. 2-[(E)-2-(3,5-dimethoxyphenyl)vinyl]-5-(phenylsulfonyl)-5H-pyrrolo[2,3-b]pyrazine

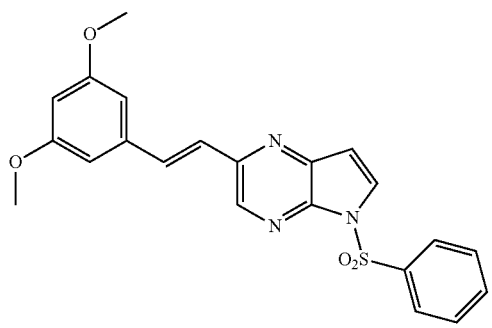 [SMILES: COc1cc(/C=C/c2cnc3c(ccn3S(=O)(=O)c3ccccc3)n2)cc(OC)c1]

A stirred mixture of 2-bromo-5-(phenylsulfonyl)-5H-pyrrolo[2,3-b]pyrazine (929 mg, 2.75 mmol), 2-[(E)-2-(3,5-dimethoxyphenyl)vinyl]-4,4,5,5-tetramethyl-1,3,2-dioxaborolane (from Aldrich, cat#676160, 838 mg, 2.89 mmol), [1,1'-bis(diphenylphosphino)ferrocene]-dichloropalladium (II), complex with dichloromethane (1:1) (140 mg, 0.171 mmol), and potassium phosphate (1.20 g, 5.65 mmol) in 1,4-dioxane (20 mL)/water (9.6 mL) was heated at 88° C. After 1 hour, the reaction mixture was quenched with saturated aq. $NH_4Cl$ and extracted with methylene chloride. The combined organic layers were dried over $MgSO_4$, filtered, and then concentrated. The residue was purified on silica gel (eluting with 0 to 50% EtOAc in hexanes) to give the desired product (1.10 g, 95%). LCMS calculated for $C_{22}H_{20}N_3O_4S$ $(M+H)^+$: m/z=422.2. Found: 422.2.

Step 3. 2-[2-(3,5-dimethoxyphenyl)ethyl]-5-(phenylsulfonyl)-5H-pyrrolo[2,3-b]pyrazine

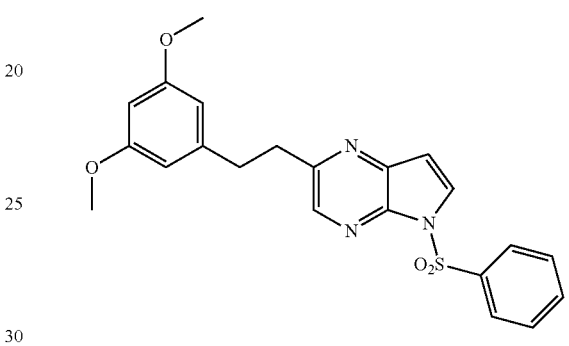

To a stirred solution of 2-[(E)-2-(3,5-dimethoxyphenyl)vinyl]-5-(phenylsulfonyl)-5H-pyrrolo[2,3-b]pyrazine (1.10 g, 2.61 mmol) in tetrahydrofuran (8 mL)/methanol (10 mL), was added Pd/C (10% w/w, 580 mg, 0.545 mmol). The resulted mixture was stirred under $H_2$ (45 psi) at ambient temperature. After 24 hours, the palladium catalyst was removed by filtration, and the filtrate was concentrated under reduced pressure to afford the desired product (1.05 g, 90%), which was used directly in the next step without further purification. LCMS calculated for $C_{22}H_{22}N_3O_4S$ $(M+H)^+$: m/z=424.2. Found: 424.2; $^1$H NMR (400 MHz, $CDCl_3$): δ 8.18-8.15 (m, 3H), 7.97 (d, J=4.4 Hz, 1H), 7.63-7.59 (m, 1H), 7.53-7.48 (m, 2H), 6.80 (d, J=4.4 Hz, 1H), 6.34 (d, J=2.0 Hz, 2H), 6.30 (t, J=2.4 Hz, 1H), 3.73 (s, 6H), 3.19-3.15 (m, 2H), 3.02-2.98 (m, 2H) ppm.

Step 4. 6-bromo-2-[2-(3,5-dimethoxyphenyl)ethyl]-5-(phenylsulfonyl)-5H-pyrrolo[2,3-b]pyrazine

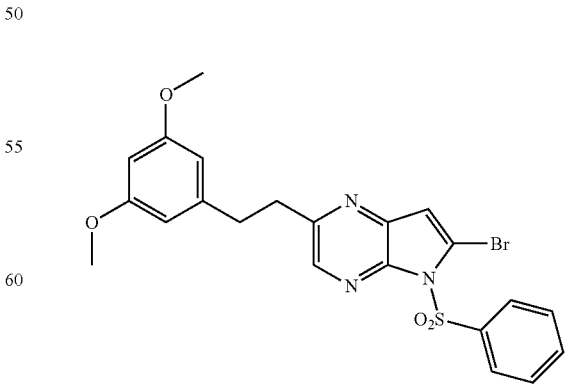

To a stirred solution of N,N-diisopropylamine (0.610 mL, 4.25 mmol) in tetrahydrofuran (2.0 mL) at −78° C., n-butyllithium (2.5M in hexanes, 1.70 mL, 4.25 mmol) was added dropwise. After the white precipitate formed, the mixture was warmed up to 0° C. for 10 minutes. The resulting resulted solution was added to a stirred solution of 2-[2-(3,5-dimethoxyphenyl)ethyl]-5-(phenylsulfonyl)-5H-pyrrolo[2,3-b]pyrazine (1.30 g, 3.07 mmol) in tetrahydrofuran (10 mL) at −78° C. After 30 min, a solution of 1,2-dibromo-1,1,2,2-tetrachloroethane (1.10 g, 3.38 mmol) in tetrahydrofuran (6 mL) was added dropwise. After another 1 hour, the reaction mixture was quenched with saturated aq. NH$_4$Cl, then extracted with methylene chloride. The combined organic layers were dried over MgSO$_4$, and then concentrated. The residue was purified on silica gel (eluting with 0 to 50% EtOAc in hexanes) to give the desired product (1.30 g, 84%). LCMS calculated for C$_{22}$H$_{21}$BrN$_3$O$_4$S (M+H)$^+$: m/z=502.0. Found: 502.0; $^1$H NMR (400 MHz, CDCl$_3$): δ 8.15-8.12 (m, 3H), 7.68-7.58 (m, 1H), 7.51-7.47 (m, 2H), 6.88 (s, 1H), 6.31 (d, J=2.0 Hz, 2H), 6.28 (t, J=2.5 Hz, 1H), 3.72 (s, 6H), 3.16-3.12 (m, 2H), 2.99-2.96 (m, 2H) ppm.

Step 5. 2-[2-(3,5-dimethoxyphenyl)ethyl]-6-[4-(4-methylpiperazin-1-yl)phenyl]-5H-pyrrolo[2,3-b]pyrazine

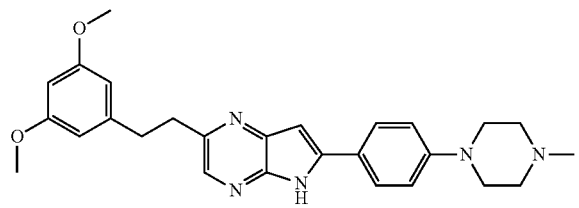

A stirred mixture of 6-bromo-2-[2-(3,5-dimethoxyphenyl)ethyl]-5-(phenylsulfonyl)-5H-pyrrolo[2,3-b]pyrazine (30.0 mg, 59.7 μmol), 1-methyl-4-[4-(4,4,5,5-tetramethyl-1,3,2-dioxaborolan-2-yl)phenyl]piperazine (from Alfa Aesar, cat#H51659, 19.8 mg, 6.57 μmol), [1,1'-bis(diphenylphosphino)ferrocene]dichloropalladium(II), complex with dichloro-methane (1:1) (4.9 mg, 5.97 μmol), and potassium phosphate (25.4 mg, 119 μmol) in water (0.2 mL)/1,4-dioxane (1 mL) was heated at 88° C. After 1 hour, the volatiles were removed under vacuum and the residue was dissolved in methanol (1 mL). Potassium carbonate (16.5 mg, 119 μmol) was added and the reaction mixture was warmed up to 60° C. After 1 hour, the reaction mixture was cooled to ambient temperature and was purified on RP-HPLC (XBridge C18 column, eluting with a gradient of acetonitrile/water containing 0.05% TFA, at flow rate of 30 mL/min) to give the desired product (10.1 mg, 44%) as its (trifluoroacetic acid) TFA salt. LCMS calculated for C$_{27}$H$_{32}$N$_5$O$_2$ (M+H)$^+$: m/z=458.2. Found: 458.2; $^1$H NMR (400 MHz, DMSO-d$_6$): δ 12.21 (s, 1H), 9.73 (s, 1H), 8.01 (s, 1H), 7.89 (d, J=9.2 Hz, 2H), 7.12 (d, J=9.2 Hz, 2H), 6.93 (d, J=2.0 Hz, 1H), 6.38 (d, J=2.4 Hz, 2H), 6.28 (t, J=2.4 Hz, 1H), 4.01 (d, J=14.0 Hz, 2H), 3.67 (s, 6H), 3.52 (d, J=12.8 Hz, 2H), 3.19-2.93 (m, 8H), 2.86 (d, J=4.0 Hz, 3H) ppm.

Example 2

2-[2-(3,5-dimethoxyphenyl)ethyl]-6-[4-(4-ethylpiperazin-1-yl)phenyl]-5H-pyrrolo[2,3-b]pyrazine

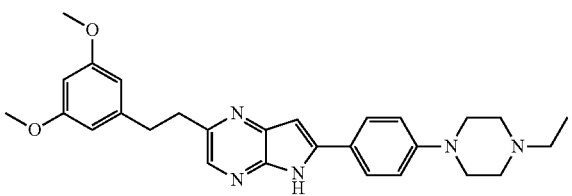 [SMILES: CCN1CCN(c2ccc(-c3cc4nc(CCc5cc(OC)cc(OC)c5)cnc4[nH]3)cc2)CC1]

This compound was prepared using procedures analogous to those for Example 1, Step 5, with 1-ethyl-4-[4-(4,4,5,5-tetramethyl-1,3,2-dioxaborolan-2-yl)phenyl]piperazine (from Ark Pharm, cat#AK-40362) replacing 1-methyl-4-[4-(4,4,5,5-tetramethyl-1,3,2-dioxaborolan-2-yl)phenyl]piperazine. LCMS calculated for C$_{28}$H$_{34}$N$_5$O$_2$ (M+H)$^+$: m/z=472.3. Found: 472.3.

Example 3

2-(3,5-dimethoxyphenethyl)-6-phenyl-5H-pyrrolo[2,3-b]pyrazine

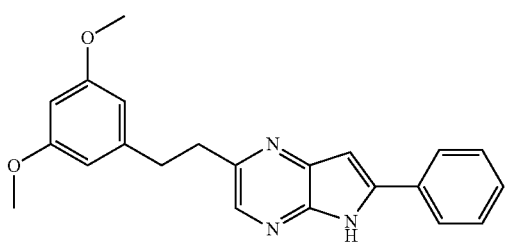 [SMILES: COc1cc(CCc2cnc3[nH]c(-c4ccccc4)cc3n2)cc(OC)c1]

This compound was prepared using procedures analogous to those for Example 1, Step 5, with phenylboronic acid replacing 1-methyl-4-[4-(4,4,5,5-tetramethyl-1,3,2-dioxaborolan-2-yl)phenyl]piperazine. LCMS calculated for C$_{22}$H$_{22}$N$_3$O$_2$ (M+H)$^+$: m/z=360.2. Found: 360.2.

Example 4

6-(2,6-difluorophenyl)-2-(3,5-dimethoxyphenethyl)-5H-pyrrolo[2,3-b]pyrazine

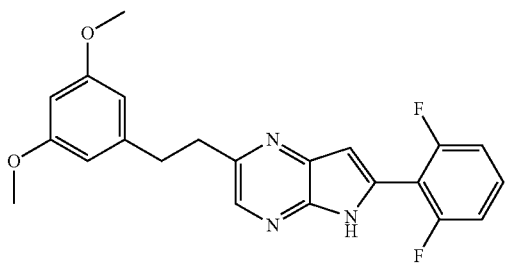 [SMILES: COc1cc(CCc2cnc3[nH]c(-c4c(F)cccc4F)cc3n2)cc(OC)c1]

This compound was prepared using procedures analogous to those for Example 1, Step 5, with 2,6-difluorophenylboronic acid replacing 1-methyl-4-[4-(4,4,5,5-tetramethyl-1,3,2-dioxaborolan-2-yl)phenyl]piperazine. LCMS calculated for $C_{22}H_{20}F_2N_3O_2$ (M+H)$^+$: m/z=396.2. Found: 396.1.

Example 5

2-[2-(3,5-dimethoxyphenyl)ethyl]-6-(4-methoxyphenyl)-5H-pyrrolo[2,3-b]pyrazine

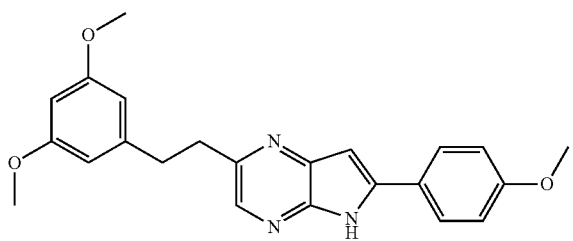

This compound was prepared using procedures analogous to those for Example 1, Step 5, with (4-methoxyphenyl)boronic acid replacing 1-methyl-4-[4-(4,4,5,5-tetramethyl-1,3,2-dioxaborolan-2-yl)phenyl]piperazine. LCMS calculated for $C_{23}H_{24}N_3O_3$ (M+H)$^+$: m/z=390.2. Found: 390.2; $^1$H NMR (300 MHz, CDCl$_3$): δ 9.90 (s, 1H), 7.90 (s, 1H), 7.63 (d, J=8.7 Hz, 2H), 6.97 (d, J=9.0 Hz, 2H), 6.78 (d, J=1.8 Hz, 1H), 6.33 (d, J=2.4 Hz, 2H), 6.23 (t, J=2.4 Hz, 1H), 3.82 (s, 3H), 3.68 (s, 6H), 3.15-3.10 (m, 2H), 3.02-2.97 (m, 2H) ppm.

Example 6

N-(4-{2-[2-(3,5-dimethoxyphenyl)ethyl]-5H-pyrrolo[2,3-b]pyrazin-6-yl}phenyl)acetamide

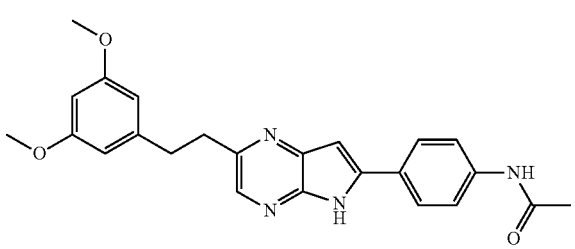 [SMILES: COc1cc(CCc2cnc3[nH]c(-c4ccc(NC(C)=O)cc4)cc3n2)cc(OC)c1]

This compound was prepared using procedures analogous to those for Example 1, Step 5, with [4-(acetylamino)phenyl]boronic acid replacing 1-methyl-4-[4-(4,4,5,5-tetramethyl-1,3,2-dioxaborolan-2-yl)phenyl]piperazine. LCMS calculated for $C_{24}H_{25}N_4O_3$ (M+H)$^+$: m/z=417.2. Found: 417.2.

Example 7

4-{2-[2-(3,5-dimethoxyphenyl)ethyl]-5H-pyrrolo[2,3-b]pyrazin-6-yl}-N,N-dimethylbenzamide

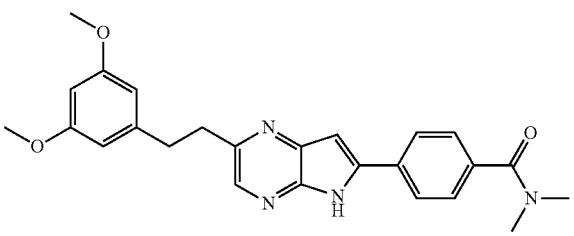

This compound was prepared using procedures analogous to those for Example 1, Step 5, with {4-[(dimethylamino)carbonyl]phenyl}boronic acid replacing 1-methyl-4-[4-(4,4,5,5-tetramethyl-1,3,2-dioxaborolan-2-yl)phenyl]piperazine. LCMS calculated for $C_{25}H_{27}N_4O_3$ (M+H)$^+$: m/z=431.2. Found: 431.2.

Example 8

2-[2-(3,5-dimethoxyphenyl)ethyl]-6-[4-(trifluoromethyl)phenyl]-5H-pyrrolo[2,3-b]pyrazine

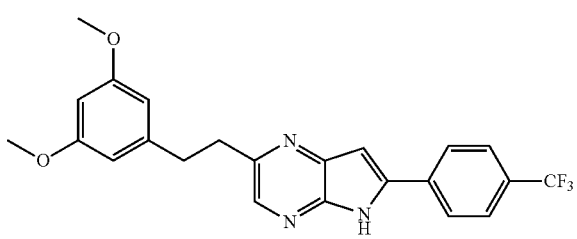 [SMILES: COc1cc(CCc2cnc3[nH]c(-c4ccc(C(F)(F)F)cc4)cc3n2)cc(OC)c1]

This compound was prepared using procedures analogous to those for Example 1, Step 5, with (4-trimethylphenyl)boronic acid replacing 1-methyl-4-[4-(4,4,5,5-tetramethyl-1,3,2-dioxaborolan-2-yl)phenyl]piperazine. LCMS calculated for $C_{23}H_{21}F_3N_3O_2$ (M+H)$^+$: m/z=428.2. Found: 428.1.

Example 9

2-[2-(3,5-dimethoxyphenyl)ethyl]-6-(2-methylphenyl)-5H-pyrrolo[2,3-b]pyrazine

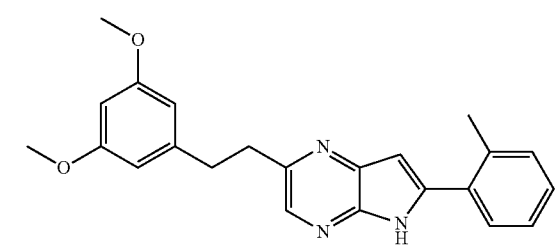 [SMILES: COc1cc(CCc2cnc3[nH]c(-c4ccccc4C)cc3n2)cc(OC)c1]

This compound was prepared using procedures analogous to those for Example 1, Step 5, with (2-methylphenyl)boronic acid replacing 1-methyl-4-[4-(4,4,5,5-tetramethyl- 1,3,2-dioxaborolan-2-yl)phenyl]piperazine. LCMS calculated for $C_{23}H_{24}N_3O_2$ (M+H)$^+$: m/z=374.2. Found: 374.2.

Example 10

2-{2-[2-(3,5-dimethoxyphenyl)ethyl]-5H-pyrrolo[2,3-b]pyrazin-6-yl}benzonitrile

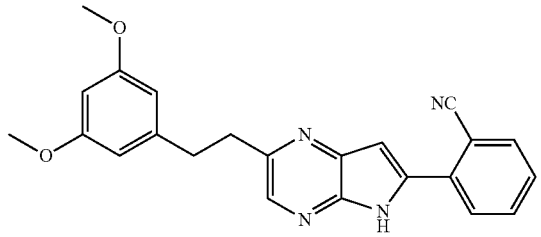 [SMILES: COc1cc(CCc2cnc3[nH]c(-c4ccccc4C#N)cc3n2)cc(OC)c1]

This compound was prepared using procedures analogous to those for Example 1, Step 5, with (2-cyanophenyl)boronic acid replacing 1-methyl-4-[4-(4,4,5,5-tetramethyl-1,3,2-dioxaborolan-2-yl)phenyl]piperazine. LCMS calculated for $C_{23}H_{21}N_4O_2$ (M+H)$^+$: m/z=385.2. Found: 385.2.

Example 11

2-[2-(3,5-dimethoxyphenyl)ethyl]-6-[4-(piperidin-1-ylmethyl)phenyl]-5H-pyrrolo[2,3-b]pyrazine

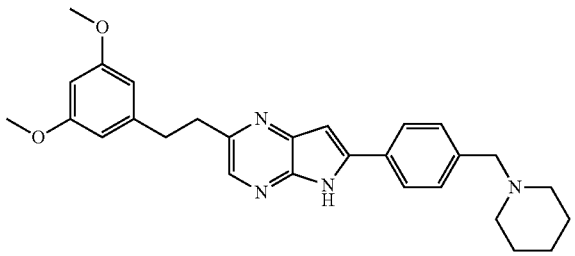 [SMILES: COc1cc(CCc2cnc3[nH]c(-c4ccc(CN5CCCCC5)cc4)cc3n2)cc(OC)c1]

This compound was prepared using procedures analogous to those for Example 1, Step 5, with 1-[4-(4,4,5,5-tetramethyl-1,3,2-dioxaborolan-2-yl)benzyl]piperidine (from Frontier, cat#P10017) replacing 1-methyl-4-[4-(4,4,5,5-tetramethyl-1,3,2-dioxaborolan-2-yl)phenyl]piperazine. LCMS calculated for $C_{28}H_{33}N_4O_2$ (M+H)$^+$: m/z=457.2. Found: 457.3.

Example 12

2-[2-(3,5-dimethoxyphenyl)ethyl]-6-[4-(methoxymethyl)phenyl]-5H-pyrrolo[2,3-b]pyrazine

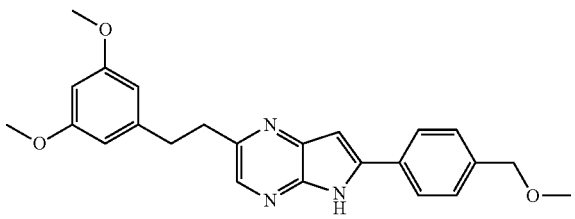

This compound was prepared using procedures analogous to those for Example 1, Step 5, with [4-(methoxymethyl)phenyl]boronic acid replacing 1-methyl-4-[4-(4,4,5,5-tetramethyl-1,3,2-dioxaborolan-2-yl)phenyl]piperazine. LCMS calculated for $C_{24}H_{26}N_3O_3$ (M+H)$^+$: m/z=404.2. Found: 404.2.

Example 13

(4-{2-[2-(3,5-dimethoxyphenyl)ethyl]-5H-pyrrolo[2,3-b]pyrazin-6-yl}phenyl)methanol

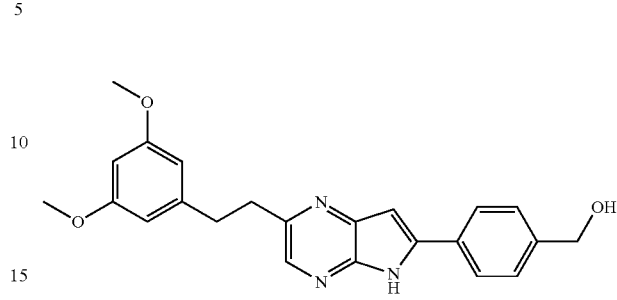

This compound was prepared using procedures analogous to those for Example 1, Step 5, with 4-hydroxymethylbenzeneboronic acid replacing 1-methyl-4-[4-(4,4,5,5-tetramethyl-1,3,2-dioxaborolan-2-yl)phenyl]piperazine. LCMS calculated for $C_{23}H_{24}N_3O_3$ (M+H)$^+$: m/z=390.2. Found: 390.1.

Example 14

(4-{2-[2-(3,5-dimethoxyphenyl)ethyl]-5H-pyrrolo[2,3-b]pyrazin-6-yl}phenyl)acetonitrile

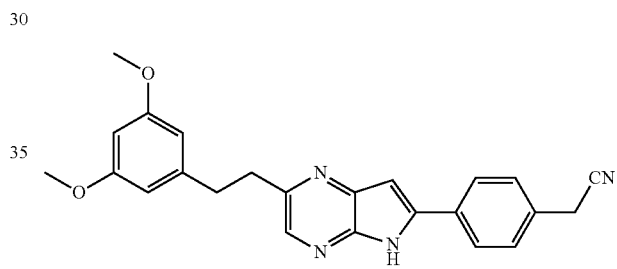

This compound was prepared using procedures analogous to those for Example 1, Step 5, with [4-(cyanomethyl)phenyl]boronic acid replacing 1-methyl-4-[4-(4,4,5,5-tetramethyl-1,3,2-dioxaborolan-2-yl)phenyl]piperazine. LCMS calculated for $C_{24}H_{23}N_4O_2$ (M+H)$^+$: m/z=399.2. Found: 399.2.

Example 15

4-{2-[2-(3,5-dimethoxyphenyl)ethyl]-5H-pyrrolo[2,3-b]pyrazin-6-yl}benzoic acid

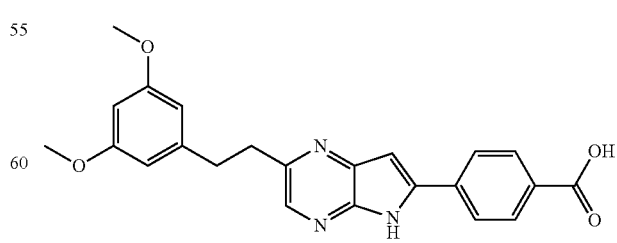

This compound was prepared using procedures analogous to those for Example 1, Step 5, with 4-(dihydroxyboryl)benzoic acid replacing 1-methyl-4-[4-(4,4,5,5-tetramethyl- 1,3,2-dioxaborolan-2-yl)phenyl]piperazine. LCMS calculated for $C_{23}H_{22}N_3O_4$ (M+H)$^+$: m/z=404.2. Found: 404.2.

Example 16

2-[2-(3,5-dimethoxyphenyl)ethyl]-6-[6-(4-methylpiperazin-1-yl)pyridin-3-yl]-5H-pyrrolo[2,3-b]pyrazine

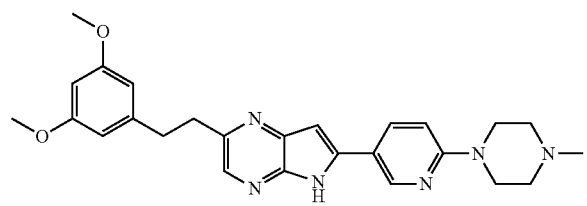

This compound was prepared using procedures analogous to those for Example 1, Step 5, with 1-methyl-4-[5-(4,4,5,5-tetramethyl-1,3,2-dioxaborolan-2-yl)pyridin-2-yl]piperazine (from Frontier, cat#P1824) replacing 1-methyl-4-[4-(4,4,5,5-tetramethyl-1,3,2-dioxaborolan-2-yl)phenyl]piperazine. LCMS calculated for $C_{26}H_{21}N_6O_2$ (M+H)$^+$: m/z=459.2. Found: 459.3.

Example 17

5-{2-[2-(3,5-dimethoxyphenyl)ethyl]-5H-pyrrolo[2,3-b]pyrazin-6-yl}-N-methylpyridine-2-carboxamide

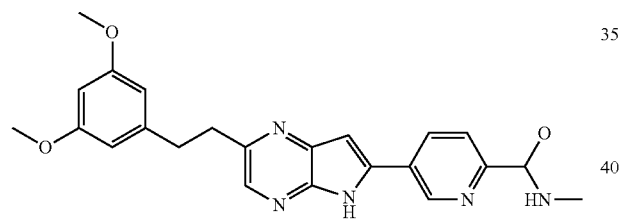

This compound was prepared using procedures analogous to those for Example 1, Step 5, with {6-[(methylamino)carbonyl]pyridin-3-yl}boronic acid (from Frontier, cat#M10074) replacing 1-methyl-4-[4-(4,4,5,5-tetramethyl-1,3,2-dioxaborolan-2-yl)phenyl]piperazine. LCMS calculated for $C_{23}H_{24}N_5O_3$ (M+H)$^+$: m/z=418.2. Found: 418.3.

Example 18

2-[2-(3,5-dimethoxyphenyl)ethyl]-6-[5-(morpholin-4-ylcarbonyl)pyridin-3-yl]-5H-pyrrolo[2,3-b]pyrazine

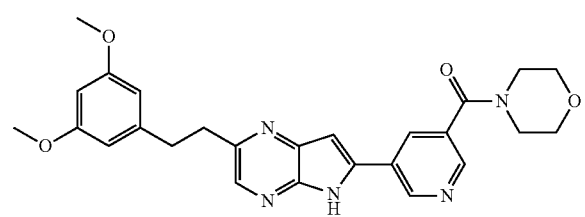 [SMILES: COc1cc(CCc2cnc3[nH]c(-c4cncc(C(=O)N5CCOCC5)c4)cc3n2)cc(OC)c1]

This compound was prepared using procedures analogous to those for Example 1, Step 5, with 4-{[5-(4,4,5,5-tetramethyl-1,3,2-dioxaborolan-2-yl)pyridin-3-yl]carbonyl}morpholine (from Frontier, cat#M1818) replacing 1-methyl-4-[4-(4,4,5,5-tetramethyl-1,3,2-dioxaborolan-2-yl)phenyl]piperazine. LCMS calculated for $C_{26}H_{28}N_5O_4$ (M+H)$^+$: m/z=474.2. Found: 474.2.

Example 19

4-{2-[2-(3,5-dimethoxyphenyl)ethyl]-5H-pyrrolo[2,3-b]pyrazin-6-yl}thiophene-2-carboxylic acid

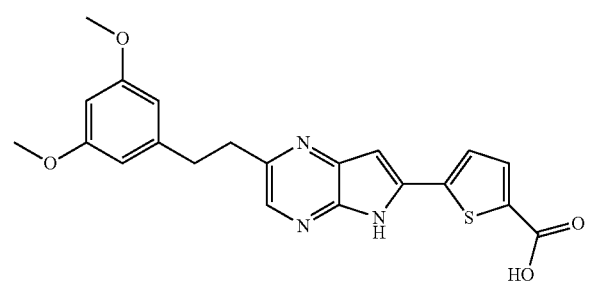 [SMILES: COc1cc(CCc2cnc3[nH]c(-c4ccc(C(=O)O)s4)cc3n2)cc(OC)c1]

This compound was prepared using procedures analogous to those for Example 1, Step 5, with 4-(dihydroxyboryl)thiophene-2-carboxylic acid (from Frontier, cat#C1695) replacing 1-methyl-4-[4-(4,4,5,5-tetramethyl-1,3,2-dioxaborolan-2-yl)phenyl]piperazine. LCMS calculated for $C_{21}H_{20}N_3O_4S$ (M+H)$^+$: m/z=410.1. Found: 410.1.

Example 20

5-{2-[2-(3,5-dimethoxyphenyl)ethyl]-5H-pyrrolo[2,3-b]pyrazin-6-yl}-N,N-dimethylpyrimidin-2-amine

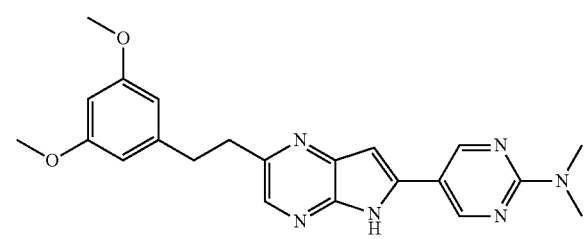

This compound was prepared using procedures analogous to those for Example 1, Step 5, with N,N-dimethyl-5-(4,4,5,5-tetramethyl-1,3,2-dioxaborolan-2-yl)pyrimidin-2-amine (from Frontier, cat#D1773) replacing 1-methyl-4-[4-(4,4,5,5-tetramethyl-1,3,2-dioxaborolan-2-yl)phenyl]piperazine. LCMS calculated for $C_{22}H_{25}N_6O_2$ (M+H)$^+$: m/z=405.2. Found: 405.2.

Example 21

6-(1,3-benzodioxol-5-yl)-2-[2-(3,5-dimethoxyphenyl)ethyl]-5H-pyrrolo[2,3-b]pyrazine

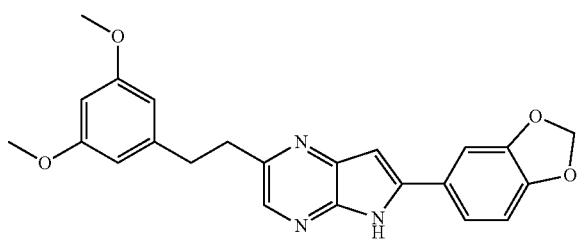 [SMILES: COc1cc(CCc2cnc3[nH]c(-c4ccc5c(c4)OCO5)cc3n2)cc(OC)c1]

This compound was prepared using procedures analogous to those for Example 1, Step 5, with 1,3-benzodioxol-5-ylboronic acid replacing 1-methyl-4-[4-(4,4,5,5-tetramethyl-1,3,2-dioxaborolan-2-yl)phenyl]piperazine. LCMS calculated for $C_{23}H_{22}N_3O_4$ $(M+H)^+$: m/z=404.2. Found: 404.2.

Example 22

2-[2-(3,5-dimethoxyphenyl)ethyl]-6-[4-(1-methylpiperidin-4-yl)phenyl]-5H-pyrrolo[2,3-b]pyrazine

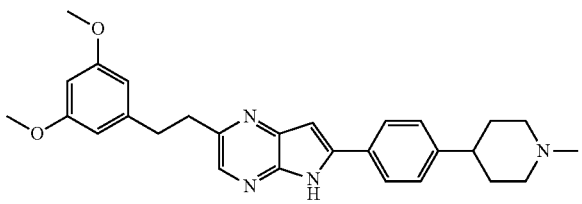

Step 1. 1-methyl-4-[4-(4,4,5,5-tetramethyl-1,3,2-dioxaborolan-2-yl)phenyl]piperidine

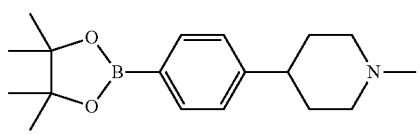

To a stirred solution of 4-(4-bromophenyl)-1-methylpiperidine (from J&W PharmLab, cat#60-0498, 200 mg, 0.787 mmol) and 4,4,4',4',5,5,5',5'-octamethyl-2,2'-bi(1,3,2-dioxaborolane) (0.210 g, 0.826 mmol) in 1,4-dioxane (1.62 mL, 20.7 mmol) [1,1'-bis(diphenylphosphino)ferrocene]dichloropalladium(II) complex with dichloromethane (1:1) (27.0 mg, 33.1 µmol), potassium acetate (0.160 g, 1.63 mmol), and 1,1'-bis(diphenylphosphino)ferrocene (19.0 mg, 3.43 µmol) was added sequentially. The reaction mixture was then warmed up to 90° C. After 3 hours, the reaction mixture was quenched with saturated aq. NH$_4$Cl, extracted with methylene chloride. The combined organic layers were dried over MgSO$_4$, and then concentrated to give the desired product (190 mg, 80%). LCMS calculated for $C_{18}H_{29}BNO_2$ $(M+H)^+$: m/z=302.2. Found: 302.2.

Step 2. 2-[2-(3,5-dimethoxyphenyl)ethyl]-6-[4-(1-methylpiperidin-4-yl)phenyl]-5H-pyrrolo[2,3-b]pyrazine

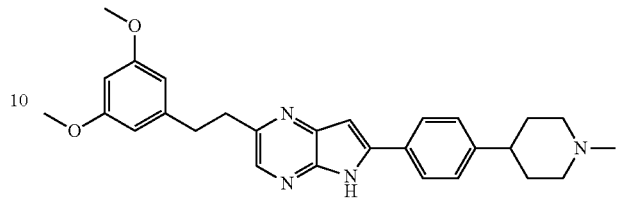

This compound was prepared using procedures analogous to those for Example 1, Step 5, with 1-methyl-4-[4-(4,4,5,5-tetramethyl-1,3,2-dioxaborolan-2-yl)phenyl]piperidine (from Example 22, Step 1) replacing 1-methyl-4-[4-(4,4,5,5-tetramethyl-1,3,2-dioxaborolan-2-yl)phenyl]piperazine. LCMS calculated for $C_{28}H_{33}N_4O_2$ $(M+H)^+$: m/z=457.3. Found: 457.2.

Example 23

2-[2-(3,5-dimethoxyphenyl)ethyl]-6-(1-methyl-1,2,3,6-tetrahydropyridin-4-yl)-5H-pyrrolo[2,3-b]pyrazine

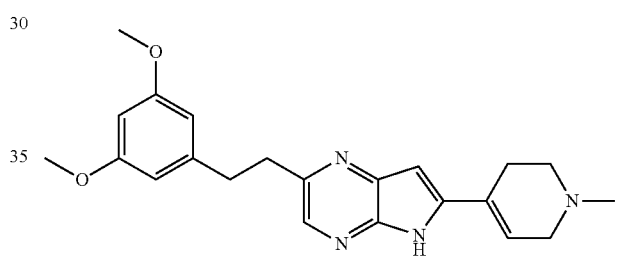

This compound was prepared using procedures analogous to those for Example 1, Step 5, with 1-methyl-4-(4,4,5,5-tetramethyl-1,3,2-dioxaborolan-2-yl)-1,2,3,6-tetrahydropyridine replacing 1-methyl-4-[4-(4,4,5,5-tetramethyl-1,3,2-dioxaborolan-2-yl)phenyl]piperazine. LCMS calculated for $C_{22}H_{27}N_4O_2$ $(M+H)^+$: m/z=379.2. Found: 379.3.

Example 24

2-[2-(3,5-dimethoxyphenyl)ethyl]-6-(1-methylpiperidin-4-yl)-5H-pyrrolo[2,3-b]pyrazine

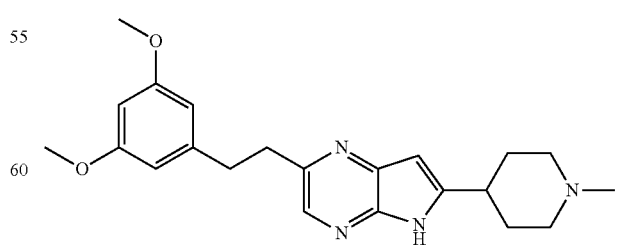

To a stirred solution of 2-[2-(3,5-dimethoxyphenyl)ethyl]-6-(1-methyl-1,2,3,6-tetrahydropyridin-4-yl)-5H-pyrrolo[2,3-b]pyrazine (from Example 23, 10 mg, 26.4 µmol) in methanol (1 mL), Pd/C (10% w/w, 3.2 mg, 3.0 µmol) was added. The reaction mixture was then stirred under the atmosphere of $H_2$ at ambient temperature. After 3 hours, the palladium catalyst was filtered and the crude mixture was purified on RP-HPLC (XBridge C18 column, eluting with a gradient of acetonitrile/water containing 0.05% TFA, at flow rate of 30 mL/min) to give the desired product (3.0 mg, 30%) as its TFA salt. LCMS calculated for $C_{22}H_{29}N_4O_2$ (M+H)$^+$: m/z=381.2. Found: 381.3.

Example 25

2-[2-(3,5-dimethoxyphenyl)ethyl]-N-methyl-5H-pyrrolo[2,3-b]pyrazine-6-carboxamide

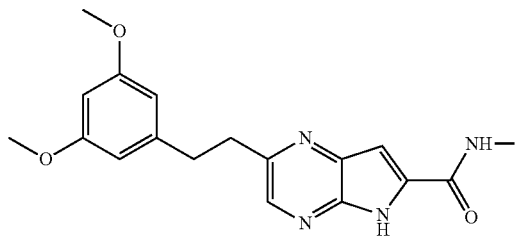

Step 1. 2-(3,5-dimethoxyphenethyl)-5-(phenylsulfonyl)-5H-pyrrolo[2,3-b]pyrazine-6-carboxylic acid

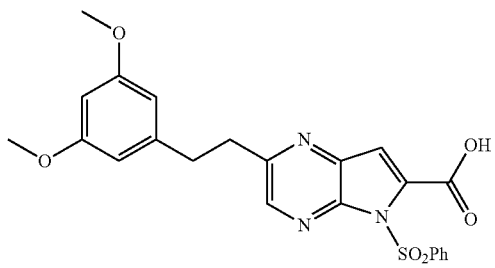

To a stirred solution of N,N-diisopropylamine (64.8 µL, 0.463 mmol) in tetrahydrofuran (0.3 mL) at −78° C., n-butyllithium (2.5M in hexanes, 0.185 mL, 0.463 mmol) was added dropwise. After the white precipitate formed, the reaction mixture was warmed up to 0° C. for 10 minutes. The resulted solution was transferred to a stirred solution of 2-[2-(3,5-dimethoxyphenyl)ethyl]-5-(phenylsulfonyl)-5H-pyrrolo[2,3-b]pyrazine (from example 1, step 4, 130 mg, 0.310 mmol) in tetrahydrofuran (2 mL) at −78° C. A dark red solution was formed. After 15 minutes, dry $CO_2$ (prepared by passing $CO_2$ through drying tube) was bubbled into the reaction mixture. After another 15 minutes, the reaction mixture was quenched with saturated aq. $NH_4Cl$, extracted with methylene chloride. The combined organic layers were dried over $MgSO_4$, and then concentrated to afford the desired product (135 mg, 94%). LCMS calculated for $C_{23}H_{22}N_3O_6S$ (M+H)$^+$: m/z=468.1. Found: 468.0.

Step 2. 2-[2-(3,5-dimethoxyphenyl)ethyl]-N-methyl-5H-pyrrolo[2,3-b]pyrazine-6-carboxamide

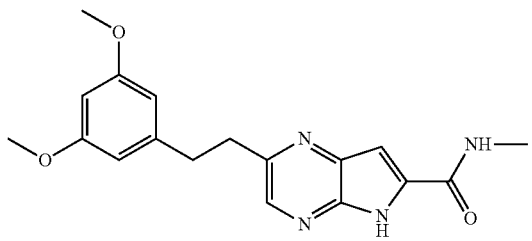

To a stirred solution of 2-(3,5-dimethoxyphenethyl)-5-(phenylsulfonyl)-5H-pyrrolo[2,3-b]pyrazine-6-carboxylic acid (27 mg, 57.8 µmol) in N,N-dimethylformamide (2 mL), methylamine (2.0M in THF, 57.8 µL, 0.116 mmol), HATU (43.9 mg, 0.116 mmol) and N,N-diisopropylethylamine (40.2 µL, 0.231 mmol) were added sequentially at ambient temperature. After 1 hour, the reaction was quenched with saturated aq. $NH_4Cl$, then extracted with methylene chloride. The combined organic layers were dried over $MgSO_4$, and then concentrated. The residue was dissolved in methanol (2.0 mL), and potassium carbonate (16.0 mg, 0.116 mmol) was added. The reaction mixture was then warmed up to 60° C. After 1 hour, the crude mixture was allowed to warm to room temperature and was then purified on RP-HPLC (XBridge C18 column, eluting with a gradient of acetonitrile/water containing 0.05% TFA, at a flow rate of 30 mL/min) to give the desired product (6.0 mg, 30%) as its TFA salt. LCMS calculated for $C_{18}H_{21}N_4O_3$ (M+H)$^+$: m/z=341.2. Found: 341.1.

Example 26

2-[2-(3,5-dimethoxyphenyl)ethyl]-N,N-dimethyl-5H-pyrrolo[2,3-b]pyrazine-6-carboxamide

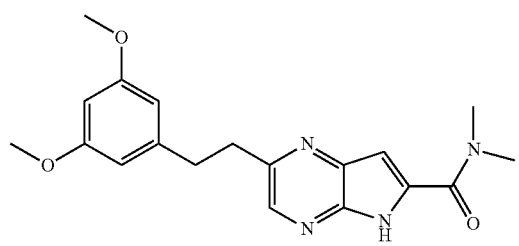

This compound was prepared using procedures analogous to those for Example 15, Step 2, with dimethylamine (2.0M in THF) replacing methylamine (2.0M in THF). LCMS calculated for $C_{19}H_{23}N_4O_2$ (M+H)$^+$: m/z=355.2. Found: 355.2.

Example 27

3-{2-[2-(3,5-dimethoxyphenyl)ethyl]-5H-pyrrolo[2,3-b]pyrazin-6-yl}-N,N-diethylprop-2-yn-1-amine

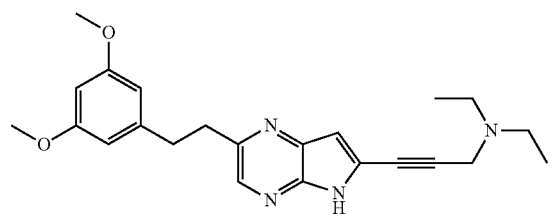 [SMILES: CCN(CC)CC#Cc1cc2nc(CCc3cc(OC)cc(OC)c3)cnc2[nH]1]

A solution of N,N-diethylprop-2-yn-1-amine (10.6 mg, 95.5 μmol), bis(triphenylphosphine)palladium(II) chloride (2.8 mg, 4.0 μmol), copper(I) iodide (1.2 mg, 6.4 mol), triethylamine (17.0 μL, 120 μmol), and 6-bromo-2-[2-(3,5-dimethoxyphenyl)ethyl]-5-(phenylsulfonyl)-5H-pyrrolo[2,3-b]pyrazine (from Example 1, Step 4, 40.0 mg, 79.7 μmol) in N,N-dimethylformamide (1.0 mL) was stirred at ambient temperature overnight. The reaction was quenched with saturated aq. NH₄Cl, then extracted with methylene chloride. The combined organic layers were dried over MgSO₄, and then concentrated. The residue was dissolved in methanol (2.0 mL) and potassium carbonate (22.0 mg, 0.159 mmol) was added. The reaction mixture was then warmed up to 60° C. After 1 hour, the crude mixture was allowed to warm to room temperature and was purified on RP-HPLC (XBridge C18 column, eluting with a gradient of acetonitrile/water containing 0.05% TFA, at flow rate of 30 mL/min) to give the desired product (6.0 mg, 20%) as its TFA salt. LCMS calculated for $C_{23}H_{29}N_4O_2$ (M+H)⁺: m/z=393.2. Found: 393.1.

Example 28

3-{2-[2-(3,5-dimethoxyphenyl)ethyl]-5H-pyrrolo[2,3-b]pyrazin-6-yl}-N,N-diethylpropan-1-amine

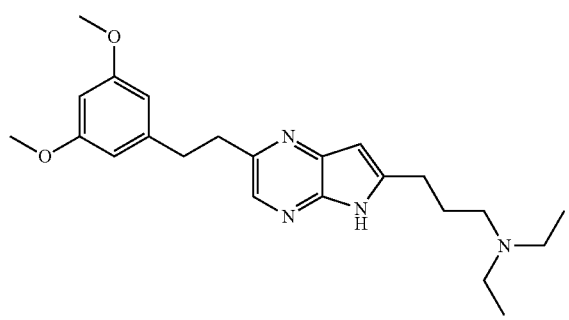 [SMILES: CCN(CC)CCCc1cc2nc(CCc3cc(OC)cc(OC)c3)cnc2[nH]1]

To a stirred solution of 3-{2-[2-(3,5-dimethoxyphenyl)ethyl]-5H-pyrrolo[2,3-b]pyrazin-6-yl}-N,N-diethylprop-2-yn-1-amine (from Example 27, 5 mg, 12.7 μmol) in methanol (2 mL), Pd/C (10% w/w, 5.0 mg, 4.7 μmol) was added. The resulted mixture was stirred under H₂ at ambient temperature. After 1.5 hours, the palladium catalyst was filtered and the crude mixture was purified on RP-HPLC (XBridge C18 column, eluting with a gradient of acetonitrile/water containing 0.05% TFA, at flow rate of 30 mL/min) to give the desired product (2.4 mg, 50%) as its TFA salt. LCMS calculated for $C_{23}H_{33}N_4O_2$ (M+H)⁺: m/z=397.3. Found: 397.3.

Example 29

2-[2-(3,5-dimethoxyphenyl)ethyl]-6-(1H-pyrazol-4-yl)-5H-pyrrolo[2,3-b]pyrazine

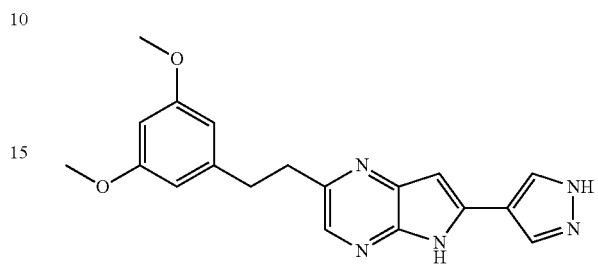

This compound was prepared using procedures analogous to those for Example 1, Step 5, with 4-(4,4,5,5-tetramethyl-1,3,2-dioxaborolan-2-yl)-1H-pyrazole replacing 1-methyl-4-[4-(4,4,5,5-tetramethyl-1,3,2-dioxaborolan-2-yl)phenyl]piperazine. LCMS calculated for $C_{19}H_{20}N_5O_2$ (M+H)⁺: m/z=350.2. Found: 350.2.

Example 30

2-[2-(3,5-dimethoxyphenyl)ethyl]-6-(1-methyl-1H-pyrazol-4-yl)-5H-pyrrolo[2,3-b]pyrazine

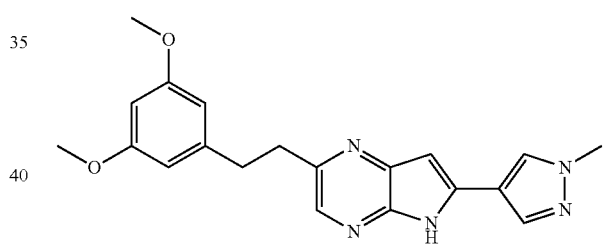

This compound was prepared using procedures analogous to those for Example 1, Step 5, with 1-methyl-4-(4,4,5,5-tetramethyl-1,3,2-dioxaborolan-2-yl)-1H-pyrazole replacing 1-methyl-4-[4-(4,4,5,5-tetramethyl-1,3,2-dioxaborolan-2-yl)phenyl]piperazine. LCMS calculated for $C_{20}H_{22}N_5O_2$ (M+H)⁺: m/z=364.2. Found: 364.2.

Example 31

2-[2-(3,5-dimethoxyphenyl)ethyl]-6-[1-(2-morpholin-4-ylethyl)-1H-pyrazol-4-yl]-5H-pyrrolo[2,3-b]pyrazine

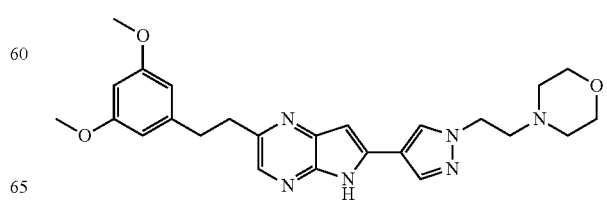

This compound was prepared using procedures analogous to those for Example 1, Step 5, with 4-{2-[4-(4,4,5,5-tetramethyl-1,3,2-dioxaborolan-2-yl)-1H-pyrazol-1-yl]ethyl}morpholine (from Combi-Blocks, cat#PN-8727) replacing 1-methyl-4-[4-(4,4,5,5-tetramethyl-1,3,2-dioxaborolan-2-yl)phenyl]piperazine. LCMS calculated for $C_{25}H_{31}N_6O_3$ (M+H)$^+$: m/z=463.2. Found: 463.2.

Example 32

2-[2-(3,5-dimethoxyphenyl)ethyl]-6-[1-(tetrahydro-2H-pyran-4-yl)-1H-pyrazol-4-yl]-5H-pyrrolo[2,3-b]pyrazine

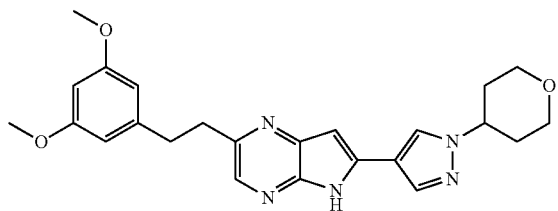 [SMILES: COc1cc(CCc2cnc3[nH]c(-c4cnn(C5CCOCC5)c4)cc3n2)cc(OC)c1]

Step 1. tetrahydro-2H-pyran-4-yl methanesulfonate

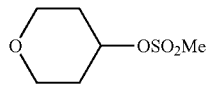

To a stirred solution of tetrahydro-4H-pyran-4-ol (100.0 μL, 1.05 mmol) in methylene chloride (8.0 mL) at 0° C., triethylamine (183 μL, 1.31 mmol) and methanesulfonyl chloride (89.3 μL, 1.15 mmol) were added sequentially. After 1.5 h, the reaction was quenched with water and extracted with methylene chloride. The combined organic layers were dried over MgSO$_4$, and then concentrated to give the desired product (190 mg, 100%), which was used directly in the next step. $^1$H NMR (400 MHz, CDCl$_3$): δ 4.92-4.87 (m, 1H), 3.97-3.92 (m, 2H), 3.57-3.52 (m, 2H), 3.04 (s, 3H), 2.07-2.02 (m, 2H), 1.92-1.83 (m, 2H) ppm.

Step 2. 1-(tetrahydro-2H-pyran-4-yl)-4-(4,4,5,5-tetramethyl-1,3,2-dioxaborolan-2-yl)-1H-pyrazole

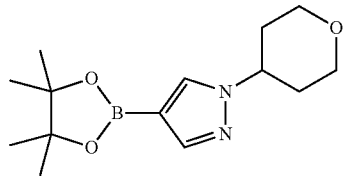 [SMILES: CC1(C)OB(c2cnn(C3CCOCC3)c2)OC1(C)C]

A mixture of 4-(4,4,5,5-tetramethyl-1,3,2-dioxaborolan-2-yl)-1H-pyrazole (30.0 mg, 0.154 mmol), and tetrahydro-2H-pyran-4-yl methanesulfonate (0.150 g, 0.460 mmol) in acetonitrile (1.0 mL) was stirred at 90° C. for 2 hours. The reaction was quenched with water, extracted with ethyl acetate. The combined organic layer was dried over MgSO$_4$, then filtered and concentrated under reduced pressure to afford the desired product (35 mg, 80%), which was used directly in the next step without further purification. LCMS calculated for $C_{14}H_{24}BN_2O_3$ (M+H)$^+$: m/z=279.2. Found: 279.2.

Step 3. 2-[2-(3,5-dimethoxyphenyl)ethyl]-6-[1-(tetrahydro-2H-pyran-4-yl)-1H-pyrazol-4-yl]-5H-pyrrolo[2,3-b]pyrazine

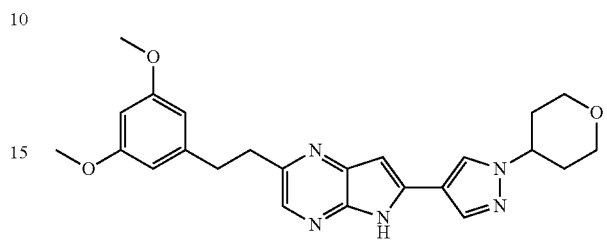

A stirred mixture of 6-bromo-2-[2-(3,5-dimethoxyphenyl)ethyl]-5-(phenylsulfonyl)-5H-pyrrolo[2,3-b]pyrazine (15.0 mg, 29.8 μmol), [1,1'-bis(diphenylphosphino)ferrocene]-dichloropalladium(II) complexed with dichloromethane (1:1) (1.30 mg, 1.59 μmol), 1-(tetrahydro-2H-pyran-4-yl)-4-(4,4,5,5-tetramethyl-1,3,2-dioxaborolan-2-yl)-1H-pyrazole (8.9 mg, 32.0 μmol), and potassium phosphate (13.5 mg, 63.6 μmol) in water (0.2 mL)/1,4-dioxane (0.40 mL) was heated at 88° C. After 1 hour, the volatiles were removed under vacuum and the residues were dissolved in methanol (1 mL). Potassium carbonate (8.8 mg, 63.7 μmol) was added and the reaction mixture was then warmed up to 60° C. After 1 hour, the reaction mixture was cooled to ambient temperature and was purified on RP-HPLC (XBridge C18 column, eluting with a gradient of acetonitrile/water containing 0.05% TFA, at flow rate of 30 mL/min) to give the desired product (2.5 mg) as its TFA salt. LCMS calculated for $C_{24}H_{28}N_5O_3$ (M+H)$^+$: m/z=434.2. Found: 434.2.

Example 33

1-(4-{2-[2-(3,5-dimethoxyphenyl)ethyl]-5H-pyrrolo[2,3-b]pyrazin-6-yl}-1H-pyrazol-1-yl)-2-methylpropan-2-ol

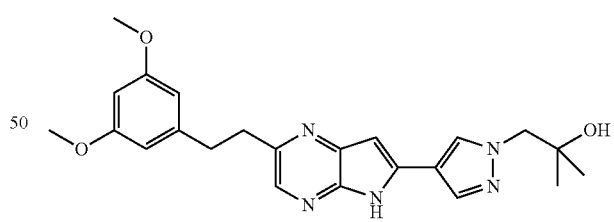

Step 1. 2-methyl-1-[4-(4,4,5,5-tetramethyl-1,3,2-dioxaborolan-2-yl)-1H-pyrazol-1-yl]propan-2-ol

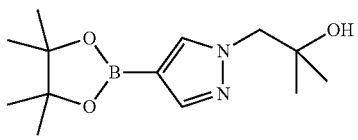 [SMILES: CC(C)(O)Cn1cc(B2OC(C)(C)C(C)(C)O2)cn1]

A mixture of 4-(4,4,5,5-tetramethyl-1,3,2-dioxaborolan-2-yl)-1H-pyrazole (30.0 mg, 0.154 mmol), 2,2-dimethyloxirane (25.8 μL, 0.309 mmol), and cesium carbonate (0.150 g, 0.460 mmol) in acetonitrile (1.0 mL) was stirred at 90° C. for 5 hours. The reaction mixture was cooled to ambient temperature, quenched with water, and extracted with methylene chloride. The combined organic layers were dried over MgSO$_4$, then filtered and concentrated under reduced pressure to give the desired product (32 mg, 78%). LCMS calculated for $C_{13}H_{24}BN_2O_3$ (M+H)$^+$: m/z=267.2. Found: 267.2.

Step 2. 1-(4-{2-[2-(3,5-dimethoxyphenyl)ethyl]-5H-pyrrolo[2,3-b]pyrazin-6-yl}-1H-pyrazol-1-yl)-2-methylpropan-2-ol

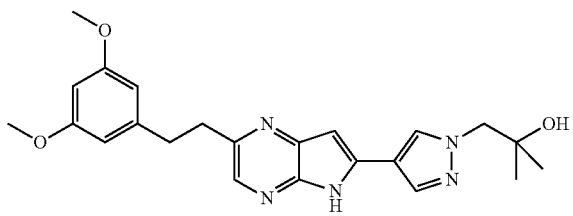 [SMILES: COc1cc(CCc2cnc3[nH]c(-c4cnn(CC(C)(C)O)c4)cc3n2)cc(OC)c1]

A stirred mixture of 6-bromo-2-[2-(3,5-dimethoxyphenyl)ethyl]-5-(phenylsulfonyl)-5H-pyrrolo[2,3-b]pyrazine (from Example 1, Step 5, 15.0 mg, 29.8 μmol), [1,1'-bis(diphenylphosphino)ferrocene]dichloro-palladium(II) complexed with dichloromethane (1:1) (1.30 mg, 1.59 μmol), 2-methyl-1-[4-(4,4,5,5-tetramethyl-1,3,2-dioxaborolan-2-yl)-1H-pyrazol-1-yl]propan-2-ol (8.5 mg, 31.8 μmol), and potassium phosphate (13.5 mg, 63.7 μmol) in water (0.2 mL)/1,4-dioxane (0.4 mL) was heated at 88° C. After 1 hour, the volatiles were removed under vacuum and the residues were dissolved in methanol (1.0 mL). Potassium carbonate (8.3 mg, 59.7 μmol) was added and the reaction mixture was warmed up to 60° C. After 1 hour, the reaction mixture was cooled to ambient temperature and was purified on RP-HPLC (XBridge C18 column, eluting with a gradient of acetonitrile/water containing 0.05% TFA, at flow rate of 30 mL/min) to give the desired product (3.0 mg) as its TFA salt. LCMS calculated for $C_{23}H_{28}N_5O_3$ (M+H)$^+$: m/z=422.2. Found: 422.3.

Example 34

2-(4-{2-[2-(3,5-dimethoxyphenyl)ethyl]-5H-pyrrolo[2,3-b]pyrazin-6-yl}-1H-pyrazol-1-yl)-N,N-dimethylethanamine

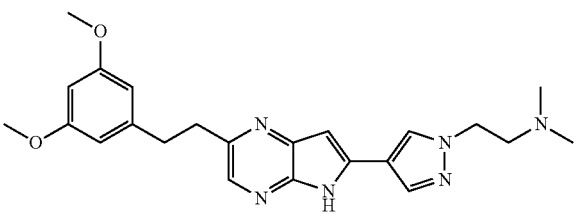

Step 1. N,N-dimethyl-2-[4-(4,4,5,5-tetramethyl-1,3,2-dioxaborolan-2-yl)-1H-pyrazol-1-yl]ethanamine

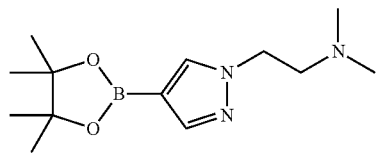

A mixture of 4-(4,4,5,5-tetramethyl-1,3,2-dioxaborolan-2-yl)-1H-pyrazole (60.0 mg, 0.309 mmol), β-dimethylaminoethyl chloride hydrochloride (49.0 mg, 0.340 mmol) and cesium carbonate (0.302 g, 0.928 mmol) in acetonitrile (1 mL) was stirred at 90° C. overnight. The reaction mixture was cooled to ambient temperature, quenched with water, and extracted with methylene chloride. The combined organic layers were dried over MgSO$_4$, then filtered and concentrated under reduced pressure to give the desired product (60 mg, 88%). LCMS calculated for $C_{13}H_{25}BN_3O_2$ (M+H)$^+$: m/z=266.2. Found: 266.2.

Step 2. 2-(4-{2-[2-(3,5-dimethoxyphenyl)ethyl]-5H-pyrrolo[2,3-b]pyrazin-6-yl}-1H-pyrazol-1-yl)-N,N-dimethylethanamine

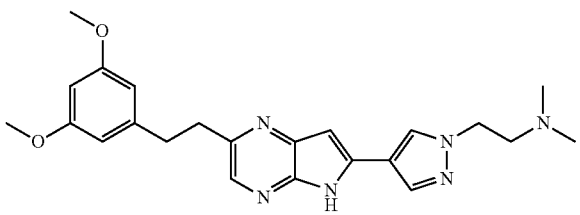

A stirred mixture of 6-bromo-2-[2-(3,5-dimethoxyphenyl)ethyl]-5-(phenylsulfonyl)-5H-pyrrolo[2,3-b]pyrazine (from example 1, step 4, 20.0 mg, 0.0398 mmol), [1,1'-bis(diphenylphosphino)ferrocene]dichloropalladium(II) complexed with dichloromethane (1:1) (1.30 mg, 1.59 μmol), N,N-dimethyl-2-[4-(4,4,5,5-tetramethyl-1,3,2-dioxaborolan-2-yl)-1H-pyrazol-1-yl]ethanamine (8.44 mg, 0.0318 mmol), and potassium phosphate (13.5 mg, 0.0637 mmol) in water (0.2 mL)/1,4-dioxane (0.4 mL) was heated at 88° C. After 1 hour, the volatiles were removed under vacuum and the residues were dissolved in methanol (2.0 mL). Potassium carbonate (8.8 mg, 63.7 μmol) was added and the reaction mixture was warmed up to 60° C. After 1 hour, the reaction mixture was cooled to ambient temperature and was purified on RP-HPLC (XBridge C18 column, eluting with a gradient of acetonitrile/water containing 0.05% TFA, at flow rate of 30 mL/min) to give the desired product (3.0 mg) as its TFA salt. LCMS calculated for $C_{23}H_{29}N_6O_2$ (M+H)$^+$: m/z=421.2. Found: 421.2.

Example 35

3-cyclopentyl-3-(4-{2-[2-(3,5-dimethoxyphenyl)ethyl]-5H-pyrrolo[2,3-b]pyrazin-6-yl}-1H-pyrazol-1-yl)propanenitrile

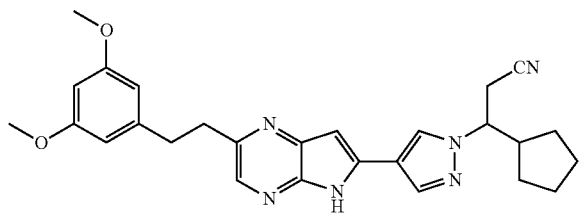 [SMILES: COc1cc(CCc2cnc3[nH]c(-c4cnn(C(CC#N)C5CCCC5)c4)cc3n2)cc(OC)c1]

Step 1. 2-[2-(3,5-dimethoxyphenyl)ethyl]-5-(phenylsulfonyl)-6-(1H-pyrazol-4-yl)-5H-pyrrolo[2,3-b]pyrazine

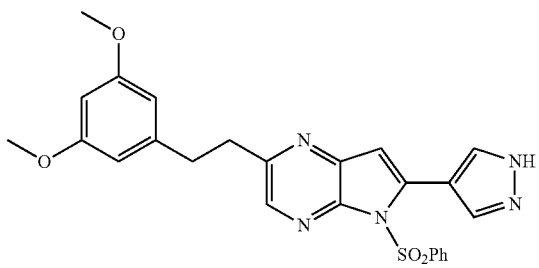

A stirred mixture of 6-bromo-2-[2-(3,5-dimethoxyphenyl)ethyl]-5-(phenylsulfonyl)-5H-pyrrolo[2,3-b]pyrazine (180 mg, 0.358 mmol), tert-butyl-4-(4,4,5,5-tetramethyl-1,3,2-dioxaborolan-2-yl)-1H-pyrazole-1-carboxylate (106 mg, 0.360 mmol), [1,1'-bis(diphenyl-phosphino)ferrocene]dichloropalladium(II) complexed with dichloromethane (1:1) (29.2 mg, 0.0358 mmol), and potassium phosphate (153 mg, 0.719 mmol) in water (2 mL)/1,4-dioxane (5 mL) was heated at 88° C. After 1 hour, the reaction mixture was cooled to ambient temperature, quenched with water, and extracted with methylene chloride. The combined organic layers were dried over MgSO$_4$, and then concentrated. The residue was purified on silica gel (eluting with 0 to 50% EtOAc in hexanes) to give the desired product (132 mg, 75%). LCMS calculated for $C_{25}H_{24}N_5O_4S$ (M+H)$^+$: m/z=490.2. Found: 490.2.

Step 2. 3-cyclopentyl-3-(4-{2-[2-(3,5-dimethoxyphenyl)ethyl]-5H-pyrrolo[2,3-b]pyrazin-6-yl}-1H-pyrazol-1-yl)propanenitrile

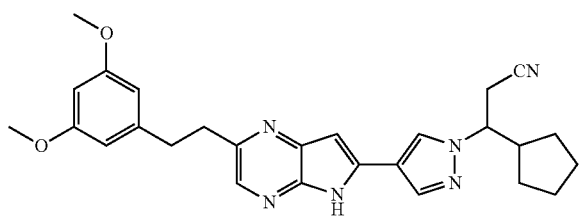 [SMILES: COc1cc(CCc2cnc3[nH]c(-c4cnn(C(CC#N)C5CCCC5)c4)cc3n2)cc(OC)c1]

To a stirred solution of 2-[2-(3,5-dimethoxyphenyl)ethyl]-5-(phenylsulfonyl)-6-(1H-pyrazol-4-yl)-5H-pyrrolo[2,3-b]pyrazine (25.0 mg, 51.1 μmol) in acetonitrile (1.0 mL), 1,8-diazabicyclo[5.4.0]undec-7-ene (9.2 μL, 61.5 μmol) and (2E)-3-cyclopentylacrylonitrile (from Adesis, cat#9-245, 6.8 μL, 61.7 μmol) were added sequentially at room temperature. After 16 hours, the volatiles were removed and the crude mixture was purified on RP-HPLC (XBridge C18 column, eluting with a gradient of acetonitrile/water containing 0.05% TFA, at flow rate of 30 mL/min) to give the desired product (4.2 mg) as its TFA salt. LCMS calculated for $C_{27}H_{31}N_6O_2$ (M+H)$^+$: m/z=471.2. Found: 471.2.

Example 36

3-(4-(2-(3,5-dimethoxyphenethyl)-5H-pyrrolo[2,3-b]pyrazin-6-yl)-1H-pyrazol-1-l)butanenitrile

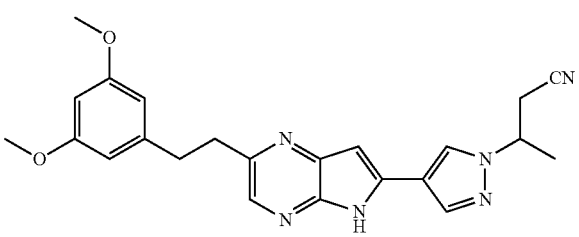 [SMILES: COc1cc(CCc2cnc3[nH]c(-c4cnn(C(C)CC#N)c4)cc3n2)cc(OC)c1]

This compound was prepared using procedures analogous to those for Example 35, Step 2, with 2-butenenitrile replacing (2E)-3-cyclopentylacrylonitrile. LCMS calculated for $C_{23}H_{25}N_6O_2$ (M+H)$^+$: m/z=417.2. Found: 417.2.

Example 37

2-[2-(3,5-dimethoxyphenyl)ethyl]-6-[1-(1-methylpiperidin-4-yl)-1H-pyrazol-4-yl]-5H-pyrrolo[2,3-b]pyrazine

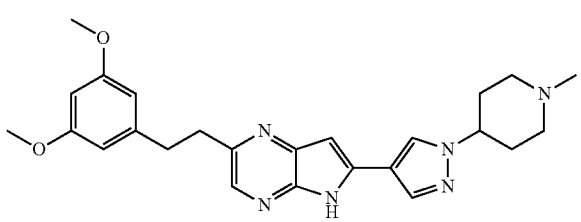

Step 1. 1-methylpiperidin-4-yl methanesulfonate

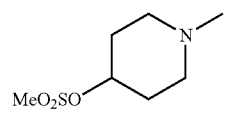

4-Hydroxy-N-methylpiperidine (200 μL, 1.70 mmol) was dissolved in methylene chloride (10 mL) and then cooled to 0° C. Triethylamine (296 μL, 2.13 mmol) was added, followed by the addition of methanesulfonyl chloride (145

μL, 1.87 mmol). After 1.5 hours, the reaction was quenched with water, and extracted with methylene chloride. The combined organic layers were dried over MgSO$_4$, then concentrated under vacuum to give the desired product (280 mg, 88%). LCMS calculated for C$_7$H$_{16}$NO$_3$S (M+H)$^+$: m/z=194.1. Found: 194.1.

Step 2. 2-[2-(3,5-dimethoxyphenyl)ethyl]-6-[1-(1-methylpiperidin-4-yl)-1H-pyrazol-4-yl]-5H-pyrrolo[2,3-b]pyrazine

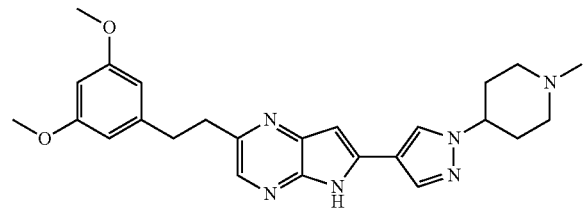

To a stirred solution of 2-[2-(3,5-dimethoxyphenyl)ethyl]-5-(phenylsulfonyl)-6-(1H-pyrazol-4-yl)-5H-pyrrolo[2,3-b]pyrazine (from Example 35, Step 1, 50.0 mg, 0.102 mmol) in N,N-dimethylformamide (2.0 mL), sodium hydride (6.13 mg, 0.153 mmol) was added at 0° C. After 15 minutes, a solution of 1-methylpiperidin-4-yl methanesulfonate (23.7 mg, 0.122 mmol) in N,N-dimethylformamide (1 mL) was added. The reaction mixture was then warmed up to 55° C. After 2 hours, the reaction was quenched with water, and extracted with methylene chloride. The combined organic layers were dried over MgSO$_4$, then filtered and concentrated. The crude mixture was purified on RP-HPLC (XBridge C18 column, eluting with a gradient of acetonitrile/water containing 0.05% TFA, at flow rate of 30 mL/min) to give the desired product (2.2 mg) as its TFA salt. LCMS calculated for C$_{25}$H$_{31}$N$_6$O$_2$ (M+H)$^+$: m/z=447.3. Found: 447.3.

Example 38

2-(4-{2-[2-(3,5-dimethoxyphenyl)ethyl]-5H-pyrrolo[2,3-b]pyrazin-6-yl}-1H-pyrazol-1-yl)ethanol

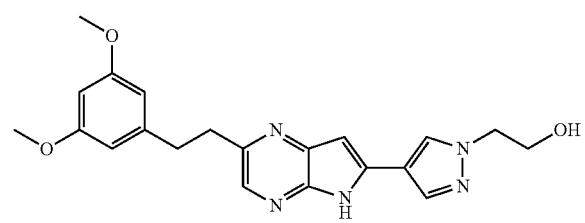 [SMILES: COc1cc(CCc2cnc3[nH]c(-c4cnn(CCO)c4)cc3n2)cc(OC)c1]

To a stirred solution of 2-[2-(3,5-dimethoxyphenyl)ethyl]-5-(phenylsulfonyl)-6-(1H-pyrazol-4-yl)-5H-pyrrolo[2,3-b]pyrazine (from Example 35, Step 1, 30.0 mg, 0.0613 mmol) in acetonitrile (1 mL), cesium carbonate (20.0 mg, 0.0613 mmol) and (2-bromoethoxy) (tert-butyl)dimethylsilane (13.1 μL, 0.0613 mmol) were added sequentially at ambient temperature. The reaction mixture was warmed up to 60° C. After 2 hours, the reaction was quenched with water, and extracted with methylene chloride. The combined organic layers were dried over MgSO$_4$, concentrated. The residue was dissolved in methylene chloride (1.0 m)/trifluoroacetic acid (1.0 mL) at ambient temperature. After 2 hours, the volatiles were removed under vacuum and the residues were dissolved in methanol (2.0 mL). Potassium carbonate (16.9 mg, 0.122 mmol) was added and the reaction mixture was warmed up to 60° C. After 1 hour, the crude mixture was purified on RP-HPLC (XBridge C18 column, eluting with a gradient of acetonitrile/water containing 0.05% TFA, at flow rate of 30 mL/min) to give the desired product (3.5 mg) as its TFA salt. LCMS calculated for C$_{21}$H$_{24}$N$_5$O$_3$ (M+H)$^+$: m/z=394.2. Found: 394.2.

Example 39

(2S)-1-(4-{2-[2-(3,5-dimethoxyphenyl)ethyl]-5H-pyrrolo[2,3-b]pyrazin-6-yl}-1H-pyrazol-1-yl)propan-2-ol

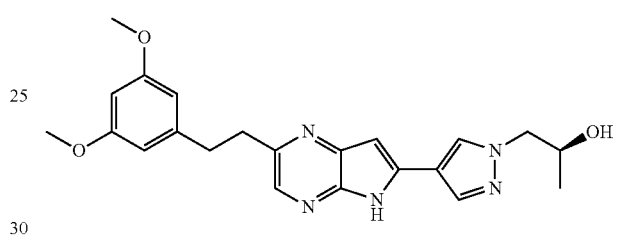

To a stirred solution of 2-[2-(3,5-dimethoxyphenyl)ethyl]-5-(phenylsulfonyl)-6-(1H-pyrazol-4-yl)-5H-pyrrolo[2,3-b]pyrazine (from Example 35, Step 1, 30.0 mg, 0.0613 mmol) and (S)-(−)-methyloxirane (8.56 μL, 0.122 mmol) in isopropyl alcohol (2 mL)/N,N-dimethylformamide (0.5 mL), triethylamine (17.1 μL, 0.122 mmol) was added at ambient temperature. The reaction mixture was then warmed up to 90° C. After 2 hours, the volatiles were removed and the residue was dissolved in methanol (2 mL). Potassium carbonate (16.9 mg, 0.122 mmol) was added and the reaction mixture was warmed up to 60° C. After 30 minutes, the crude mixture was purified on RP-HPLC (XBridge C18 column, eluting with a gradient of acetonitrile/water containing 0.05% TFA, at flow rate of 30 mL/min) to give the desired product (3.8 mg) as its TFA salt. LCMS calculated for C$_{22}$H$_{26}$N$_5$O$_3$ (M+H)$^+$: m/z=408.2. Found: 408.2.

Example 40

1-[2-(4-{2-[2-(3,5-dimethoxyphenyl)ethyl]-5H-pyrrolo[2,3-b]pyrazin-6-yl}-1H-pyrazol-1-yl)ethyl]piperidin-4-ol

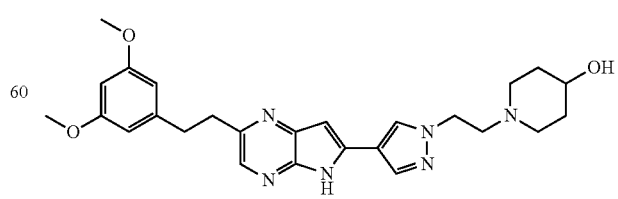

To a stirred solution of 1-piperidineethanol (7.9 mg, 0.0613 mmol) and triphenylphosphine (16.1 mg, 0.0613 mmol) in tetrahydrofuran (1.0 mL), diethyl azodicarboxylate (9.65 µL, 0.0613 mmol) was added at ambient temperature. After 15 minutes, a solution of 2-[2-(3,5-dimethoxyphenyl)ethyl]-5-(phenylsulfonyl)-6-(1H-pyrazol-4-yl)-5H-pyrrolo[2,3-b]pyrazine (from Example 35, Step 1, 25 mg, 0.0510 mmol) in tetrahydrofuran (0.5 mL) was added. After 16 hours, the reaction was quenched with saturated aqueous NaHCO$_3$, extracted with methylene chloride. The combined organic layers were dried over MgSO$_4$, and then concentrated. The residue was dissolved in methanol (2 mL) and potassium carbonate (14.1 mg, 0.102 mmol) was added. The reaction mixture was then warmed up to 60° C. After 30 minutes, the crude mixture was cooled to ambient temperature and purified on RP-HPLC (XBridge C18 column, eluting with a gradient of acetonitrile/water containing 0.05% TFA, at flow rate of 30 mL/min) to give the desired product (3.2 mg) as its TFA salt. LCMS calculated for $C_{26}H_{33}N_6O_3$ (M+H)$^+$: m/z=477.3. Found: 477.2.

Example 41

2-[2-(3,5-dimethoxyphenyl)ethyl]-6-[1-(2-piperidin-1-ylethyl)-1H-pyrazol-4-yl]-5H-pyrrolo[2,3-b]pyrazine

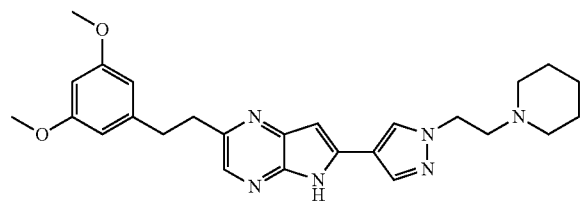 [SMILES: COc1cc(CCc2cnc3[nH]c(-c4cnn(CCN5CCCCC5)c4)cc3n2)cc(OC)c1]

This compound was prepared using procedures analogous to those for Example 40, with 2-(piperidin-1-yl)ethanol replacing 1-piperidineethanol. LCMS calculated for $C_{26}H_{33}N_6O_2$ (M+H)$^+$: m/z=461.3. Found: 461.2.

Example 42

2-[2-(3,5-dimethoxyphenyl)ethyl]-6-{1-[2-(4-methylpiperazin-1-yl)ethyl]-1H-pyrazol-4-yl}-5H-pyrrolo[2,3-b]pyrazine

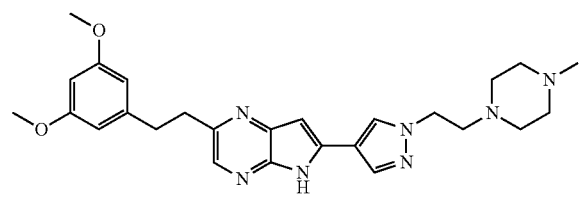

This compound was prepared using procedures analogous to those for Example 40, with 2-(4-methylpiperazin-1-yl)ethanol replacing 1-piperidineethanol. LCMS calculated for $C_{26}H_{34}N_7O_2$ (M+H)$^+$: m/z=476.3. Found: 476.2.

Example 43

2-(4-{2-[2-(3,5-dimethoxyphenyl)ethyl]-5H-pyrrolo[2,3-b]pyrazin-6-yl}-1H-pyrazol-1-yl)-N,N-dimethylacetamide

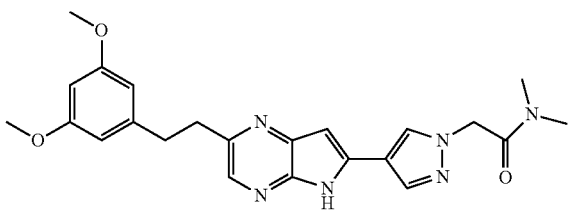

Step 1. {4-[2-[2-(3,5-dimethoxyphenyl)ethyl]-5-(phenylsulfonyl)-5H-pyrrolo[2,3-b]pyrazin-6-yl]-1H-pyrazol-1-yl}acetic acid

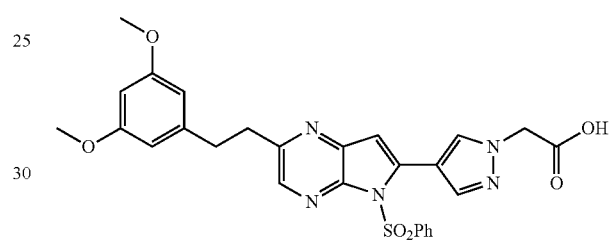

A stirred mixture of 6-bromo-2-[2-(3,5-dimethoxyphenyl)ethyl]-5-(phenylsulfonyl)-5H-pyrrolo[2,3-b]pyrazine (from Example 1, Step 4, 40.0 mg, 79.7 µmol), [1,1'-bis(diphenylphosphino)ferrocene]dichloropalladium(II) complexed with dichloromethane (1:1) (3.25 mg, 3.98 µmol), tert-butyl [4-(4,4,5,5-tetramethyl-1,3,2-dioxaborolan-2-yl)-1H-pyrazol-1-yl]acetate (24.5 mg, 79.6 µmol), and potassium phosphate (33.8 mg, 0.159 mmol) in water (0.5 mL)/1,4-dioxane (1.0 mL) was heated at 88° C. After 1 hour, the reaction was quenched with saturated aqueous NH$_4$Cl, extracted with methylene chloride. The combined organic layers were dried over MgSO$_4$, and then concentrated. The residue was dissolved in methylene chloride (1 mL) and trifluoroacetic acid (1 mL) was added at ambient temperature. After 2 hours, the volatiles were removed under vacuum to afford the desired product (40 mg, 92%). LCMS calculated for $C_{27}H_{26}N_5O_6S$ (M+H)$^+$: m/z=548.2. Found: 548.2.

Step 2. 2-(4-{2-[2-(3,5-dimethoxyphenyl)ethyl]-5H-pyrrolo[2,3-b]pyrazin-6-yl}-1H-pyrazol-1-yl)-N,N-dimethylacetamide

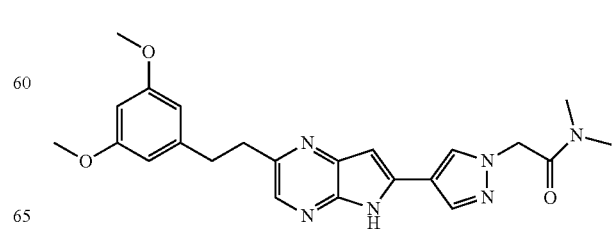

To a stirred solution of {4-[2-[2-(3,5-dimethoxyphenyl)ethyl]-5-(phenylsulfonyl)-5H-pyrrolo[2,3-b]pyrazin-6-yl]-1H-pyrazol-1-yl}acetic acid (10.0 mg, 18.3 μmol) in N,N-dimethylformamide (1.0 mL), N,N-dimethylamine (2.0M in THF, 13.7 μL, 27.4 μmol), N,N,N',N'-tetramethyl-O-(7-azabenzotriazol-1-yl)uronium hexafluorophosphate (8.33 mg, 21.9 μmol) and N,N-diisopropylethylamine (12.7 μL, 73.0 μmol) were added sequentially at ambient temperature. After 1 hour, the reaction was quenched with saturated aqueous NH$_4$Cl, extracted with methylene chloride. The combined organic layers were dried over MgSO$_4$, and then concentrated. The residue was dissolved in methanol (2.0 mL) and potassium carbonate (5.05 mg, 36.5 μmol) was added. The reaction mixture was then warmed up to 60° C. After 2 hours, the crude mixture was cooled to ambient temperature and purified on RP-HPLC (XBridge C18 column, eluting with a gradient of acetonitrile/water containing 0.05% TFA, at flow rate of 30 mL/min) to give the desired product (2.8 mg) as its TFA salt. LCMS calculated for C$_{23}$H$_{27}$N$_6$O$_3$ (M+H)$^+$: m/z=435.2. Found: 435.3.

Example 44

2-(4-(2-(3,5-dimethoxyphenethyl)-5H-pyrrolo[2,3-b]pyrazin-6-yl)-1H-pyrazol-1-yl)-1-(4-methylpiperazin-1-yl)ethanone

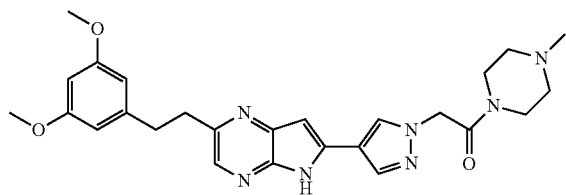

This compound was prepared using procedures analogous to those for Example 43, Step 2, with 1-methylpiperazine replacing N,N-dimethylamine (2.0M in THF). LCMS calculated for C$_{26}$H$_{32}$N$_7$O$_3$ (M+H)$^+$: m/z=490.3. Found: 490.3.

Example 45

2-[2-(3,5-dimethoxyphenyl)ethyl]-6-[4-(4-methylpiperazin-1-yl)phenyl]-5H-pyrrolo[2,3-b]pyrazine-7-carbonitrile

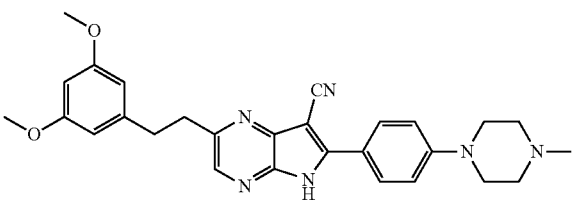

To a stirred solution of 2-[2-(3,5-dimethoxyphenyl)ethyl]-6-[4-(4-methylpiperazin-1-yl)phenyl]-5H-pyrrolo[2,3-b]pyrazine (from Example 1, Step 5, 50.0 mg, 10.9 μmol) in N,N-dimethylformamide (2 mL), chlorosulfonyl isocyanate (24.0 μL, 27.6 μmol) was added at 0° C. The reaction mixture was then warmed to ambient temperature and kept stirring overnight. The volatiles were removed and the residue was purified on RP-HPLC (XBridge C18 column, eluting with a gradient of acetonitrile/water containing 0.05% TFA, at flow rate of 30 mL/min) to give the desired product (1.2 mg) as its TFA salt. LCMS calculated for C$_{28}$H$_{31}$N$_6$O$_2$ (M+H)$^+$: m/z=483.2. Found: 483.2.

Example 46

7-bromo-2-[2-(3,5-dimethoxyphenyl)ethyl]-6-[4-(4-methylpiperazin-1-yl)phenyl]-5H-pyrrolo[2,3-b]pyrazine

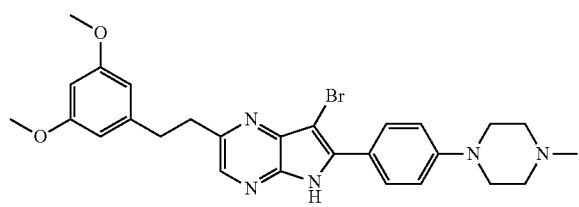

To a stirred solution of 2-[2-(3,5-dimethoxyphenyl)ethyl]-6-[4-(4-methylpiperazin-1-yl)phenyl]-5H-pyrrolo[2,3-b]pyrazine (from Example 1, Step 5, 120 mg, 0.262 mmol) in methylene chloride (2 mL), a solution of N-bromosuccinimide (46.7 mg, 0.262 mmol) in methylene chloride (1 mL) was added dropwise at 0° C. After 30 minutes, the reaction was quenched with saturated aqueous NaHCO$_3$, then extracted with methylene chloride. The combined organic layers were dried over MgSO$_4$, and then concentrated. The residue was purified on silica gel (eluting with 0 to 10% MeOH in dichloromethane (DCM)) to give the desired product (110 mg, 78%). LCMS calculated for C$_{27}$H$_{31}$BrN$_5$O$_2$ (M+H)$^+$: m/z=536.2. Found: 536.2.

Example 47

7-chloro-2-[2-(3,5-dimethoxyphenyl)ethyl]-6-[4-(4-methylpiperazin-1-yl)phenyl]-5H-pyrrolo[2,3-b]pyrazine

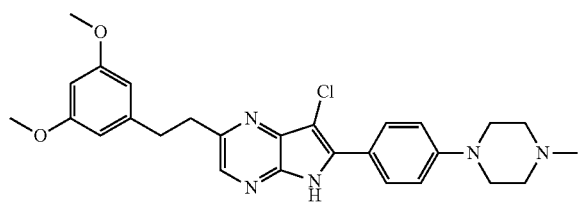

This compound was prepared using procedures analogous to those for Example 30, with N-chlorosuccinimide replacing N-bromosuccinimide. LCMS calculated for C$_{27}$H$_{31}$ClN$_5$O$_2$ (M+H)$^+$: m/z=492.2. Found: 492.3.

Example 48

2-[2-(2-chloro-3,5-dimethoxyphenyl)ethyl]-6-[4-(4-methylpiperazin-1-yl)phenyl]-5H-pyrrolo[2,3-b]pyrazine

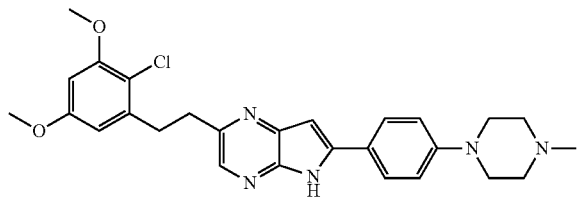

Step 1. 2-[2-(3,5-dimethoxyphenyl)ethyl]-6-[4-(4-methylpiperazin-1-yl)phenyl]-5-(phenylsulfonyl)-5H-pyrrolo[2,3-b]pyrazine

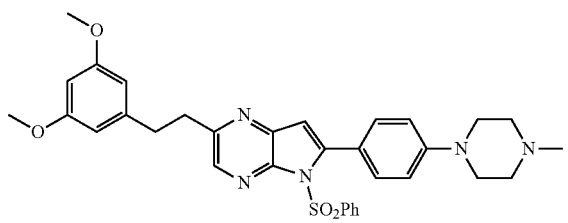

A stirred mixture of 6-bromo-2-[2-(3,5-dimethoxyphenyl)ethyl]-5-(phenylsulfonyl)-5H-pyrrolo[2,3-b]pyrazine (from Example 1, step 4, 30.0 mg, 59.7 μmol), 1-methyl-4-[4-(4,4,5,5-tetramethyl-1,3,2-dioxaborolan-2-yl)phenyl]piperazine (from Alfa Aesar, cat#H51659, 19.8 mg, 6.57 μmol), [1,1'-bis(diphenylphosphino)ferrocene]dichloropalladium (II) complexed with dichloromethane (1:1) (4.9 mg, 5.97 mmol), and potassium phosphate (25.4 mg, 119 μmol) in water (0.2 mL)/1,4-dioxane (1 mL) was heated at 88° C. After another 1 hour, the reaction mixture was quenched with saturated aq. NH$_4$Cl, extracted with methylene chloride. The combined organic layers were dried over MgSO$_4$, then concentrated to give the desired product (25 mg, 70%). LCMS calculated for C$_{33}$H$_{36}$N$_5$O$_4$S (M+H)$^+$: m/z=598.3. Found: 598.3.

Step 2. 2-[2-(2-chloro-3,5-dimethoxyphenyl)ethyl]-6-[4-(4-methylpiperazin-1-yl)phenyl]-5H-pyrrolo[2,3-b]pyrazine

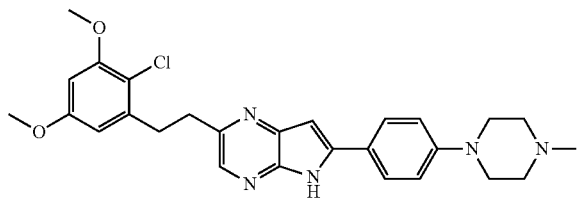

To a stirred solution of 2-[2-(3,5-dimethoxyphenyl)ethyl]-6-[4-(4-methylpiperazin-1-yl)phenyl]-5-(phenylsulfonyl)-5H-pyrrolo[2,3-b]pyrazine (25 mg, 41.9 μmol) in methylene chloride (2 mL) at 0° C., a solution of sulfuryl chloride (6.0 μL, 75 μmol) in methylene chloride (1 mL) was added dropwise. After 30 minutes, the volatiles were removed and the residue was dissolved in methanol (2 mL) and potassium carbonate (27.5 mg, 0.199 mmol) was added. The reaction mixture was then warmed up to 60° C. After 30 minutes, the crude mixture was purified on RP-HPLC (XBridge C18 column, eluting with a gradient of acetonitrile/water containing 0.05% TFA, at flow rate of 30 mL/min) to give the desired product (2.5 mg) as its TFA salt. LCMS calculated for C$_{27}$H$_{31}$ClN$_5$O$_2$ (M+H)$^+$: m/z=492.2. Found: 492.2.

Example 49

2-[2-(2,6-dichloro-3,5-dimethoxyphenyl)ethyl]-6-[4-(4-methylpiperazin-1-yl)phenyl]-5H-pyrrolo[2,3-b]pyrazine

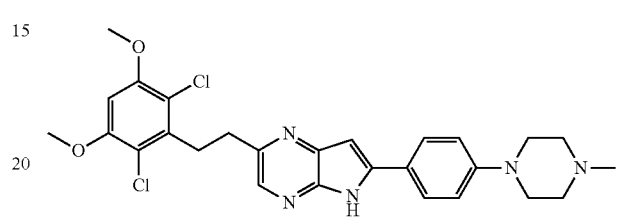

This compound was prepared using procedures same with those for Example 48. LCMS calculated for C$_{27}$H$_{30}$C$_{12}$N$_5$O$_2$ (M+H)$^+$: m/z=526.2. Found: 526.2.

Example 50

2-[2-(3,5-dimethoxyphenyl)ethyl]-N-methyl-6-[4-(4-methylpiperazin-1-yl)phenyl]-5H-pyrrolo[2,3-b]pyrazine-7-carboxamide

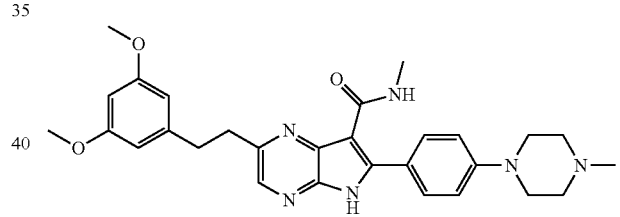

Step 1. 7-bromo-2-[2-(3,5-dimethoxyphenyl)ethyl]-6-[4-(4-methylpiperazin-1-yl)phenyl]-5-{[2-(trimethylsilyl)ethoxy]methyl}-5H-pyrrolo[2,3-b]pyrazine

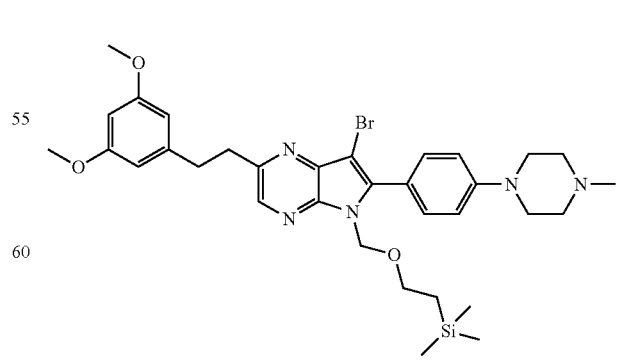

To a stirred solution of 7-bromo-2-[2-(3,5-dimethoxyphenyl)ethyl]-6-[4-(4-methylpiperazin-1-yl)phenyl]-5H-pyrrolo[2,3-b]pyrazine (from Example 46, 110 mg, 0.205 mmol) in tetrahydrofuran (2 mL), sodium hydride (12.0 mg, 0.300 mmol) was added at 0° C. After 10 min, [β-(trimethylsilyl)ethoxy]methyl chloride (55.7 µL, 0.315 mmol) was added dropwise. After another 1 hour, the reaction was quenched with saturated aqueous NH$_4$Cl, extracted with methylene chloride. The combined organic layers were dried over MgSO$_4$, and then concentrated. The residue was purified on silica gel (eluting with 0 to 8% MeOH in DCM) to give the desired product (55 mg, 31%). LCMS calculated for $C_{33}H_{45}BrN_5O_3Si$ (M+H)$^+$: m/z=666.2. Found: 666.3.

Step 2. 2-[2-(3,5-dimethoxyphenyl)ethyl]-6-[4-(4-methylpiperazin-1-yl)phenyl]-5-{[2-(trimethylsilyl)ethoxy]methyl}-5H-pyrrolo[2,3-b]pyrazine-7-carboxylic acid

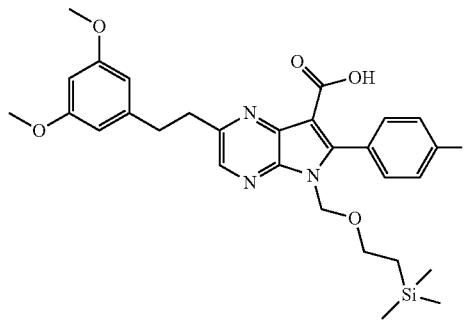

The a stirred solution of 7-bromo-2-[2-(3,5-dimethoxyphenyl)ethyl]-6-[4-(4-methylpiperazin-1-yl)phenyl]-5-{[2-(trimethylsilyl)ethoxy]methyl}-5H-pyrrolo[2,3-b]-pyrazine (55 mg, 82.7 µmol) in tetrahydrofuran (2 mL), n-butyllithium (2.5M in hexanes, 50 µL, 0.125 mmol) was added at −78° C. After 10 minutes, dry CO$_2$ (prepared by passing the CO$_2$ through drying tube) was bubbled into the reaction. After 20 minutes, the reaction was quenched with saturated aqueous NH$_4$Cl, then extracted with methylene chloride. The combined organic layers were dried over MgSO$_4$, then concentrated to give the crude product (50 mg), which was used directly in the next step. LCMS calculated for $C_{34}H_{46}BN_5O_5Si$ (M+H)$^+$: m/z=632.3. Found: 632.3.

Step 3. 2-[2-(3,5-dimethoxyphenyl)ethyl]-N-methyl-6-[4-(4-methylpiperazin-1-yl)phenyl]-5H-pyrrolo[2,3-b]pyrazine-7-carboxamide

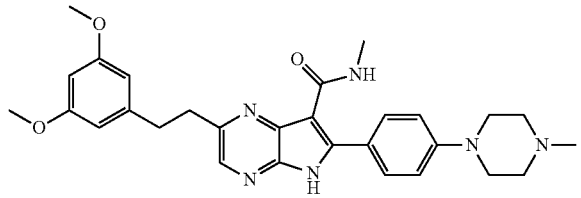

To a stirred solution of crude 2-[2-(3,5-dimethoxyphenyl)ethyl]-6-[4-(4-methylpiperazin-1-yl)phenyl]-5-{[2-(trimethylsilyl)ethoxy]methyl}-5H-pyrrolo[2,3-b]pyrazine-7-carboxylic acid (20 mg, 31.6 µmol) in N,N-dimethylformamide (2 mL), HATU (12.0 mg, 31.6 µmol), 2.0M methylamine in THF (15.8 µL, 31.6 µmol) and N,N-diisopropylethylamine (11.0 µL, 63.3 mol) were added sequentially at ambient temperature. After 1 hour, the reaction was quenched with saturated aqueous NH$_4$Cl, extracted with methylene chloride. The combined organic layers were dried over MgSO$_4$, concentrated. The residue was dissolved in methylene chloride (1 mL) and trifluoroacetic acid (1 mL) was added at ambient temperature. After 2 hours, the volatiles were removed under vacuum and the residue was dissolved in methanol (1 mL), followed by the addition of ethylenediamine (0.1 mL). After another 1 hour, the reaction mixture was purified on RP-HPLC (XBridge C18 column, eluting with a gradient of acetonitrile/water containing 0.05% TFA, at flow rate of 30 mL/min) to give the desired product (3.5 mg) as its TFA salt. LCMS calculated for $C_{29}H_{35}N_6O_3$ (M+H)$^+$: m/z=515.3. Found: 515.2.

Example 51

2-[2-(3,5-dimethoxyphenyl)ethyl]-7-methyl-6-[4-(4-methylpiperazin-1-yl)phenyl]-5H-pyrrolo[2,3-b]pyrazine

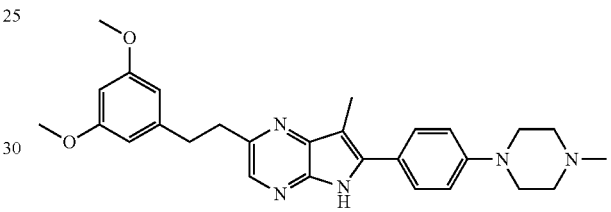

To a stirred solution of 7-bromo-2-[2-(3,5-dimethoxyphenyl)ethyl]-6-[4-(4-methylpiperazin-1-yl)phenyl]-5H-pyrrolo[2,3-b]pyrazine (from Example 46, 20.0 mg, 37.3 mol) and Pd(dppf)Cl$_2$ (2.7 mg, 3.7 µmol) in 1,4-dioxane (0.8 mL), dimethylzinc (2.0M in toluene, 47 µL, 94.0 µmol) was added at ambient temperature. The reaction mixture was then warmed up to 90° C. After 4 hours, the volatiles were removed and the residue was purified on RP-HPLC (XBridge C18 column, eluting with a gradient of acetonitrile/water containing 0.05% TFA, at flow rate of 30 mL/min) to give the desired product (4.2 mg) as its TFA salt. LCMS calculated for $C_{28}H_{34}N_5O_2$ (M+H)$^+$: m/z=472.2. Found: 472.2.

Example 52

2-[2-(3,5-dimethoxyphenyl)ethyl]-7-ethyl-6-[4-(4-methylpiperazin-1-yl)phenyl]-5H-pyrrolo[2,3-b]pyrazine

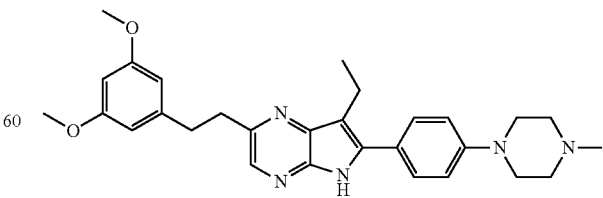

A stirred mixture of 7-bromo-2-[2-(3,5-dimethoxyphenyl)ethyl]-6-[4-(4-methylpiperazin-1-yl)phenyl]-5H-pyrrolo[2,3-b]pyrazine (from Example 46, 10.0 mg, 18.6 mol), [1,1'- bis(diphenylphosphino)ferrocene]dichloropalladium(II) complexed with dichloromethane (1:1) (1.22 mg, 1.49 µmol), 4,4,5,5-tetramethyl-2-vinyl-1,3,2-dioxaborolane (2.53 µL, 14.9 µmol), and potassium phosphate (6.33 mg, 29.8 µmol) in water (0.2 mL)/1,4-dioxane (0.5 mL) was heated at 88° C. After 1 hour, the volatiles were removed and the residue was dissolved in methanol (1 mL). Pd/C (10% w/w, 1.59 mg, 1.49 µmol) was then added. The reaction mixture was stirred under $H_2$ at ambient temperature. After 2 hours, the crude mixture was purified on RP-HPLC (XBridge C18 column, eluting with a gradient of acetonitrile/water containing 0.05% TFA, at flow rate of 30 mL/min) to give the desired product (3.2 mg) as its TFA salt. LCMS calculated for $C_{29}H_{36}N_5O_2$ $(M+H)^+$: m/z=486.2. Found: 486.2; $^1H$ NMR (400 MHz, DMSO-$d_6$): δ 11.76 (s, 1H), 9.68 (s, 1H), 8.03 (s, 1H), 7.61 (d, J=9.0 Hz, 2H), 7.16 (d, J=9.0 Hz, 2H), 6.39 (d, J=2.4 Hz, 2H), 6.28 (t, J=2.0 Hz, 1H), 3.99 (d, J=11.5 Hz, 2H), 3.68 (s, 6H), 3.53 (d, J=12.0 Hz, 2H), 3.20-2.97 (m, 8H), 2.91 (q, J=7.5 Hz, 2H), 2.87 (s, 3H), 1.28 (t, J=7.5 Hz, 3H) ppm.

Example 53

2-Chloro-4-(2-(3,5-dimethoxyphenethyl)-5H-pyrrolo[2,3-b]pyrazin-6-yl)-N-isopropylbenzamide

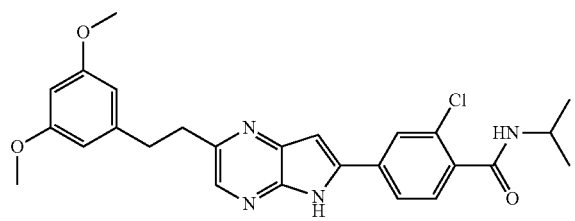 [SMILES: COc1cc(CCc2cnc3[nH]c(-c4ccc(C(=O)NC(C)C)c(Cl)c4)cc3n2)cc(OC)c1]

Step 1. 6-Bromo-2-[2-(3,5-dimethoxyphenyl)ethyl]-5H-pyrrolo[2,3-b]pyrazine

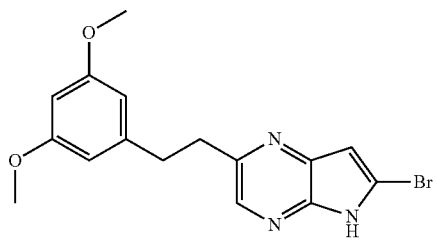 [SMILES: COc1cc(CCc2cnc3[nH]c(Br)cc3n2)cc(OC)c1]

6.0M Potassium hydroxide in water (0.50 mL, 3.0 mmol) was added to a solution of 6-bromo-2-[2-(3,5-dimethoxyphenyl)ethyl]-5-(phenyl sulfonyl)-5H-pyrrolo[2,3-b]pyrazine (0.5 g, 0.9952 mmol) (from Example 1, Step 4) in THF (10 mL) and then the mixture was stirred at 70 OC for 3 hours. Most of the solvent was removed and the residue was treated with saturated ammonium chloride. The formed precipitate was filtered, washed with water, and dried to provide the desired product (0.34 g, 94%). LCMS calculated for $C_{16}H_{17}BrN_3O$ $(M+H)^+$: m/z=362.0. Found 362.0.

Step 2. 2-Chloro-4-(2-(3,5-dimethoxyphenethyl)-5H-pyrrolo[2,3-b]pyrazin-6-yl)-N-isopropylbenzamide

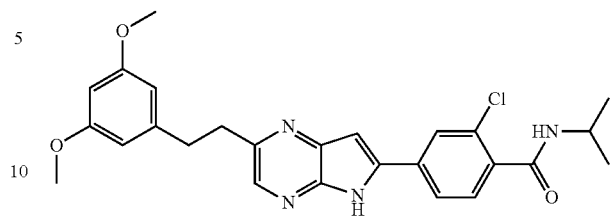

A mixture of 6-bromo-2-[2-(3,5-dimethoxyphenyl)ethyl]-5H-pyrrolo[2,3-b]pyrazine (10.0 mg, 0.0276 mmol), 2-chloro-N-isopropyl-4-(4, 4, 5, 5-tetramethyl-1, 3, 2-dioxaborolan-2-yl)benzamide (13.0 mg, 0.041 mmol, from Combi-Blocks), sodium carbonate (5.8 mg, 0.055 mmol) and dichloro(bis{di-tert-butyl[4-(dimethylamino)phenyl]phosphoranyl})-palladium (0.59 mg, 0.00083 mmol) in 1,4-dioxane (0.5 mL)/water (0.1 mL) was evacuated and refilled with $N_2$ three times. The reaction was then stirred at 110° C. overnight. The mixture was purified by RP-HPLC (pH=2, TFA as the media) to afford the desired product as TFA salt. LCMS calculated for $C_{26}H_{28}ClN_4O_3$ $(M+H)^+$: m/z=479.2. Found 479.1.

Example 54

5-(2-(3,5-Dimethoxyphenethyl)-5H-pyrrolo[2,3-b]pyrazin-6-yl)-2-fluoro-N,N-dimethylbenzamide

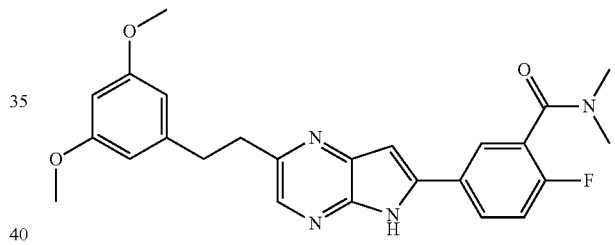

The compound was prepared by using procedure analogous to those described for the synthesis of Example 53, Step 2 starting from 6-bromo-2-[2-(3,5-dimethoxyphenyl)ethyl]-5H-pyrrolo[2,3-b]pyrazine and 3-(dimethylcarbamoyl)-4-fluorophenylboronic acid (from Combi-Blocks). LCMS calculated for $C_{25}H_{26}FN_4O_3$ $(M+H)^+$: m/z=449.2. Found 449.1.

Example 55

2-(3,5-Dimethoxyphenethyl)-6-(2-(4-methylpiperazin-1-yl)pyridin-4-yl)-5H-pyrrolo[2,3-b]pyrazine

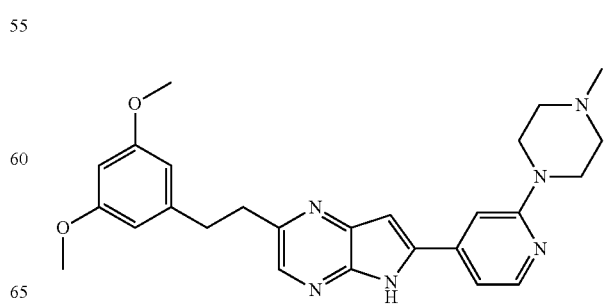

The compound was prepared by using procedure analogous to those described for the synthesis of Example 53, Step 2 starting from 6-bromo-2-[2-(3,5-dimethoxyphenyl)ethyl]-5H-pyrrolo[2,3-b]pyrazine and 1-methyl-4-[4-(4,4,5,5-tetramethyl-1,3,2-dioxaborolan-2-yl)pyridin-2-yl]piperazine (from Boron Molecular). LCMS calculated for $C_{26}H_{31}N_6O_2$ (M+H)$^+$: m/z=459.2. Found 459.1.

Example 56

2-Chloro-4-(2-(3,5-dimethoxyphenethyl)-5H-pyrrolo[2,3-b]pyrazin-6-yl)-N,N-dimethylbenzamide

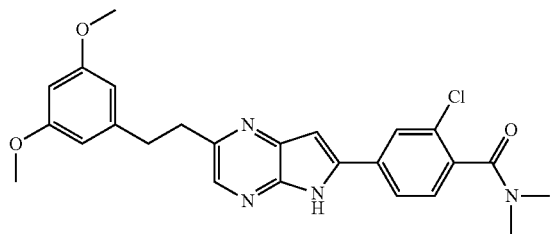 [SMILES: COc1cc(CCc2cnc3[nH]c(-c4ccc(C(=O)N(C)C)c(Cl)c4)cc3n2)cc(OC)c1]

The compound was prepared by using procedures analogous to those described for the synthesis of Example 53, Step 2 starting from 6-bromo-2-[2-(3,5-dimethoxyphenyl)ethyl]-5H-pyrrolo[2,3-b]pyrazine and 3-chloro-4-(dimethylcarbamoyl)phenylboronic acid (from Combi-Blocks). LCMS calculated for $C_{25}H_{26}ClN_4O_3$ (M+H)$^+$: m/z=465.2. Found 465.1.

Example 57

4-(2-(3,5-Dimethoxyphenethyl)-5H-pyrrolo[2,3-b]pyrazin-6-yl)-2-fluoro-N-methylbenzamide

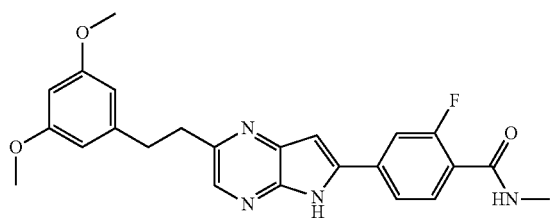 [SMILES: CNC(=O)c1ccc(-c2cc3nc(CCc4cc(OC)cc(OC)c4)cnc3[nH]2)cc1F]

The compound was prepared by using procedures analogous to those described for the synthesis of Example 53, Step 2 starting from 6-bromo-2-[2-(3,5-dimethoxyphenyl)ethyl]-5H-pyrrolo[2,3-b]pyrazine and 3-fluoro-4-(methylcarbamoyl)phenylboronic acid (from Combi-Blocks). LCMS calculated for $C_{24}H_{24}FN_4O_3$ (M+H)$^+$: m/z=435.2. Found 435.2.

Example 58

5-(2-(3,5-Dimethoxyphenethyl)-5H-pyrrolo[2,3-b]pyrazin-6-yl)pyrimidin-2-amine

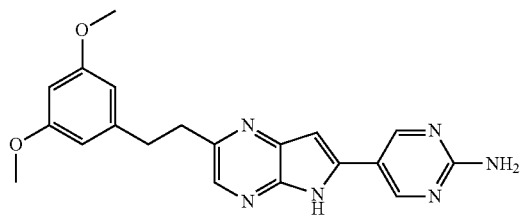 [SMILES: COc1cc(CCc2cnc3[nH]c(-c4cnc(N)nc4)cc3n2)cc(OC)c1]

The compound was prepared by using procedures analogous to those described for the synthesis of Example 53, Step 2 starting from 6-bromo-2-[2-(3,5-dimethoxyphenyl)ethyl]-5H-pyrrolo[2,3-b]pyrazine and 5-(4, 4, 5, 5-tetramethyl-1,3,2-dioxaborolan-2-yl)pyrimidin-2-amine (from Boron Molecular). LCMS calculated for $C_{20}H_{21}N_6O_2$ (M+H)$^+$: m/z=377.2. Found 377.1.

Example 59

5-(2-(3,5-Dimethoxyphenethyl)-5H-pyrrolo[2,3-b]pyrazin-6-yl)-N,N-dimethylpicolinamide

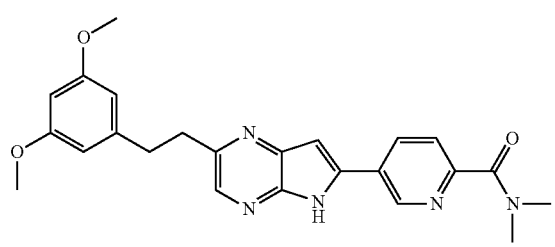 [SMILES: COc1cc(CCc2cnc3[nH]c(-c4ccc(C(=O)N(C)C)nc4)cc3n2)cc(OC)c1]

The compound was prepared by using procedures analogous to those described for the synthesis of Example 53, Step 2 starting from 6-bromo-2-[2-(3,5-dimethoxyphenyl)ethyl]-5H-pyrrolo[2,3-b]pyrazine and N,N-dimethyl-5-(4,4,5,5-tetramethyl-1,3,2-dioxaborolan-2-yl)pyridine-2-carboxamide (from PepTech Corp. Encyclopedia of Amino Acid Analogs and Boronic Acids). LCMS calculated for $C_{24}H_{26}N_5O_3$ (M+H)$^+$: m/z=432.2. Found 432.1.

Example 60

4-(2-(3,5-Dimethoxyphenethyl)-5H-pyrrolo[2,3-b]pyrazin-6-yl)picolinonitrile

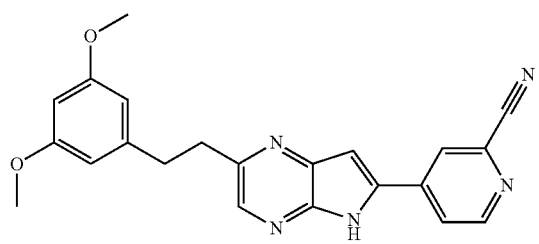 [SMILES: COc1cc(CCc2cnc3[nH]c(-c4ccnc(C#N)c4)cc3n2)cc(OC)c1]

The compound was prepared by using procedures analogous to those described for the synthesis of Example 53, Step 2 starting from 6-bromo-2-[2-(3,5-dimethoxyphenyl)ethyl]-5H-pyrrolo[2,3-b]pyrazine and 4-(4,4,5,5-tetramethyl-1,3,2-dioxaborolan-2-yl)pyridine-2-carbonitrile (from Combi-Blocks). LCMS calculated for $C_{22}H_{20}N_5O_2$ (M+H)$^+$: m/z=386.2. Found 386.2.

Example 61

2-(3,5-Dimethoxyphenethyl)-6-(6-methoxypyridin-3-yl)-5H-pyrrolo[2,3-b]pyrazine

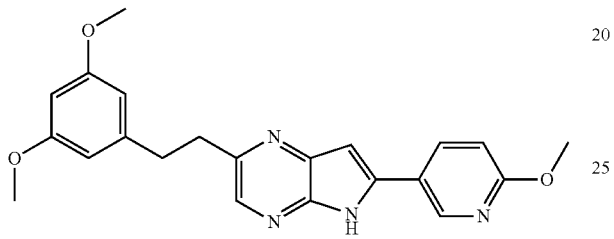

The compound was prepared by using procedures analogous to those described for the synthesis of Example 53, Step 2 starting from 6-bromo-2-[2-(3,5-dimethoxyphenyl)ethyl]-5H-pyrrolo[2,3-b]pyrazine and (6-methoxypyridin-3-yl)boronic acid (from Aldrich). LCMS calculated for $C_{22}H_{23}N_4O_3$ (M+H)$^+$: m/z=391.2. Found: m/z=391.1.

Example 62

2-(3,5-Dimethoxyphenethyl)-6-(1-methyl-1H-indazol-5-yl)-5H-pyrrolo[2,3-b]pyrazine

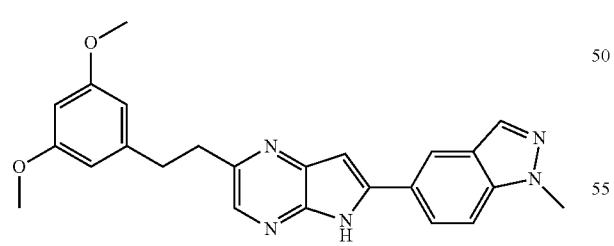

The compound was prepared by using procedures analogous to those described for the synthesis of Example 53, Step 2 starting from 6-bromo-2-[2-(3,5-dimethoxyphenyl)ethyl]-5H-pyrrolo[2,3-b]pyrazine and 1-methyl-5-(4,4,5,5-tetramethyl-1,3,2-dioxaborolan-2-yl)-1H-indazole (from Combi-Blocks). LCMS calculated for $C_{24}H_{24}N_5O_{52}$ (M+H)$^+$: m/z=414.2. Found 414.2.

Example 63

2-(3,5-Dimethoxyphenethyl)-6-(1-methyl-1H-indazol-6-yl)-5H-pyrrolo[2,3-b]pyrazine

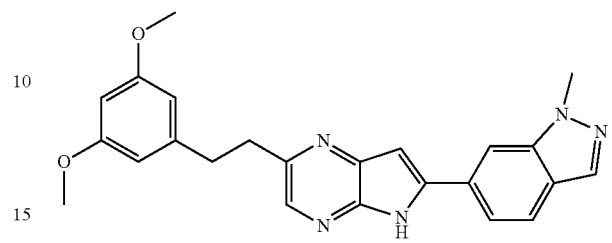

The compound was prepared by using procedures analogous to those described for the synthesis of Example 53, Step 2 starting from 6-bromo-2-[2-(3,5-dimethoxyphenyl)ethyl]-5H-pyrrolo[2,3-b]pyrazine and 1-methyl-6-(4,4,5,5-tetramethyl-1,3,2-dioxaborolan-2-yl)-1H-indazole (from Combi-Blocks). LCMS calculated for $C_{24}H_{24}N_5O_{52}$ (M+H)$^+$: m/z=414.2. Found 414.2.

Example 64

2-(3,5-Dimethoxyphenethyl)-6-(2-(piperazin-1-yl)pyridin-4-yl)-5H-pyrrolo[2,3-b]pyrazine

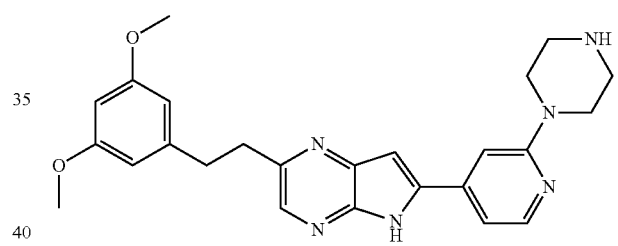

The compound was prepared by using procedure analogous to those described for the synthesis of Example 53, Step 2 starting from 6-bromo-2-[2-(3,5-dimethoxyphenyl)ethyl]-5H-pyrrolo[2,3-b]pyrazine and 1-[4-(4,4,5,5-tetramethyl-1,3,2-dioxaborolan-2-yl)pyridin-2-yl]piperazine (from Aldrich). LCMS calculated for $C_{25}H_{29}N_6O_2$ (M+H)$^+$: m/z=445.2. Found 445.2.

Example 65

5-(2-(3,5-Dimethoxyphenethyl)-5H-pyrrolo[2,3-b]pyrazin-6-yl)-2-fluorobenzonitrile

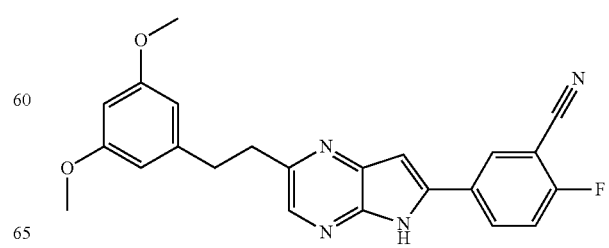

The compound was prepared by using procedures analogous to those described for the synthesis of Example 53, Step 2 starting from 6-bromo-2-[2-(3,5-dimethoxyphenyl)ethyl]-5H-pyrrolo[2,3-b]pyrazine and (4-cyano-3-fluorophenyl)boronic acid (from Aldrich). LCMS calculated for $C_{23}H_{20}FN_4O_2$ (M+H)$^+$: m/z=403.2. Found 403.2.

Example 66

7-(2-(3,5-Dimethoxyphenethyl)-5H-pyrrolo[2,3-b]pyrazin-6-yl)pyrido[2,3-b]pyrazine

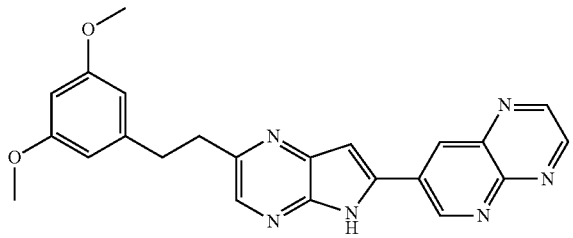 [SMILES: COc1cc(CCc2cnc3[nH]c(-c4cnc5nccnc5c4)cc3n2)cc(OC)c1]

The compound was prepared by using procedures analogous to those described for the synthesis of Example 53, Step 2 starting from 6-bromo-2-[2-(3,5-dimethoxyphenyl)ethyl]-5H-pyrrolo[2,3-b]pyrazine and 7-(4,4,5,5-tetramethyl-1,3,2-dioxaborolan-2-yl)pyrido[2,3-b]pyrazine (from Combi-Blocks). LCMS calculated for $C_{23}H_{21}N_6O_2$ (M+H)$^+$: m/z=413.2. Found 413.2.

Example 67

N-(5-(2-(3,5-Dimethoxyphenethyl)-5H-pyrrolo[2,3-b]pyrazin-6-yl)pyridin-2-yl)acetamide

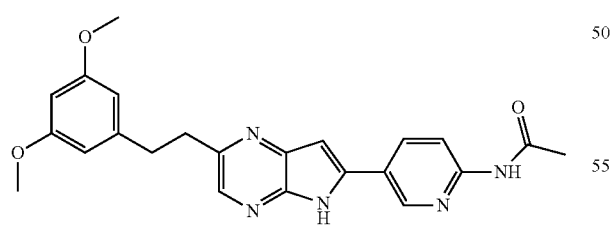

The compound was prepared by using procedures analogous to those described for the synthesis of Example 53, Step 2 starting from 6-bromo-2-[2-(3,5-dimethoxyphenyl)ethyl]-5H-pyrrolo[2,3-b]pyrazine and N-[5-(4,4,5,5-tetramethyl-1,3,2-dioxaborolan-2-yl)pyridin-2-yl]acetamide (from Combi-Blocks). LCMS calculated for $C_{23}H_{24}N_5O_3$ (M+H)$^+$: m/z=418.2. Found 418.1.

Example 68

1-(5-(2-(3,5-Dimethoxyphenethyl)-5H-pyrrolo[2,3-b]pyrazin-6-yl)pyridin-2-yl)pyrrolidin-2-one

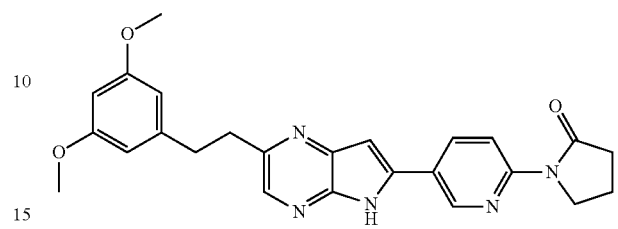

The compound was prepared by using procedures analogous to those described for the synthesis of Example 53, Step 2 starting from 6-bromo-2-[2-(3,5-dimethoxyphenyl)ethyl]-5H-pyrrolo[2,3-b]pyrazine and 1-[5-(4,4,5,5-tetramethyl-1,3,2-dioxaborolan-2-yl)pyridin-2-yl]pyrrolidin-2-one (from JPM2 Pharmaceuticals). LCMS calculated for $C_{25}H_{26}N_5O_3$ (M+H)$^+$: m/z=444.2. Found 444.2.

Example 69

4-(5-(2-(3,5-Dimethoxyphenethyl)-5H-pyrrolo[2,3-b]pyrazin-6-yl)pyridin-3-yl)morpholine

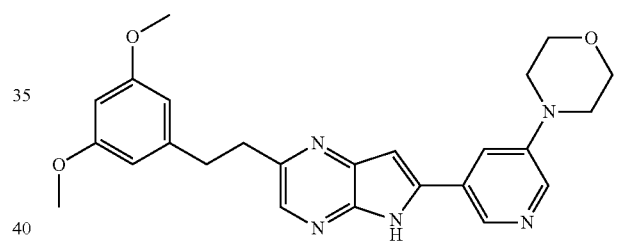

The compound was prepared by using procedures analogous to those described for the synthesis of Example 53, Step 2 starting from 6-bromo-2-[2-(3,5-dimethoxyphenyl)ethyl]-5H-pyrrolo[2,3-b]pyrazine and 4-[5-(4,4,5,5-tetramethyl-1,3,2-dioxaborolan-2-yl)pyridin-3-yl]morpholine (from Small Molecules). LCMS calculated for $C_{25}H_{28}N_5O_3$ (M+H)$^+$: m/z=446.2. Found 446.1.

Example 70

2-(3,5-Dimethoxyphenethyl)-6-(1H-indazol-5-yl)-5H-pyrrolo[2,3-b]pyrazine

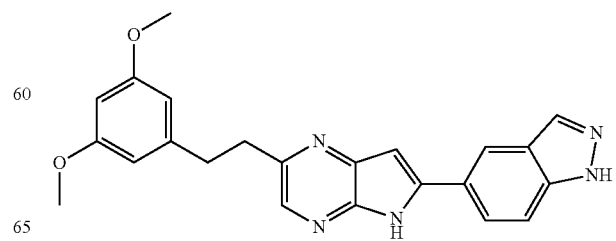

The compound was prepared by using procedures analogous to those described for the synthesis of Example 53, Step 2 starting from 6-bromo-2-[2-(3,5-dimethoxyphenyl)ethyl]-5H-pyrrolo[2,3-b]pyrazine and 2-[2-(3,5-dimethoxyphenyl)-ethyl]-6-(1H-indazol-5-yl)-5H-pyrrolo[2,3-b]pyrazine (from Combi-Blocks). LCMS calculated for $C_{23}H_{22}N_5O_2$ (M+H)$^+$: m/z=400.2. Found 400.1.

Example 71

2-(4-(4-(2-(3,5-Dimethoxyphenethyl)-5H-pyrrolo[2,3-b]pyrazin-6-yl)phenyl)piperazin-1-yl)ethanol

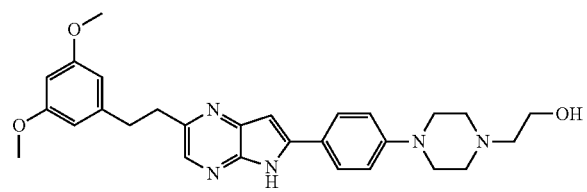 [SMILES: COc1cc(CCc2cnc3[nH]c(-c4ccc(N5CCN(CCO)CC5)cc4)cc3n2)cc(OC)c1]

Step 1. 1-(2-{[t-Butyl(dimethyl)silyl]oxy}ethyl)-4-[4-(4,4,5,5-tetramethyl-1,3,2-dioxaborolan-2-yl)phenyl]piperazine

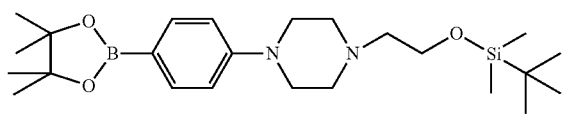 [SMILES: CC1(C)OB(c2ccc(N3CCN(CCO[Si](C)(C)C(C)(C)C)CC3)cc2)OC1(C)C]

A mixture of 1-[4-(4,4,5,5-tetramethyl-1,3,2-dioxaborolan-2-yl)phenyl]piperazine (0.1 g, 0.5 mmol, from Boron Molecular), (2-bromoethoxy)(tert-butyl)dimethylsilane (0.18 g, 0.75 mmol) and cesium carbonate (0.32 g, 1.0 mmol) in acetonitrile (2.0 mL) was stirred at 40° C. overnight. The residue was purified by flash chromatography on a silica gel column with ethyl acetate in hexanes (0-30%) to afford the desired product (0.2 g, 88%). LCMS calculated for $C_{24}H_{44}BN_2O_3Si$ (M+H)$^+$: m/z=447.3. Found 447.3.

Step 2. 2-(4-(4-(2-(3,5-Dimethoxyphenethyl)-5H-pyrrolo[2,3-b]pyrazin-6-yl)phenyl)piperazin-1-yl)ethanol

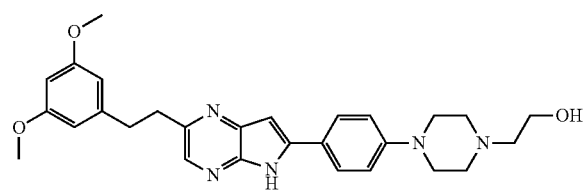 [SMILES: COc1cc(CCc2cnc3[nH]c(-c4ccc(N5CCN(CCO)CC5)cc4)cc3n2)cc(OC)c1]

A mixture of 6-bromo-2-[2-(3,5-dimethoxyphenyl)ethyl]-5H-pyrrolo[2,3-b]pyrazine (10.0 mg, 0.0276 mmol), 1-(2-{[t-butyl(dimethyl)silyl]oxy}ethyl)-4-[4-(4,4,5,5-tetramethyl-1,3,2-dioxaborolan-2-yl)phenyl]piperazine (18.0 mg, 0.041 mmol), sodium carbonate (5.8 mg, 0.055 mmol), and dichloro(bis{di-tert-butyl[4-(dimethylamino)phenyl]phosphoranyl})-palladium (0.59 mg, 0.00083 mmol) in 1,4-dioxane (0.5 mL)/water (0.1 mL) was evacuated and refilled with N$_2$ three times. The reaction was then stirred at 110° C. overnight. The mixture was filtered and then to the filtrate was added conc. HCl (0.05 mL) and then the reaction was stirred at room temperature for 2 hours. The mixture was purified by RP-HPLC (pH=2, TFA as the media) to afford the desired product as TFA salt. LCMS calculated for $C_{28}H_{34}N_5O_3$ (M+H)$^+$: m/z=488.3. Found 488.2.

Example 72

5-(2-(3,5-Dimethoxyphenethyl)-5H-pyrrolo[2,3-b]pyrazin-6-yl)-2-(4-methylpiperazin-1-yl)benzonitrile

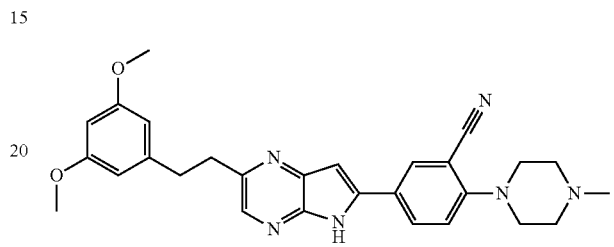

Step 1. 5-Bromo-2-(4-methylpiperazin-1-yl)benzonitrile

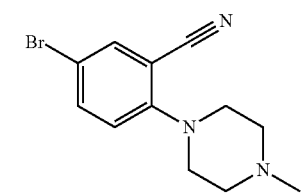 [SMILES: CN1CCN(c2ccc(Br)cc2C#N)CC1]

A mixture of 5-bromo-2-fluorobenzonitrile (0.20 g, 1.0 mmol), 1-methylpiperizine (0.15 g, 1.5 mmol) and triethylamine (0.20 g, 2.0 mmol) in 1-butanol (3.0 mL) was heated at 140° C. for 2 hours. The solvent was removed under reduced pressure and the residue was diluted with ethyl acetate, washed with water, brine, dried over Na$_2$SO$_4$, filtered and concentrated to provide the desired product (0.26 g, 92%). LCMS calculated for $C_{12}H_{15}BrN_3$ (M+H)$^+$: m/z=280.0. Found 280.0.

Step 2. 2-(4-Methylpiperazin-1-yl)-5-(4,4,5,5-tetramethyl-1,3,2-dioxaborolan-2-yl)benzonitrile

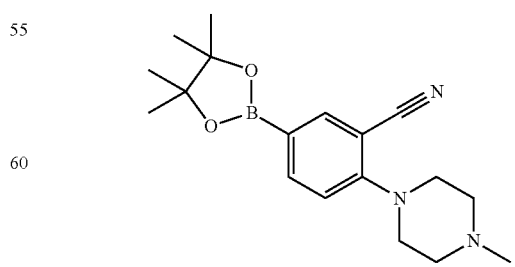

A mixture of 5-bromo-2-(4-methylpiperazin-1-yl)benzonitrile (0.28 g, 1.0 mmol), 4,4,5,5,4',4',5',5'-octamethyl-[2, 2']bi[[1,3,2]dioxaborolanyl](0.38 g, 1.5 mmol), potassium acetate (0.29 g, 3.0 mmol), and the [1,1'-bis(diphenylphosphino)ferrocene]-dichloropalladium(II) complexed with dichloromethane (1:1) (0.041 g, 0.050 mmol) in 1,4-dioxane (5.0 mL) was degassed with nitrogen and then the reaction was stirred at 100° C. overnight. The mixture was filtered through silica gel and washed with methanol. The solvent was concentrated. The residue was purified by flash chromatography on a silica gel column with methanol in methylene chloride (0-8%) to afford the desired product (0.2 g, 88%). LCMS calculated for $C_{18}H_{27}BN_3O_2$ (M+H)$^+$: m/z=328.2. Found 328.1.

Step 3. 5-(2-(3,5-Dimethoxyphenethyl)-5H-pyrrolo[2,3-b]pyrazin-6-yl)-2-(4-methylpiperazin-1-yl)benzonitrile

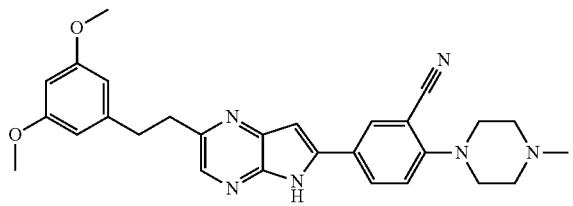 [SMILES: COc1cc(CCc2cnc3[nH]c(-c4ccc(N5CCN(C)CC5)c(C#N)c4)cc3n2)cc(OC)c1]

The compound was prepared by using procedures analogous to those described for the synthesis of Example 53, Step 2 starting from 6-bromo-2-[2-(3,5-dimethoxyphenyl)ethyl]-5H-pyrrolo[2,3-b]pyrazine and 2-(4-methylpiperazin-1-yl)-5-(4,4,5,5-tetramethyl-1,3,2-dioxaborolan-2-yl)benzonitrile. LCMS calculated for $C_{28}H_{31}N_6O_2$ (M+H)$^+$: m/z=483.2. Found 483.3.

Example 73

4-(2-(3,5-Dimethoxyphenethyl)-5H-pyrrolo[2,3-b]pyrazin-6-yl)-N-methylpicolinamide

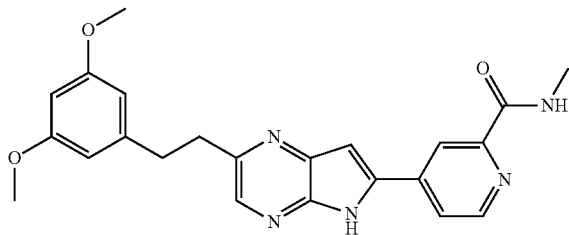 [SMILES: CNC(=O)c1cc(-c2cc3nc(CCc4cc(OC)cc(OC)c4)cnc3[nH]2)ccn1]

Step 1. 4-(2-(3,5-Dimethoxyphenethyl)-5-(phenylsulfonyl)-5H-pyrrolo[2,3-b]pyrazin-6-yl)picolinonitrile

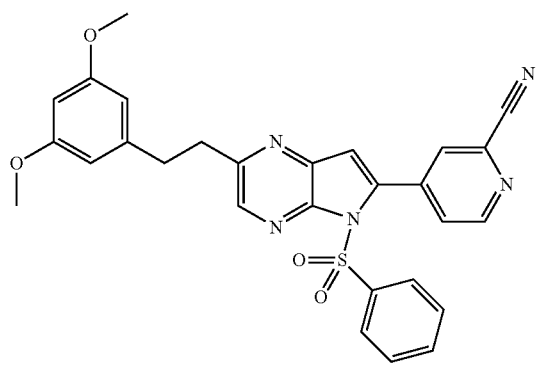 [SMILES: COc1cc(CCc2cnc3c(cc(-c4ccnc(C#N)c4)n3S(=O)(=O)c3ccccc3)n2)cc(OC)c1]

A mixture of 6-bromo-2-[2-(3,5-dimethoxyphenyl)ethyl]-5-(phenylsulfonyl)-5H-pyrrolo[2,3-b]pyrazine (60.0 mg, 0.119 mmol) (from Example 1, Step 4), 4-(4,4,5,5-tetramethyl-1,3,2-dioxaborolan-2-yl)pyridine-2-carbonitrile (0.041 g, 0.18 mmol from Combi-Blocks), sodium carbonate (25 mg, 0.24 mmol) and [1,1'-bis(diphenylphosphino)ferrocene]dichloropalladium(II) complexed with dichloromethane (1:1) (20. mg, 0.024 mmol) in acetonitrile (1 mL)/water (0.2 mL) was evacuated and the refilled with N$_2$ and then stirred at 100° C. for 3 hours. The mixture was diluted with ethyl acetate, washed with saturated NaHCO$_3$, water, brine, then dried over Na$_2$SO$_4$, filtered and concentrated. The residue was purified by flash chromatography on a silica gel column with ethyl acetate in methylene chloride (0-60%) to afford the desired product (0.055 g, 85%). LCMS calculated for $C_{28}H_{24}N_5O_4S$ (M+H)$^+$: m/z=526.2. Found 526.2.

Step 2. 4-(2-(3,5-Dimethoxyphenethyl)-5H-pyrrolo[2,3-b]pyrazin-6-yl)picolinic acid

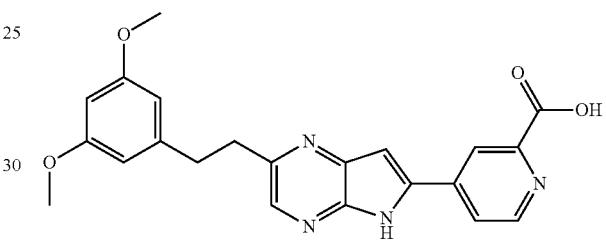

6.0M Potassium hydroxide in water (0.2 mL, 1 mmol) was added to a solution of 4-[2-[2-(3,5-dimethoxyphenyl)ethyl]-5-(phenylsulfonyl)-5H-pyrrolo[2,3-b]pyrazin-6-yl]pyridine-2-carbonitrile (50.0 mg, 0.0951 mmol) in THF (0.5 mL) and then the reaction was stirred at 90° C. for 5 hours. The mixture was then acidified to pH=2 by adding conc. HCl and then the solvent was removed to provide the desired crude product which was used in the next step directly. LCMS calculated for $C_{22}H_{21}N_4O_4$ (M+H)$^+$: m/z=405.2. Found 405.2.

Step 3. 4-(2-(3,5-Dimethoxyphenethyl)-5H-pyrrolo[2,3-b]pyrazin-6-yl)-N-methylpicolinamide

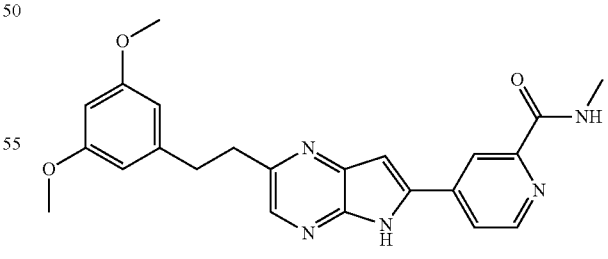

2.0M Methylamine in THF (0.1 mL, 0.3 mmol) was added to a solution of 4-{2-[2-(3,5-dimethoxyphenyl)ethyl]-5H-pyrrolo[2,3-b]pyrazin-6-yl}pyridine-2-carboxylic acid (6.10 mg, 0.0151 mmol) and benzotriazole-1-yl-oxy-tris-(dimethylamino)-phosphonium hexafluorophosphate (10 mg, 0.02 mmol) in dimethylformamide (DMF) (0.5 mL) at r.t followed by adding triethylamine (6.3 µL, 0.045 mmol) and

Example 74

4-(2-(3,5-Dimethoxyphenethyl)-5H-pyrrolo[2,3-b]pyrazin-6-yl)-N,N-dimethylpicolinamide

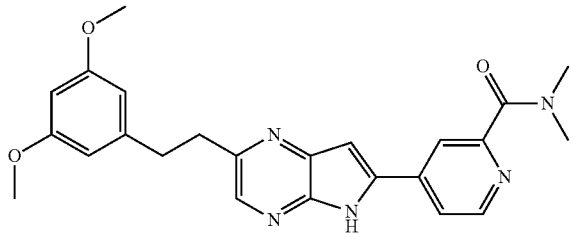 [SMILES: COc1cc(CCc2cnc3[nH]c(-c4ccnc(C(=O)N(C)C)c4)cc3n2)cc(OC)c1]

The compound was prepared by using procedures analogous to those described for the synthesis of Example 73, Step 3 starting from 4-{2-[2-(3,5-dimethoxyphenyl)ethyl]-5H-pyrrolo[2,3-b]pyrazin-6-yl}pyridine-2-carboxylic acid and N,N-dimethyl amine (2.0M in THF). LCMS calculated for $C_{24}H_{26}N_5O_3$ (M+H)$^+$: m/z=432.2. Found 432.2.

Example 75

(4-(2-(3,5-Dimethoxyphenethyl)-5H-pyrrolo[2,3-b]pyrazin-6-yl)pyridin-2-yl)(3-hydroxyazetidin-1-yl)methanone

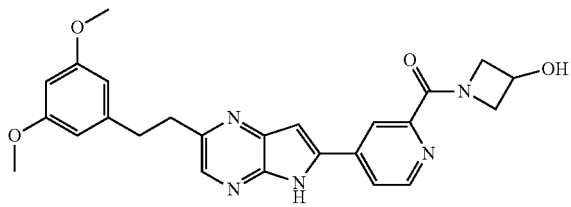 [SMILES: COc1cc(CCc2cnc3[nH]c(-c4ccnc(C(=O)N5CC(O)C5)c4)cc3n2)cc(OC)c1]

The compound was prepared by using procedure analogous to those described for the synthesis of Example 73, Step 3 starting from 4-{2-[2-(3,5-dimethoxyphenyl)ethyl]-5H-pyrrolo[2,3-b]pyrazin-6-yl}pyridine-2-carboxylic acid and 3-hydroxyazetidine hydrochloride (from Oakwood). LCMS calculated for $C_{25}H_{26}N_5O_4$ (M+H)$^+$: m/z=460.2. Found 460.2.

Example 76

1-(4-(2-(3,5-Dimethoxyphenethyl)-5H-pyrrolo[2,3-b]pyrazin-6-yl)phenyl)-4-methylpiperazin-2-one

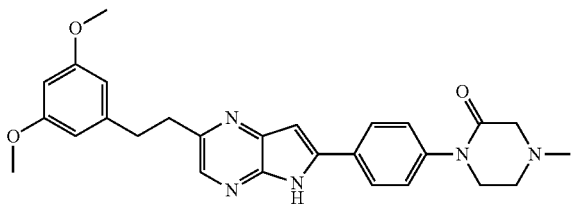 [SMILES: COc1cc(CCc2cnc3[nH]c(-c4ccc(N5CCN(C)CC5=O)cc4)cc3n2)cc(OC)c1]

then the reaction was stirred at room temperature for 2 hours. The mixture was purified by RP-HPLC (pH=2, TFA as the media) to afford the desired product as TFA salt. LCMS calculated for $C_{23}H_{24}N_5O_3$ (M+H)$^+$: m/z=418.2. Found 418.1.

Step 1. 1-(4-Bromophenyl)-4-methylpiperazin-2-one

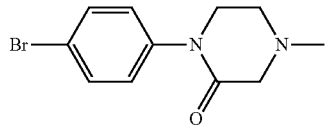

Sodium triacetoxyborohydride (0.25 g, 1.2 mmol) was added to a solution of 1-(4-bromophenyl)piperazin-2-one (200.0 mg, 0.7840 mmol, from J&W PharmLab product) and 11.0M formaldehyde in water (0.21 mL, 2.4 mmol) in methylene chloride (3 mL, 50 mmol) and then the reaction was stirred at rt for 1 hour. The mixture was diluted with methylene chloride, washed with saturated NaHCO$_3$, water, brine, then dried over Na$_2$SO$_4$, filtered and concentrated to provide the product which was used in the next step. LCMS calculated for $C_{11}H_{14}BrN_2O$ (M+H)$^+$: m/z=269.0. Found 269.0.

Step 2. 4-Methyl-1-(4-(4,4,5,5-tetramethyl-1,3,2-dioxaborolan-2-yl)phenyl)piperazin-2-one

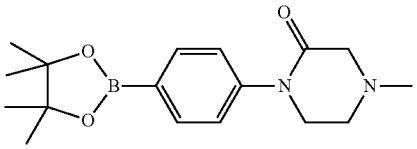

The compound was prepared by using procedure analogous to those described for the synthesis of Example 72, Step 2 starting from 1-(4-bromophenyl)-4-methylpiperazin-2-one. LCMS calculated for $C_{17}H_{26}BN_2O_3$ (M+H)$^+$: m/z=317.2. Found 317.2.

Step 3. 1-(4-(2-(3,5-Dimethoxyphenethyl)-5H-pyrrolo[2,3-b]pyrazin-6-yl)phenyl)-4-methylpiperazin-2-one

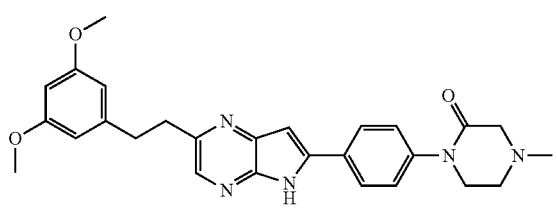 [SMILES: COc1cc(CCc2cnc3[nH]c(-c4ccc(N5CCN(C)CC5=O)cc4)cc3n2)cc(OC)c1]

A mixture of 6-bromo-2-[2-(3,5-dimethoxyphenyl)ethyl]-5H-pyrrolo[2,3-b]pyrazine (10.0 mg, 0.0276 mmol), 4-methyl-1-[4-(4,4,5,5-tetramethyl-1,3,2-dioxaborolan-2-yl)phenyl]piperazin-2-one (13 mg, 0.041 mmol), sodium carbonate (5.8 mg, 0.055 mmol) and dichloro(bis{di-tert-butyl[4-(dimethylamino)-phenyl]phosphoranyl})-palladium (0.59 mg, 0.00083 mmol) in 1,4-dioxane (0.5 mL)/water (0.1 mL) was evacuated and refilled with N$_2$ three times. The reaction was stirred at 110° C. overnight. The mixture was purified by RP-HPLC (pH=2, TFA as the media) to afford the desired product as TFA salt. LCMS calculated for $C_{27}H_{30}N_5O_3$ (M+H)$^+$: m/z=472.2. Found 472.2.

Example 77

1-(4-(2-(3,5-Dimethoxyphenethyl)-5H-pyrrolo[2,3-b]pyrazin-6-yl)phenyl)piperidin-4-ol

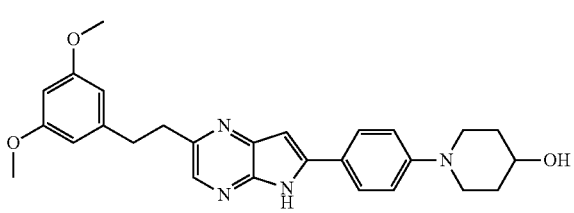 [SMILES: COc1cc(CCc2cnc3[nH]c(-c4ccc(N5CCC(O)CC5)cc4)cc3n2)cc(OC)c1]

Step 1. 1-(4-(4,4,5,5-Tetramethyl-1,3,2-dioxaborolan-2-yl)phenyl)piperidin-4-ol

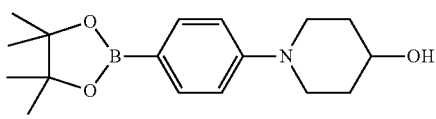

Sodium tetrahydroborate (0.012 g, 0.33 mmol) was added to a mixture of 1-[4-(4,4,5,5-tetramethyl-1,3,2-dioxaborolan-2-yl)phenyl]piperidin-4-one (0.050 g, 0.17 mmol, from Combi-Blocks) in methanol (1.0 mL) at 0° C. and then the reaction was stirred at 0° C. for 1 hour. The solvent was removed and the residue was treated with water and then filtered. The residue was dried to provide the desired product as a white solid. LCMS calculated for $C_{17}H_{27}BNO_3$ (M+H)$^+$: m/z=304.2. Found 304.1.

Step 2. 1-(4-(2-(3,5-Dimethoxyphenethyl)-5H-pyrrolo[2,3-b]pyrazin-6-yl)phenyl)piperidin-4-ol

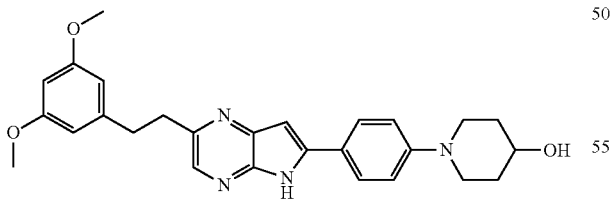

The compound was prepared by using procedure analogous to those described for the synthesis of Example 53, Step 2 starting from 6-bromo-2-[2-(3,5-dimethoxyphenyl)ethyl]-5H-pyrrolo[2,3-b]pyrazine and 1-(4-(4,4,5,5-tetramethyl-1,3,2-dioxaborolan-2-yl)phenyl)piperidin-4-ol. LCMS calculated for $C_{27}H_{31}N_4O_3$ (M+H)$^+$: m/z=459.2. Found 459.3.

Example 78

2-(3,5-Dimethoxyphenethyl)-6-(3-(piperazin-1-yl)phenyl)-5H-pyrrolo[2,3-b]pyrazine

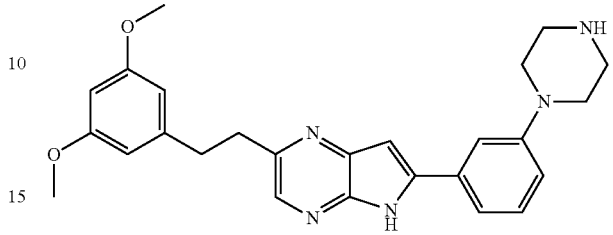

The compound was prepared by using procedures analogous to those described for the synthesis of Example 53, Step 2 starting from 6-bromo-2-[2-(3,5-dimethoxyphenyl)ethyl]-5H-pyrrolo[2,3-b]pyrazine and 1-[3-(4,4,5,5-tetramethyl-1,3,2-dioxaborolan-2-yl)phenyl]piperazine. LCMS calculated for $C_{26}H_{30}N_5O_2$ (M+H)$^+$: m/z=444.2. Found 444.2.

Example 79

2-(3,5-Dimethoxyphenethyl)-6-(3-(4-methylpiperazin-1-yl)phenyl)-5H-pyrrolo[2,3-b]pyrazine

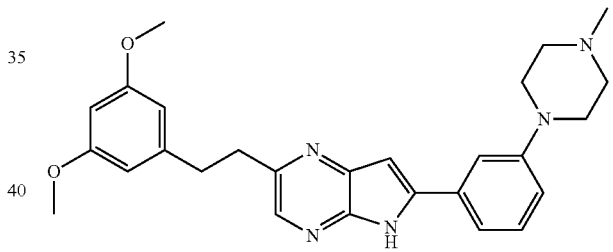

Step 1. 1-Methyl-4-(3-(4,4,5,5-tetramethyl-1,3,2-dioxaborolan-2-yl)phenyl)piperazine

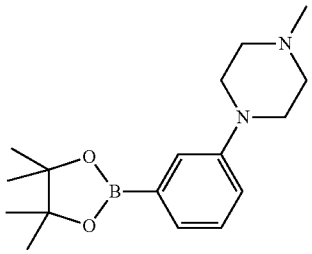

Sodium triacetoxyborohydride (0.066 g, 0.31 mmol) was added to a solution of 1-[3-(4,4,5,5-tetramethyl-1,3,2-dioxaborolan-2-yl)phenyl]piperazine (60.0 mg, 0.208 mmol, from Boron Molecular) and 11.0M aqueous formaldehyde (0.057 mL, 0.62 mmol) in methylene chloride (0.8 mL, 10 mmol) and then the reaction was stirred at r.t. for 1 hour. The mixture was diluted with methylene chloride, washed with saturated NaHCO₃, water, brine, then dried over Na₂SO₄, filtered and concentrated to provide the product which was used in the next step. LCMS calculated for $C_{17}H_{28}BN_2O_2$ (M+H)⁺: m/z=303.2. Found 303.2.

Step 2. 2-(3,5-Dimethoxyphenethyl)-6-(3-(4-methylpiperazin-1-yl)phenyl)-5H-pyrrolo[2,3-b]pyrazine

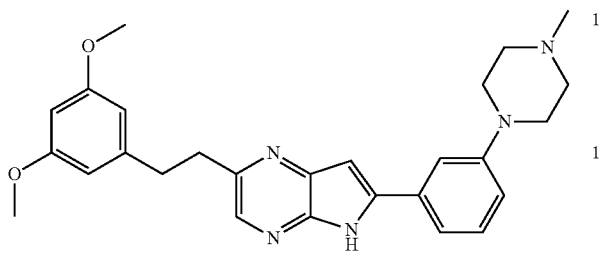

The compound was prepared by using procedures analogous to those described for the synthesis of Example 53, Step 2 starting from 6-bromo-2-[2-(3,5-dimethoxyphenyl)ethyl]-5H-pyrrolo[2,3-b]pyrazine and 1-methyl-4-(3-(4,4,5,5-tetramethyl-1,3,2-dioxaborolan-2-yl)phenyl)piperazine. LCMS calculated for $C_{27}H_{32}N_5O_3$ (M+H)⁺: m/z=458.3. Found 458.3.

Example 80

5-(2-(3,5-Dimethoxyphenethyl)-5H-pyrrolo[2,3-b]pyrazin-6-yl)indolin-2-one

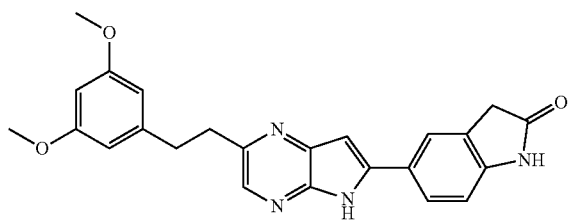 [SMILES: COc1cc(CCc2cnc3[nH]c(-c4ccc5c(c4)CC(=O)N5)cc3n2)cc(OC)c1]

The compound was prepared by using procedures analogous to those described for the synthesis of Example 53, Step 2 starting from 6-bromo-2-[2-(3,5-dimethoxyphenyl)ethyl]-5H-pyrrolo[2,3-b]pyrazine and 5-(4,4,5,5-tetramethyl-1,3,2-dioxaborolan-2-yl)indolin-2-one (from CombiBlocks) LCMS calculated for $C_{24}H_{23}N_4O_3$ (M+H)⁺: m/z=415.2. Found 415.3.

Example 81

4-(4-(2-(3,5-Dimethoxyphenethyl)-5H-pyrrolo[2,3-b]pyrazin-6-yl)phenyl)-1-methylpiperazin-2-one

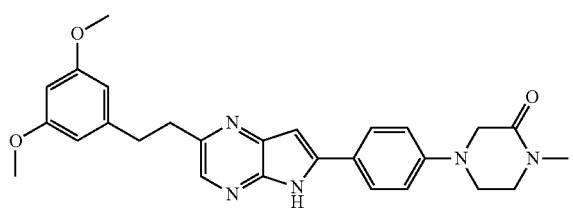 [SMILES: COc1cc(CCc2cnc3[nH]c(-c4ccc(N5CCN(C)C(=O)C5)cc4)cc3n2)cc(OC)c1]

Step 1. 4-(4-Bromophenyl)-1-methylpiperazin-2-one

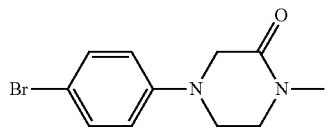

A mixture of 1,4-dibromobenzene (470 mg, 2.0 mmol), 1-methylpiperazin-2-one hydrochloride (150 mg, 1.0 mmol, from J&W PharmLab), palladium acetate (6.7 mg, 0.030 mmol), (9,9-dimethyl-9H-xanthene-4,5-diyl)bis(diphenylphosphine) (0.035 g, 0.060 mmol), and cesium carbonate (0.98 g, 3.0 mmol) in toluene (5.0 mL) was evacuated and refilled with nitrogen three times and then the reaction was stirred at 105° C. overnight. The mixture was diluted with ethyl acetate, washed with water, brine, then dried over Na₂SO₄, filtered and concentrated. The residue was purified by flash chromatography on a silica gel column with ethyl acetate in hexane (0-60%) to afford the desired product (0.26 g, 49%). LCMS calculated for $C_{11}H_{14}BrN_2O$ (M+H)⁺: m/z=269.0. Found 269.0.

Step 2. 1-Methyl-4-(4-(4,4,5,5-tetramethyl-1,3,2-dioxaborolan-2-yl)phenyl)piperazin-2-one

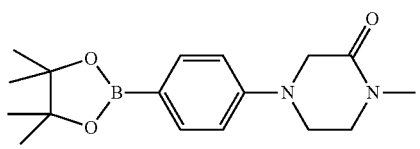

The compound was prepared by using procedures analogous to those described for the synthesis of Example 72, Step 2 starting from 4-(4-bromophenyl)-1-methylpiperazin-2-one. LCMS calculated for $C_{17}H_{26}BN_2O_3$ (M+H)⁺: m/z=317.2. Found 317.1.

Step 3. 4-(4-(2-(3,5-Dimethoxyphenethyl)-5H-pyrrolo[2,3-b]pyrazin-6-yl)phenyl)-1-methylpiperazin-2-one

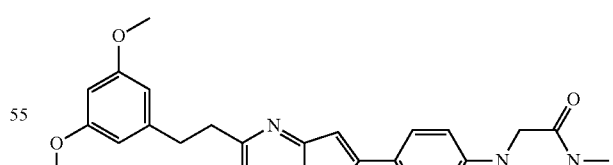

The compound was prepared by using procedures analogous to those described for the synthesis of Example 53, Step 2 starting from 6-bromo-2-[2-(3,5-dimethoxyphenyl)ethyl]-5H-pyrrolo[2,3-b]pyrazine and 1-methyl-4-(4-(4,4,5,5-tetramethyl-1,3,2-dioxaborolan-2-yl)phenyl)piperazin-2-one. LCMS calculated for $C_{27}H_{30}N_5O_3$ (M+H)⁺: m/z=472.2. Found 472.1.

Example 82

2-(2-Fluoro-3,5-dimethoxyphenethyl)-6-(4-(4-methylpiperazin-1-yl)phenyl)-5H-pyrrolo[2,3-b]pyrazine

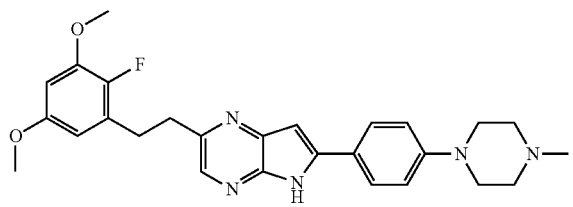 [SMILES: COc1cc(CCc2cnc3[nH]c(-c4ccc(N5CCN(C)CC5)cc4)cc3n2)c(F)c(OC)c1]

Step 1. 6-Bromo-2-(2-fluoro-3,5-dimethoxyphenethyl)-5-(phenylsulfonyl)-5H-pyrrolo[2,3-b]pyrazine

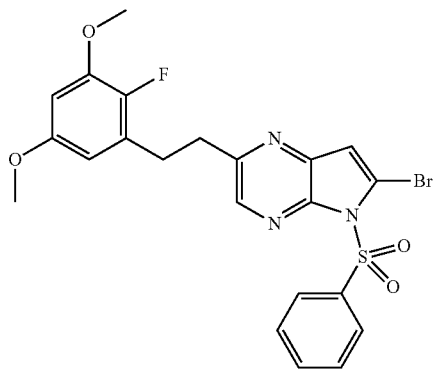 [SMILES: COc1cc(CCc2cnc3c(cc(Br)n3S(=O)(=O)c3ccccc3)n2)c(F)c(OC)c1]

A mixture of 6-bromo-2-[2-(3,5-dimethoxyphenyl)ethyl]-5-(phenylsulfonyl)-5H-pyrrolo[2,3-b]pyrazine (25.0 mg, 0.0498 mmol) and 1-(chloromethyl)-4-fluoro-1,4-diazoniabicyclo[2.2.2]octane ditetrafluoroborate (17.6 mg, 0.0498 mmol) in acetonitrile (0.3 mL)/water (0.06 mL) was stirred at 50° C. overnight. The solvent was removed and the residue was used in the next step w/o purification. LCMS calculated for $C_{22}H_{20}BrFN_3O_4S$ $(M+H)^+$: m/z=520.0. Found 520.0.

Step 2. 2-[2-(2-Fluoro-3,5-dimethoxyphenyl)ethyl]-6-[4-(4-methylpiperazin-1-yl)phenyl]-5-(phenylsulfonyl)-5H-pyrrolo[2,3-b]pyrazine

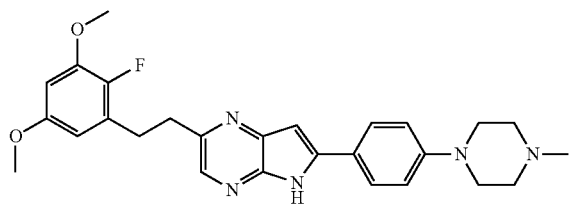 [SMILES: COc1cc(CCc2cnc3[nH]c(-c4ccc(N5CCN(C)CC5)cc4)cc3n2)c(F)c(OC)c1]

A mixture of 6-bromo-2-[2-(2-fluoro-3,5-dimethoxyphenyl)ethyl]-5-(phenylsulfonyl)-5H-pyrrolo[2,3-b]pyrazine (20.0 mg, 0.0384 mmol), 1-methyl-4-[4-(4,4,5,5-tetramethyl-1,3,2-dioxaborolan-2-yl)phenyl]piperazine (17 mg, 0.058 mmol), sodium carbonate (8.1 mg, 0.077 mmol) in 1,4-dioxane (0.7 mL)/water (0.1 mL) was evacuated and refilled with $N_2$ three times. The reaction was stirred at 110° C. for 3 h and then filtered. The filtrate was concentrated, the residue was redissolved in THF (0.5 mL), and then 6.0M KOH (0.1 mL) was added. The resulting mixture was stirred at 65° C. overnight and then purified by RP-HPLC (pH=2, TFA as the media) to afford the desired product as TFA salt. LCMS calculated for $C_{27}H_{31}FN_5O_2$ $(M+H)^+$: m/z=476.2. Found 476.2.

Example 83

2-[2-(2,6-difluoro-3,5-dimethoxyphenyl)ethyl]-6-(5-methyl-1H-pyrazol-4-yl)-5H-pyrrolo[2,3-b]pyrazine

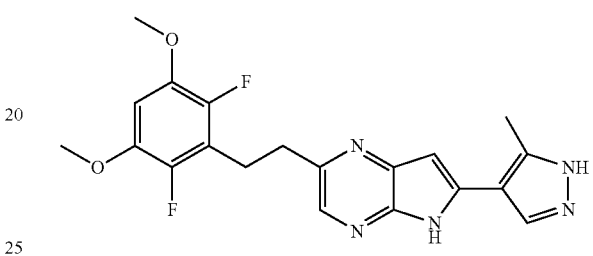

Step 1. 2,4-difluoro-3-iodo-1,5-dimethoxybenzene

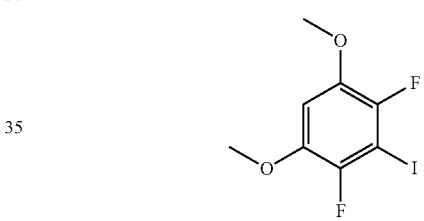

To a stirred slurry of 2,6-difluoro-3,5-dimethoxyaniline (1.00 g, 5.29 mmol) in 6.0M hydrogen chloride in water (9.00 mL, 54.0 mmol), a solution of sodium nitrite (0.383 g, 5.55 mmol) in water (2 mL) was added dropwise over 15 minutes at 0° C. After another 15 minutes, the resulting orange-red slurry was added to a solution of potassium iodide (3.50 g, 21.1 mmol) in water (5 mL) in small portions at 0° C. After addition, the reaction mixture was allowed to warm to room temperature and then it was stirred for 1 hour. Solid precipitated which was filtered out. The solid was washed with water and dried under vacuum to give the desired product (1.15 g, 70%). $^1$H NMR (400 MHz, CDCl$_3$): δ 6.68 (t, J=8.0 Hz, 1H), 3.88 (s, 6H) ppm.

Step 2. [(2,6-difluoro-3,5-dimethoxyphenyl)ethynyl](trimethyl)silane

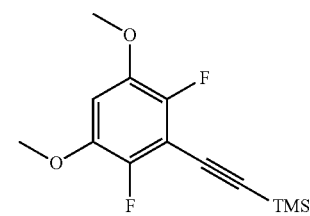 [SMILES: COc1cc(OC)c(F)c(C#C[Si](C)(C)C)c1F]

To a stirred mixture of 2,4-difluoro-3-iodo-1,5-dimethoxybenzene (740 mg, 2.47 mmol), (trimethylsilyl)acetylene (0.697 mL, 4.93 mmol), copper(I) iodide (38 mg, 0.20 mmol), and triethylamine (0.52 mL, 3.7 mmol) in N,N-dimethylformamide (DMF) (4 mL, 50 mmol), bis(triphenylphosphine)palladium(II) chloride (86 mg, 0.12 mmol) was added. The reaction mixture was stirred at room temperature for 70 hours. The reaction was quenched with saturated aq. NH$_4$Cl, then extracted with methylene chloride. The combined organic layers were dried over MgSO$_4$, then concentrated. The residue was purified on silica gel (eluting with 0 to 30% EtOAc in hexanes) to give the desired product (630 mg, 94%).

Step 3.
3-ethynyl-2,4-difluoro-1,5-dimethoxybenzene

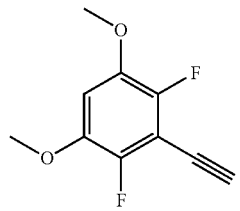

To a stirred solution of [(2,6-difluoro-3,5-dimethoxyphenyl)ethynyl](trimethyl)-silane (630 mg, 2.33 mmol) in tetrahydrofuran (2 mL)/methanol (2 mL), cesium fluoride (354 mg, 2.33 mmol) was added at room temperature. After 1 hour, the reaction was quenched with saturated aq. NH$_4$Cl, then extracted with methylene chloride. The combined organic layers were dried over MgSO$_4$, concentrated to give the desired product (440 mg, 95%). $^1$H NMR (300 MHz, CDCl$_3$): δ 6.62 (t, J=7.8 Hz, 1H), 3.89 (s, 7H) ppm.

Step 4. 2-[(2,6-difluoro-3,5-dimethoxyphenyl)ethynyl]-5-(phenylsulfonyl)-5H-pyrrolo[2,3-b]pyrazine

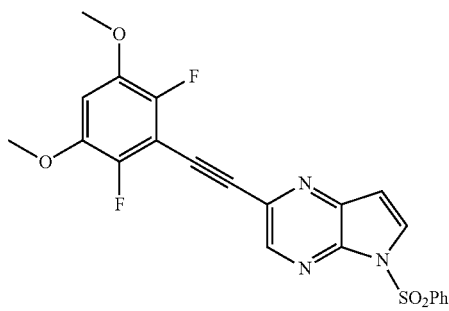

To a stirred solution of 3-ethynyl-2,4-difluoro-1,5-dimethoxybenzene (340 mg, 1.72 mmol) and 2-bromo-5-(phenylsulfonyl)-5H-pyrrolo[2,3-b]pyrazine (696 mg, 2.06 mmol, from Example 1, Step 1) in N,N-dimethylformamide (4 mL), copper(I) iodide (26 mg, 0.14 mmol), bis(triphenylphosphine)palladium(II) chloride (60.0 mg, 0.0885 mmol) and triethylamine (0.36 mL, 2.6 mmol) were added sequentially at room temperature. After 14 hours, the reaction was quenched with saturated aq. NH$_4$Cl, then extracted with methylene chloride. The combined organic layers were dried over MgSO$_4$, then concentrated. The residue was purified on silica gel (eluting with 0 to 50% ethyl acetate (EtOAc) in hexanes) to give the desired product (490 mg, 63%). LCMS calculated for C$_{22}$H$_{15}$F$_2$N$_3$O$_4$S (M+H)$^+$: m/z=456.1. Found: 456.1.

Step 5. 2-[2-(2,6-difluoro-3,5-dimethoxyphenyl)ethyl]-5-(phenylsulfonyl)-5H-pyrrolo[2,3-b]pyrazine

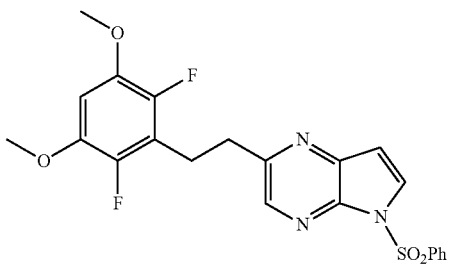

To a stirred solution of 2-[(2,6-difluoro-3,5-dimethoxyphenyl)ethynyl]-5-(phenylsulfonyl)-5H-pyrrolo[2,3-b]pyrazine (490 mg, 1.08 mmol) in tetrahydrofuran (8 mL)/methanol (10 mL), Pd/C (10% w/w, 365 mg, 0.343 mmol) was added. The resulting mixture was stirred under H$_2$ at ambient temperature. After 24 hr, the catalyst was removed by filtration, and the filtrate was concentrated under reduced pressure. The residue was purified on silica gel (eluting with 0 to 60% EtOAc in hexanes) to give the desired product (400 mg, 81%). LCMS calculated for C$_{22}$H$_{19}$F$_2$N$_3$O$_4$S (M+H)$^+$: m/z=460.1. Found: 460.1.

Step 6. 6-bromo-2-[2-(2,6-difluoro-3,5-dimethoxyphenyl)ethyl]-5-(phenylsulfonyl)-5H-pyrrolo[2,3-b]pyrazine

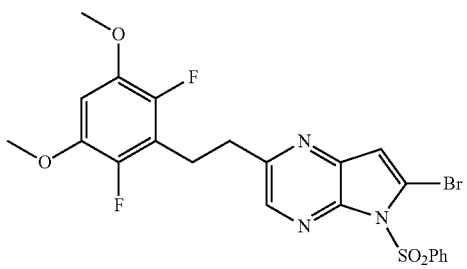

To a stirred solution of N,N-diisopropylamine (0.150 mL, 1.07 mmol) in tetrahydrofuran (0.48 mL) at −78° C., n-butyllithium (2.5M in hexanes, 0.428 mL, 1.07 mmol) was added dropwise. After a white precipitate formed, the mixture was warmed up to 0° C. for 10 minutes. The resulting solution was added to a stirred solution of 2-[2-(2,6-difluoro-3,5-dimethoxyphenyl)ethyl]-5-(phenylsulfonyl)-5H-pyrrolo[2,3-b]pyrazine (400 mg, 0.871 mmol) in tetrahydrofuran (3 mL) at −78° C. After 10 minutes, a solution of 1,2-dibromo-1,1,2,2-tetrachloroethane (0.283 g, 0.870 mmol) in tetrahydrofuran (2 mL) was added dropwise. After another 1 hour, the reaction mixture was quenched with saturated aq. NH$_4$Cl, then extracted with methylene chloride. The combined organic layers were dried over MgSO$_4$, then concentrated. The residue was purified on silica gel (eluting with 0 to 50% EtOAc in hexanes) to give the desired product (330 g, 70%). LCMS calculated for $C_{22}H_{19}BrF_2N_3O_4S$ (M+H)$^+$: m/z=538.0. Found: 538.0.

Step 7. 2-[2-(2,6-difluoro-3,5-dimethoxyphenyl) ethyl]-6-(5-methyl-1H-pyrazol-4-yl)-5H-pyrrolo[2,3-b]pyrazine

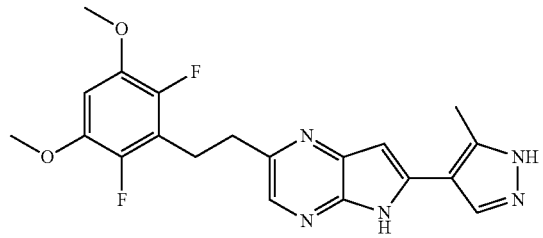 [SMILES: COc1cc(OC)c(F)c(CCc2cnc3[nH]c(-c4cn[nH]c4C)cc3n2)c1F]

A stirred mixture of 6-bromo-2-[2-(2,6-difluoro-3,5-dimethoxyphenyl)ethyl]-5-(phenylsulfonyl)-5H-pyrrolo[2,3-b]pyrazine (15 mg, 28 μmol), (3-methyl-1H-pyrazol-4-yl) boronic acid (4.2 mg, 33 μmol), [1,1'-bis (diphenylphosphino)ferrocene]-dichloropalladium(II) complexed with dichloromethane (1:1) (1.8 mg, 2.2 μmol), and potassium phosphate (9.5 mg, 45 μmol) in water (0.2 mL)/1,4-dioxane (1 mL) was heated at 88° C. After 1 hour, the volatiles were removed under vacuum and the residue was dissolved in methanol (1 mL). Potassium carbonate (7.7 mg, 56 μmol) was added and the reaction mixture was warmed up to 60° C. After 0.5 hour, the reaction mixture was cooled to ambient temperature and was purified on RP-HPLC (XBridge C18 column, eluting with a gradient of acetonitrile/water containing 0.05% TFA, at flow rate of 30 mL/min) to give the desired product (5.1 mg, 46%) as its TFA salt. LCMS calculated for $C_{20}H_{20}F_2N_5O_2$ (M+H)$^+$: m/z=400.2. Found: 400.2.

Example 84

2-(2,6-difluoro-3,5-dimethoxyphenethyl)-6-(1-methyl-1H-pyrazol-4-yl)-5H-pyrrolo[2,3-b]pyrazine

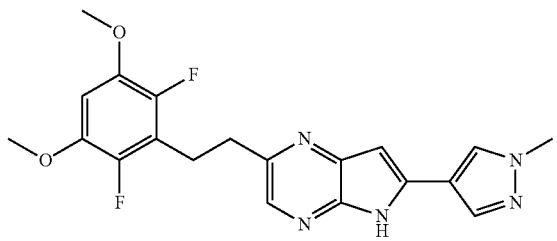

This compound was prepared using procedures analogous to those for Example 83, Step 7, with 1-methyl-4-(4,4,5,5-tetramethyl-1,3,2-dioxaborolan-2-yl)-1H-pyrazole replacing (3-methyl-1H-pyrazol-4-yl)boronic acid LCMS calculated for $C_{20}H_{20}F_2N_5O_2$ (M+H)$^+$: m/z=400.2. Found: 400.1.

Example 85

2-(2-(2,6-difluoro-3,5-dimethoxyphenethyl)-5H-pyrrolo[2,3-b]pyrazin-6-yl)benzonitrile

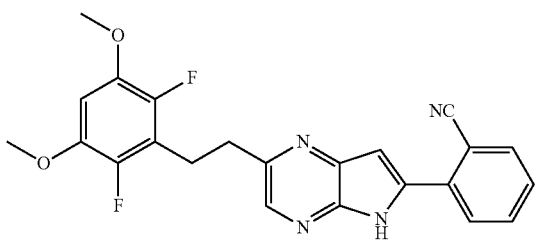 [SMILES: COc1cc(OC)c(F)c(CCc2cnc3[nH]c(-c4ccccc4C#N)cc3n2)c1F]

This compound was prepared using procedures analogous to those for Example 83, Step 7, with 2-(4,4,5,5-tetramethyl-1,3,2-dioxaborolan-2-yl)benzonitrile replacing (3-methyl-1H-pyrazol-4-yl)boronic acid LCMS calculated for $C_{23}H_{19}F_2N_4O_2$ (M+H)$^+$: m/z=421.1. Found: 421.1.

Example 86

2-(2,6-difluoro-3,5-dimethoxyphenethyl)-6-(2-methoxypyridin-3-yl)-5H-pyrrolo[2,3-b]pyrazine

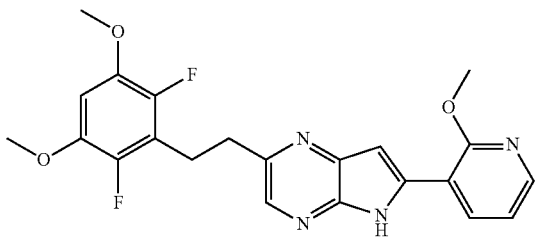 [SMILES: COc1cc(OC)c(F)c(CCc2cnc3[nH]c(-c4cccnc4OC)cc3n2)c1F]

This compound was prepared using procedures analogous to those for Example 83, Step 7, with 2-methoxy-3-(4,4,5,5-tetramethyl-1,3,2-dioxaborolan-2-yl)pyridine replacing (3-methyl-1H-pyrazol-4-yl)boronic acid LCMS calculated for $C_{22}H_{21}F_2N_4O_3$ (M+H)$^+$: m/z=427.2. Found: 427.2.

Example 87

2-(4-(2-(2,6-difluoro-3,5-dimethoxyphenethyl)-5H-pyrrolo[2,3-b]pyrazin-6-yl)-1H-pyrazol-1-yl)-N,N-dimethylethanamine

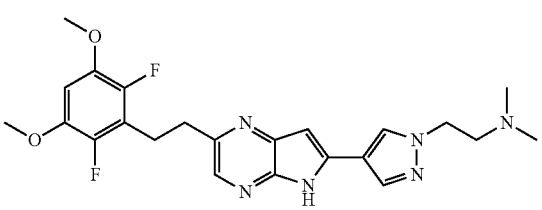

This compound was prepared using procedures analogous to those for Example 83, Step 7, with N,N-dimethyl-2-(4-(4,4,5,5-tetramethyl-1,3,2-dioxaborolan-2-yl)-1H-pyrazol-1-yl)ethanamine (from Example 34, Step 1) replacing (3-methyl-1H-pyrazol-4-yl)boronic acid LCMS calculated for $C_{23}H_{27}F_2N_6O_2$ (M+H)$^+$: m/z=457.2. Found: 457.3.

Example 88

1-(4-(2-(2,6-difluoro-3,5-dimethoxyphenethyl)-5H-pyrrolo[2,3-b]pyrazin-6-yl)-1H-pyrazol-1-yl)-2-methylpropan-2-ol

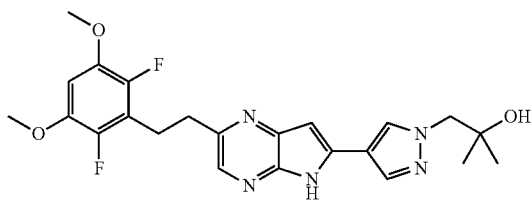 [SMILES: COc1cc(OC)c(F)c(CCc2cnc3[nH]c(-c4cnn(CC(C)(C)O)c4)cc3n2)c1F]

This compound was prepared using procedures analogous to those for Example 83, Step 7, with 2-methyl-1-(4-(4,4,5,5-tetramethyl-1,3,2-dioxaborolan-2-yl)-1H-pyrazol-1-yl)propan-2-ol (from Example 33, Step 1) replacing (3-methyl-1H-pyrazol-4-yl)boronic acid LCMS calculated for $C_{23}H_{26}F_2N_5O_3$ (M+H)$^+$: m/z=458.2. Found: 458.2.

Example 89

2-(2,6-difluoro-3,5-dimethoxyphenethyl)-N-methyl-5H-pyrrolo[2,3-b]pyrazine-6-carboxamide

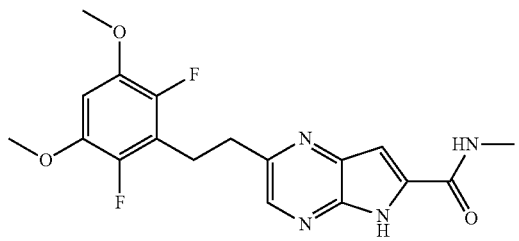

This compound was prepared using procedures analogous to those for Example 25, with 2-(2,6-difluoro-3,5-dimethoxyphenethyl)-5-(phenylsulfonyl)-5H-pyrrolo[2,3-b]pyrazine (from Example 83, Step 5) replacing 2-[2-(3,5-dimethoxyphenyl)ethyl]-5-(phenylsulfonyl)-5H-pyrrolo[2,3-b]pyrazine LCMS calculated for $C_{18}H_{19}F_2N_4O_3$ (M+H)$^+$: m/z=377.2. Found: 377.2.

Example A

FGFR Enzymatic Assay

The inhibitor potency of compounds was measured in an enzyme assay that measures peptide phosphorylation using FRET measurements to detect product formation. Inhibitors were serially diluted in DMSO and a volume of 0.5 µL was transferred to the wells of a 384-well plate. For FGFR3, a 10 µL volume of FGFR3 enzyme (Millipore) diluted in assay buffer (50 mM HEPES, 10 mM MgCl$_2$, 1 mM EGTA, 0.01% Tween-20, 5 mM DTT, pH 7.5) was added to the plate and pre-incubated for 5-10 minutes. Appropriate controls (enzyme blank and enzyme with no inhibitor) were included on the plate. The assay was initiated by the addition of a 10 µL solution containing biotinylated EQEDEPEGDYFEWLE peptide substrate (SEQ ID NO: 1) and ATP (final concentrations of 500 nM and 140 µM respectively) in assay buffer to the wells. The plate was incubated at 25° C. for 1 hr. The reactions were ended with the addition of 10 µL/well of quench solution (50 mM Tris, 150 mM NaCl, 0.5 mg/mL BSA, pH 7.8; added fresh 30 mM EDTA and Perkin Elmer Lance Reagents for HTRF at 3.75 nM Eu-antibody PY20 and 180 nM APC-Streptavidin). The plate was allowed to equilibrate for ~1 hr before scanning the wells on a PheraStar plate reader.

FGFR1 and FGFR2 were measured under equivalent conditions with the following changes in enzyme and ATP concentrations: FGFR1, 0.02 nM and 210 µM, respectively and FGFR2, 0.01 nM and 100 µM, respectively.

GraphPad prism3 was used to analyze the data. The IC$_{50}$ values were derived by fitting the data to the equation for a sigmoidal dose-response with a variable slope. Y=Bottom+(Top−Bottom)/(1+10^((Log IC$_{50}$−X)*HillSlope)) where X is the logarithm of concentration and Y is the response.

The compounds of the invention were found to be inhibitors of one or more of FGFR1, FGFR2, and FGFR3 according to the above-described assay. IC$_{50}$ data is provided below in Table 1. The symbol "+" indicates an IC$_{50}$ less than 100 nM, the symbol "++" indicates an IC$_{50}$ of 100 to 500 nM, and the symbol "+++" indicates an IC$_{50}$ greater than 500 nM but less than 2700 nM. "N/P" means not provided.

TABLE 1

| Example No. | FGFR1 IC$_{50}$ (nM) | FGFR2 IC$_{50}$ (nM) | FGFR3 IC$_{50}$ (nM) |
| --- | --- | --- | --- |
| 1 | + | + | + |
| 2 | + | + | + |
| 3 | + | + | + |
| 4 | + | ++ | +++ |
| 5 | + | + | + |
| 6 | + | + | ++ |
| 7 | + | + | ++ |
| 8 | + | ++ | ++ |
| 9 | + | ++ | +++ |
| 10 | + | + | +++ |
| 11 | + | + | + |
| 12 | + | + | + |
| 13 | + | + | + |
| 14 | + | + | ++ |
| 15 | + | + | + |
| 16 | + | + | ++ |
| 17 | + | + | ++ |
| 18 | + | + | +++ |
| 19 | + | + | ++ |
| 20 | + | ++ | >1000 |
| 21 | ++ | ++ | >2000 |
| 22 | + | + | + |
| 23 | + | + | ++ |
| 24 | ++ | +++ | >2000 |
| 25 | ++ | ++ | >2000 |
| 26 | +++ | +++ | >2000 |
| 27 | + | ++ | >2000 |
| 28 | ++ | +++ | >2000 |
| 29 | + | + | ++ |
| 30 | + | + | ++ |
| 31 | + | + | + |
| 32 | + | + | + |
| 33 | + | + | + |
| 34 | + | + | + |
| 35 | + | + | + |
| 36 | + | + | + |
| 37 | + | + | ++ |
| 38 | + | + | ++ |
| 39 | + | + | + |
| 40 | + | + | + |
| 41 | + | + | + |
| 42 | + | + | ++ |

TABLE 1-continued

| Example No. | FGFR1 IC$_{50}$ (nM) | FGFR2 IC$_{50}$ (nM) | FGFR3 IC$_{50}$ (nM) |
|---|---|---|---|
| 43 | + | + | ++ |
| 44 | + | + | + |
| 45 | + | + | + |
| 46 | + | + | + |
| 47 | + | + | + |
| 48 | + | + | + |
| 49 | + | + | + |
| 50 | + | + | +++ |
| 51 | + | + | + |
| 52 | + | + | + |
| 53 | + | + | + |
| 54 | + | + | ++ |
| 55 | + | + | ++ |
| 56 | + | + | + |
| 57 | + | + | + |
| 58 | + | + | ++ |
| 59 | + | + | ++ |
| 60 | + | + | ++ |
| 61 | + | + | ++ |
| 62 | + | + | + |
| 63 | + | + | ++ |
| 64 | + | + | + |
| 65 | + | + | N/P |
| 66 | + | + | >2000 |
| 67 | + | + | ++ |
| 68 | + | + | ++ |
| 69 | + | + | ++ |
| 70 | + | + | ++ |
| 71 | + | + | + |
| 72 | + | + | = |
| 73 | + | + | + |
| 74 | + | + | ++ |
| 75 | + | + | ++ |
| 76 | + | + | + |
| 77 | + | + | + |
| 78 | + | + | + |
| 79 | + | + | + |
| 80 | + | + | + |
| 81 | + | + | + |
| 82 | + | + | + |
| 83 | + | + | + |
| 84 | + | + | + |
| 85 | + | + | + |
| 86 | + | + | + |
| 87 | + | + | + |
| 88 | + | + | + |
| 89 | + | + | >400 |

Example B

FGFR3 Cell Proliferation/Survival Assays

A recombinant cell line over-expressing human FGFR3 was developed by stable transfection of the mouse pro-B Ba/F3 cells (obtained from the Deutsche Sammlung von Mikroorganismen und Zellkulturen) with a plasmid encoding the full length human FGFR3. Cells were sequentially selected for puromycin resistance and proliferation in the presence of heparin and FGF1. A single cell clone was isolated and characterized for functional expression of FGFR3. This Ba/F3-FGFR3 clone is used in cell proliferation assays, and compounds are screened for their ability to inhibit cell proliferation/survival. The Ba/F3-FGFR3 cells are seeded into 96 well, black cell culture plates at 3500 cells/well in RPMI1640 media containing 2% FBS, 20 ug/mL Heparin and 5 ng/mL FGF1. The cells were treated with 10 μL of 10× concentrations of serially diluted compounds (diluted with medium lacking serum from 5 mM DSMO dots) to a final volume of 100 μL/well. After 72 hour incubation, 100 μL of Cell Titer Glo® reagent (Promega Corporation) that measures cellular ATP levels is added to each well. After 20 minute incubation with shaking, the luminescence is read on a plate reader. The luminescent readings are converted to percent inhibition relative to DMSO treated control wells, and the IC$_{50}$ values are calculated using GraphPad Prism software. Compounds having an IC$_{50}$ of 10 μM or less are considered active. Other non-recombinant cancer cell lines representing a variety of tumor types including KMS-11 (multiple myeloma), RT112 (bladder cancer), KatoIII (gastric cancer), and H-1581 (lung) are used in similar proliferation assays. In some experiments, MTS reagent, Cell Titer 96® AQueous One Solution Reagent (Promega Corporation) is added to a final concentration of 333 μg/mL in place Cell Titer Glo and read at 490/650 nm on a plate reader.

Example C

Cell-Based FGFR Phosphorylation Assays

The inhibitory effect of compounds on FGFR phosphorylation in relevant cell lines (Ba/F3-FGFR3, KMS-11, RT112, KatoIII, H-1581 cancer cell lines and HUVEC cell line) can be assessed using immunoassays specific for FGFR phosphorylation. Cells are starved in media with reduced serum (0.5%) and no FGF1 for 4 to 48 h depending upon the cell line then treated with various concentrations of individual inhibitors for 1-4 hours. For some cell lines, such as Ba/F3-FGFR3 and KMS-11, cells are stimulated with Heparin (20 μg/mL) and FGF1 (10 ng/mL) for 10 min. Whole cell protein extracts are prepared by incubation in lysis buffer with protease and phosphatase inhibitors [50 mM HEPES (pH 7.5), 150 mM NaCl, 1.5 mM MgCl$_2$, 10% Glycerol, 1% Triton X-100, 1 mM sodium orthovanadate, 1 mM sodium fluoride, aprotinin (2 μg/mL), leupeptin (2 μg/mL), pepstatin A (2 μg/mL), and phenylmethylsulfonyl fluoride (1 mM)] at 4° C. Protein extracts are cleared of cellular debris by centrifugation at 14,000×g for 10 minutes and quantified using the BCA (bicinchoninic acid) microplate assay reagent (Thermo Scientific).

Phosphorylation of FGFR receptor in protein extracts was determined using immunoassays including western blotting, enzyme-linked immunoassay (ELISA) or bead-based immunoassays (Luminex). For detection of phosphorylated FGFR2, a commercial ELISA kit DuoSet IC Human Phospho-FGF R2α ELISA assay (R&D Systems, Minneapolis, Minn.) can be used. For the assay KATOlll cells are plated in 0.2% FBS supplemented Iscove's medium (5×104 cells/well/per 100 μL) into 96-well flat-bottom tissue culture treated plates (Corning, Corning, N.Y.), in the presence or absence of a concentration range of test compounds and incubated for 4 hours at 37° C., 5% CO$_2$. The assay is stopped with addition of 200 μL of cold PBS and centrifugation. The washed cells are lysed in Cell Lysis Buffer (Cell Signaling, #9803) with Protease Inhibitor (Calbiochem, #535140) and PMSF (Sigma, #P7626) for 30 min on wet ice. Cell lysates were frozen at −800° C. before testing an aliquot with the DuoSet IC Human Phospho-FGF R2α ELISA assay kit. GraphPad prism3 was used to analyze the data. The IC$_{50}$ values were derived by fitting the data to the equation for a sigmoidal dose-response with a variable slope.

For detection of phosphorylated FGFR3, a bead based immunoassay was developed. An anti-human FGFR3 mouse mAb (R&D Systems, cat#MAB7661) was conjugated to Luminex MAGplex microspheres, bead region 20 and used as the capture antibody. RT-112 cells were seeded into multi-well tissue culture plates and cultured until 70% confluence. Cells were washed with PBS and starved in RPMI+0.5% FBS for 18 hr. The cells were treated with 10 µL of 10× concentrations of serially diluted compounds for 1 hr at 37° C., 5% $CO_2$ prior to stimulation with 10 ng/mL human FGF1 and 20 µg/mL Heparin for 10 min. Cells were washed with cold PBS and lysed with Cell Extraction Buffer (Invitrogen) and centrifuged. Clarified supernatants were frozen at −800° C. until analysis.

For the assay, cell lysates are diluted 1:10 in Assay Diluent and incubated with capture antibody-bound beads in a 96-well filter plate for 2 hours at room temperature on a plate shaker. Plates are washed three times using a vacuum manifold and incubated with anti-phospho-FGF R1-4 (Y653/Y654) rabbit polyclonal antibody (R&D Systems cat#AF3285) for 1 hour at RT with shaking. Plates are washed three times. The diluted reporter antibody, goat anti-rabbit-RPE conjugated antibody (Invitrogen Cat. #LHB0002) is added and incubated for 30 minutes with shaking. Plates are washed three times. The beads are suspended in wash buffer with shaking at room temperature for 5 minutes and then read on a Luminex 200 instrument set to count 50 events per sample, gate settings 7500-13500. Data is expressed as mean fluorescence intensity (MFI). MFI from compound treated samples are divided by MFI values from DMSO controls to determine the percent inhibition, and the $IC_{50}$ values are calculated using the GraphPad Prism software.

Example D

FGFR Cell-Based Signaling Assays

Activation of FGFR leads to phosphorylation of Erk proteins. Detection of pErk is monitored using the Cellu'Erk HTRF (Homogeneous Time Resolved Flurorescence) Assay (CisBio) according to the manufacturer's protocol. KMS-11 cells are seeded into 96-well plates at 40,000 cells/well in RPMI medium with 0.25% FBS and starved for 2 days. The medium is aspirated and cells are treated with 30 µL of 1× concentrations of serially diluted compounds (diluted with medium lacking serum from 5 mM DSMO dots) to a final volume of 30 µL/well and incubated for 45 min at room temperature. Cells are stimulated by addition of 10 µL of Heparin (100 µg/mL) and FGF1 (50 ng/mL) to each well and incubated for 10 min at room temperature. After lysis, an aliquot of cell extract is transferred into 384-well low volume plates, and 4 µL of detection reagents are added followed by incubation for 3 hr at room temperature. The plates are read on a PheraStar instrument with settings for HTRF. The normalized fluorescence readings are converted to percent inhibition relative to DMSO treated control wells, and the $IC_{50}$ values are calculated using the GraphPad Prism software. Compounds having an $IC_{50}$ of 1 µM or less are considered active.

Example E

VEGFR2 Kinase Assay

Enzyme reactions (40 µL) are run in black 384 well polystyrene plates for 1 hour at 25° C. Wells are dotted with 0.8 µL of test compound in dimethyl sulfoxide (DMSO). The assay buffer contains 50 mM Tris, pH 7.5, 0.01% Tween-20, 10 mM $MgCl_2$, 1 mM EGTA, 5 mM DTT, 0.5 µM Biotin-labeled EQEDEPEGDYFEWLE peptide substrate (SEQ ID NO: 1), 1 mM ATP, and 0.1 nM enzyme (Millipore catalogue number 14-630). Reactions are stopped by addition of 20 µL Stop Buffer (50 mM Tris, pH=7.8, 150 mM NaCl, 0.5 mg/mL BSA, 45 mM EDTA) with 225 nM LANCE Streptavidin Surelight® APC (PerkinElmer catalogue number CR130-100) and 4.5 nM LANCE Eu-W1024 anti phosphotyrosine (PY20) antibody (PerkinElmer catalogue number AD0067). After 20 minutes of incubation at room temperature, the plates are read on a PheraStar FS plate reader (BMG Labtech). $IC_{50}$ values can be calculated using GraphPad Prism.

Various modifications of the invention, in addition to those described herein, will be apparent to those skilled in the art from the foregoing description. Such modifications are also intended to fall within the scope of the appended claims. Each reference, including all patent, patent applications, and publications, cited in the present application is incorporated herein by reference in its entirety.

What is claimed is:

1. A method of modulating fibroblast growth factor receptor activity in a patient, wherein said patient suffers from cancer, comprising administering to said patient a therapeutically effective amount of a compound of Formula I:

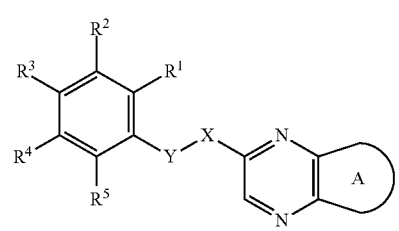

or a pharmaceutically acceptable salt thereof, wherein:
X and Y are each independently selected from $CH_2$, O, and S, wherein no more than one of X and Y is selected from O and S;
ring A is

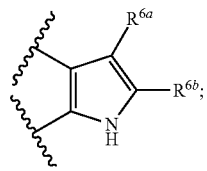

$R^1$, $R^2$, $R^3$, $R^4$, and $R^5$ are each independently selected from H, halo, $C_{1-6}$ alkyl, $C_{2-6}$ alkenyl, $C_{2-6}$ alkynyl, $C_{1-6}$ haloalkyl, CN, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)OR^a$, $NR^eC(O)NR^cR^d$, $C(=NR^e)R^b$, $C(=NR^e)NR^cR^d$, $NR^cC(=NR^e)NR^cR^d$, $NR^cS(O)R^b$, $NR^cS(O)_2R^b$, $NR^cS(O)_2NR^cR^d$, $S(O)R^b$, $S(O)NR^cR^d$, $S(O)_2R^b$, and $S(O)_2NR^cR^d$; wherein said $C_{1-6}$ alkyl, $C_{2-6}$ alkenyl, and $C_{2-6}$ alkynyl, are each optionally substituted with 1, 2, or 3 substituents independently selected from halo, $C_{1-6}$ haloalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $C(=NR^e)NR^cR^d$, $NR^cC(=NR^e)NR^cR^d$, $NR^cR^d$, $NR^cC(O)R^b$, $NR^cC(O)OR^a$, $NR^cC(O)NR^cR^d$, $NR^cS(O)R^b$, $NR^cS(O)_2R^b$, $NR^cS(O)_2NR^cR^d$, $S(O)R^b$, $S(O)NR^cR^d$, $S(O)_2R^b$, and $S(O)_2NR^cR^d$;

each $R^a$, $R^b$, $R^c$, and $R^d$ is independently selected from H, $C_{1-6}$ alkyl, $C_{1-4}$ haloalkyl, $C_{2-6}$ alkenyl, and $C_{2-6}$ alkynyl;

$R^e$ is selected from H, $C_{1-4}$ alkyl, CN, and $C_{1-4}$ alkoxy;

$R^{6a}$ and $R^{6b}$ are each independently selected from H, halo, $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-10 membered heteroaryl, 4-10 membered heterocycloalkyl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $C(=NR^{e1})R^{b1}$, $C(=NR^{e1})NR^{c1}R^{d1}$, $NR^{c1}C(=R^{e1})NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, and $S(O)_2NR^{c1}R^{d1}$; wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, and 4-10 membered heterocycloalkyl are each optionally substituted with 1, 2, 3, 4, or 5 substituents independently selected from $R^9$;

each $R^9$ is independently selected from $Cy^1$, halo, $C_{1-6}$ alkyl, $C_{2-6}$ alkenyl, $C_{2-6}$ alkynyl, $C_{1-6}$ haloalkyl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $C(=NR^{e1})NR^{c1}R^{d1}$, $NR^{c1}C(=NR^{e1})NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, and $S(O)_2NR^{c1}R^{d1}$, wherein said $C_{1-6}$ alkyl, $C_{2-6}$ alkenyl, and $C_{2-6}$ alkynyl are each optionally substituted with 1, 2, or 3 substituents independently selected from $Cy^1$, halo, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $C(=NR^{e1})NR^{c1}R^{d1}$, $NR^{c1}C(=NR^{e1})NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, and $S(O)_2NR^{c1}R^{d1}$;

each $Cy^1$ is independently selected from $C_{6-10}$ aryl, $C_{3-10}$ cycloalkyl, 5-10 membered heteroaryl, and 4-10 membered heterocycloalkyl, each of which is optionally substituted by 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-10 membered heteroaryl, 4-10 membered heterocycloalkyl, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)OR^{a2}$, $NR^{c2}C(O)NR^{c2}R^{d2}$, $C(=NR^{e2})R^{b2}$, $C(=NR^{e2})NR^{c2}R^{d2}$, $NR^{c2}C(=NR^{e2})NR^{c2}R^{d2}$, $NR^{c2}S(O)R^{b2}$, $NR^{c2}S(O)_2R^{b2}$, $NR^{c2}S(O)_2NR^{c2}R^{d2}$, $S(O)R^{b2}$, $S(O)NR^{c2}R^{d2}$, $S(O)_2R^{b2}$, and $S(O)_2NR^{c2}R^{d2}$; wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, and 4-10 membered heterocycloalkyl are each optionally substituted with 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $C(=NR^{e2})NR^{c2}R^{d2}$, $NR^{c2}C(=NR^{e2})NR^{c2}R^{d2}$, $NR^{c2}R^{d2}$, $NR^{c2}C(O)R^{b2}$, $NR^{c2}C(O)OR^{a2}$, $NR^{c2}C(O)NR^{c2}R^{d2}$, $NR^{c2}S(O)R^{b2}$, $NR^{c2}S(O)_2R^{b2}$, $NR^{c2}S(O)_2NR^{c2}R^{d2}$, $S(O)R^{b2}$, $S(O)NR^{c2}R^{d2}$, $S(O)_2R^{b2}$, and $S(O)_2NR^{c2}R^{d2}$;

each $R^{a1}$, $R^{b1}$, $R^{c1}$, $R^{d1}$, $R^{a2}$, $R^{b2}$, $R^{c2}$, and $R^{d2}$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl, $C_{3-10}$ cycloalkyl-$C_{1-4}$ alkyl, (5-10 membered heteroaryl)-$C_{1-4}$ alkyl, and (4-10 membered heterocycloalkyl)-$C_{1-4}$ alkyl, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl, $C_{3-10}$ cycloalkyl-$C_{1-4}$ alkyl, (5-10 membered heteroaryl)-$C_{1-4}$ alkyl, and (4-10 membered heterocycloalkyl)-$C_{1-4}$ alkyl are optionally substituted with 1, 2, 3, 4, or 5 substituents independently selected from $C_{1-4}$ alkyl, $C_{1-4}$ haloalkyl, halo, CN, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)OR^{a3}$, $C(=NR^{e3})NR^{c3}R^{d3}$, $NR^{c3}C(=NR^{e3})NR^{c3}R^{d3}$, $S(O)R^{b3}$, $S(O)NR^{c3}R^{d3}$, $S(O)_2R^{b3}$, $NR^{c3}S(O)_2R^{b3}$, $NR^{c3}S(O)_2NR^{c3}R^{d3}$, and $S(O)_2NR^{c3}R^{d3}$;

or any $R^{c1}$ and $R^{d1}$ together with the N atom to which they are attached form a 4-, 5-, 6-, or 7-membered heterocycloalkyl group optionally substituted with 1, 2, or 3 substituents independently selected from $C_{1-6}$ alkyl, $C_{3-7}$ cycloalkyl, 4-7 membered heterocycloalkyl, $C_{6-10}$ aryl, 5-6 membered heteroaryl, $C_{1-6}$ haloalkyl, halo, CN, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)NR^{c3}R^{d3}$, $NR^{c3}C(O)OR^{a3}$, $C(=NR^{e3})NR^{c3}R^{d3}$, $NR^{c3}C(=NR^{e3})NR^{c3}R^{d3}$, $S(O)R^{b3}$, $S(O)NR^{c3}R^{d3}$, $S(O)_2R^{b3}$, $NR^{c3}S(O)_2R^{b3}$, $NR^{c3}S(O)_2NR^{c3}R^{d3}$, and $S(O)_2NR^{c3}R^{d3}$, wherein said $C_{1-6}$ alkyl, $C_{3-7}$ cycloalkyl, 4-7 membered heterocycloalkyl, $C_{6-10}$ aryl, and 5-6 membered heteroaryl are optionally substituted by 1, 2, or 3 substituents independently selected from halo, CN, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)NR^{c3}R^{d3}$, $NR^{c3}C(O)OR^{a3}$, $C(=NR^{e3})NR^{c3}R^{d3}$, $NR^{c3}C(=NR^{e3})NR^{c3}R^{d3}$, $S(O)R^{b3}$, $S(O)NR^{c3}R^{d3}$, $S(O)_2R^{b3}$, $NR^{c3}S(O)_2R^{b3}$, $NR^{c3}S(O)_2NR^{c3}R^{d3}$, and $S(O)_2NR^{c3}R^{d3}$;

or any $R^{c2}$ and $R^{d2}$ together with the N atom to which they are attached form a 4-, 5-, 6-, or 7-membered heterocycloalkyl group optionally substituted with 1, 2, or 3 substituents independently selected from $C_{1-6}$ alkyl, $C_{3-7}$ cycloalkyl, 4-7 membered heterocycloalkyl, $C_{6-10}$ aryl, 5-6 membered heteroaryl, $C_{1-6}$ haloalkyl, halo, CN, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)NR^{c3}R^{d3}$, $NR^{c3}C(O)OR^{a3}$, $C(=NR^{e3})NR^{c3}R^{d3}$, $NR^{c3}C(=NR^{e3})NR^{c3}R^{d3}$, $S(O)R^{b3}$, $S(O)NR^{c3}R^{d3}$, $S(O)_2R^{b3}$, $NR^{c3}S(O)_2R^{b3}$, $NR^{c3}S(O)_2NR^{c3}R^{d3}$, and $S(O)_2NR^{c3}R^{d3}$, wherein said $C_{1-6}$ alkyl, $C_{3-7}$ cycloalkyl, 4-7 membered heterocycloalkyl, $C_{6-10}$ aryl, and 5-6 membered heteroaryl are optionally substituted by 1, 2, or 3 substituents independently selected from halo, CN, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)NR^{c3}R^{d3}$, $NR^{c3}C(O)OR^{a3}$, $C(=NR^{e3})NR^{c3}R^{d3}$, $NR^{c3}C(=NR^{e3})NR^{c3}R^{d3}$, $S(O)R^{b3}$, $S(O)NR^{c3}R^{d3}$, $S(O)_2R^{b3}$, $NR^{c3}S(O)_2R^{b3}$, $NR^{c3}S(O)_2NR^{c3}R^{d3}$, and $S(O)_2NR^{c3}R^{d3}$;

each $R^{c1}$ and $R^{c2}$ is independently selected from H, $C_{1-4}$ alkyl, CN, $OR^{a3}$, $SR^{b3}$, $S(O)_2R^{b3}$, $C(O)R^{b3}$, $S(O)_2NR^{c3}R^{d3}$, and $C(O)NR^{c3}R^{d3}$;

each $R^{a3}$, $R^{b3}$, $R^{c3}$, and $R^{d3}$ is independently selected from H, $C_{1-4}$ alkyl, $C_{1-4}$ haloalkyl, $C_{2-4}$ alkenyl, and $C_{2-4}$ alkynyl, wherein said $C_{1-4}$ alkyl, $C_{2-4}$ alkenyl, and $C_{2-4}$ alkynyl are optionally substituted with 1, 2, or 3 substituents independently selected from OH, CN, amino, halo, $C_{1-4}$ alkyl, $C_{1-4}$ alkoxy, $C_{1-4}$ alkylthio, $C_{1-4}$ alkylamino, di($C_{1-4}$ alkyl)amino, $C_{1-4}$ haloalkyl, and $C_{1-4}$ haloalkoxy;

or any $R^{c3}$ and $R^{d3}$ together with the N atom to which they are attached form a 4-, 5-, 6-, or 7-membered heterocycloalkyl group optionally substituted with 1, 2, or 3 substituents independently selected from OH, CN, amino, halo, $C_{1-6}$ alkyl, $C_{1-4}$ alkoxy, $C_{1-4}$ alkylthio, $C_{1-4}$ alkylamino, di($C_{1-4}$ alkyl)amino, $C_{1-4}$ haloalkyl, and $C_{1-4}$ haloalkoxy; and each $R^{e3}$ is independently selected from H, $C_{1-4}$ alkyl, and CN.

2. The method of claim 1, wherein said cancer is selected from the group consisting of bladder cancer, breast cancer, cervical cancer, colorectal cancer, endometrial cancer, gastric cancer, head and neck cancer, kidney cancer, liver cancer, lung cancer, ovarian cancer, prostate cancer, esophageal cancer, gall bladder cancer, pancreatic cancer, thyroid cancer, skin cancer, leukemia, multiple myeloma, chronic lymphocytic lymphoma, adult T cell leukemia, B-cell lymphoma, acute myelogenous leukemia, Hodgkin's or non-Hodgkin's lymphoma, Waldenstrom's macroglubulinemia, hairy cell lymphoma, Burkett's lymphoma, glioblastoma, melanoma, myeloproliferative neoplasms, squamous cell carcinoma, adenocarcinoma and rhabdosarcoma.

3. The method of claim 1, wherein said cancer is selected from the group consisting of bladder cancer, breast cancer, cervical cancer, colorectal cancer, endometrial cancer, gastric cancer, head and neck cancer, kidney cancer, liver cancer, lung cancer, ovarian cancer, prostate cancer, esophageal cancer, gall bladder cancer, pancreatic cancer, thyroid cancer, and skin cancer.

4. The method of claim 1, wherein said cancer is selected from the group consisting of leukemia, multiple myeloma, chronic lymphocytic lymphoma, adult T cell leukemia, B-cell lymphoma, acute myelogenous leukemia, Hodgkin's or non-Hodgkin's lymphoma, Waldenstrom's macroglubulinemia, hairy cell lymphoma, Burkett's lymphoma, glioblastoma, melanoma, and rhabdosarcoma.

5. The method of claim 1, wherein at least two of $R^1$, $R^2$, $R^3$, $R^4$, and $R^5$ are other than H.

6. The method of claim 1, wherein at least three of $R^1$, $R^2$, $R^3$, $R^4$, and $R^5$ are other than H.

7. The method of claim 1, wherein at least four of $R^1$, $R^2$, $R^3$, $R^4$, and $R^5$ are other than H.

8. The method of claim 1, wherein $R^1$, $R^2$, $R^3$, $R^4$, and $R^5$ are each independently selected from H, halo, and $OR^a$.

9. The method of claim 1, wherein $R^1$, $R^2$, $R^3$, $R^4$, and $R^5$ are each independently selected from H, F, and $OCH_3$.

10. The method of claim 1, wherein $R^1$ is H, $R^2$ is $OCH_3$, $R^3$ is H, $R^4$ is $OCH_3$, and $R^5$ is H.

11. The method of claim 1, wherein $R^1$ is F, $R^2$ is $OCH_3$, $R^3$ is H, $R^4$ is $OCH_3$, and $R^5$ is F.

12. The method of claim 1, wherein $R^{6a}$ is H, halo, $C_{1-6}$ alkyl, CN, or $C(O)NR^{c1}R^{d1}$.

13. The method of claim 1, wherein $R^{6a}$ is H, Br, Cl, $CH_3$, $CH_2CH_3$, CN, or $C(O)NHCH_3$.

14. The method of claim 1, wherein $R^{6a}$ is H.

15. The method of claim 1, wherein $R^{6b}$ is other than H.

16. The method of claim 1, wherein $R^{6b}$ is $C_{1-6}$ alkyl, $C_{2-6}$ alkynyl, $C_{6-10}$ aryl, 5-10 membered heteroaryl, 4-10 membered heterocycloalkyl, or $C(O)NR^{c1}R^{d1}$; wherein said $C_{1-6}$ alkyl, $C_{2-6}$ alkynyl, $C_{6-10}$ aryl, 5-10 membered heteroaryl, and 4-10 membered heterocycloalkyl are each optionally substituted with 1, 2, 3, 4, or 5 substituents independently selected from $R^9$.

17. The method of claim 1, wherein $R^{6b}$ is propyl, propynyl, phenyl, thienyl, pyrazolyl, pyridyl, pyrimidinyl, benzo[d][1,3]dioxolyl, 1,2,3,6-tetrahydropyridinyl, 1H-indazolyl, piperidinyl, pyrido[2,3-b]pyrazinyl, indolin-2-onyl, $C(O)NHCH_3$, or $C(O)N(CH_3)_2$; wherein said propyl, propynyl, phenyl, thienyl, pyrazolyl, pyridyl, pyrimidinyl, benzo[d][1,3]dioxolyl, 1,2,3,6-tetrahydropyridinyl, 1H-indazolyl, piperidinyl, pyrido[2,3-b]pyrazinyl, and indolin-2-onyl are each optionally substituted with 1, 2, or 3 substituents independently selected from $R^9$.

18. The method of claim 1, wherein $R^9$ is $Cy^1$, halo, $C_{1-6}$ alkyl, $C_{1-6}$ haloalkyl, CN, $OR^{a1}$, $C(O)NR^{c1}R^{d1}$, $C(O)OR^{a1}$, $NR^{c1}R^{d1}$, or $NR^{c1}C(O)R^{b1}$, wherein said $C_{1-6}$ alkyl is optionally substituted with 1, 2, or 3 substituents independently selected from $Cy^1$, halo, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $C(=NR^{e1})NR^{c1}R^{d1}$, $NR^{c1}C(=NR^{e1})NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, and $S(O)_2NR^{c1}R^{d1}$.

19. The method of claim 1, wherein X and Y are both $CH_2$.

20. The method of claim 1, wherein the compound is a compound of Formula IIa:

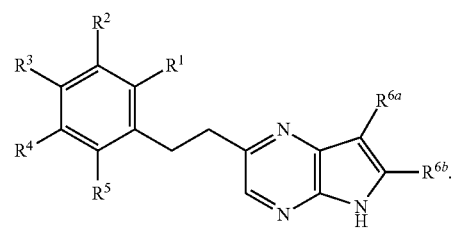

IIa

21. The method of claim 1, wherein the compound is a compound of Formula IIb:

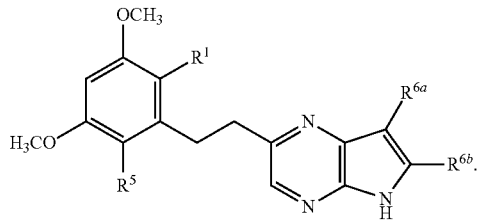

22. The method of claim 1, wherein the compound is selected from the group consisting of:
2-[2-(3,5-dimethoxyphenyl)ethyl]-6-[4-(4-methylpiperazin-1-yl)phenyl]-5H-pyrrolo[2,3-b]pyrazine;
2-[2-(3,5-dimethoxyphenyl)ethyl]-6-[4-(4-ethylpiperazin-1-yl)phenyl]-5H-pyrrolo[2,3-b]pyrazine;
2-(3,5-dimethoxyphenethyl)-6-phenyl-5H-pyrrolo[2,3-b]pyrazine;
6-(2,6-difluorophenyl)-2-(3,5-dimethoxyphenethyl)-5H-pyrrolo[2,3-b]pyrazine;
2-[2-(3,5-dimethoxyphenyl)ethyl]-6-(4-methoxyphenyl)-5H-pyrrolo[2,3-b]pyrazine;
N-(4-{2-[2-(3,5-dimethoxyphenyl)ethyl]-5H-pyrrolo[2,3-b]pyrazin-6-yl}phenyl)acetamide;
4-{2-[2-(3,5-dimethoxyphenyl)ethyl]-5H-pyrrolo[2,3-b]pyrazin-6-yl}-N,N-dimethylbenzamide;
2-[2-(3,5-dimethoxyphenyl)ethyl]-6-[4-(trifluoromethyl)phenyl]-5H-pyrrolo[2, 3-b]pyrazine;
2-[2-(3,5-dimethoxyphenyl)ethyl]-6-(2-methylphenyl)-5H-pyrrolo[2,3-b]pyrazine;
2-{2-[2-(3,5-dimethoxyphenyl)ethyl]-5H-pyrrolo[2,3-b]pyrazin-6-yl}benzonitrile;
2-[2-(3,5-dimethoxyphenyl)ethyl]-6-[4-(piperidin-1-ylmethyl)phenyl]-5H-pyrrolo[2,3-b]pyrazine;
2-[2-(3,5-dimethoxyphenyl)ethyl]-6-[4-(methoxymethyl)phenyl]-5H-pyrrolo[2,3-b]pyrazine;
(4-{2-[2-(3,5-dimethoxyphenyl)ethyl]-5H-pyrrolo[2,3-b]pyrazin-6-yl}phenyl)methanol;
(4-{2-[2-(3,5-dimethoxyphenyl)ethyl]-5H-pyrrolo[2,3-b]pyrazin-6-yl}phenyl)acetonitrile;
4-{2-[2-(3,5-dimethoxyphenyl)ethyl]-5H-pyrrolo[2,3-b]pyrazin-6-yl}benzoic acid;
2-[2-(3,5-dimethoxyphenyl)ethyl]-6-[6-(4-methylpiperazin-1-yl)pyridin-3-yl]-5H-pyrrolo[2,3-b]pyrazine;
5-{2-[2-(3,5-dimethoxyphenyl)ethyl]-5H-pyrrolo[2,3-b]pyrazin-6-yl}-N-methylpyridine-2-carboxamide;
2-[2-(3,5-dimethoxyphenyl)ethyl]-6-[5-(morpholin-4-ylcarbonyl)pyridin-3-yl]-5H-pyrrolo[2,3-b]pyrazine;
4-{2-[2-(3,5-dimethoxyphenyl)ethyl]-5H-pyrrolo[2,3-b]pyrazin-6-yl}thiophene-2-carboxylic acid;
5-{2-[2-(3,5-dimethoxyphenyl)ethyl]-5H-pyrrolo[2,3-b]pyrazin-6-yl}-N,N-dimethylpyrimidin-2-amine;
6-(1,3-benzodioxol-5-yl)-2-[2-(3,5-dimethoxyphenyl)ethyl]-5H-pyrrolo[2,3-b]pyrazine;
2-[2-(3,5-dimethoxyphenyl)ethyl]-6-[4-(1-methylpiperidin-4-yl)phenyl]-5H-pyrrolo[2,3-b]pyrazine;
2-[2-(3,5-dimethoxyphenyl)ethyl]-6-(1-methyl-1,2,3,6-tetrahydropyridin-4-yl)-5H-pyrrolo[2,3-b]pyrazine;
2-[2-(3,5-dimethoxyphenyl)ethyl]-6-(1-methylpiperidin-4-yl)-5H-pyrrolo[2,3-b]pyrazine;
2-[2-(3,5-dimethoxyphenyl)ethyl]-N-methyl-5H-pyrrolo[2,3-b]pyrazine-6-carboxamide;
2-[2-(3,5-dimethoxyphenyl)ethyl]-N,N-dimethyl-5H-pyrrolo[2,3-b]pyrazine-6-carboxamide;
3-{2-[2-(3,5-dimethoxyphenyl)ethyl]-5H-pyrrolo[2,3-b]pyrazin-6-yl}-N,N-diethylprop-2-yn-1-amine;
3-{2-[2-(3,5-dimethoxyphenyl)ethyl]-5H-pyrrolo[2,3-b]pyrazin-6-yl}-N,N-diethylpropan-1-amine;
2-[2-(3,5-dimethoxyphenyl)ethyl]-6-(1H-pyrazol-4-yl)-5H-pyrrolo[2,3-b]pyrazine;
2-[2-(3,5-dimethoxyphenyl)ethyl]-6-(1-methyl-1H-pyrazol-4-yl)-5H-pyrrolo[2,3-b]pyrazine;
2-[2-(3,5-dimethoxyphenyl)ethyl]-6-[1-(2-morpholin-4-ylethyl)-1H-pyrazol-4-yl]-5H-pyrrolo[2,3-b]pyrazine;
2-[2-(3,5-dimethoxyphenyl)ethyl]-6-[1-(tetrahydro-2H-pyran-4-yl)-1H-pyrazol-4-yl]-5H-pyrrolo[2,3-b]pyrazine;
1-(4-{2-[2-(3,5-dimethoxyphenyl)ethyl]-5H-pyrrolo[2,3-b]pyrazin-6-yl}-1H-pyrazol-1-yl)-2-methylpropan-2-ol;
2-(4-{2-[2-(3,5-dimethoxyphenyl)ethyl]-5H-pyrrolo[2,3-b]pyrazin-6-yl}-1H-pyrazol-1-yl)-N,N-dimethylethanamine;
3-cyclopentyl-3-(4-{2-[2-(3,5-dimethoxyphenyl)ethyl]-5H-pyrrolo[2,3-b]pyrazin-6-yl}-1H-pyrazol-1-yl)propanenitrile;
3-(4-(2-(3,5-dimethoxyphenethyl)-5H-pyrrolo[2,3-b]pyrazin-6-yl)-1H-pyrazol-1-1)butanenitrile;
2-[2-(3,5-dimethoxyphenyl)ethyl]-6-[1-(1-methylpiperidin-4-yl)-1H-pyrazol-4-yl]-5H-pyrrolo[2,3-b]pyrazine;
2-(4-{2-[2-(3,5-dimethoxyphenyl)ethyl]-5H-pyrrolo[2,3-b]pyrazin-6-yl}-1H-pyrazol-1-yl)ethanol;
(2S)-1-(4-{2-[2-(3,5-dimethoxyphenyl)ethyl]-5H-pyrrolo[2,3-b]pyrazin-6-yl}-1H-pyrazol-1-yl)propan-2-ol;
1-[2-(4-{2-[2-(3,5-dimethoxyphenyl)ethyl]-5H-pyrrolo[2,3-b]pyrazin-6-yl}-1H-pyrazol-1-yl)ethyl]piperidin-4-ol;
2-[2-(3,5-dimethoxyphenyl)ethyl]-6-[1-(2-piperidin-1-ylethyl)-1H-pyrazol-4-yl]-5H-pyrrolo[2,3-b]pyrazine;
2-[2-(3,5-dimethoxyphenyl)ethyl]-6-{1-[2-(4-methylpiperazin-1-yl)ethyl]-1H-pyrazol-4-yl}-5H-pyrrolo[2,3-b]pyrazine;
2-(4-{2-[2-(3,5-dimethoxyphenyl)ethyl]-5H-pyrrolo[2,3-b]pyrazin-6-yl}-1H-pyrazol-1-yl)-N,N-dimethylacetamide;
2-(4-(2-(3,5-dimethoxyphenethyl)-5H-pyrrolo[2,3-b]pyrazin-6-yl)-1H-pyrazol-1-yl)-1-(4-methylpiperazin-1-yl)ethanone;
2-[2-(3,5-dimethoxyphenyl)ethyl]-6-[4-(4-methylpiperazin-1-yl)phenyl]-5H-pyrrolo[2,3-b]pyrazine-7-carbonitrile;
7-bromo-2-[2-(3,5-dimethoxyphenyl)ethyl]-6-[4-(4-methylpiperazin-1-yl)phenyl]-5H-pyrrolo[2,3-b]pyrazine;
7-chloro-2-[2-(3,5-dimethoxyphenyl)ethyl]-6-[4-(4-methylpiperazin-1-yl)phenyl]-5H-pyrrolo[2,3-b]pyrazine;
2-[2-(2-chloro-3,5-dimethoxyphenyl)ethyl]-6-[4-(4-methylpiperazin-1-yl)phenyl]-5H-pyrrolo[2,3-b]pyrazine;
2-[2-(2,6-dichloro-3,5-dimethoxyphenyl)ethyl]-6-[4-(4-methylpiperazin-1-yl)phenyl]-5H-pyrrolo[2,3-b]pyrazine;
2-[2-(3,5-dimethoxyphenyl)ethyl]-N-methyl-6-[4-(4-methylpiperazin-1-yl)phenyl]-5H-pyrrolo[2,3-b]pyrazine-7-carboxamide;

2-[2-(3,5-dimethoxyphenyl)ethyl]-7-methyl-6-[4-(4-methylpiperazin-1-yl)phenyl]-5H-pyrrolo[2,3-b]pyrazine;
2-[2-(3,5-dimethoxyphenyl)ethyl]-7-ethyl-6-[4-(4-methylpiperazin-1-yl)phenyl]-5H-pyrrolo[2,3-b]pyrazine;
2-Chloro-4-(2-(3,5-dimethoxyphenethyl)-5H-pyrrolo[2,3-b]pyrazin-6-yl)-N-isopropylbenzamide;
5-(2-(3,5-Dimethoxyphenethyl)-5H-pyrrolo[2,3-b]pyrazin-6-yl)-2-fluoro-N,N-dimethylbenzamide;
2-(3,5-Dimethoxyphenethyl)-6-(2-(4-methylpiperazin-1-yl)pyridin-4-yl)-5H-pyrrolo[2,3-b]pyrazine;
2-Chloro-4-(2-(3,5-dimethoxyphenethyl)-5H-pyrrolo[2,3-b]pyrazin-6-yl)-N,N-dimethylbenzamide;
4-(2-(3,5-Dimethoxyphenethyl)-5H-pyrrolo[2,3-b]pyrazin-6-yl)-2-fluoro-N-methylbenzamide;
5-(2-(3,5-Dimethoxyphenethyl)-5H-pyrrolo[2,3-b]pyrazin-6-yl)pyrimidin-2-amine;
5-(2-(3,5-Dimethoxyphenethyl)-5H-pyrrolo[2,3-b]pyrazin-6-yl)-N,N-dimethylpicolinamide;
4-(2-(3,5-Dimethoxyphenethyl)-5H-pyrrolo[2,3-b]pyrazin-6-yl)picolinonitrile;
2-(3,5-Dimethoxyphenethyl)-6-(6-methoxypyridin-3-yl)-5H-pyrrolo[2,3-b]pyrazine;
2-(3,5-Dimethoxyphenethyl)-6-(1-methyl-1H-indazol-5-yl)-5H-pyrrolo[2,3-b]pyrazine;
2-(3,5-Dimethoxyphenethyl)-6-(1-methyl-1H-indazol-6-yl)-5H-pyrrolo[2,3-b]pyrazine;
2-(3,5-Dimethoxyphenethyl)-6-(2-(piperazin-1-yl)pyridin-4-yl)-5H-pyrrolo[2,3-b]pyrazine;
5-(2-(3,5-Dimethoxyphenethyl)-5H-pyrrolo[2,3-b]pyrazin-6-yl)-2-fluorobenzonitrile;
7-(2-(3,5-Dimethoxyphenethyl)-5H-pyrrolo[2,3-b]pyrazin-6-yl)pyrido[2,3-b]pyrazine;
N-(5-(2-(3,5-Dimethoxyphenethyl)-5H-pyrrolo[2,3-b]pyrazin-6-yl)pyridin-2-yl)acetamide;
1-(5-(2-(3,5-Dimethoxyphenethyl)-5H-pyrrolo[2,3-b]pyrazin-6-yl)pyridin-2-yl)pyrrolidin-2-one;
4-(5-(2-(3,5-Dimethoxyphenethyl)-5H-pyrrolo[2,3-b]pyrazin-6-yl)pyridin-3-yl)morpholine;
2-(3,5-Dimethoxyphenethyl)-6-(1H-indazol-5-yl)-5H-pyrrolo[2,3-b]pyrazine;
2-(4-(4-(2-(3,5-Dimethoxyphenethyl)-5H-pyrrolo[2,3-b]pyrazin-6-yl)phenyl)piperazin-1-yl)ethanol;
5-(2-(3,5-Dimethoxyphenethyl)-5H-pyrrolo[2,3-b]pyrazin-6-yl)-2-(4-methylpiperazin-1-yl)benzonitrile;
4-(2-(3,5-Dimethoxyphenethyl)-5H-pyrrolo[2,3-b]pyrazin-6-yl)-N-methylpicolinamide;
4-(2-(3,5-Dimethoxyphenethyl)-5H-pyrrolo[2,3-b]pyrazin-6-yl)-N,N-dimethylpicolinamide;
(4-(2-(3,5-Dimethoxyphenethyl)-5H-pyrrolo[2,3-b]pyrazin-6-yl)pyridin-2-yl)(3-hydroxyazetidin-1-yl)methanone;
1-(4-(2-(3,5-Dimethoxyphenethyl)-5H-pyrrolo[2,3-b]pyrazin-6-yl)phenyl)-4-methylpiperazin-2-one;
1-(4-(2-(3,5-Dimethoxyphenethyl)-5H-pyrrolo[2,3-b]pyrazin-6-yl)phenyl)piperidin-4-ol;
2-(3,5-Dimethoxyphenethyl)-6-(3-(piperazin-1-yl)phenyl)-5H-pyrrolo[2,3-b]pyrazine;
2-(3,5-Dimethoxyphenethyl)-6-(3-(4-methylpiperazin-1-yl)phenyl)-5H-pyrrolo[2,3-b]pyrazine;
5-(2-(3,5-Dimethoxyphenethyl)-5H-pyrrolo[2,3-b]pyrazin-6-yl)indolin-2-one;
4-(4-(2-(3,5-Dimethoxyphenethyl)-5H-pyrrolo[2,3-b]pyrazin-6-yl)phenyl)-1-methylpiperazin-2-one;
2-(2-Fluoro-3,5-dimethoxyphenethyl)-6-(4-(4-methylpiperazin-1-yl)phenyl)-5H-pyrrolo[2,3-b]pyrazine;
2-[2-(2,6-difluoro-3, 5-dimethoxyphenyl)ethyl]-6-(5-methyl-1H-pyrazol-4-yl)-5H-pyrrolo[2,3-b]pyrazine;
2-(2,6-difluoro-3, 5-dimethoxyphenethyl)-6-(1-methyl-1H-pyrazol-4-yl)-5H-pyrrolo[2,3-b]pyrazine;
2-(2-(2,6-difluoro-3, 5-dimethoxyphenethyl)-5H-pyrrolo[2,3-b]pyrazin-6-yl)benzonitrile;
2-(2, 6-difluoro-3,5-dimethoxyphenethyl)-6-(2-methoxypyridin-3-yl)-5H-pyrrolo[2,3-b]pyrazine;
2-(4-(2-(2, 6-difluoro-3,5-dimethoxyphenethyl)-5H-pyrrolo[2,3-b]pyrazin-6-yl)-1H-pyrazol-1-yl)-N,N-dimethylethanamine;
1-(4-(2-(2, 6-difluoro-3,5-dimethoxyphenethyl)-5H-pyrrolo[2,3-b]pyrazin-6-yl)-1H-pyrazol-1-yl)-2-methylpropan-2-ol; and
2-(2, 6-difluoro-3, 5-dimethoxyphenethyl)-N-methyl-5H-pyrrolo[2,3-b]pyrazine-6-carboxamide,
or a pharmaceutically acceptable salt thereof.

* * * * *

UNITED STATES PATENT AND TRADEMARK OFFICE
CERTIFICATE OF CORRECTION

PATENT NO. : 9,745,311 B2  
APPLICATION NO. : 15/181903  
DATED : August 29, 2017  
INVENTOR(S) : Liang Lu et al.

Page 1 of 2

It is certified that error appears in the above-identified patent and that said Letters Patent is hereby corrected as shown below:

In the Claims

Column 99, Line 20, Claim 1, delete "$NR^eC(O)NR^cR^d$," and insert -- $NR^cC(O)NR^cR^d$, --.

Column 100, Line 45, Claim 1, delete "$NR^{c3}\ S(O)_2R^{b3}$," and insert -- $NR^{c3}S(O)_2R^{b3}$, --.

Column 100, Line 45, Claim 1, delete "$NR^{c3}\ S(O)_2NR^{c3}R^{d3}$," and insert -- $NR^{c3}S(O)_2NR^{c3}R^{d3}$, --.

Column 100, Lines 66-67, Claim 1, delete "$NR^{c3}\ S(O)_2NR^{c3}R^{d3}$," and insert -- $NR^{c3}S(O)_2NR^{c3}R^{d3}$, --.

Column 101, Line 21, Claim 1, delete "$NR^{c3}\ S(O)_2R^{b3}$," and insert -- $NR^{c3}S(O)_2R^{b3}$, --.

Column 101, Lines 21-22, Claim 1, delete "$NR^{c3}\ S(O)_2NR^{c3}R^{d3}$," and insert -- $NR^{c3}S(O)_2NR^{c3}R^{d3}$, --.

Column 101, Line 23, Claim 1, delete "$R^{c1}$" and insert -- $R^{e1}$ --.

Column 101, Line 23, Claim 1, delete "$R^{c2}$" and insert -- $R^{e2}$ --.

Column 103, Line 33, Claim 22, delete "[2, 3-b]" and insert -- [2,3-b] --.

Column 106, Line 25, Claim 22, delete "-3, 5-" and insert -- -3,5- --.

Column 106, Line 27, Claim 22, delete "-3, 5-" and insert -- -3,5- --.

Column 106, Line 29, Claim 22, delete "-3, 5-" and insert -- -3,5- --.

Column 106, Line 31, Claim 22, delete "2-(2, 6-" and insert -- 2-(2,6- --.

Signed and Sealed this  
Fourteenth Day of August, 2018

Andrei Iancu  
*Director of the United States Patent and Trademark Office*

Column 106, Line 33, Claim 22, delete "-(2, 6-" and insert -- -(2,6- --.

Column 106, Line 37, Claim 22, delete "-(2, 6-" and insert -- -(2,6- --.

Column 106, Line 40, Claim 22, delete "2-(2, 6-" and insert -- 2-(2,6- --.

Column 106, Line 40, Claim 22, delete "-3, 5-" and insert -- -3,5- --.

SEQUENCE LISTING

```
<160> NUMBER OF SEQ ID NOS: 1

<210> SEQ ID NO 1
<211> LENGTH: 15
<212> TYPE: PRT
<213> ORGANISM: Artificial Sequence
<220> FEATURE:
<223> OTHER INFORMATION: synthetic peptide

<400> SEQUENCE: 1

Glu Gln Glu Asp Glu Pro Glu Gly Asp Tyr Phe Glu Trp Leu Glu
1               5                   10                  15
```